US010124028B2

(12) United States Patent
Champion et al.

(10) Patent No.: US 10,124,028 B2
(45) Date of Patent: Nov. 13, 2018

(54) ONCOLYTIC ADENOVIRUS ENCODING A B7 PROTEIN OR ACTIVE FRAGMENT

(71) Applicant: PSIOXUS THERAPEUTICS LIMITED, Oxfordshire (GB)

(72) Inventors: Brian Robert Champion, Oxfordshire (GB); Alice Claire Noel Brown, Oxfordshire (GB)

(73) Assignee: PSIOXUS THERAPEUTICS LIMITED, Oxfordshire (GB)

( * ) Notice: Subject to any disclaimer, the term of this patent is extended or adjusted under 35 U.S.C. 154(b) by 77 days.

(21) Appl. No.: 15/231,422

(22) Filed: Aug. 8, 2016

(65) Prior Publication Data

US 2017/0056458 A1 Mar. 2, 2017

Related U.S. Application Data

(63) Continuation-in-part of application No. PCT/EP2016/059609, filed on Apr. 29, 2016.

(30) Foreign Application Priority Data

Apr. 30, 2015 (GB) .................................. 1507419.8
Sep. 24, 2015 (GB) .................................. 1516936.0
Dec. 14, 2015 (GB) .................................. 1522013.0

(51) Int. Cl.

| | |
|---|---|
| ***A61K 35/761*** | (2015.01) |
| ***C12N 7/00*** | (2006.01) |
| ***C07K 14/705*** | (2006.01) |
| ***C12N 15/86*** | (2006.01) |
| ***C07K 14/52*** | (2006.01) |
| ***C07K 14/56*** | (2006.01) |
| ***C07K 16/28*** | (2006.01) |
| *A61K 39/00* | (2006.01) |

(52) U.S. Cl.

CPC .......... *A61K 35/761* (2013.01); *C07K 14/523* (2013.01); *C07K 14/56* (2013.01); *C07K 14/70532* (2013.01); *C07K 16/2809* (2013.01); *C12N 7/00* (2013.01); *C12N 15/86* (2013.01); *A61K 2039/505* (2013.01); *C07K 2317/56* (2013.01); *C07K 2317/622* (2013.01); *C07K 2319/03* (2013.01); *C07K 2319/74* (2013.01); *C12N 2710/10321* (2013.01); *C12N 2710/10332* (2013.01); *C12N 2710/10343* (2013.01); *C12N 2710/10371* (2013.01)

(58) Field of Classification Search

None

See application file for complete search history.

(56) References Cited

U.S. PATENT DOCUMENTS

| | | | |
|---|---|---|---|
| 7,510,868 B2 | 3/2009 | Harden et al. | |
| 8,052,965 B2 * | 11/2011 | van Beusechem | C07K 14/4746 424/93.2 |
| 2006/0292682 A1 | 12/2006 | Hawkins et al. | |

FOREIGN PATENT DOCUMENTS

| | | | |
|---|---|---|---|
| CN | 102586327 | A | 7/2012 |
| DE | 102005055128 | A1 | 5/2007 |
| WO | 2000/015823 | A1 | 3/2000 |
| WO | 2001/053506 | A2 | 7/2001 |
| WO | 2005/118825 | A2 | 12/2005 |
| WO | 2015/059303 | A1 | 4/2015 |
| WO | 2015077624 | A1 | 5/2015 |
| WO | 2016174200 | A1 | 11/2016 |

OTHER PUBLICATIONS

Kuhn et al. (PLoS ONE, Jun. 2008, vol. 3, Issue 6, p. 1-11).*
Accession No. EF011630 (Kuhn 2006).*
Paul et al., "The combination of a chemokine, cytokine and TCR-based T cell stimulus for effective gene therapy of cancer", Cancer Immunol Immunother. Dec. 2002;51(11-12):645-54. Epub Oct. 9, 2002.
Choi et al., "Concurrent delivery of GM-CSF and B7-1 using an oncolytic adenovirus elicits potent antitumor effect", Gene Ther. Jul. 2006;13(13):1010-20. Epub Mar. 9, 2006.
Hermiston and Kuhn, "Armed therapeutic viruses: strategies and challenges to arming oncolytic viruses with therapeutic genes", Cancer Gene Ther. Dec. 2002;9(12):1022-35. Review.
Hobbs et al., "Efficient activation of viral genomes by levels of herpes simplex virus ICP0 insufficient to affect cellular gene expression or cell survival", J Virol. Apr. 2001;75(7):3391-403.
Hu et al., "A simplified system for generating oncolytic adenovirus vector carrying one or two transgenes", Cancer Gene Ther. Mar. 2008;15(3):173-82. Epub Dec 21, 2007.
Jiang et al., "The Controlled Transgene Expression in Oncolytic Adenoviral Vectors with Major Late Promoter for Therapy of Cancer", Molecular Therapy vol. 13, Supplement 1, May 2006, S251.
Lee et al., "Enhanced Antitumor Effect of Oncolytic Adenovirus Expressing Interleukin-12 and B7-1 in an Immunocompetent Murine Model", Clin Cancer Res. Oct. 1, 2006;12(19):5859-68.
Putzer et al., "Improved Treatment of Pancreatic Cancer by IL-12 and B7.1 Costimulation: Antitumor Efficacy and Immunoregulation in a Nonimmunogenic Tumor Model", Mol Ther. Apr. 2002;5(4):405-12.

(Continued)

*Primary Examiner* — Agnieszka Boesen
(74) *Attorney, Agent, or Firm* — Saul Ewing Arnstein & Lehr LLP; Debora Plehn-Dujowich

(57) ABSTRACT

The present disclosure provides a replication competent oncolytic adenovirus with selectivity for cancer cells, wherein the adenovirus comprises a transgene under the control of a promoter endogenous to the virus, wherein the transgene comprises a DNA sequence encoding a B7 protein or an active fragment thereof, compositions comprising same, methods of generating the viruses, and use of the viruses and compositions in treatment, particularly in the treatment of cancer.

18 Claims, 70 Drawing Sheets

Specification includes a Sequence Listing.

(56) References Cited

OTHER PUBLICATIONS

International Search Report and Written Opinion issued in PCT/EP2016/059609 dated Jul. 11, 2016 (16 pages).
Non-Final Office Action for U.S. Appl. No. 14/896,294 dated Apr. 6, 2018.
Jin, et al., Identification of novel insertion sites in the Ad5 genome that utilize the Ad splicing machinery for therapeutic gene expression, Mol Ther. 12(6) ,2005 ,1052-1063.

* cited by examiner

Fig. 1A Antigen Presenting Cell or Tumor Cell
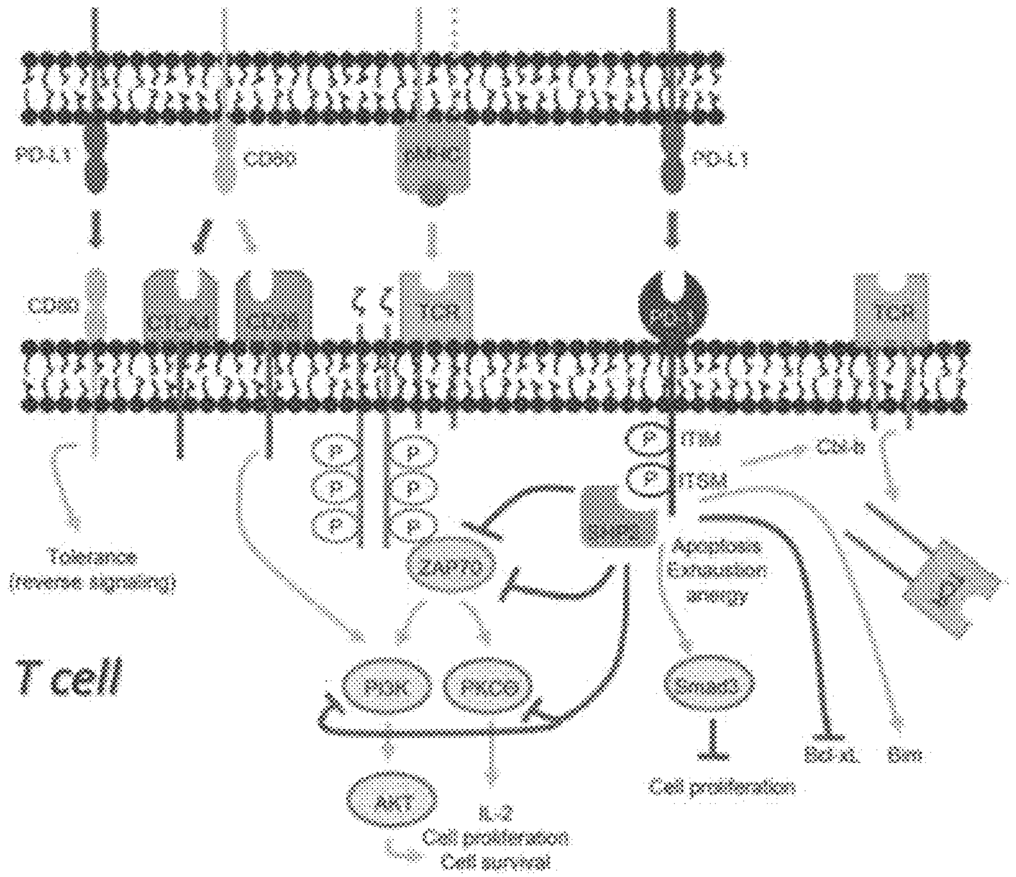
Fig. 1B
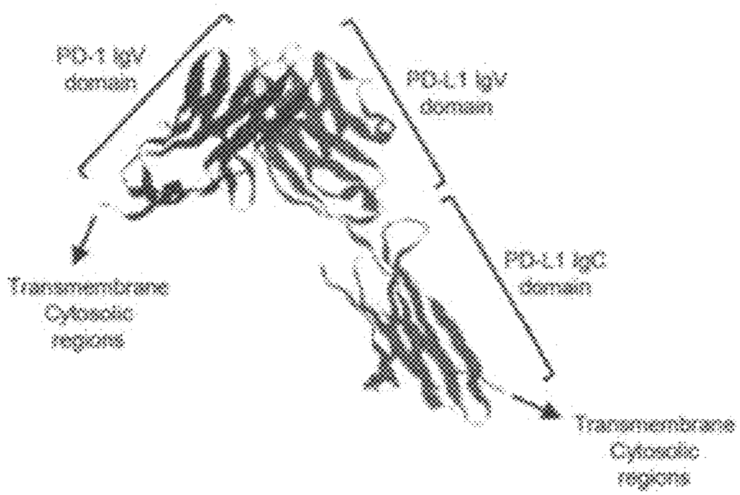

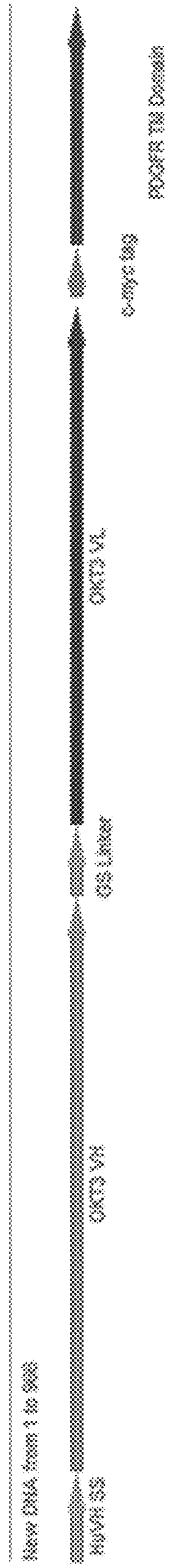
Fig. 3G ORF cassette for scFv antibody

E

Fig. 13A
A
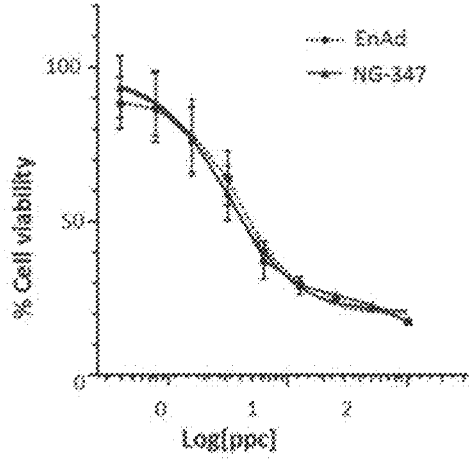
Fig. 13B
B
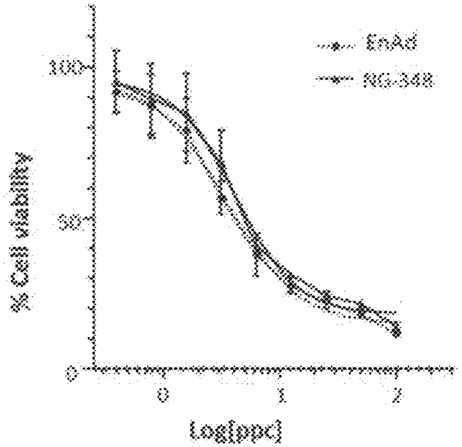
Fig. 13C
| VIRUS | TITRE (vp/mL) | INFECTIOUS TITRE (IFU/mL) | Infectivity Ratio (P:I) |
|---|---|---|---|
| EnAd (Ref 1) | 3e12 | 7.83e10 | 38.3 |
| EnAd (Ref 2) | 3e12 | 9.37e10 | 32.0 |
| NG-347 | 3.78e12 | 1.67e11 | 22.7 |
| NG-348 | 6.68e12 | 3.31e11 | 20.2 |

CD3+CD4+
T cells
35.8
A549: T cells
40.4
EnAd: A549: T cells
34.5
NG-348: A549: T cells
90.3

CD3+CD4-
T cells
7.41
A549: T cells
9.03
EnAd: A549: T cells
10.3
NG-348: A549: T cells
68.5
SSC
CD25

ONCOLYTIC ADENOVIRUS ENCODING A B7 PROTEIN OR ACTIVE FRAGMENT

CROSS REFERENCE TO RELATED APPLICATIONS

The present invention is a continuation-in-part of International Application No. PCT/EP2016/059609, filed Apr. 29, 2016, which designated the U.S. and claims the benefit of priority to United Kingdom Patent Application Nos. GB 1507419.8 filed Apr. 30, 2015; GB 1516936.0 filed Sep. 24, 2015; and GB 1522013.0 filed Dec. 14, 2015, each of which is hereby incorporated by reference in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Nov. 14, 2016, is named STPS145_US_SeqList.txt and is 527 kilobytes in size.

TECHNICAL FIELD

The present disclosure relates to an oncolytic adenovirus comprising a transgene encoding at least a B7 protein such as CD80 or an active fragment thereof, compositions comprising the same and use of the virus and compositions in treatment, particularly in the treatment of cancer.

BACKGROUND

Cancer is still a huge social burden to society in terms of the hardship and suffering of patients and their loved ones, and also in terms of the high financial cost of treating, caring for and supporting patients. It is now thought that the immune system of healthy individuals clears cancerous cells routinely. However, in those patients with cancer one or more of the defense mechanisms involved in this clearance is/are down regulated or turned off completely.

It is now known that tumors change their microenvironment to make it more permissive to their growth. This occurs by the tumor releasing extracellular signals that, for example, promote tumor angiogenesis and/or induce local immune suppression or immune tolerance.

It is clear from many different preclinical and clinical studies that the microenvironment within tumours can suppress the development and activity of anti-tumour immune responses, with a wide variety of mechanisms being shown to potentially play a role. In particular immuno-suppressive mechanisms ultimately prevent T-cell responses from mediating the killing of tumour cells. Suppressive mechanisms may include the exclusion of T-cells from entering tumour tissues, inhibiting activation of T-cells that do enter the tumour and the modulation of tumour cell proteins which reduces the ability of T-cells to recognize or respond to them. The importance of such immunosuppressive pathways in supporting tumour progression has been particularly highlighted by the clinical efficacy shown by antibodies to receptors in two such suppressive pathways, CTLA4 and PD-1/PDL1, which has led to their marketing approval for the treatment of melanoma and other cancers.

B7 is a type of peripheral membrane protein found on activated antigen presenting cells (APCs) that, when paired with either a CD28 or CD152 (CTLA-4) surface protein on a T cell, can produce a co-stimulatory signal or a co-inhibitory signal to enhance or decrease the activity of a MHC-TCR signal between the antigen presenting cell (APC) and the T cell, respectively. Besides being present on activated APCs, B7 can also be found on T-cells themselves.

There are several steps to activation of the immune system against an antigen. The T cell receptor must first interact with a complex of its specific peptide antigen (Ag) bound to a major histocompatibility complex (MHC) surface protein. The CD4 or CD8 proteins on the T-cell surface interact with the MHC to help stabilize the MHC/Ag interaction with the T-cell receptor complex, which comprises both the antigen-binding chain dimers (alpha/beta or gamma/delta) and the CD3 signaling complex (comprising gamma, delta, epsilon and zeta chains). This is also referred to as "Signal 1" and its main purpose is to provide the initial signaling and guarantee antigen specificity of the T cell activation.

However, MHC binding is insufficient by itself for stimulating full effector T cell differentiation and activation. In fact, lack of further stimulatory signals can render the T cell anergic. The co-stimulatory signals necessary to continue the immune response can come from B7-CD28 and CD40-CD40L interactions. There are other activation signals which play a role in immune responses. For example, in the TNF family of molecules, the protein 4-1BB (CD137) on the T cell may bind to 4-1BBL on the APC.

The B7 (CD80/B7-1 and/or CD86/B7-2) protein is present on the APC surface, and it interacts with the CD28 receptor on the T cell surface. This is one source of "Signal 2" (cytokines can also contribute to T-cell activation, which may be referred to as "Signal 3"). This interaction produces a series of downstream signals which promote the target T cell's survival, activation and differentiation into an effector cell that can mediate aspects of the immune response, such as killing of virus infected cells or tumour cells, and the recruitment of inflammatory cells.

Usually for initiating a T-cell response, the stimulatory signal and the co-stimulatory signal are provided by an antigen presenting cell in order to induce both CD4 and CD8 T-cell responses. But effector CD8 T-cells recognize their antigen associated with MHC class I molecules which are present on most nucleated cells, including tumour cells.

The present inventors have reason to believe that the signals to activate T cells do not need to come from the same cell or cell type. Therefore it would be useful to provide one or more of these signals (i.e. the stimulatory signal and/or the co-stimulatory signal) to the immune system, for example on the surface of a cancer cell.

Currently there is much interest in inhibiting PD-1 (programmed cell death protein 1) and/or its ligand PDL1 (also known as B7-H1) activity because this pathway is thought to play an important role in down-regulating immune responses, for example in cancers.

However, some work done suggests that CD80 (B7-1) not only acts as a T-cell co-stimulator by binding to CD28 on the T-cell, it can also bind to PDL1, for example when expressed in the same cell membrane, and block PDL1-PD1 inhibitory signaling interactions. Thus, by acting in two different ways, CD80 may be a viable and potentially more useful molecule for restoring or enhancing the activation of human T cells. Soluble forms of CD80 also seem to be capable of counteracting PDL1-PD1 mediated T cell inhibition, see for example Haile et al Soluble CD80 Restores T Cell Activation and Overcomes Tumor Cell Programmed Death Ligand 1—Mediated Immune Suppression J Immunol 2013; 191: 2829-2836. A CD80-Fc fusion protein has been generated and is being tested for safety and efficacy, see the Journal of Immunology, 2014, 193: 3835-3841.

The present inventors believe that the B7 proteins or an active fragment thereof delivered and expressed by an oncolytic virus, for example on the surface of a cancer cell, would be useful in activating the patient's own immune system to fight the cancer.

Furthermore, B7 proteins, such as CD80, if simply administered systemically have the potential to stimulate immune responses systemically in an undesirable way. The present inventors believe that a more sophisticated delivery of these proteins is required to create a suitable therapeutic window where beneficial therapeutic effects are realized and off target effects are minimized.

SUMMARY OF THE DISCLOSURE

Thus there is provided an oncolytic adenovirus with selectivity for cancer cells, wherein the adenovirus comprises a transgene under the control of a promoter endogenous to the virus, wherein the transgene comprises a DNA sequence encoding a B7 protein or an active fragment thereof. This is beneficial because the oncolytic viruses according to the present disclosure preferentially infect cancer cells and thus penetrate the microenvironment created by the cancer. Once in the cancer cells the B7 proteins encoded by the virus can be expressed, for example on the cell surface (i.e. cancer cell surface). This is advantageous because the B7 protein is then in the desired location where it can be biologically active.

In one embodiment the B7 protein encoded comprises a sequence capable of anchoring the protein on the surface of a cell, for example a transmembrane domain sequence, GPI anchor or the like.

Thus in one embodiment the cancer cell is infected with a virus of the present disclosure which expresses a B7 protein or molecule, in particular on the surface of the cancer cell, wherein the B7 protein is suitable for providing at least the co-stimulatory signal i.e. signal 2 to activate a T cell, and/or may bind to and inhibit the activity of PD-L1 expressed on the surface of the cancer cell or other cells in the local microenvironment.

In one embodiment the B7 sequence comprises a transmembrane element from a B7 protein, for example a transmembrane element native to the particular B7 protein or a transmembrane domain from a "different" B7 protein to that being particularly expressed.

B7 proteins are surface expressed proteins and can also be employed to carry additional proteins to the cancer cell surface, for example where at least the transmembrane domain of a B7 protein is attached to an additional protein.

Thus in one aspect there is provided a replication competent oncolytic adenovirus with selectivity for cancer cells, wherein the adenovirus comprises a transgene under the control of a promoter endogenous to the virus, wherein the transgene comprises a DNA sequence encoding a B7 protein or an active fragment thereof.

Also provided is a replication competent oncolytic virus according to claim 1, wherein the B7 protein or active fragment thereof is independently selected from the group comprising B7-1, B7-2, B7-DC, B7-H1, B7-H2, B7-H3, B7-H4, B7-H5 and B7-H6, in particular wherein the B7 protein is B7-1 (CD80) or an active fragment thereof.

In one embodiment the replication competent oncolytic virus is a group B adenovirus.

In one embodiment the replication competent oncolytic virus is a chimeric virus.

In one embodiment the replication competent oncolytic virus has a backbone is enadenotucirev (also referred to as EnAd).

In one embodiment the replication competent oncolytic virus has a formula (I):

5'ITR-B1-BA-B2-BX-BB-BY-B3-3'ITR (I)

$B_1$ comprises: E1A, E1B or E1A-E1B;

$B_A$ is E2B-L1-L2-L3-E2A-L4;

$B_2$ is a bond or comprises E3 or a transgene, for example under an endogenous or exogenous promoter;

$B_X$ is a bond or a DNA sequence comprising: a restriction site, one or more transgenes or both;

$B_B$ comprises L5;

$B_Y$ comprises a transgene encoding a B7 protein or an active fragment thereof; and $B_3$ is a bond or comprises E4.

In one embodiment the replication competent oncolytic virus according to any one of claims 1 to 7, wherein the B7 protein or active fragment thereof comprises a transmembrane sequence, for example a transmembrane domain from a PDGF receptor, or GPI anchor suitable for anchoring the protein or fragment in a cell membrane.

In one embodiment the replication competent oncolytic virus further comprises a second transgene, for example encoding a polypeptide selected from the group comprising a cytokine, a chemokine, an antagonistic antibody molecule or fragment thereof, and an agonistic antibody molecule or fragment thereof.

In one embodiment the second and third transgene, for example encoding two different polypeptides selected from the group comprising a cytokine, a chemokine, an antibody, such as an antagonistic antibody molecule or fragment thereof, or an agonistic antibody molecule or fragment thereof.

In one embodiment the second or third transgene encodes a cytokine, selected from the group comprising IL-2, IFN-alpha, IFN-beta, IFN-gamma, Flt3 ligand, GM-CSF, IL-15, and IL-12.

In one embodiment the second or third transgene encodes a chemokine, selected from the group comprising MIP1α, IL-8, CCL5, CCL17, CCL20, CCL22, CXCL9, CXCL10, CXCL11, CXCL13, CXCL12, CCL2, CCL19 and CCL21.

In one embodiment a cytokine and a chemokine combination is encoded by the virus selected from the group comprising Mip1α and Flt3 ligand, and MIP1α and IFNα.

In one embodiment the virus encodes an antibody molecule or fragment thereof for example comprising a transmembrane sequence or GPI anchor such that it is a cell membrane-anchored form or a transmembrane domain, for example from a PDGF receptor.

In one embodiment the antibody molecule or binding fragment thereof comprises an anti-human CD3 antigen binding domain.

In one embodiment the antibody molecule is an inhibitor, for example selected from the group comprising an inhibitor of an angiogenesis factor, such as an anti-VEGF antibody molecule, and inhibitor of T cell deactivation factors, such an anti-CTLA-4 antibody molecule.

In one embodiment the antibody molecule is an agonist, for example of one or more selected from the group comprising CD40, GITR, OX40, CD27 and 4-1BB.

In one embodiment an exogenous protein or proteins encoded by the virus is/are a form suitable for expression on a cancer cell surface.

SUMMARY OF THE FIGURES

FIG. 1A shows some of the key molecules involved in T-cell recognition of antigen presenting cells or tumor cells, and some of the signaling events induced in the responding T-cell.

FIG. 1B shows the structure of PDL1 and interaction with the IgV domain of PD1

FIG. 3G shows a schematic of the open reading frame (ORF) of the OKT3 scFv.

FIG. 8E shows similar CD80 expression was seen with both A549 and HT-29 tumour cells.

FIG. 13C shows infectivity of EnAd, NG-347 and NG-348 viruses in an HT-29 cytotoxicity assay.

FIG. 18A shows CD25 is upregulated on human $CD3^+$ $CD4^+$ T-cells following co-culture with NG-348 infected A549 cells in comparison to T-cells co-cultured with unifected A549 cells or A549 cells infected with EnAd.

FIG. 18B shows CD25 is upregulated on human $CD3^+$ $CD4^+$ T-cells following co-culture with NG-348 infected A549 cells in comparison to T-cells co-cultured with unifected A549 cells or A549 cells infected with EnAd.

Thus FIGS. 18A-D show CD25 is upregulated on both $CD4^+$ and $CD4^+$ (primarily CD8) human $CD3^+$ T cell subsets following co-culture with NG-348 infected A549 cells, but not when infection was with EnAd.

Thus, FIGS. 19A-B show low level of HLA-DR expression on human $CD3^+$ T cells following co-culture with NG-348 or EnAd infected A549 cells.

Thus FIGS. 21A-D show induction of CD107a expression on the surface of both $CD4^+$ and $CD4^+$ $CD3^+$ T cell subsets following co-culture with NG-348 infected A549 cells, but not when infection was with EnAd.

Thus, FIGS. 24A-B show CD69 is upregulated on more human $CD3^+$ T-cells following co-culture with NG-347 infected A549 cells than when infection was with EnAd.

SUMMARY OF THE SEQUENCE LISTING

Figure 2:
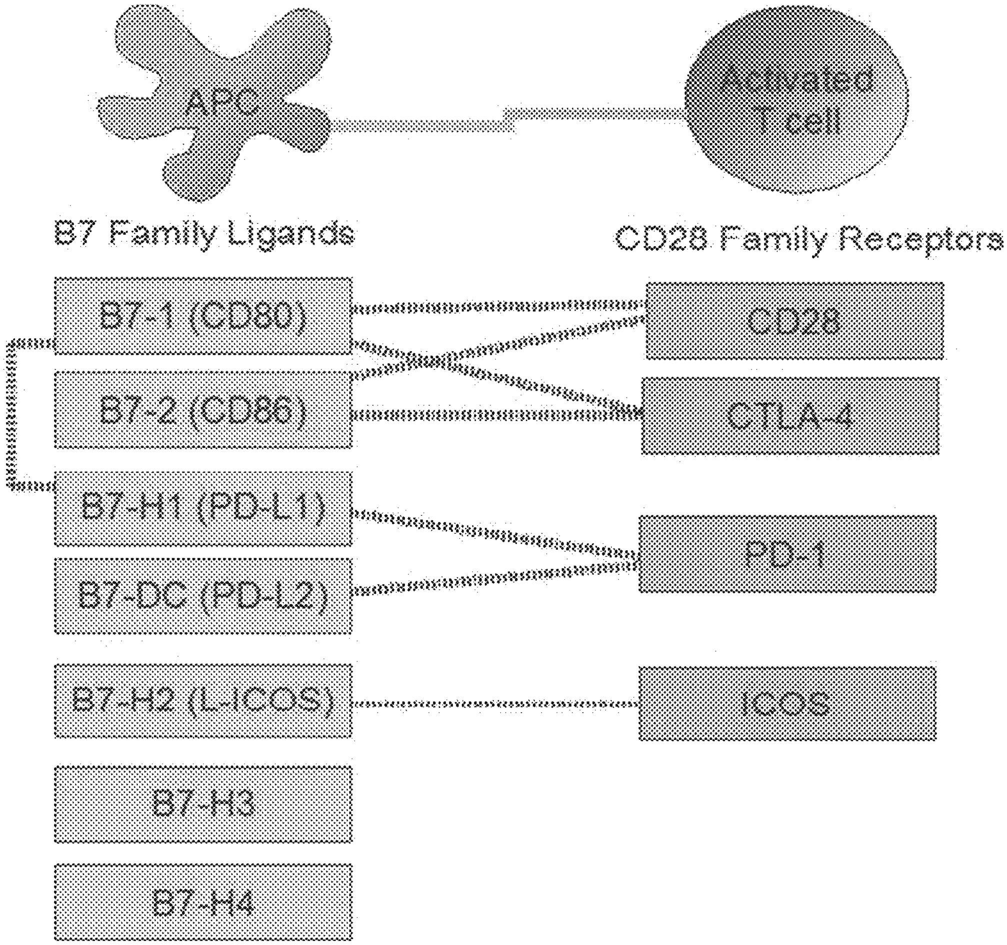
FIG. 2 shows some of the B7 family ligands and binding partners from the CD28 family of receptors

SEQ ID NO: 1 shows $B_Y$ DNA sequence corresponding to and including by 29345-29379 of the EnAd genome.

SEQ ID NO: 2 PDGF TM domain

SEQ ID NO: 3 SPLICE ACCEPTOR SEQUENCE

SEQ ID NO: 4 SPLICE ACCEPTOR SEQUENCE

SEQ ID NO: 5 poly adenylation sequence (SV40 late polyA sequence)

SEQ ID NO: 6 Internal Ribosome Entry Sequence (IRES)

SEQ ID NO: 7 High efficiency self-cleavable P2A peptide sequence

SEQ ID NO: 8 High efficiency self-cleavable F2A peptide sequence

SEQ ID NO: 9 High efficiency self-cleavable E2A peptide sequence

SEQ ID NO: 10 High efficiency self-cleavable T2A peptide sequence

SEQ ID NO: 11 Human CD80 amino acid sequence

SEQ ID NO: 12 Human Interferona amino acid sequence

SEQ ID NO: 13 Human soluble Flt3 ligand amino acid sequence

SEQ ID NO: 14 Human Macrophage Inflammatory protein 1a amino acid sequence (LD78b isoform)

SEQ ID NO: 15 Membrane anchored form of the anti-human CD3 single chain Fv

SEQ ID NO: 16 NG-330 virus genome sequence comprising the EnAd genome with a transgene cassette that encodes the T lymphocyte activation antigen, CD80, inserted in the region $B_Y$. The transgene cassette contains a 5' SSA, human CD80 cDNA sequence and a 3' poly(A)

SEQ ID NO: 17 NG-343 virus genome sequence comprising the EnAd genome with a transgene cassette that encodes IFNα, and CD80, inserted in the region $B_Y$. The transgene cassette contains a 5' SSA, IFNα cDNA sequence, P2A peptide, CD80 cDNA sequence and a 3' poly(A)

SEQ ID NO: 18 NG-345 virus genome sequence comprising the EnAd genome with a transgene cassette that encodes Flt3 Ligand, MIP1a and IFNα, inserted in the region $B_Y$. The transgene cassette contains a 5' SSA, Flt3 Ligand cDNA, P2A peptide sequence, MIP1α cDNA sequence SEQ ID NO: 19 NG-346 virus genome sequence comprising the EnAd genome with a transgene cassette that encodes Flt3 Ligand, MIP1a and CD80, inserted in the region $B_Y$. The transgene cassette contains a 5' SSA, Flt3 Ligand cDNA sequence, P2A peptide sequence, MIP1α cDNA SEQ ID NO: 20 NG-347 virus genome sequence comprising the EnAd genome with a transgene cassette that encodes IFNα, MIP1α and CD80, inserted in the region By. The transgene cassette contains a 5' SSA, IFNα cDNA sequence, P2A peptide sequence, MIP1α cDNA sequence, T2A SEQ ID NO: 21 EnAd Genome SEQ ID NO: 22 E2B region of EnAd genome (BP 10355-5068)

SEQ ID NO: 23 E3 REGION FROM EnAd

SEQ ID NO: 24 A non-coding sequence for inclusion into $B_X$

SEQ ID NO: 25 A non-coding sequence for inclusion into By

SEQ ID NO: 26-34 Hinge linker sequences

SEQ ID NO: 35-74 Flexible linker sequence

SEQ ID NO: 75 & 76 Rigid linker sequence

SEQ ID NO: 77-90 Linker sequence

SEQ ID NO: 91 PDGFR receptor A

SEQ ID NO: 92 PDGFR receptor B

SEQ ID NO: 93 Insulin like growth factor 1

SEQ ID NO: 94 IL6-R

SEQ ID NO: 95 CD28

SEQ ID NO: 96 NG-348 virus genome sequence comprising the EnAd genome with a transgene cassette that encodes a membrane-anchored chimeric form of the single chain Fv anti-human CD3e and the T lymphocyte activation antigen, CD80 inserted in the region By.

SEQ ID NO: 97 Nucleic acid encoding membrane tethered OKT3-scFv

SEQ ID NO: 98 Transgene Cassette sequence for NG-348

SEQ ID NO: 99 Membrane anchored form of the anti-human CD3 scFv with C-terminal V5 tag SEQ ID NO: 100 V5 tag (9 amino acid variant)

SEQ ID NO: 101 NG-348A virus genome sequence comprising the EnAd genome with a transgene cassette that encodes a membrane-anchored chimeric form of the single chain Fv anti-human CD3e with C-terminal V5 tag and the T lymphocyte activation antigen, CD80 inserted in the region SEQ ID NO: 102 NG-420 virus genome sequence comprising the EnAd genome with a transgene cassette that encodes a membrane-anchored chimeric form of the single chain Fv anti-human CD3e inserted in the region $B_Y$. The transgene cassette contains a 5' SSA SEQ ID NO: 103 NG-420A virus genome sequence comprising the EnAd genome with a transgene cassette that encodes a membrane-anchored chimeric form of the single chain Fv anti-human CD3e and a C-terminal V5 tag, inserted in the region $B_Y$. The transgene cassette contains a SEQ ID NO: 104 Linker SEQ ID NO: 105 Sequence comprising a start codon SEQ ID NO: 106 c-myc tag SEQ ID NO: 107 c-myc tag with amino acid spacer at the N and C-terminal SEQ ID NO: 108 spacer-c-myc tag-spacer PDGF TM domain SEQ ID NO: 109 Fully synthetic EnAd genome with incorporated cloning site for transgene cassette insertion as in plasmid pEnAd2.4

DETAILED DESCRIPTION OF THE DISCLOSURE

B7 is a family of proteins.

A B7 protein encoded in an oncolytic viruses of the present disclosure can be useful because the extracellular domain of the protein family member generally modulates a biological function, for example the B7-1 extracellular domain may be employed to prime or stimulate T cells. The actual biological function is specific to the extracellular domain of each given B7 protein (i.e. generally different proteins members of the B7 family have different functions). Other functions of B7 proteins, such as B7-1 and/or B7-2 may include the ability to bind CD28 and/or CTLA-4, and in particular to signal or activate the relevant signaling cascade or cascades.

In addition or alternatively the transmembrane domain of the B7 proteins can be employed to direct proteins encoded by a virus of the present disclosure to the surface of a cancer cell, for example by fusing the transmembrane domain to the C-terminus of the relevant protein.

B7 protein as employed herein, unless the context indicates otherwise, refers to the full length sequence of a protein from the B7 family or a sequence at least 95% similar or identical thereto (such as 96%, 97%, 98%, 99% or 100% similar or identical thereto along the entirety of the relevant sequence). The B7 family includes B7-1, B7-2, B7-DC, B7-H1, B7-H2, B7-H3, B7-H4, B7-H5, B7-H6, B7-H7. When the full length protein is employed then at least one normal biological function of the protein will generally be present.

Full length, protein as employed in respect of the B7 family, refers to at least the extracellular domain, including chimeric B7 proteins wherein the sequence of the chimaera has the structure and a function of a B7 protein and wherein the sequences that make up the chimaera are selected from proteins in the B7 family. The elements in a fragment or full length B7 protein may be from the same or different B7 proteins. Thus in one embodiment the B7 fragment or protein is chimeric.

The chimeric B7 proteins as employed herein refer to where substantially all the sequences making up the chimaera are from a B7 protein, for example at least 98% of the sequence of the chimaera is fragments of B7 proteins fused together. Thus a chimeric fragment as employed herein refers a fragment comprising a sequence from two or more different B7 proteins.

In one embodiment the full length B7 protein comprises the extracellular domain, for example from a single B7 protein, such as B7-1 and/or B7-2.

In one embodiment the full length B7 protein comprises the extracellular domain and the transmembrane domain, for example from the same B7 protein or alternatively the extracellular domain from a B7 protein (such as B7-1 and/or B7-2) and a transmembrane domain or equivalent, such as lipid membrane anchor, from a completely different protein.

In one embodiment a full length chimeric B7 protein may comprise an extracellular domain of one B7 protein (such as B7-1 and/or B7-2) and the transmembrane from a different B7 protein.

In one embodiment the full length B7 protein comprises the extracellular domain, the transmembrane domain and intracellular domain, for example all from the same B7 protein or from two or more different B7 proteins.

Active fragment of a B7 protein as employed herein refers to a fragment that has at least one function of a B7 protein, for example to facilitate expression on the cancer cell surface or other biological function of a B7 protein.

In one embodiment the fragment has at least 50% of the activity of the full-length protein, such as 60, 65, 70, 75, 80, 85, 90, 95 or 100% of the activity of the full-length protein.

In one embodiment the active fragment comprises or consists of a B7 extracellular domain or a sequence at least 95% similar or identical thereto, such as 96, 97, 98, 99 or 100% similar or identical.

In one embodiment the B7 fragment comprises or consists of a transmembrane domain from a B7 protein in particular one described herein, such as B7-1. Employing the latter is thought to contribute expression on the cell surface.

In one embodiment the active B7 fragment may be part of an extracellular domain.

An active fragment, for example a transmembrane fragment or a larger fragment comprising more B7 domains may be employed in a fusion protein with an additional protein, for example to facilitate expression of the additional protein on the cancer cell surface.

Larger fragment as employed herein does not refer to size or weight per se but to a larger repertoire of sequence information (i.e. the fragment comprises sequences from at least two B7 domains) which in turn may provide more functionality.

In one embodiment the larger fragment comprises some biological activity of the relevant B7 protein. In one embodiment an active B7 fragment is a fragment that retains the essential biological activity of the full-length protein, for example the ability to prime or activate T cells.

The activity of a given protein fragment may be analysed in a relevant in vitro assay, for example using full-length protein as a comparator, for example employing an assay described in the Examples herein. Where the active fragment is a transmembrane domain the activity can be assessed by analysing the surface expression on cells of the relevant protein to which the transmembrane domain is attached, for example using an assay described in the Examples herein.

When the full-length B7 protein is part of a fusion protein then the B7 portion may be linked to the additional protein by an amide bond between the end of one sequence and the beginning of the next protein sequence or connected by a linker. Examples of linkers are given below.

A full length B7 protein comprising a transmembrane domain can be employed to present the extracellular domain of the B7 protein and the protein or fragment fused or linked thereto on the surface of the infected cancer cell. Generally in this embodiment the B7 protein will be attached to the surface of the cancer cell and the "other" protein will be at the N-terminus and on the extracellular side of the cancer cell surface.

Having said that the proteins can be arrange as desired, for example with the B7 extracellular domain at the N-terminal, fused or linked at its C-terminal to the next protein or fragment, which in turn is fused or linked at the C-terminal to the transmembrane domain, for example a transmembrane domain from a B7 protein.

Generally when a full-length B7 protein is employed in a fusion protein then both the B7 protein and the additional protein will have a biological function.

Fusion protein as employed herein refers to at least two proteins or fragments or a combination of at least one protein and at least one fragment fused directly or connected to each other, for example by a linker.

Fused as employed herein generally refers to an amide bond between the end of one polypeptide (or protein/fragment) and the beginning of the next polypeptide (or protein/fragment).

Linked, unless the context indicates otherwise, refers to wherein two entities, such as two polypeptide sequences are connected via a linker. A linker is a sequence which is not naturally present in either polypeptide or a sequence, which is not present in that particular position relative to both polypeptides.

In one embodiment the fusion protein comprises a B7 protein or an active fragment thereof. Fusion proteins comprising B7 fragments or protein and additional proteins are not referred to as chimeric proteins herein. Generally fusion protein as employed herein refers to a combination of a B7 protein or fragment thereof and another non-B7-protein/fragment.

Only proteins containing fragments from different B7 proteins are referred to as chimeric herein, as described supra.

In one embodiment fusion proteins of the present disclosure do not comprise a B7 protein or active fragment thereof and are encoded by a virus of the present disclosure in addition to the B7 protein or fragment thereof.

Thus viruses of the present disclosure may encode entities in addition to the B7 protein or active fragment thereof, such entities include further proteins.

B7 Family

In one embodiment the B7 is independently selected from B7-1, B7-2, B7-DC, B7-H1, B7-H2, B7-H3, B7-H4, B7-H5, B7-H6, B7-H7, active fragments of the same, and combinations thereof. In one embodiment the B7 protein is B7-1 (CD80), B7-2 (CD86) or an active fragment of any of the same and combinations thereof, in particular B7-1 or an active fragment thereof.

B7 proteins include B7-1 (also known as CD80 uniprot number P33681), B7-2 (also known as CD86 uniprot number P42081). These proteins bind CD28 and CTLA-4.

In one embodiment CD80 has the following sequence:

SEQ ID NO: 11

```
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVSQDPETELYAV

SSKLDFNMTTNHSFMCLIKYGHLRVNQTFNWNTTKQEHFPDNLLPSWAIT

LISVNGIFVICCLTYCFAPRCRERRRNERLRRESVRPV
```

Other B7 proteins include B7-DC (also known as PDCD1LG2 and PD-L2 uniprot number Q9BQ51), B7-H1 (also known as PD-L1 and CD274: Uniprot number Q9NZQ7). Both these proteins bind PD-1.

Programmed death-ligand 1 (PD-L1) is a 40 kDa type 1 transmembrane protein that has been speculated to play a major role in suppressing the immune system. It appears that upregulation of PD-L1 may allow cancers to evade the host immune system. An analysis of 196 tumor specimens from patients with renal cell carcinoma found that high tumor expression of PD-L1 was associated with increased tumor aggressiveness and a 4.5-fold increased risk of death. Ovarian cancer patients with higher expression of PD-L1 had a significantly poorer prognosis than those with lower expression. PD-L1 expression correlated inversely with intraepithelial $CD8^+$ T-lymphocyte count, suggesting that PD-L1 on tumor cells may suppress antitumor $CD8^+$ T cells. The effect might be tumor type dependent; a study on patients with non-small cell lung cancer showed that greater PD-L1 protein and mRNA expression is associated with increased local lymphocytic infiltrate and longer survival. A number of anti-PDL1 antibodies have been shown to be of interest for treating several cancers in clinical trials.

In one embodiment the B7-DC and/or B7-H1 protein or fragment thereof employed in the virus of the present disclosure does not stimulate immune suppression, for example is mutated to remove the immune suppressive function.

Alternatively, a virus encoding B7-H1 extracellular domain in an unmutated form may be employed to treat appropriate cancers, where upregulation of PD-L1 is associated with a good/improved prognosis, such as lung cancer.

In one embodiment at least the cytoplasmic (intracellular domain) of B7-DC and/or B7-H1 is deleted or non-functional. Whilst not wishing to be bound by theory there is evidence to suggest that removal of the intracellular domain reduces the cancer cells resistance to lysis Blood 2008, April 1; 111(7) 3635-3643.

In one embodiment only the transmembrane domain fragment of B7-DC and/or B7-H1 is employed. In one embodiment the following proteins are not provided as full-length proteins B7-DC and B7-H1 with a relevant biological activity.

Other B7 proteins include B7-H2 (also known as ICOSLG, B7RP1, CD275: Uniprot number 075144) which binds ICOS, B7-H3 (also known as CD276: Uniprot number Q5ZPR3), B7-H4 (also known as VTCN1: Uniprot number Q727D3), B7-H5 (also known as VISTA, Platelet receptor Gi24, SISP1), B7-H6 (also known as NCR3LG1, NR3L1) which binds NKp30, B7-H7 (also known as HHLA2) which binds CD28H.

In one embodiment the fragment only comprises the transmembrane domain of any one B7-H2, B7-H3, B7-H4, B7-H5, B7-H6 and B7-H7.

Individual proteins include single proteins, that is proteins or active fragments thereof that are not part of a fusion protein (including chimeric proteins), and also fusion proteins. In one embodiment the individual proteins are single proteins (including active fragments thereof).

In one embodiment the cytoplasmic domain of the B7 protein is present. In one embodiment the cytoplasmic domain is absent. The absence of the cytoplasmic domain may reduce or eliminate intracellular signaling to the cancer cell, which is relevant to one or more embodiments discussed below.

"Transmembrane Domains"

In one embodiment a transmembrane domain other than one derived from a B7 protein is employed to express a protein (including a fusion protein) encoded by a virus of the present disclosure on the surface of an infected cancer cell, for example the transmembrane domain can be employed to present an active B7 protein fragment or another protein of interest on the surface of the infected cancer cell. Alternatively it can be employed to present a fusion protein, for example comprising a B7 protein or active fragment thereof on said surface. In one embodiment the transmembrane domain from a PDGF receptor or fragment thereof is employed to express a B7 and/or another protein on the cancer cell surface.

In one embodiment a transmembrane tether or anchor sequence employed in the present disclosure comprises a PDGFR TM domain (e.g. ala513-arg561), such as AVGQDTQEVIVVPHSLPFKVVVISAILALVVLTIISLIILIMLWQKPR (SEQ ID NO: 2).

In one embodiment a tether or anchor sequence employed in the present disclosure comprises a tag attached, for example to a PDGF receptor or fragment thereof, such as PDGFR TM domain, in particular SEQ ID NO: 2.

Suitable tags include His-tags, Flag-tags, c-myc tag and the like. More specifically the tether or anchor may comprise a c-myc tag eg. of SEQ ID NO: 106 EQKLISEEDL followed by a PDGFR TM domain is employed, (for example ala513-arg561), such as shown in SEQ ID NO: 2 AVGQDTQEVIVVPHSLPFKVVVISAILALVVLTIISLIILIMLWQKKPR.

In one embodiment the c-myc tag comprises a spacer or spacer amino acids at the 3' and/or 5' end, for example gsEQKLISEEDLn (SEQ ID NO: 107 wherein the lower case letters represent the amino acids which are added to the tag as spacers).

In one embodiment the tether or anchor sequence employed is gsEQKLISEEDLnAVGQDTQEVIVVPHSLPFKVVVISAILALVVLTIISLIILIMLWQKKPR (SEQ ID NO: 108) wherein the lower case letter represent amino acid spacers).

Generally the protein/polypeptide to which the tether or anchor is attached does not comprise a stop codon.

An exogenous protein or proteins encoded by the virus according to the present disclosure will generally comprise a leader sequence (also referred to as a signal peptide). A leader sequence is, for example a sequence about 5 to 30 amino acids long located at the N-terminal of the protein or polypeptide.

In one embodiment the leader sequence for the protein to be expressed on the cancer cell surface is human, for example HuVHSS.

In one embodiment the structure of the ORF cassette is as follows:

LS-POLY-TAG-TM_D wherein

LS is a leader sequence, for example a human leader sequence;

POLY is a polynucleotide encoding polypeptide or proteins of interest, in particular one disclosed herein;

TAG is a tag for example one disclosed herein, such as c-myc, in particular SEQ ID NO: 100 or 106;

TM_D is a TM domain for example a PDGFR TM domain, for example SEQ ID NO: 2.

When the polypeptide is a scFv then the ORF may be as follows:

LS-$VAR_1$-LINK-$VAR_2$-TAG-TM_D wherein

LS is a leader sequence, for example a human leader sequence;

$VAR_1$ is a polynucleotide encoding a variable region such as VH region;

LINK is a linker, for example as disclosed herein, such as a linker based on the units of $G_4S$, in particular SEQ ID NO: 104 GGGGSGGGGSGGGGS;

$VAR_2$ is a polynucleotide encoding a variable region, such as a VL region;

TAG is a tag, for example one disclosed herein, such as c-myc, in particular SEQ ID NO: 100 or 106;

TM_D is a TM domain for example a PDGFR TM domain, for example SEQ ID NO: 2.

The disclosure also extends to embodiments, in particular those described specifically herein, which comprise a tag at the N- or C-termini of the polypeptide chains, such that it resides inside or on the outside of the membrane. Thus a C-termini tag located inside the membrane is advantageous because it is not likely to interfere with the binding or function of the polypeptide.

Having said this expressing the tag on the N-terminal of a surface expressed protein may be useful in some situations because may facilitate isolation, identification and purification of cells expressing the protein.

In one embodiment a combination of a transmembrane domain and a secretory signal sequence is employed to express a protein encoded by the virus (for example as described herein) on the surface of an infected cancer cell. The present inventors have shown that the proteins encoded are expressed only on cells which are permissive to infection by the oncolytic virus, i.e. cancer cells.

In one embodiment the fragment employed to express the protein on the surface of the infected cancer cell (such as the transmembrane fragment) is selected from about 20 to 25 hydrophobic amino acids which form a transmembrane alpha helix, for example from the proteins including PDGF receptor, insulin-like growth factor receptor, IL-6 receptor, CD28, glycophorin, LDL receptor, influenza HA protein, insulin receptor, Asialoglycoprotein receptor, Transferrin receptor.

In one embodiment the fragment employed to express the protein on the surface of the infected cancer cell (such as the transmembrane fragment) is selected from the group comprising TM domain sequences (minimal portions) given in SEQ ID NO: 91, 92, 93, 94 or 95:

| SEQ ID NO: | Name | SEQUENCE |
|---|---|---|
| 91 | PDGFR Receptor A | AVLVLLVIVIISLIVLVVIW |
| 92 | PDGFR Receptor B | VVISAILALVVLTIISLIILI |
| 93 | INSULIN-LIKE GROWTH FACTOR 1 | IIIGPPLIFVFLFSVVIGSIYLFL |
| 94 | IL6-R | SSSVPLPTFLVAGGSLAFGTLLCIAIVL |
| 95 | CD28 | FWVLVVVGGVLACYSLLVTVAFIIFWV |

In one embodiment the transmembrane domain employed is derived from a G protein-coupled receptor or S antigen from hepatitis B.

In one embodiment a fusion protein comprising a full length extracellular domain of a B7 protein or fragment and also a transmembrane domain derived from a protein other than B7 is arranged such that the B7 protein is located at the terminal end of the fusion protein distal from the cancer cell surface, that is on the outside of the cancer cell facing the extracellular space.

Viruses

Having the DNA sequence encoding a B7 protein or an active fragment under the control of an endogenous promoter is also advantageous because the protein is expressed in accordance with the virus life cycle as opposed to being constitutively expressed. In the present situation continuous expression under an exogenous promoter, for example a strong promoter like the CMV promoter, may produce more B7 protein than is necessary for a therapeutic effect and may result in off-target effects.

Alternatives to transmembrane domains for expressing proteins on the surface of the infected cancer cell include approaches employing glycophospholipid anchor (also referred to as a GPI anchor) attached to the C-terminal amino acid of the extracellular protein or fragment (Low et al 1986, Cross 1987, Low and Saltiel 1988, Ferguson and William 1988). Suitable glycophospholipid anchors, for use in the present disclosure include those from Thy-1, N-CAM and DAF.

In one embodiment oncolytic virus according to present disclosure is an adenovirus, for example a group B adenovirus. In one embodiment the virus according to the present disclosure is a chimeric virus, for example EnAd. In one embodiment the adenovirus is replication competent.

In one embodiment the virus is replication deficient and provided as a viral vector.

In one embodiment the sequence encoding the B7 protein or active fragment thereof is located between the stop codon and polyA recognition site of the adenoviral gene L5 and the stop codon and polyA recognition site of the gene E4.

In one embodiment the sequence encoding the B7 protein or active fragment thereof is located between about by 29356 and about 29357 of the EnAd genome, for example as shown in SEQ ID NO: 21, or a position equivalent thereto. The skilled person will understand that the absolute numerical value of the location can change based on how the numbering is allocated. However, the relative position of the inserted gene remains the same irrespective of the absolute numerical values employed.

In one embodiment the oncolytic adenovirus according to the present disclosure has a formula (I):

$$5'ITR-B_1-B_A-B_2-B_X-B_B-B_Y-B_3-3'ITR \quad (I)$$

wherein:

$B_1$ comprises: E1A, E1B or E1A-E1B;

$B_A$ is E2B-L1-L2-L3-E2A-L4;

$B_2$ is a bond or comprises E3 or a transgene, for example under an endogenous or exogenous promoter;

$B_X$ is a bond or a DNA sequence comprising: a restriction site, one or more transgenes or both;

$B_B$ comprises L5;

$B_Y$ comprises a transgene encoding a B7 protein or an active fragment thereof; and $B_3$ is a bond or comprises E4.

In one embodiment the oncolytic virus has a formula (Ia):

$$5'ITR-B_1-B_A-B_2-B_B-B_Y-B_3-3'ITR \quad (Ia)$$

wherein:

$B_1$ is a bond or comprises: E1A, E1B or E1A-E1B (in particular E1A, E1B or E1A-E1B);

$B_A$ is E2B-L1-L2-L3-E2A-L4;

$B_2$ is a bond or comprises E3;

$B_B$ comprises L5;

$B_Y$ comprises a transgene encoding a B7 protein or an active fragment thereof; and $B_3$ is a bond or comprises E4.

In one embodiment the virus genome in constructs of formula (I) and/or (Ia) is from Ad11 or EnAd, in particular EnAd.

In one embodiment the transgene encoding the B7 protein or active fragment thereof, is under the control of an endogenous promoter, for example the major late promoter.

Regulatory Elements

In one embodiment $B_Y$ comprises a transgene cassette, said cassette comprising a transgene encoding a B7 protein or fragment thereof and a regulatory element, such as combination of regulatory elements.

In one embodiment the regulatory element is splice acceptor sequence.

In one embodiment the regulatory element is a Kozak sequence.

In one embodiment, for example where the transgene encodes a polycistronic RNA molecule, the regulatory element is an IRES sequence.

In one embodiment the regulatory sequence is a high efficiency self-cleavable peptide sequence such as P2A, T2A, F2A, E2A.

In one embodiment the regulatory sequence is a polyA tail.

In one embodiment there are at least two regulatory sequences, for example a splice acceptor and a Kozak sequence or a splice acceptor and a polyA tail, or a splice acceptor and an IRES sequence, or a splice acceptor and a P2A sequence.

In one embodiment there are at least three regulator sequences, for example a splice acceptor sequence, a Kozak sequence and polyA tail, or a splice acceptor sequence an IRES or 2A sequence and a polyA tail; or a splice acceptor sequence, Kozak sequence and an IRES or 2A sequence.

In one embodiment there are at least four regulatory sequences, for example a splice acceptor sequence, a Kozak sequence, an IRES or 2A sequence and a polyA tail, in particular located between L5 and E4 in the order splice acceptor sequence, Kozak sequence, IRES or 2A sequence and a polyA tail.

In one embodiment the transgene encodes a polycistronic RNA molecule comprising both an IRES and a 2A regulatory sequence.

Proteins Encoded by the Virus

In one embodiment the virus of the present disclosure encodes multiple proteins for expression on the surface of the infected cancer cell wherein at least one is a B7 protein or an active fragment thereof, for example two, three, four or more different proteins are encoded, in particular two or three proteins are encoded by the virus for expression on the cancer cell surface or secretion into the extracellular space. Protein in this context includes a fusion protein. In one embodiment the virus of the present disclosure encodes two different B7 proteins, active fragments thereof or combinations of the same, for example both for expression on a cancer cell surface.

In one embodiment the virus according to the present disclosure encodes one or two protein for cell surface expression and one or two proteins which are not capable of being anchored on the cell surface, for example are intended to act with the cancer cell or are for secretion/release from the cells.

In one embodiment a B7 protein or active fragment is encoded by the virus of the present disclosure for expression on the surface of the cancer cell and a soluble form, which is released or secreted from the cell, of the same B7 protein or a different B7 protein (including active fragments) is also encoded by the virus.

In one embodiment at least two different B7 proteins or active fragments are encoded by a virus of the present disclosure.

In one embodiment at least one protein expressed on the cell surface is a B7 protein and at least one non-cell-anchored (e.g. secreted) proteins is a non-B7 protein.

In one embodiment the multiple proteins may be encoded to be expressed as separate proteins which are independently processed and expressed in the cancer cell membrane. The independence of the proteins on the surface of the cancer cell may make a positive contribution to the immune activation. Whilst not wishing to be bound by theory, lipid packing can influence the fluidity (i.e. the viscosity) of the lipid bilayer in the membrane of the cancer cell. Viscosity of the membrane can affect the rotation and orientation of proteins and other bio-molecules within the membrane, thereby affecting the functions of these molecules. Thus when the proteins encoded by the virus are located as individual and separate proteins within the membrane of the infected cancer cell, the fluidity of the lipid bilayer allows independent movement of the molecules which may be a particularly suitable format, for example similar to a natural format that is conducive to biological function.

In one embodiment the independently processed and expressed proteins are located (anchored) in different locations, such as physically separate locations, in the cancer cell membrane.

In one embodiment one or more proteins (for example all the proteins) encoded by the virus and expressed on the surface of the infected cancer cell are not fusion proteins.

As described supra in some embodiment the proteins are expressed as a fusion protein.

In one embodiment the virus of the present disclosure provides one or more separate independent proteins for cell surface expression and one or more fusion proteins for cell surface expression.

Thus in one embodiment the virus according to the present disclosure comprises DNA sequences encoding said multiple proteins for expression, for example on the surface or the infected cancer cell.

Thus in one embodiment the virus according to the present disclosure comprises two or more transgenes, in the same or different locations in the virus genome. When located at the same position in the virus genome the multiple proteins will still be expressed independently at the surface of the cancer cell.

In one embodiment the multiple proteins (including fusion proteins) are encoded in different locations in the virus genome, for example in E3, $B_X$ and/or $B_Y$ and are expressed separately on the surface of the infected cancer cell.

In one embodiment the multiple proteins (including fusion proteins) are encoded in the same location in the virus genome and expressed together on the infected cancer cell surface, for example where the proteins encoded are provided as a fusion protein, in particular wherein the fusion protein comprises a B7 protein or an active fragment thereof.

In one embodiment the B7 protein in the fusion protein is a full length protein, in particular a protein described herein, such as B7-1 and/or B7-2, fused or linked to another protein of interest or an active fragment thereof. In one embodiment, the fusion protein comprises a transmembrane from a B7 protein. In one embodiment the B7 is an active fragment excluding the transmembrane domain. In the latter embodiment a transmembrane other than one derived from a B7 protein may be employed to ensure the fusion protein is presented on the surface of the infected cancer cell.

In one embodiment the multiple proteins are encoded in the same location in the virus and are expressed as one or more fusion proteins together on the surface of the infected cancer cell.

When the location of the gene(s) encoding a protein or protein(s) of interest in the virus is the same then the genes may, for example be linked by an IRES sequence or a 2A peptide.

In one embodiment the virus according to the present disclosure comprises a "second" transgene and optionally a third transgene (i.e. one or more of said multiple proteins, for example encoding a polypeptide selected from the group comprising a cytokine, a chemokine, a ligand, and an antibody molecule, such as an antagonistic antibody molecule, and an agonistic antibody molecule.

In one embodiment the additional protein or proteins is/are independently selected from the group comprising an antibody, antibody fragment or protein ligand that binds CD3, CD28, CD80, CD86, 4-1BB, GITR, OX40, CD27, CD40 and combinations, for example in forms suitable for expression on the surface of a cancer cell.

In one embodiment the additional protein is an anti-CD3 antibody, for example independently selected from a Muromonab-CD3 (also known as OKT3), otelixizumab (also known as TRX4), teplizumab (also known as hOKT3γ1 (Ala-Ala)), or visilizumab.

In one embodiment the anti-CD3 antibody is in the form of an antibody fragment, for example an scFv that is part of a fusion protein with the transmembrane region of another protein, for example the transmembrane domain from the PDGF receptor or from the cell surface form of IgG In one embodiment an antibody molecule is an inhibitor (antagonistic antibody) is independently selected from the group comprising an inhibitor of an angiogenesis factor, such as an anti-VEGF antibody molecule, and inhibitor of T cell deactivation factors, such as an anti-CTLA-4, anti-PD1 or anti-PDL1 antibody molecule. In one embodiment antibody molecule is an agonist independently selected from the group comprising antibodies to CD40, GITR, OX40, CD27 and 4-1BB.

In one embodiment an additional transgene encodes a cytokine, or soluble variant thereof selected from the group comprising IL-2, IFNα, IFNβ, IFNγ, GM-CSF, IL-15, IL-12 and fms-related tyrosine kinase 3 ligand (FLT3L). Advantageously, one or more of this group of proteins expressed by the virus, in particular as a free protein secreted from the cancer cell, may be particularly suitable for stimulating an immune response in vivo to the cancer cell.

In one embodiment an additional transgene encodes a chemokine, selected from the group comprising MIP1-alpha, IL-8, CCL5, CCL17, CCL20, CCL22, CXCL9, CXCL10, CXCL11, CXCL13, CXCL12, CCL2, CCL19 and CCL21. Advantageously, one or more of this group of proteins is expressed by the virus as a free protein which may be secreted from the cancer cell may be particularly suitable for attracting immune cells and stimulating an immune response to the cancer cell in vivo.

In one embodiment in addition to at least the B7 protein or active fragment thereof expressed on the surface of the infected cancer cell, one or more molecules are also expressed on the surface and/or secreted.

Thus in one embodiment the virus encodes B7-1, B7-2 or an active fragment of any one of the same or a combination thereof.

Thus in one embodiment the virus encodes B7-1, B7-2 or an active fragment of any one of the same or a combination thereof for expression on the surface of the infected cancer cell and an anti-CD3 (agonist) antibody or antibody binding fragment (such as a scFv) also for expression on the cancer cell surface, in particular where the proteins are expressed as individual proteins on the cell surface.

Thus in one embodiment the virus encodes B7-1, B7-2 or an active fragment of any one of the same or a combination thereof for expression on the surface of the infected cancer cell and an anti-VEGF (antagonist) antibody or a binding fragment thereof also for expression on the cancer cell surface or for release from the cancer cell, for example by secretion or after lysis/death of the infected cancer cell.

Thus in one embodiment the virus encodes B7-1, B7-2 or an active fragment of any one of the same or a combination thereof for expression on the surface of the infected cancer cell and an antibody, antibody fragment or protein ligand that binds CD3, CD28, CD80, CD86, 4-1BB, GITR, OX40, CD27, CD40 also for expression on the cancer cell surface or for release from the cancer cell, for example by secretion or release after lysis/death of the infected cancer cell.

Thus in one embodiment the virus encodes B7-1, B7-2 or an active fragment of any one of the same or a combination thereof for expression on the surface of the infected cancer cell and a cytokine selected from IL-2, IFN-alpha, IFN-beta, IFN-gamma, GM-CSF, IL-15, IL-12, and FLT3L, for example for release from the cancer cell, in particular by secretion or release after cell lysis/death of the infected cancer cell.

Thus in one embodiment the virus encodes B7-1, B7-2 or an active fragment of any one of the same or a combination thereof for expression on the surface of the infected cancer cell and a chemokine selected from MIP1-alpha, IL-8, CCL5, CCL17, CCL20, CCL22, CXCL9, CXCL10, CXCL11, CXCL13, CXCL12, CCL2, CCL19, CCL21, for example for release from the cancer cell, in particular by secretion or release after cell lysis/death of the infected cancer cell.

Thus in one embodiment the virus encodes B7-1, B7-2 or an active fragment of any one of the same or a combination thereof for expression on the surface of the infected cancer cell and an anti-CD3 (agonist) antibody or antibody binding fragment (such as a scFv) also for expression on the cancer cell surface (in particular where the proteins are expressed as individual proteins on the cell surface) and further encodes a cytokine or chemokine selected from IL-2, IFN-alpha, IFN-gamma, GM-CSF, IL-15, IL-12, FLT3L, MIP1-alpha, IL-8, CCL5, CCL17, CCL20, CCL22, CXCL9, CXCL10, CXCL11, CXCL13, CXCL12, CCL2, CCL19, CCL21 for example for release from the cancer cell, in particular by secretion or after cell lysis/death of the infected cancer cell.

Thus in one embodiment the virus encodes B7-1, B7-2 or an active fragment of any one of the same or a combination thereof for expression on the surface of the infected cancer cell and an anti-CD3 (agonist) antibody or antibody fragment (such as a scFv) also for expression on the cancer cell surface (in particular where the proteins are expressed as individual proteins on the cell surface) and further encodes an antibody, antibody fragment or protein ligand that binds CD28, CD80, CD86, 4-1BB, GITR, OX40, CD27, CD40 or an anti-VEGF (antagonist) antibody also for expression on the cancer cell surface or for release from the cancer cell, for example by secretion or release after lysis/death of the infected cancer cell.

Thus in one embodiment the virus encodes B7-1, B7-2 or an active fragment of any one of the same or a combination thereof for expression on the surface of the infected cancer cell and two different cytokines or chemokines selected from IL-2, IFNα, IFNβ, IFNγ, GM-CSF, IL-15, and IL-12, FLT3L, MIP1α, IL-8, CCL5, CCL17, CCL20, CCL22, CXCL9, CXCL10, CXCL11, CXCL13, CXCL12, CCL2, CCL19, CCL21, for example for release from the cancer cell, in particular by secretion of after cell lysis/death of the infected cancer cell.

Thus in one embodiment the virus encodes B7-1, B7-2 or an active fragment of any one of the same or a combination thereof for expression on the surface of the infected cancer cell and an anti-CD3 (agonist) antibody or antibody binding fragment (such as a scFv) also for expression on the cancer cell surface (in particular where the proteins are expressed as individual proteins on the cell surface) and further encodes a cytokine independently selected from IL-2, IFNα, IFNγ, GM-CSF, IL-15, and IL-12, and or a chemokine selected from RANTES (CCL5), MIP1α (LD78α (CCL3) or LD78β (CCL3L1) isoforms), MIP1β which can be released from the cancer cell, in particular by secretion before and release after cell lysis/death of the infected cancer cell.

In one embodiment which in particular may be combined with any of the embodiments above the virus further encodes an anti-PD-1 antibody (an antagonist).

In one embodiment the protein or proteins encoded in the transgene cassette for cell membrane expression may also comprise a peptide linker or spacer between the transmembrane domain and the extracellular ligand binding domain. Such linkers or spacers may add flexibility to the cell surface expressed protein that enhances the ability of the protein to interact with its target molecule, for example on an adjacent cell. Such linkers or spacers may also be designed or selected to promote dimerisation or trimerisation of the proteins at the cell surface, via disulphide bond formation or protein-protein interactions. For example the hinge regions of immunoglobulin molecules or CD8 may be employed to enhance both flexibility and dimerisation In one embodiment the protein or proteins encoded in the transgene cassette may also comprise a peptide tag. The peptide tag may include c-myc, poly-histidine, V5 or FLAG tags and can be located on the N-terminus or C-terminus of the polypeptide, either intracellularly or extracellularly, or may be encoded within the protein for example in an extracellular loop or between the transmembrane domain and the extracellular domain. Peptide tags can be used as spacers or linkers between different protein domains, for example the transmembrane and the extracellular domain, and can be used for detection or purification or detection of the protein, or cells expressing the protein.

In one embodiment the one or more additional transgenes (other than the gene encoding the B7 protein or fragment thereof) is under the control of an exogenous or endogenous promoter, for example an endogenous promoter. In one embodiment a transgene in the E3 region ($B_2$) is under control of an exogenous promoter.

In one embodiment the one or more additional transgenes genes are between the E3 region and the fibre L5 in the adenovirus genome, for example at a position $B_X$ in the construct of formula (I), in particular under the control of an exogenous promoter. thus in one embodiment a transgene in $B_X$ is under the control of an exogenous.

In one embodiment the one or more additional transgenes genes are between the E4 region and the fibre L5 in the adenovirus genome, for example at a position $B_Y$ in the construct of formula (I) or (Ia), in particular under the control of an endogenous promoter, such as the major late promoter. This may be in addition to the B7 protein or active fragment thereof encoded in the region $B_Y$.

In one embodiment there is provided a composition comprising an oncolytic adenovirus according to the present disclosure, for example a pharmaceutical composition, in particular comprising a pharmaceutically acceptable excipient, such as a diluent or carrier.

In one embodiment there is provided an oncolytic adenovirus according to the present disclosure or a composition comprising the same, for use in treatment, in particular for use in the treatment of cancer.

In one embodiment there is provided a method of treating a patient in need thereof comprising administering a therapeutically effective amount of an oncolytic virus according to the present disclosure or a composition, such as a pharmaceutical composition comprising the same.

In one embodiment there is provided use of an oncolytic adenovirus according to the present disclosure or a composition comprising the same for the manufacture of a medicament for the treatment of cancer, in particular carcinomas, for example colorectal, lung, bladder, renal, pancreatic, hepatic, head and neck, breast or ovarian cancer.

In one embodiment there is provided a polynucleotide comprising a genomic sequence of at least 50% of a virus according to the present disclosure (for example 55, 60, 65, 70, 75, 80, 85, 90, 91, 92, 93, 94, 95, 96, 97, 98, 99 or 100%) and comprising a sequence encoding a B7 protein or an active fragment thereof, for example a B7 protein disclosed herein, such as B7-1 or an active fragment thereof. In one embodiment the polynucleotide sequence is in the form of a plasmid.

In one embodiment there is provided a host cell, for example a mammalian cell, such as a HEK293 cell or a derivative thereof, comprising an oncolytic virus according to the present disclosure or a polynucleotide sequence according to the present disclosure.

In one embodiment there is provided a process for preparing an oncolytic adenovirus according to the present disclosure comprising a step of inserting a polynucleotide encoding B7 protein or an active fragment thereof into an oncolytic adenovirus.

In one embodiment there is provided a process of replicating a virus according to the present disclosure comprising the step of culture host cells in the presence of the virus under conditions suitable for replication. Generally the method will comprise a further step of harvesting the virus, for example from the supernatant or after lysis of the host cells.

Definitions

Oncolytic virus with selectivity for cancer cells as employed herein refers to a virus that preferentially kills cancer cells, for example because it preferentially infects cancer cells and/or the virus life cycle is dependent on a gene, such as p53 that is disregulated, for example overexpressed in cancer cells. In one embodiment the oncolytic virus preferentially infects cancer cells and goes on to replicate its genome and produce capsid proteins to generate new virus particles, for example as per EnAd.

The selectivity for cancer cells (therapeutic index) can be tested as described in WO2005/118825 incorporated herein by reference.

Transgene as employed herein refers to a gene that has been inserted into the genome sequence of the adenovirus, wherein the gene is unnatural to the virus (exogenous) or not normally found in that particular location in the virus. Examples of transgenes are given herein. Transgene as employed herein also includes a functional fragment of the gene that is a portion of the gene which when inserted is suitable to perform the function or most of the function of the full-length gene, for example 50% of the function or more.

Transgene and coding sequence are used interchangeably herein in the context of inserts into the viral genome, unless the context indicates otherwise. Coding sequence as employed herein means, for example a DNA sequence encoding a functional RNA, peptide, polypeptide or protein. Typically the coding sequence is cDNA for the transgene that encodes the functional RNA, peptide, polypeptide or protein of interest. Functional RNA, peptides, polypeptide and proteins of interest are described below.

In one embodiment transgene as employed herein refers to a segment of DNA containing a gene or cDNA sequence that has been isolated from one organism and is introduced into a different organism i.e. the virus of the present disclosure. In one embodiment this non-native segment of DNA will generally retain the ability to produce functional RNA, peptide, polypeptide or protein. Transgenes employed may for example encode a single proteins or active fragment thereof, chimeric protein or a fusion protein.

Clearly the virus genome contains coding sequences of DNA. Endogenous (naturally occurring genes) in the genomic sequence of the virus are not considered a transgene, within the context of the present specification unless then have been modified by recombinant techniques such as that they are in a non-natural location or in a non-natural environment.

Thus in one embodiment the transgene inserted encodes a human or humanised protein, polypeptide or peptide.

In one embodiment the transgene comprises a DNA sequence encoding a B7 protein or an active fragment thereof. The present disclosure provides that the B7 protein or activate fragment thereof may be provided in one or more formats independently selected from a fusion protein, a simple B7 protein or an active fragment thereof.

Simple B7 protein or an active fragment thereof as employed herein refers to proteins which are essentially wild-type proteins, for example which are not part of a fusion protein and which has a sequence identical or similar to the relevant known protein, in particular the known human protein. Simple gene also includes wherein 10% of the amino acids are substituted or deleted over the whole length of the relevant protein.

GPI anchor as employed herein refers to is a glycolipid that can be attached to the C-terminus of a protein during posttranslational modification. It is composed of a phosphatidylinositol group linked through a carbohydrate-containing linker (glucosamine and mannose glycosidically bound to the inositol residue) and via an ethanolamine phosphate (EtNP) bridge to the C-terminal amino acid of a mature protein. The two fatty acids within the hydrophobic phosphatidyl-inositol group anchor the protein to the cell membrane.

Glypiated (GPI-linked) proteins generally contain a signal peptide, thus directing them into the endoplasmic reticulum (ER). The C-terminus is composed of hydrophobic amino acids that stay inserted in the ER membrane. The hydrophobic end is then cleaved off and replaced by the GPI-anchor. As the protein progresses through the secretory pathway, it is transferred via vesicles to the Golgi apparatus and finally to the extracellular space where it remains attached to the exterior leaflet of the cell membrane. Since the glypiation is the sole means of attachment of such proteins to the membrane, cleavage of the group by phospholipases will result in controlled release of the protein from the membrane. The latter mechanism is used in vitro; i.e., the membrane proteins released from the membranes in the enzymatic assay are glypiated protein.

Phospholipase C (PLC) is an enzyme that is known to cleave the phospho-glycerol bond found in GPI-anchored proteins. Treatment with PLC will cause release of GPI-linked proteins from the outer cell membrane. The T-cell marker Thy-1 and acetylcholinesterase, as well as both intestinal and placental alkaline phosphatases, are known to be GPI-linked and are released by treatment with PLC. GPI-linked proteins are thought to be preferentially located in lipid rafts, suggesting a high level of organization within plasma membrane microdomains.

A review of GPI anchors written by Ferguson, Kinoshita and Hart is available in Chapter 11 of Essentials of Glycobiology 2$^{nd}$ Edition.

Viruses

Replication competent in the context of the present specification refers to a virus that possesses all the necessary machinery to replicate in cells in vitro and in vivo, i.e. without the assistance of a packaging cell line. A viral vector, for example deleted in at least the E1A region, capable of replicating in a complementary packaging cell line is not a replication competent virus in the present context.

A viral vector is a replication deficient virus, which requires a packaging cell line (comprising a transgene) to replicate.

A replication capable virus as employed herein refers to a replication competent virus or a virus whose replication is dependent on a factor in the cancer cells, for example an upregulated factor, such as p53 or similar.

In one embodiment the adenovirus is a human adenovirus. "Adenovirus", "serotype" or adenoviral serotype" as employed herein refers to any adenovirus that can be assigned to any of the over 50 currently known adenoviral serotypes, which are classified into subgroups A-F, and further extends to any, as yet, unidentified or unclassified adenoviral serotypes. See, for example, Strauss, "Adenovirus infections in humans," in The Adenoviruses, Ginsberg, ea., Plenum Press, New York, N.Y., pp. 451-596 (1984) and Shenk, "Adenoviridae: The Viruses and Their Replication," in Fields Virology, Vol. 2, Fourth Edition, Knipe, 35ea., Lippincott Williams & Wilkins, pp. 2265-2267 (2001), as shown in Table 1.

TABLE 1

| SubGroup | Adenoviral Serotype |
|---|---|
| A | 12, 18, 31 |
| B | 3, 7, 11, 14, 16, 21, 34, 35, 51 |
| C | 1, 2, 5, 6 |
| D | 8-10, 13, 15, 17, 19, 20, 22-30, 32, 33, 36-39, 42-49 |
| E | 4 |
| F | 40, 41 |

Adenoviruses are grouped based on their capsid.

In one embodiment the adenovirus is a subgroup B, for example independently selected from the group comprising or consisting of: Ad3, Ad7, Ad11, Ad14, Ad16, Ad21, Ad34 and Ad51, such as Ad11, in particular Ad11p (the Slobitski strain). In one embodiment the adenovirus of the invention has the capsid, such as the hexon and/or fibre of a subgroup B adenovirus, such as Ad11, in particular Ad11p. In one embodiment the adenovirus is Ad11 or has the fibre and/or hexon and/or penton of Ad11, such as Ad11p.

In one embodiment the virus of the present disclosure is not a group A virus.

In one embodiment the virus of the present disclosure does not comprise an adeno death protein (ADP).

In one embodiment the virus of the present disclosure is not a group C virus.

In one embodiment the virus of the present disclosure does not comprise more and a fragment of part of an Ad5 virus.

Enadenotucirev (EnAd) is a chimeric oncolytic adenovirus, formerly known as ColoAd1 (WO2005/118825), with fibre, penton and hexon from Ad11p, hence it is a subgroup B virus. It has a chimeric E2B region, which comprises DNA from Ad11p and Ad3. Almost all of the E3 region and part of the E4 region is deleted in EnAd. Therefore, it has significant space in the genome to accommodate additional genetic material whilst remaining viable. Furthermore, because EnAd is a subgroup B adenovirus, pre-existing immunity in humans is less common than, for example, Ad5. Other examples of chimeric oncolytic viruses with Ad11 fibre, penton and hexon include OvAd1 and OvAd2 (see WO2006/060314).

EnAd seems to preferentially infect tumour cells, replicates rapidly in these cells and causes cell lysis. This, in turn, can generate inflammatory immune responses thereby stimulating the body to also fight the cancer. Part of the success of EnAd is hypothesised to be related to the fast replication of the virus in vivo.

Importantly, it has been demonstrated clinically that EnAd can be administered systemically (e.g. by intravenous or intraperitoneal injection or infusion) and then subsequently selectively infect and express proteins within tumour cells. This property of EnAd, which may be shared by Ad11p and other group B adenoviruses in particular those expressing the capsid proteins of Ad11p (such as those described herein), makes it possible to express proteins on the surface of cancer cells without having to directly inject the transgenes into the tumour, which is not feasible for many cancers.

Whilst EnAd selectively lyses tumour cells, it may be possible to introduce further beneficial properties, for example increasing the therapeutic activity of the virus or reducing side-effects of the virus by arming it with transgenes, such as a transgene which encodes a cell signalling protein or an antibody, or a transgene which encodes an entity which stimulates a cell signalling protein(s).

Advantageously arming a virus, with DNA encoding certain proteins that can be expressed inside the cancer cell, may enable the body's own defenses to be employed to combat tumour cells more effectively, for example by making the cells more visible to the immune system or by delivering a therapeutic gene/protein preferentially to target tumour cells.

In one embodiment the oncolytic adenovirus of the present disclosure stimulates the patient's immune system to fight the tumor, for example by reducing the cancers ability to suppress immune responses.

In one embodiment the oncolytic virus has a fibre, hexon and penton proteins from the same serotype, for example Ad11, in particular Ad11p, for example found at positions 30812-31789, 18254-21100 and 13682-15367 of the genomic sequence of the latter wherein the nucleotide positions are relative to Genbank ID 217307399 (accession number: GC689208).

In one embodiment the adenovirus is enadenotucirev (also known as EnAd and formerly as ColoAd1). Enadenotucirev as employed herein refers the chimeric adenovirus of SEQ ID NO: 21. It is a replication competent oncolytic chimeric adenovirus which has enhanced therapeutic properties compared to wild type adenoviruses (see WO2005/118825). EnAd has a chimeric E2B region, which features DNA from Ad11p and Ad3, and deletions in E3/E4. The structural changes in enadenotucirev result in a genome that is approximately 3.5 kb smaller than Ad11p thereby providing additional "space" for the insertion of transgenes.

Antibody molecules as employed may comprise a complete antibody molecule having full length heavy and light chains, bispecific antibody format comprising full length antibodies or a fragment of any one of the same including, but are not limited to Fab, modified Fab, Fab', modified Fab', F(ab')2, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

Antibody as employed herein, unless the context indicated otherwise refers to a full length antibody.

Antibody binding fragments refers to a fragment comprising a binding domains which, such as a VH and/or VL which retains specificity for the target antigen to which it binds and for example Fab, modified Fab, Fab', modified Fab', F(ab')2, Fv, single domain antibodies (e.g. VH or VL or VHH), scFv, bi, tri or tetra-valent antibodies, Bis-scFv, diabodies, triabodies, tetrabodies and epitope-binding fragments of any of the same.

Linkers

Linkers suitable for use in fusion proteins of the present disclosure include:

TABLE 2

Hinge linker sequences

| SEQ ID NO: | SEQUENCE |
|---|---|
| 26 | DKTHTCAA |
| 27 | DKTHTCPPCPA |
| 28 | DKTHTCPPCPATCPPCPA |
| 29 | DKTHTCPPCPATCPPCPATCPPCPA |
| 30 | DKTHTCPPCPAGKPTLYNSLVMSDTAGTCY |
| 31 | DKTHTCPPCPAGKPTHVNVSVVMAEVDGTCY |
| 32 | DKTHTCCVECPPCPA |
| 33 | DKTHTCPRCPEPKSCDTPPPCPRCPA |
| 34 | DKTHTCPSCPA |

TABLE 3

| Flexible linker sequences | |
|---|---|
| SEQ ID NO: | SEQUENCE |
| 35 | SGGGGSE |
| 36 | DKTHTS |
| 37 | (S)GGGGS |
| 38 | (S)GGGGSGGGGS |
| 39 | (S)GGGGSGGGGSGGGGS |
| 40 | (S)GGGGSGGGGSGGGGSGGGGS |
| 41 | (S)GGGGSGGGGSGGGGSGGGGSGGGGS |
| 42 | AAAGSG-GASAS |
| 43 | AAAGSG-XGGGS-GASAS |
| 44 | AAAGSG-XGGGSXGGGS-GASAS |
| 45 | AAAGSG-XGGGSXGGGSXGGGS-GASAS |
| 46 | AAAGSG-XGGGSXGGGSXGGGSXGGGS-GASAS |
| 47 | AAAGSG-XS-GASAS |
| 48 | PGGNRGTTTTRRPATTTGSSPGPTQSHY |
| 49 | ATTTGSSPGPT |
| 50 | ATTTGS |
| — | GS |
| 51 | EPSGPISTINSPPSKESHKSP |
| 52 | GTVAAPSVFIFPPSD |
| 53 | GGGGIAPSMVGGGGS |
| 54 | GGGGKVEGAGGGGGS |
| 55 | GGGGSMKSHDGGGGS |
| 56 | GGGGNLITIVGGGGS |
| 57 | GGGGVVPSLPGGGGS |
| 58 | GGEKSIPGGGGS |
| 59 | RPLSYRPPFPFGFPSVRP |
| 60 | YPRSIYIRRRHPSPSLTT |
| 61 | TPSHLSHILPSFGLPTFN |
| 62 | RPVSPFTFPRLSNSWLPA |
| 63 | SPAAHFPRSIPRPGPIRT |
| 64 | APGPSAPSHRSLPSRAFG |
| 65 | PRNSIHFLHPLLVAPLGA |
| 66 | MPSLSGVLQVRYLSPPDL |
| 67 | SPQYPSPLTLTLPPHPSL |
| 68 | NPSLNPPSYLHRAPSRIS |
| 69 | LPWRTSLLPSLPLRRRP |
| 70 | PPLFAKGPVGLLSRSFPP |
| 71 | VPPAPVVSLRSAHARPPY |

TABLE 3-continued

| Flexible linker sequences | |
|---|---|
| SEQ ID NO: | SEQUENCE |
| 72 | LRPTPPRVRSYTCCPTP- |
| 73 | PNVAHVLPLLTVPWDNLR |
| 74 | CNPLLPLCARSPAVRTFP |

(S) is optional in sequences 37 to 41,

Examples of rigid linkers include the peptide sequences GAPAPAAPAPA (SEQ ID NO: 75), PPPP (SEQ ID NO: 76) and PPP.

Other linkers are shown in Table 4:

TABLE 4

| SEQ ID NO: | SEQUENCE |
|---|---|
| 77 | DLCLRDWGCLW |
| 78 | DICLPRWGCLW |
| 79 | MEDICLPRWGCLWGD |
| 80 | QRLMEDICLPRWGCLWEDDE |
| 81 | QGLIGDICLPRWGCLWGRSV |
| 82 | QGLIGDICLPRWGCLWGRSVK |
| 83 | EDICLPRWGCLWEDD |
| 84 | RLMEDICLPRWGCLWEDD |
| 85 | MEDICLPRWGCLWEDD |
| 86 | MEDICLPRWGCLWED |
| 87 | RLMEDICLARWGCLWEDD |
| 88 | EVRSFCTRWPAEKSCKPLRG |
| 89 | RAPESFVCYWETICFERSEQ |
| 90 | EMCYFPGICWM |

Definitions Relevant to Formula (I) and (Ia)

A bond refers to a covalent bond connecting the one DNA sequence to another DNA sequence, for example connecting one section of the virus genome to another. Thus when a variable in formula (I) and (Ia) herein represents a bond the feature or element represented by the bond is absent i.e. deleted.

As the structure of adenoviruses is, in general, similar the elements below are discussed in terms of the structural elements and the commonly used nomenclature referring thereto, which are known to the skilled person. When an element is referred to herein then we refer to the DNA sequence encoding the element or a DNA sequence encoding the same structural protein of the element in an adenovirus. The latter is relevant because of the redundancy of the DNA code. The viruses' preference for codon usage may need to be considered for optimised results.

Any structural element from an adenovirus employed in the viruses of the present disclosure may comprise or consist of the natural sequence or may have similarity over the given length of at least 95%, such as 96%, 97%, 98%, 99% or 100%. The original sequence may be modified to omit 10%, 9%, 8%, 7%, 6%, 5%, 4%, 3%, 2% or 1% of the genetic material. The skilled person is aware that when making changes the reading frames of the virus must be not disrupted such that the expression of structural proteins is disrupted.

In one embodiment the given element is a full-length sequence i.e. the full-length gene. Full length gene as employed herein refers to at least the entirety of the coding sequence of a gene, but may include any associated non-coding regions, especially if they are relevant to the function of the gene.

In one embodiment the given element is less than a full-length and retains the same or corresponding function as the full-length sequence.

In one embodiment for a given element which is optional in the constructs of the present disclosure, the DNA sequence may be less than a full-length and have no functionality, for example the E3 region may be totally or partly deleted. However, it may be useful to delete essentially all the E3 region as this optimises the space available for inserting transgenes.

The structural genes encoding structural or functional proteins of the adenovirus are generally linked by non-coding regions of DNA. Thus there is some flexibility about where to "cut" the genomic sequence of the structural element of interest (especially non-coding regions thereof) for the purpose of inserting a transgene into the viruses of the present disclosure. Thus for the purposes of the present specification, the element will be considered a structural element of reference to the extent that it is fit for purpose and does not encode extraneous material. Thus, if appropriate the gene will be associated with suitable non-coding regions, for example as found in the natural structure of the virus.

Thus in one embodiment an insert, such as DNA encoding a restriction site and/or transgene, is inserted into a non-coding region of genomic virus DNA, such as an intron or intergenic sequence. Having said this some non-coding regions of adenovirus may have a function, for example in alternative splicing, transcription regulation or translation regulation, and this may need to be taken into consideration.

The sites identified herein, that are associated with the L5 region, are suitable for accommodating a variety of DNA sequences encoding complex entities such as RNAi, cytokines, single chain or multimeric proteins, such as antibodies.

Gene as employed herein refers to coding and any non-coding sequences associated therewith, for example introns and associated exons. In one embodiment a gene comprises or consists of only essential structural components, for example coding region.

Below follows a discussion relating to specific structural elements of adenoviruses.

The Inverted Terminal Repeat (ITR) sequences are common to all known adenoviruses (so named because of their symmetry) and are the viral chromosome origins of replication. Another property of these sequences is their ability to form a hairpin.

The 5'ITR as employed herein refers to part or all of an ITR from the 5' end of an adenovirus, which retains the function of the ITR when incorporated into an adenovirus in an appropriate location. In one embodiment the 5'ITR comprises or consists of the sequence from about 1 bp to 138 bp of SEQ ID NO: 21 or a sequence 90, 95, 96, 97, 98 or 99% identical thereto along the whole length, in particular the sequence consisting of from about 1 bp to 138 bp of SEQ ID NO: 21.

The 3'ITR as employed herein refers to part or all of an ITR from 3' end of an adenovirus which retains the function of the ITR when incorporated into an adenovirus in an appropriate location. In one embodiment the 3'ITR comprises or consists of the sequence from about 32189 bp to 32326 bp of SEQ ID NO: 21 or a sequence 90, 95, 96, 97, 98 or 99% identical thereto along the whole length, in particular the sequence consisting of from about 32189 bp to 32326 bp of SEQ ID NO: 21.

B1 as employed herein refers to the DNA sequence encoding: part or all of an E1A from an adenovirus, part or all of the E1B region of an adenovirus, and independently part or all of E1A and E1B region of an adenovirus.

When B1 is a bond then E1A and E1B sequences will be omitted from the virus. In one embodiment B1 is a bond and thus the virus is a vector.

In one embodiment B1 further comprises a transgene. It is known in the art that the E1 region can accommodate a transgene which may be inserted in a disruptive way into the E1 region (i.e. in the "middle" of the sequence) or part or all of the E1 region may be deleted to provide more room to accommodate genetic material.

E1A as employed herein refers to the DNA sequence encoding part or all of an adenovirus E1A region. The latter here is referring to the polypeptide/protein E1A. It may be mutated such that the protein encoded by the E1A gene has conservative or non-conservative amino acid changes (e.g. 1, 2, 3, 4 or 5 amino acid changes, additions and/or deletions over the whole length) such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same as appropriate.

E1B as employed herein refers to the DNA sequence encoding part or all of an adenovirus E1B region (i.e. polypeptide or protein), it may be mutated such that the protein encoded by the E1B gene/region has conservative or non-conservative amino acid changes (e.g. 1, 2, 3, 4 or 5 amino acid changes, additions and/or deletions over the whole length) such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same as appropriate.

Thus B1 can be modified or unmodified relative to a wild-type E1 region, such as a wild-type E1A and/or E1B. The skilled person can easily identify whether E1A and/or E1B are present or (part) deleted or mutated.

Wild-type as employed herein refers to a known adenovirus or a sequence from a known adenovirus. A known adenovirus is one that has been identified and named, regardless of whether the sequence information is available.

In one embodiment B1 has the sequence from 139 bp to 3932 bp of SEQ ID NO: 21.

$B_A$ as employed herein refers to the DNA sequence encoding the E2B-L1-L2-L3-E2A-L4 regions including any non-coding sequences, as appropriate (in particular corresponding to the natural sequence from an adenovirus). Generally this sequence will not comprise a transgene. In one embodiment the sequence is substantially similar or identical to a contiguous sequence from a known adenovirus, for example a serotype shown in Table 1, in particular a group B virus, for example Ad3, Ad7, Ad11, Ad14, Ad16, Ad21, Ad34, Ad35, Ad51 or a combination thereof, such as Ad3, Ad11 or a combination thereof. In one embodiment is E2B-L1-L2-L3-E2A-L4 refers to comprising these elements and other structural elements associated with the region, for example BA will generally include the sequence encoding the protein IV2a, for example as follows: IV2A IV2a-E2B-L1-L2-L3-E2A-L4.

In one embodiment the E2B region is chimeric. That is, comprises DNA sequences from two or more different adenoviral serotypes, for example from Ad3 and Ad11, such as Ad11p. In one embodiment the E2B region has the sequence from 5068 bp to 10355 bp of SEQ ID NO: 21 or a sequence 95%, 96%, 97%, 98% or 99% identical thereto over the whole length.

In one embodiment the E2B in component $B_A$ comprises the sequences shown in SEQ ID NO: 22 (which corresponds to SEQ ID NO: 3 disclosed in WO2005/118825).

In one embodiment $B_A$ has the sequence from 3933 bp to 27184 bp of SEQ ID NO: 21.

E3 as employed herein refers to the DNA sequence encoding part or all of an adenovirus E3 region (i.e. protein/polypeptide), it may be mutated such that the protein encoded by the E3 gene has conservative or non-conservative amino acid changes (e.g. 1, 2, 3, 4 or 5 amino acid changes, additions and/or deletions over the whole length), such that it has the same function as wild-type (the corresponding unmutated protein); increased function in comparison to wild-type protein; decreased function, such as no function in comparison to wild-type protein or has a new function in comparison to wild-type protein or a combination of the same, as appropriate.

In one embodiment the E3 region is form an adenovirus serotype given in Table 1 or a combination thereof, in particular a group B serotype, for example Ad3, Ad7, Ad11 (in particular Ad11p), Ad14, Ad16, Ad21, Ad34, Ad35, Ad51 or a combination thereof, such as Ad3, Ad11 (in particular Ad11p) or a combination thereof. In one embodiment the E3 region has a sequence shown in SEQ ID NO: 23.

In one embodiment the E3 region is partially deleted, for example is 95%, 90%, 85%, 80%, 75%, 70%, 65%, 60%, 55%, 50%, 45%, 40%, 35%, 30%, 25%, 20%, 15%, 10%, 5% deleted.

In one embodiment $B_2$ is a bond, wherein the DNA encoding the E3 region is absent.

In one embodiment the DNA encoding the E3 region can be replaced or interrupted by a transgene. As employed herein "E3 region replaced by a transgene as employed herein includes part or all of the E3 region is replaced with a transgene.

In one embodiment the $B_2$ region comprises the sequence from 27185 bp to 28165 bp of SEQ ID NO: 24.

In one embodiment $B_2$ consists of the sequence from 27185 bp to 28165 bp of SEQ ID NO: 24.

$B_X$ as employed herein refers to the DNA sequence in the vicinity of the 5' end of the L5 gene in BB. In the vicinity of or proximal to the 5' end of the L5 gene as employed herein refers to: adjacent (contiguous) to the 5' end of the L5 gene or a non-coding region inherently associated herewith i.e. abutting or contiguous to the 5' prime end of the L5 gene or a non-coding region inherently associated therewith. Alternatively, in the vicinity of or proximal to may refer to being close the L5 gene, such that there are no coding sequences between the BX region and the 5' end of L5 gene.

Thus in one embodiment $B_X$ is joined directly to a base of L5 which represents, for example the start of a coding sequence of the L5 gene.

Thus in one embodiment $B_X$ is joined directly to a base of L5 which represents, for example the start of a non-coding sequence, or joined directly to a non-coding region naturally associated with L5. A non-coding region naturally associated L5 as employed herein refers to part of all of a non-coding regions which is part of the L5 gene or contiguous therewith but not part of another gene.

In one embodiment $B_X$ comprises the sequence of SEQ ID NO: 24. This sequence is an artificial non-coding sequence wherein a DNA sequence, for example comprising a transgene (or transgene cassette), a restriction site or a combination thereof may be inserted therein. This sequence is advantageous because it acts as a buffer in that allows some flexibility on the exact location of the transgene whilst minimising the disruptive effects on virus stability and viability.

The insert(s) can occur anywhere within SEQ ID NO: 24 from the 5' end, the 3' end or at any point between bp 1 to 201, for example between base pairs 1/2, 2/3, 3/4, 4/5, 5/6, 6/7, 7/8, 8/9, 9/10, 10/11, 11/12, 12/13, 13/14, 14/15, 15/16, 16/17, 17/18, 18/19, 19/20, 20/21, 21/22, 22/23, 23/24, 24/25, 25/26, 26/27, 27/28, 28/29, 29/30, 30/31, 31/32, 32/33, 33/34, 34/35, 35/36, 36/37, 37/38, 38/39, 39/40, 40/41, 41/42, 42/43, 43/44, 44/45, 45/46, 46/47, 47/48, 48/49, 49/50, 50/51, 51/52, 52/53, 53/54, 54/55, 55/56, 56/57, 57/58, 58/59, 59/60, 60/61, 61/62, 62/63, 63/64, 64/65, 65/66, 66/67, 67/68, 68/69, 69/70, 70/71, 71/72, 72/73, 73/74, 74/75, 75/76, 76/77, 77/78, 78/79, 79/80, 80/81, 81/82, 82/83, 83/84, 84/85, 85/86, 86/87, 87/88, 88/89, 89/90, 90/91, 91/92, 92/93, 93/94, 94/95, 95/96, 96/97, 97/98, 98/99, 99/100, 100/101, 101/102, 102/103, 103/104, 104/105, 105/106, 106/107, 107/108, 108/109, 109/110, 110/111, 111/112, 112/113, 113/114, 114/115, 115/116, 116/117, 117/118, 118/119, 119/120, 120/121, 121/122, 122/123, 123/124, 124/125, 125/126, 126/127, 127/128, 128/129, 129/130, 130/131, 131/132, 132/133, 133/134, 134/135, 135/136, 136/137, 137/138, 138/139, 139/140, 140/141, 141/142, 142/143, 143/144, 144/145, 145/146, 146/147, 147/148, 148/149, 150/151, 151/152, 152/153, 153/154, 154/155, 155/156, 156/157, 157/158, 158/159, 159/160, 160/161, 161/162, 162/163, 163/164, 164/165, 165/166, 166/167, 167/168, 168/169, 169/170, 170/171, 171/172, 172/173, 173/174, 174/175, 175/176, 176/177, 177/178, 178/179, 179/180, 180/181, 181/182, 182/183, 183/184, 184/185, 185/186, 186/187, 187/188, 189/190, 190/191, 191/192, 192/193, 193/194, 194/195, 195/196, 196/197, 197/198, 198/199, 199/200 or 200/201.

In one embodiment $B_X$ comprises SEQ ID NO: 24 with a DNA sequence inserted between by 27 and by 28 or a place corresponding to between positions 28192 bp and 28193 bp of SEQ ID NO: 24.

In one embodiment $B_X$ has the sequence from 28166 bp to 28366 bp of SEQ ID NO: 21. In one embodiment $B_X$ is a bond.

$B_B$ as employed herein refers to the DNA sequence encoding the L5 region. As employed herein the L5 region refers to the DNA sequence containing the gene encoding the fibre polypeptide/protein, as appropriate in the context. The fibre gene/region encodes the fibre protein which is a major capsid component of adenoviruses. The fibre functions in receptor recognition and contributes to the adenovirus' ability to selectively bind and infect cells.

In viruses of the present disclosure the fibre can be from any adenovirus serotype and adenoviruses which are chimeric as result of changing the fibre for one of a different serotype are also envisaged with the present disclosure. In one embodiment the fibre is from a group B virus, in particular Ad11, such as Ad11p.

In one embodiment $B_B$ has the sequence from 28367 bp to 29344 bp of SEQ ID NO: 21.

DNA sequence in relation to $B_Y$ as employed herein refers to the DNA sequence in the vicinity of the 3' end of the L5 gene of $B_B$. In the vicinity of or proximal to the 3' end of the L5 gene as employed herein refers to: adjacent (contiguous) to the 3' end of the L5 gene or a non-coding region inherently associated therewith i.e. abutting or contiguous to the 3' prime end of the L5 gene or a non-coding region inherently associated therewith (i.e. all or part of an non-coding sequence endogenous to L5). Alternatively, in the vicinity of or proximal to may refer to being close the L5 gene, such that there are no coding sequences between the $B_Y$ region and the 3' end of the L5 gene.

Thus in one embodiment $B_Y$ is joined directly to a base of L5 which represents the "end" of a coding sequence.

Thus in one embodiment $B_Y$ is joined directly to a base of L5 which represents the "end" of a non-coding sequence, or joined directly to a non-coding region naturally associated with L5.

Inherently and naturally are used interchangeably herein. In one embodiment By comprises the sequence of SEQ ID NO: 25. This sequence is a non-coding sequence wherein a DNA sequence, for example comprising a transgene (or transgene cassette), a restriction site or a combination thereof may be inserted. This sequence is advantageous because it acts a buffer in that allows some flexibility on the exact location of the transgene whilst minimising the disruptive effects on virus stability and viability.

The insert(s) can occur anywhere within SEQ ID NO: 22 from the 5' end, the 3' end or at any point between by 1 to 35, for example between base pairs 1/2, 2/3, 3/4, 4/5, 5/6, 6/7, 7/8, 8/9, 9/10, 10/11, 11/12, 12/13, 13/14, 14/15, 15/16, 16/17, 17/18, 18/19, 19/20, 20/21, 21/22, 22/23, 23/24, 24/25, 25/26, 26/27, 27/28, 28/29, 29/30, 30/31, 31/32, 32/33, 33/34, or 34/35.

In one embodiment $B_Y$ comprises SEQ ID NO: 25 with a DNA sequence inserted between positions by 12 and 13 or a place corresponding to 29356 bp and 29357 bp in SEQ ID NO: 21. In one embodiment the insert is a restriction site insert. In one embodiment the restriction site insert comprises one or two restriction sites. In one embodiment the restriction site is a 19 bp restriction site insert comprising 2 restriction sites. In one embodiment the restriction site insert is a 9 bp restriction site insert comprising 1 restriction site. In one embodiment the restriction site insert comprises one or two restriction sites and at least one transgene, for example one or two or three transgenes, such as one or two transgenes. In one embodiment the restriction site is a 19 bp restriction site insert comprising 2 restriction sites and at least one transgene, for example one or two transgenes. In one embodiment the restriction site insert is a 9 bp restriction site insert comprising 1 restriction site and at least one transgene, for example one or two transgenes. In one embodiment two restriction sites sandwich one or more, such as two transgenes (for example in a transgene cassette). In one embodiment when By comprises two restrictions sites the said restriction sites are different from each other. In one embodiment said one or more restrictions sites in $B_Y$ are non-naturally occurring (such as unique) in the particular adenovirus genome into which they have been inserted. In one embodiment said one or more restrictions sites in $B_Y$ are different to other restrictions sites located elsewhere in the adenovirus genome, for example different to naturally occurring restrictions sites or restriction sites introduced into other parts of the genome, such as $B_X$. Thus in one embodiment the restriction site or sites allow the DNA in the section to be cut specifically.

In one embodiment $B_Y$ has the sequence from 29345 bp to 29379 bp of SEQ ID NO: 21. In one embodiment $B_Y$ is a bond.

In one embodiment the insert is after by 12 in SEQ ID NO: 25.

In one embodiment the insert is at about position 29356 bp of SEQ ID NO: 21.

In one embodiment the insert is a transgene cassette comprising one or more transgenes, for example 1, 2 or 3, such as 1 or 2.

E4 as employed herein refers to the DNA sequence encoding part or all of an adenovirus E4 region (i.e. polypeptide/protein region), which may be mutated such that the protein encoded by the E4 gene has conservative or non-conservative amino acid changes (e.g. 1, 2, 3, 4 or 5 amino acid changes, additions and/or deletions), and has the same function as wild-type (the corresponding non-mutated protein); increased function in comparison to wild-type protein; decreased function, such as no function in comparison to wild-type protein or has a new function in comparison to wild-type protein or a combination of the same as appropriate.

In one embodiment the E4 region is partially deleted, for example is 95%, 90%, 85%, 80%, 75%, 70%, 65%, 60%, 55%, 50%, 45%, 40%, 35%, 30%, 25%, 20%, 15%, 10% or 5% deleted. In one embodiment the E4 region has the sequence from 32188 bp to 29380 bp of SEQ ID NO: 21.

In one embodiment E4 is present except for the E4orf4 region which is deleted.

In one embodiment $B_3$ is a bond, i.e. wherein E4 is absent.

In one embodiment $B_3$ has the sequence consisting of from 32188 bp to 29380 bp of SEQ ID NO: 21.

As employed herein number ranges are inclusive of the end points.

The skilled person will appreciate that the elements in the formulas herein, such as formula (I), (Ia) are contiguous and may embody non-coding DNA sequences as well as the genes and coding DNA sequences (structural features) mentioned herein. In one or more embodiments the formulas of the present disclosure are attempting to describe a naturally occurring sequence in the adenovirus genome. In this context it will be clear to the skilled person that the formula is referring to the major elements characterising the relevant section of genome and is not intended to be an exhaustive description of the genomic stretch of DNA.

E1A, E1B, E3 and E4 as employed herein each independently refer to the wild-type and equivalents thereof, mutated or partially deleted forms of each region as described herein, in particular a wild-type sequence from a known adenovirus.

"Insert" as employed herein refers to a DNA sequence that is incorporated either at the 5' end, the 3' end or within a given DNA sequence reference segment such that it interrupts the reference sequence. A reference sequence employed as a reference point relative to which the insert is located. In the context of the present disclosure inserts generally occur within either SEQ ID NO: 24 or SEQ ID NO: 25. An insert can be either a restriction site insert, a transgene cassette or both. When the sequence is interrupted the virus will still comprise the original sequence, but generally it will be as two fragments sandwiching the insert.

In one embodiment the transgene or transgene cassette does not comprise a non-biased inserting transposon, such as a TN7 transposon or part thereof. Tn7 transposon as employed herein refers to a non-biased insertion transposon as described in WO2008/080003.

In one embodiment the transgene or transgene cassette further comprises a regulatory element or sequence.

Other Regulatory Sequences

"Regulator of gene expression" (or regulator/regulatory element) as employed herein refers to a genetic element, such as a promoter, enhancer or a splice acceptor sequence that plays a role in gene expression, typically by initiating or enhancing transcription or translation.

"Splice acceptor sequence", "splice acceptor" or "splice site" as employed herein refers to a regulatory sequence determining when an mRNA molecule will be recognised by small nuclear ribonucleoproteins of the spliceosome complex. Once assembled the spliceosome catalyses splicing between the splice acceptor site of the mRNA molecule to an upstream splice donor site producing a mature mRNA molecule that can be translated to produce a single polypeptide or protein.

Different sized splice acceptor sequences may be employed in the present invention and these can be described as short splice acceptor (small), splice acceptor (medium) and branched splice acceptor (large).

SSA as employed herein refers to a short splice acceptor, typically comprising just the splice site, for example 4 bp. SA as employed herein refers to a splice acceptor, typically comprising the short splice acceptor and the polypyrimidine tract, for example 16 bp. bSA as employed herein refers to a branched splice acceptor, typically comprising the short splice acceptor, polypyrimidine tract and the branch point, for example 26 bp.

In one embodiment the splice acceptor employed in the constructs of the disclosure are CAGG or SEQ ID NO: 3 or 4. In one embodiment the SSA has the nucleotide sequence of SEQ ID NO: CAGG. In one embodiment the SA has the nucleotide sequence of SEQ ID NO: 23. In one embodiment the bSA has the nucleotide sequence of cagg. In one embodiment the splice acceptor sequence is independently selected from the group comprising: tgctaatctt cctttctctc ttcagg (SEQ ID NO: 4), tttctctctt cagg (SEQ ID NO: 3), and cagg.

In one embodiment the splice site is immediately proceeded (i.e. followed in a 5' to 3' direction) by a consensus Kozak sequence comprising CCACC. In one embodiment the splice site and the Kozak sequence are interspersed (separated) by up to 100 or less bp. In one embodiment the Kozak sequence has the nucleotide sequence of CCACC.

Typically, when under the control of an endogenous or exogenous promoter (such as an endogenous promoter), the coding sequence will be immediately preceded by a Kozak sequence. The start of the coding region is indicated by the initiation codon (AUG), for example is in the context of the sequence (gcc)gccRccAUGg [SEQ ID NO: 105] the start of the start of the coding sequences is indicated by the bases in bold. A lower case letter denotes common bases at this position (which can nevertheless vary) and upper case letters indicate highly-conserved bases, i.e. the 'AUGG' sequence is constant or rarely, if ever, changes; 'R' indicates that a purine (adenine or guanine) is usually observed at this position and the sequence in brackets (gcc) is of uncertain significance. Thus in one embodiment the initiation codon AUG is incorporated into a Kozak sequence.

Internal Ribosome Entry DNA Sequence as employed herein refers to a DNA sequence encoding an Internal Ribosome Entry Sequence (IRES). IRES as employed herein means a nucleotide sequence that allows for initiation of translation a messenger RNA (mRNA) sequence, including initiation starting within an mRNA sequence. This is particularly useful when the cassette encodes polycistronic mRNA. Using an IRES results in a polycistronic mRNA that is translated into multiple individual proteins or peptides. In one embodiment the Internal Ribosome Entry DNA sequence has the nucleotide sequence of SEQ ID NO: 6. In one embodiment a particular IRES is only used once in the genome. This may have benefits with respect to stability of the genome.

"High self-cleavage efficiency 2A peptide" or "2A peptide" as employed herein refers to a peptide which is efficiently cleaved following translation. Suitable 2A peptides include P2A, F2A, E2A and T2A. The present inventors have noted that once a specific DNA sequence encoding a given 2A peptide is used once, the same specific DNA sequence may not be used a second time. However, redundancy in the DNA code may be utilised to generate a DNA sequence that is translated into the same 2A peptide. Using 2A peptides is particularly useful when the cassette encodes polycistronic mRNA. Using 2A peptides results in a single polypeptide chain being translated which is modified post-translation to generate multiple individual proteins or peptides.

In one embodiment the encoded P2A peptide employed has the amino acid sequence of SEQ ID NO: 7. In one embodiment the encoded F2A peptide employed has the amino acid sequence of SEQ ID NO: 8. In one embodiment the encoded E2A peptide employed has the amino acid sequence of SEQ ID NO: 9. In one embodiment the encoded T2A peptide employed has the amino acid sequence of SEQ ID NO: 10.

In one embodiment an mRNA or each mRNA encoded by transgene is/are comprise a polyadenylation signal sequence, such as typically at the end of an mRNA sequence, for example as shown in SEQ ID NO: 5. Thus in one embodiment the transgene or the transgene cassette comprises at least one sequence encoding a polyadenylation signal sequence.

"PolyA", "Polyadenylation signal" or "polyadenylation sequence" as employed herein means a DNA sequence, usually containing an AATAAA site, that once transcribed can be recognised by a multiprotein complex that cleaves and polyadenylates the nascent mRNA molecule.

In one embodiment the polyadenylation sequence has the nucleotide sequence of SEQ ID NO: 5.

In one embodiment the construct does not include a polyadenylation sequence. In one embodiment the regulator of gene expression is a splice acceptor sequence.

In one embodiment the sequence encoding a protein/polypeptide/peptide, such as an antibody or antibody binding fragment further comprises a polyadenylation signal.

In one embodiment there is provided a virus or construct with a sequence disclosed herein, for example a virus selected NG-330 (SEQ ID NO: 16); NG-334 (SEQ ID NO: 17); NG-345 (SEQ ID NO: 18); NG-346 (SEQ ID NO: 19); NG-347 (SEQ ID NO: 20) and NG-348 (SEQ ID NO: 96).

In one embodiment the virus is NG-347 (SEQ ID NO: 20) or NG-348 (SEQ ID NO: 96).

Formulations

The present disclosure relates also extends to a pharmaceutical formulation of a virus as described herein.

In one embodiment there is provided a liquid parenteral formulation, for example for infusion or injection, of a replication capable oncolytic according to the present disclosure wherein the formulation provides a dose in the range of $1\times10^{10}$ to $1\times10^{14}$ viral particles per volume of dose.

Parenteral formulation means a formulation designed not to be delivered through the GI tract. Typical parenteral delivery routes include injection, implantation or infusion. In one embodiment the formulation is provided in a form for bolus delivery.

In one embodiment the parenteral formulation is in the form of an injection. Injection includes intravenous, subcutaneous, intra-tumoral or intramuscular injection. Injection as employed herein means the insertion of liquid into the body via a syringe. In one embodiment the method of the present disclosure does not involve intra-tumoral injection.

In one embodiment the parenteral formulation is in the form of an infusion.

Infusion as employed herein means the administration of fluids at a slower rate by drip, infusion pump, syringe driver or equivalent device. In one embodiment the infusion is administered over a period in the range of 1.5 minutes to 120 minutes, such as about 3, 4, 5, 6, 7, 8, 9, 10, 11, 12, 13, 14, 15, 16, 17, 18, 19 20, 25, 30, 35, 40, 45, 50, 55, 60, 65, 70, 65, 80, 85, 90, 95, 100, 105, 110 or 115 minutes.

In one embodiment one dose of the formulation less than 100 mls, for example 30 mls, such as administered by a syringe driver.

In one embodiment the injection is administered as a slow injection, for example over a period of 1.5 to 30 minutes.

In one embodiment the formulation is for intravenous (i.v.) administration. This route is particularly effective for delivery of oncolytic virus because it allows rapid access to the majority of the organs and tissue and is particular useful for the treatment of metastases, for example established metastases especially those located in highly vascularised regions such as the liver and lungs.

Therapeutic formulations typically will be sterile and stable under the conditions of manufacture and storage. The composition can be formulated as a solution, microemulsion, liposome, or other parenteral formulation suitable for administration to a human and may be formulated as a pre-filled device such as a syringe or vial, particular as a single dose.

The formulation will generally comprise a pharmaceutically acceptable diluent or carrier, for example a non-toxic, isotonic carrier that is compatible with the virus, and in which the virus is stable for the requisite period of time.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a dispersant or surfactant such as lecithin or a non-ionic surfactant such as polysorbate 80 or 40. In dispersions the maintenance of the required particle size may be assisted by the presence of a surfactant. Examples of isotonic agents include sugars, polyalcohols such as mannitol, sorbitol, or sodium chloride in the composition.

In one embodiment parenteral formulations employed may comprise one or more of the following a buffer, for example 4-(2-hydroxyethyl)-1-piperazineethanesulfonic acid, a phosphate buffer and/or a Tris buffer, a sugar for example dextrose, mannose, sucrose or similar, a salt such as sodium chloride, magnesium chloride or potassium chloride, a detergent such as a non-ionic surfactant such as brij, PS-80, PS-40 or similar. The formulation may also comprise a preservative such as EDTA or ethanol or a combination of EDTA and ethanol, which are thought to prevent one or more pathways of possible degradation.

In one embodiment the formulation will comprise purified oncolytic virus according to the present disclosure, for example $1\times10^{10}$ to $1\times10^{14}$ viral particles per dose, such as $1\times10^{10}$ to $1\times10^{12}$ viral particles per dose. In one embodiment the concentration of virus in the formulation is in the range $2\times10^{8}$ to $2\times10^{14}$ vp/ml, such as $2\times10^{12}$ vp/ml.

In one embodiment the parenteral formulation comprises glycerol.

In one embodiment the formulation comprises oncolytic adenovirus as described herein, HEPES (N-2-hydroxyethylpiperazine-N'-2-ethanesulfonic acid), glycerol and buffer.

In one embodiment the parenteral formulation consists of virus of the disclosure, HEPES for example 5 mM, glycerol for example 5-20% (v/v), hydrochloric acid, for example to adjust the pH into the range 7-8 and water for injection.

In one embodiment 0.7 mL of virus of the disclosure at a concentration of $2\times10^{12}$ vp/mL is formulated in 5 mM HEPES, 20% glycerol with a final pH of 7.8.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure will generally contain a virus as described herein with a physiologically acceptable excipient.

These inhalable powders may include monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these with one another. Mono- or disaccharides are suitably used, such as lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The size of the particle carrying the virus is of primary importance and thus in one embodiment the virus according to the present disclosure may be adsorbed or absorbed onto a particle, such as a lactose particle of the given size.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellant gas-containing inhalable aerosols may also contain other ingredients, such as co-solvents, stabilisers, surface-active agents (surfactants), antioxidants, lubricants and means for adjusting the pH. All these ingredients are known in the art.

The propellant gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively, topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The virus of the invention can be delivered dispersed in a solvent, e.g. in the form of a solution or a suspension, for example as already described above for parenteral formulations. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The present disclosure also extends to liquid solutions or suspensions delivered intra-nasally, for example employing a device as disclosed in WO2009/068877 and US2004/0153033 both incorporated herein by reference.

Treatment

In a further aspect the present disclosure extends to a virus or a formulation thereof as described herein for use in treatment, in particular for the treatment of cancer.

In one embodiment the method of treatment is for use in the treatment of a tumour.

Tumour as employed herein is intended to refer to an abnormal mass of tissue that results from excessive cell division that is uncontrolled and progressive, also called a neoplasm. Tumours may be either benign (not cancerous) or malignant. Tumour encompasses all forms of cancer and metastases. In one embodiment the tumour is cancerous.

In one embodiment the tumour is a solid tumour. The solid tumour may be localised or metastasised.

In one embodiment the tumour is of epithelial origin.

In one embodiment the tumour is a malignancy, such as colorectal cancer, hepatoma, prostate cancer, pancreatic cancer, breast cancer, ovarian cancer, thyroid cancer, renal cancer, bladder cancer, head and neck cancer or lung cancer.

In one embodiment the tumour is a colorectal malignancy.

Malignancy as employed herein refers to cancerous cells.

In one embodiment the oncolytic adenovirus is employed in the treatment or prevention of metastasis.

In one embodiment the method or formulation herein is employed in the treatment of drug resistant cancers.

In one embodiment the virus is administered in combination with the administration of a further cancer treatment or therapy.

In one embodiment there is provided a virus or formulation according to the present disclosure for use in the manufacture of a medicament for the treatment of cancer, for example a cancer described above.

In a further aspect there is provide a method of treating cancer comprising administering a therapeutically effective amount of a virus or formulation according to the present disclosure to a patient in need thereof, for example a human patient.

In one embodiment the oncolytic virus or formulation herein is administered in combination with another therapy.

"In combination" as employed herein is intended to encompass where the oncolytic virus is administered before, concurrently and/or post cancer treatment or therapy. However, generally the treatment regimens for the combination therapy Cancer therapy includes surgery, radiation therapy, targeted therapy and/or chemotherapy.

Cancer treatment as employed herein refers to treatment with a therapeutic compound or biological agent, for example an antibody intended to treat the cancer and/or maintenance therapy thereof.

In one embodiment the cancer treatment is selected from any other anti-cancer therapy including a chemotherapeutic agent; a targeted anticancer agent, such as an antibody drug conjugate; radiotherapy, radio-isotope therapy or any combination thereof.

In one embodiment the virus of the present disclosure such as an oncolytic adenovirus may be used as a pre-treatment to the therapy, such as a surgery (neoadjuvant therapy), to shrink the tumour, to treat metastasis and/or prevent metastasis or further metastasis. The oncolytic adenovirus may be used after the therapy, such as a surgery (adjuvant therapy), to treat metastasis and/or prevent metastasis or further metastasis.

In one embodiment a virus or formulation of the present disclosure is employed in maintenance therapy.

Concurrently as employed herein is the administration of the additional cancer treatment at the same time or approximately the same time as the oncolytic adenovirus formulation. The treatment may be contained within the same formulation or administered as a separate formulation.

In one embodiment the virus is administered in combination with the administration of a chemotherapeutic agent.

Chemotherapeutic agent as employed herein is intended to refer to specific antineoplastic chemical agents or drugs that are selectively destructive to malignant cells and tissues. For example, alkylating agents, antimetabolites, anthracyclines, plant alkaloids, topoisomerase inhibitors, and other antitumour agents. Examples of specific chemotherapeutic agents include doxorubicin, 5-fluorouracil (5-FU), paclitaxel, capecitabine, irinotecan, and platins such as cisplatin and oxaliplatin. The dose may be chosen by the practitioner based on the nature of the cancer being treated.

In one embodiment the therapeutic agent is ganciclovir, which may assist in controlling immune responses and/or tumour vascularisation.

In one embodiment one or more therapies employed in the method herein are metronomic, that is a continuous or frequent treatment with low doses of anticancer drugs, often given concomitant with other methods of therapy.

Subgroup B oncolytic adenoviruses, in particular Ad11 and those derived therefrom such as EnAd may be particularly synergistic with chemotherapeutics because they seem to have a mechanism of action that is largely independent of apoptosis, killing cancer cells by a predominantly necrolytic mechanism. Moreover, the immunosuppression that occurs during chemotherapy may allow the oncolytic virus to function with greater efficiency.

Therapeutic dose as employed herein refers to the amount of virus, such as oncolytic adenovirus that is suitable for achieving the intended therapeutic effect when employed in a suitable treatment regimen, for example ameliorates symptoms or conditions of a disease, in particular without eliciting dose limiting side effects. A dose may be considered a therapeutic dose in the treatment of cancer or metastases when the number of viral particles may be sufficient to result in the following: tumour or metastatic growth is slowed or stopped, or the tumour or metastasis is found to shrink in size, and/or the life span of the patient is extended. Suitable therapeutic doses are generally a balance between therapeutic effect and tolerable toxicity, for example where the side-effect and toxicity are tolerable given the benefit achieved by the therapy.

In one embodiment there is provided systemically administering multiple doses of a parenteral formulation of an oncolytic adenovirus according to the present disclosure in a single treatment cycle, for example wherein the total dose given in each administration is in the range of $1\times10^{10}$ to $1\times10^{14}$ viral particles per dose.

In one embodiment one or more doses (for example each dose) of virus or composition comprising the same is administered such that the rate of viral particle delivery is in the range of $2\times10^{10}$ particles per minute to $2\times10'^{2}$ particles per minute.

In one embodiment a virus or therapeutic construct according to the present disclosure (including a formulation comprising same) is administered weekly, for example one week 1 the dose is administered on day 1, 3, 5, followed by one dose each subsequent week.

In one embodiment a virus or therapeutic construct according to the present disclosure (including a formulation comprising same) is administered bi-weekly or tri-weekly, for example is administered in week 1 one on days 1, 3 and 5, and on week 2 or 3 is also administered on days 1, 3 and 5 thereof. This dosing regimen may be repeated as many times as appropriate.

In one embodiment a virus or therapeutic construct according to the present disclosure (including a formulation comprising same) is administered monthly, for example in a treatment cycle or as maintenance therapy.

In one embodiment the viruses and constructs of the present disclosure are prepared by recombinant techniques. The skilled person will appreciate that the armed adenovirus genome can be manufactured by other technical means, including entirely synthesising the genome or a plasmid comprising part of all of the genome. The skilled person will appreciate that in the event of synthesising the genome the region of insertion may not comprise the restriction site nucleotides as the latter are artefacts following insertion of genes using cloning methods.

In one embodiment the armed adenovirus genome is entirely synthetically manufactured, for example as per SEQ ID NO: 109, which was employed with transgene cassettes in SEQ ID Nos: 18, 20, 96, 101, 102, 103.

The disclosure herein further extends to an adenovirus of formula (I) or a sub-formula thereof, obtained or obtainable from inserting a transgene or transgene cassette.

"Is" as employed herein means comprising.

In the context of this specification "comprising" is to be interpreted as "including".

Embodiments of the invention comprising certain features/elements are also intended to extend to alternative embodiments "consisting" or "consisting essentially" of the relevant elements/features.

Where technically appropriate, embodiments of the invention may be combined.

Technical references such as patents and applications are incorporated herein by reference.

Any embodiments specifically and explicitly recited herein may form the basis of a disclaimer either alone or in combination with one or more further embodiments.

Heading herein are employed to divide the document into sections and are not intended to be used to construe the meaning of the disclosure provided herein.

The present invention is further described by way of illustration only in the following examples.

EXAMPLES

Example 1: Production of EnAd Virus Expressing the T Cell Activating Antigen CD80

Figure 3A:
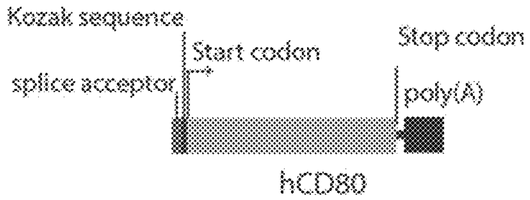
FIG. 3A shows a schematic of a transgene cassette for a virus expressing human CD80.

The plasmid pEnAd2.4 was used to generate the plasmid pNG-330 by direct insertion of a cassette encoding the human T cell activating antigen CD80 (SEQ ID NO: 11). The pNG-330 cassette contains a 5' short splice acceptor sequence CAGG, human CD80 cDNA sequence and a 3' polyadenylation sequence (SEQ ID NO: 5). A Schematic of the inserted transgene cassette is shown in FIG. 3A. Construction of the plasmid was confirmed by DNA sequencing.

Virus Production and Characterisation

References herein to viruses such as NG-330-00 are simply references to particular batched "00" of the virus NG-330. Similar nomenclature may be used for other viruses.

The plasmid pNG-330 was linearised by restriction digest with the enzyme AscI to produce the virus genome NG-330 (SEQ ID NO: 16). Digested DNA was purified by phenol/chloroform extraction and precipitated for 16 hrs, −20° C. in 300 µl>95% molecular biology grade ethanol and 10 µl 3 M Sodium Acetate. The precipitated DNA was pelleted by centrifuging at 14000 rpm, 5 mins and was washed in 500 µl 70% ethanol, before centrifuging again, 14000 rpm, 5 mins. The clean DNA pellet was air dried, resuspended in 500 µl OptiMEM containing 15 µl lipofectamine transfection reagent and incubated for 30 mins, RT. The transfection mixture was then added drop wise to a T-25 flask containing 293 cells grown to 70% confluency. After incubation of the cells with the transfection mix for 2 hrs at 37° C., 5% $CO_2$ 4 mls of cell media (DMEM high glucose with glutamine supplemented with 2% FBS) was added to the cells and the flasks was incubated 37° C., 5% $CO_2$.

The transfected 293 cells were monitored every 24 hrs and were supplemented with additional media every 48-72 hrs. The production of virus was monitored by observation of a significant cytopathic effect (CPE) in the cell monolayer. Once extensive CPE was observed the virus was harvested from 293 cells by three freeze-thaw cycles. The harvested viruses were used to re-infect 293 cells in order to amplify the virus stocks. Viable virus production during amplification was confirmed by observation of significant CPE in the cell monolayer. Once CPE was observed the virus was harvested from 293 cells by three freeze-thaw cycles. The amplified stock was used for further amplification before the virus was purified by double caesium chloride banding to produce a NG-330 virus stock.

Figure 4A:
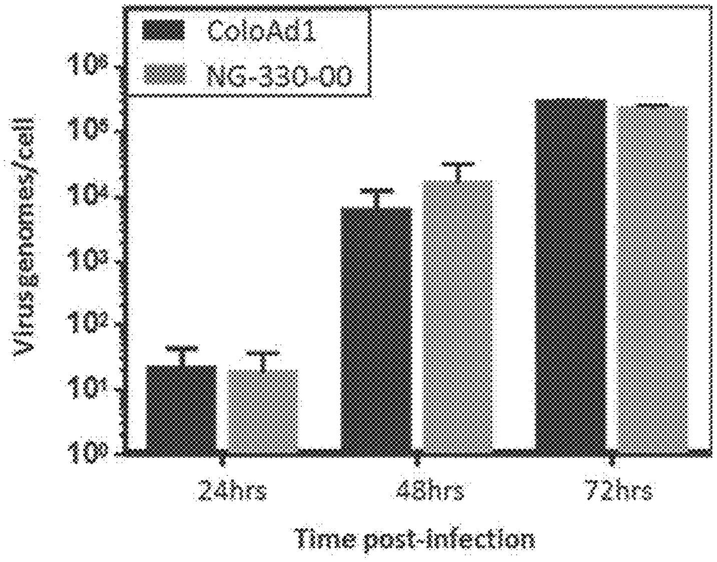
FIG. 4A shows replication of EnAd (ColoAd1) and human CD80 encoding virus NG-330 in HT-29 tumour cells.

Example 2: Characterisation of NG-330 Virus Activity Compared to EnAd in Carcinoma Cell Lines NG-330 or EnAd virus replication (assessed by qPCR), and CD80 membrane expression (assessed by flow cytometry (FIGS. 4 and 5) was compared in the colon carcinoma cell line HT-29 and lung carcinoma cell line A549. NG-330 is a virus derived from EnAd that contains a transgene cassette encoding the human T cell activating antigen, CD80 after the EnAd late gene, L5 (Fibre). A schematic of the inserted cassette is shown in FIG. 3A. Production of NG-330 virus is detailed in Example 1. A549 or HT-29 carcinoma cell lines were seeded in 6 well plates at cell densities of 7.5e5 cells/well for A549 cells or 2.e6 cells/well for HT-29 cells. Plates were incubated for 18 hrs, 37° C., 5% $CO_2$, before cells were either infected with, 100 EnAd or NG-330 virus particles per cell (ppc) or were left uninfected. Assays were carried out 24, 48 or 72 hrs post infection.

Virus Replication Assessed by qPCR

HT-29 and A549 cells lines either infected for 24, 48 or 72 hrs with 100 ppc EnAd or NG-330 or left uninfected were used for quantification of viral DNA by qPCR. Cell supernatants were collected and clarified by centrifuging for 5 mins, 1200 rpm. DNA was extracted from 10 μl of supernatant using the Sigma Genelute DNA extraction Kit, according to the manufacturer's protocol. A standard curve using EnAd virus particles (2.5e10-2.5e5vp) was also prepared and extracted using the Sigma Genelute Kit. Each extracted sample or standard was analysed by qPCR using an EnAd E3 gene specific primer-probe set.

Figure 4B:
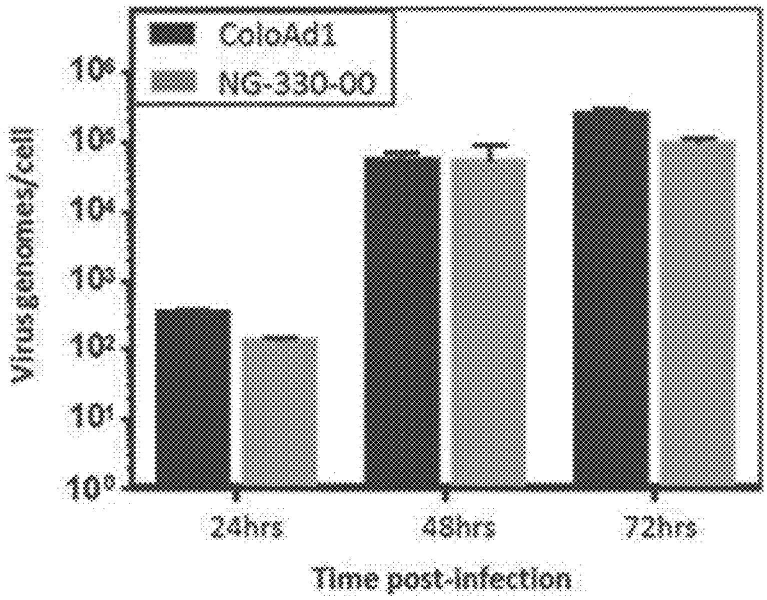
FIG. 4B shows replication of EnAd (ColoAd1) and human CD80 encoding virus NG-330 in A549 tumour cells
Figure 5A:
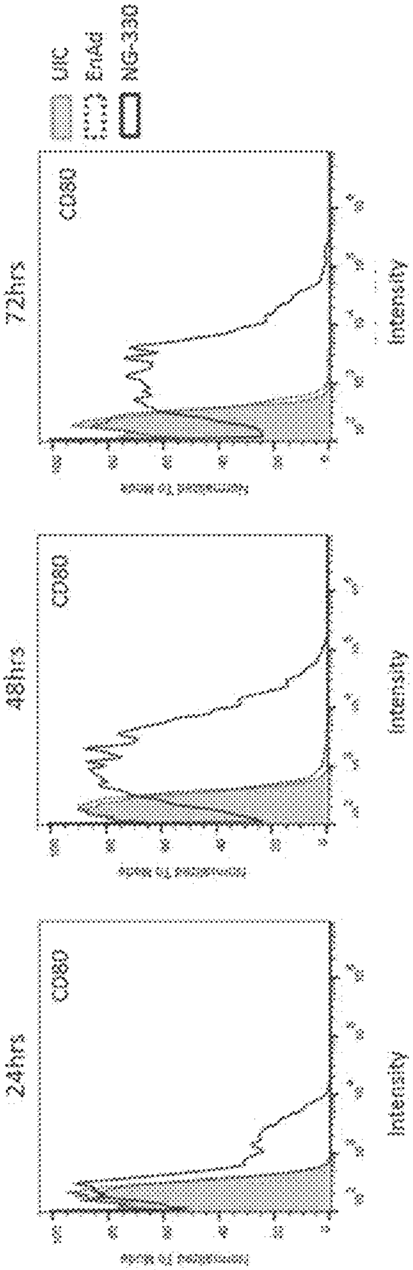
FIG. 5A shows expression of CD80 in the membrane of A549 tumour cells by fluorescent immunostaining at different times after infection with NG-330. No expression of CD80 on the cell membrane was observed with EnAd or uninfected tumour cells (UIC)
Figure 5B:
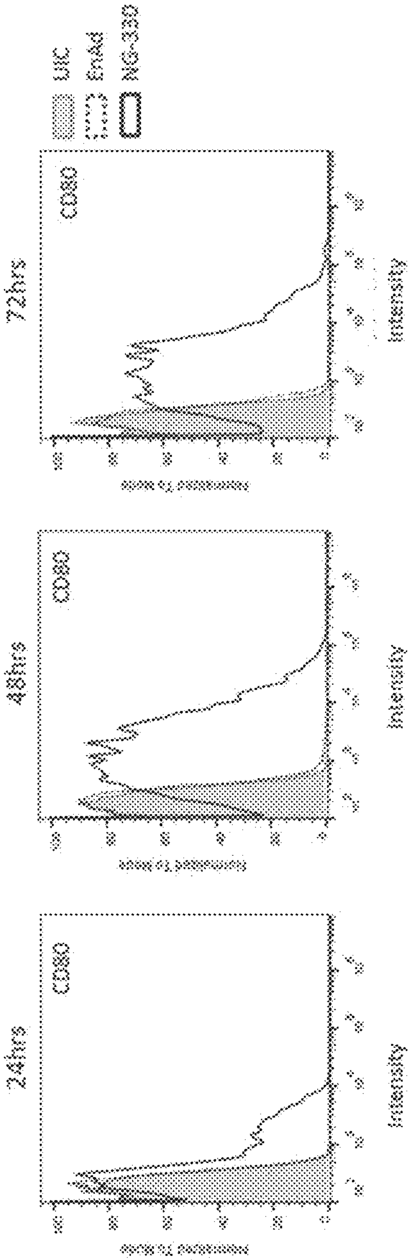
FIG. 5B shows expression of CD80 in the membrane of HT-29 tumour cells by fluorescent immunostaining at different times after infection with NG-330. No expression of CD80 on the cell membrane was observed with EnAd or uninfected tumour cells (UIC)

Quantification of the number of detected virus genomes per cell demonstrated that NG-330 and EnAd virus replication was comparable in both HT-29 (FIG. 4A) and A549 cell lines (FIG. 4B). No virus genomes could be detected in uninfected cells (data not shown).

CD80 Cell Surface Expression Assessed by Flow Cytometry

HT-29 and A549 cells lines either infected for 24, 48 or 72 hrs with 100 ppc EnAd or NG-330 or left uninfected were used for analysis of CD80 transgene expression on the cell surface. The tumour cells were removed from the plate surface by treatment with trypsin, centrifuged and then resuspended in 1% BSA/PBS. Samples were then either incubated at 5° C. for 1 hr with buffer, mouse isotype control antibody conjugated to Cy5 or anti-human CD80 antibody conjugated to Cy5 (clone 2D10). All samples were also co-stained with Zombie Aqua live/dead to differentiate viable cells. Samples were washed 3 times with 1% BSA/PBS before analysis by flow cytometry (FACS, Attune) for cell viability and CD80 protein expression on the cell surface. Analysis showed that CD80 could be detected at the cell surface in both A549 (FIG. 5A) or HT-29 (FIG. 5B) cells treated with NG-330 but not those treated with EnAd or left untreated.

Comparison of Virus Oncolytic Potency

Figure 6:
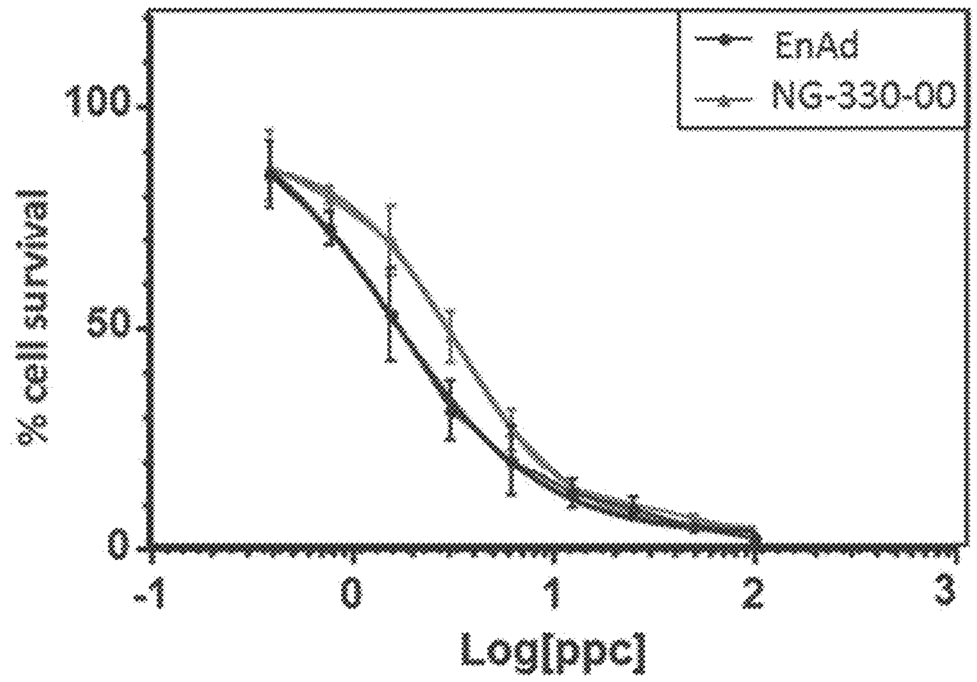
FIG. 6 shows comparable oncolytic potencies of EnAd and NG-330 in a HT-29 cytoxicity assay. Thus NG-330 retains its oncolytic properties whilst also carrying a transgene

HT-29 colon carcinoma cells were seeded in 96 well plates at a cell density of 2.5e4 cells/well. Plates were incubated for 4 hrs, 37° C., 5% $CO_2$, before cells were either infected with EnAd or NG-330 virus particles at an infection density range of 100-0.39 particles per cell (ppc). HT-29 cell viability was assessed using Cell Titre 96 MTS Reagent (Promega: G3581) 72 hrs post infection. Quantification of the % cell survival at each infection density demonstrated that NG-330 oncolytic potency was comparable to EnAd in HT29 cells (FIG. 6).

Example 3: Production of EnAd Viruses Expressing the T Cell Activating Antigen CD80 and the Cytokine IFNα

Figure 3B:
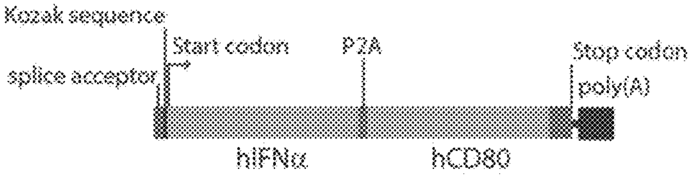
FIG. 3B shows a schematic of a transgene cassette for a virus co-expressing human IFNα and human CD80.

The plasmid pEnAd2.4 was used to generate the plasmid pNG-343 by direct insertion of a cassette encoding the human T cell activating antigen CD80 (SEQ ID NO 11) and the human cytokine interferon α (IFNα, SEQ ID NO: 12). The pNG-343 cassette contains; a 5' short splice acceptor sequence CAGG; human IFNα cDNA; a high efficiency self-cleavable P2A peptide sequence (SEQ ID NO: 7); human CD80 cDNA sequence and a 3' polyadenylation sequence (SEQ ID NO: 5). A Schematic of the inserted transgene cassette is shown in FIG. 3B. Construction of the plasmid was confirmed by DNA sequencing.

Virus Production and Characterisation

The plasmid pNG-343 was linearised by restriction digest with the enzyme AscI to produce the virus genome NG-343 (SEQ ID NO: 17)). The virus NG-343 is amplified and purified according to methods detailed in Example 1.

Example 4: Production of EnAd Viruses Expressing the Extracellular Domain of FMS-Like Tyrosine Kinase-3 Ligand, the Chemokine MIP1α and the Cytokine IFNα

Figure 3C:
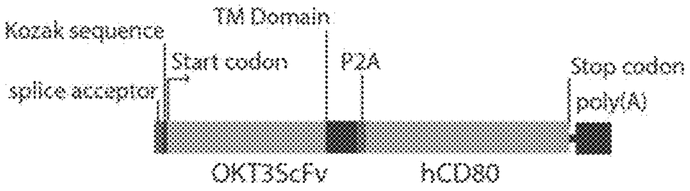
FIG. 3C shows a schematic of a transgene cassette for a virus co-expressing OKT3 scFv and human CD80.
Figure 3D:
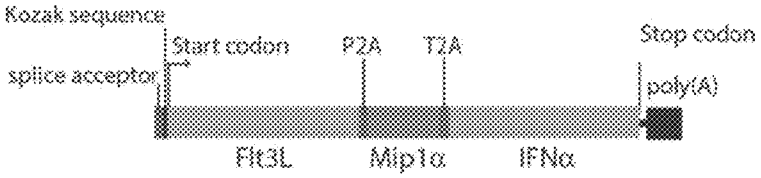
FIG. 3D shows a schematic for a virus co-expressing human Flt3L, human MIP1α and human IFNα.

The plasmid pEnAd2.4 is used to generate the plasmid pNG-345 by direct insertion of a cassette encoding a soluble variant of the FMS-like tyrosine kinase-3 ligand (Flt3L, SEQ ID NO: 13), MIP1α (isoform LD78β, SEQ ID NO: 14) and IFNα (SEQ ID NO: 12). The pNG-345 cassette contains; a 5' short splice acceptor sequence CAGG; human Flt3L cDNA; a high efficiency self-cleavable P2A peptide sequence (SEQ ID NO: 7); human MIP1α cDNA; a high efficiency self-cleavable T2A peptide sequence (SEQ ID NO: 10); human IFNα cDNA and a 3' polyadenylation sequence (SEQ ID NO: 5). A Schematic of the inserted transgene cassette is shown in FIG. 3D. Construction of the plasmid is confirmed by DNA sequencing.

Virus Production and Characterisation

The plasmid pNG-345 is linearised by restriction digest with the enzyme AscI to produce the virus genome NG-345 (SEQ ID NO: 18)). The virus NG-345 is amplified and purified according to methods detailed in Example 1.

Figure 3E:
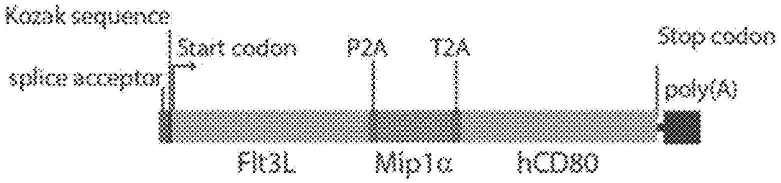
FIG. 3E shows a schematic for a virus co-expressing human Flt3L, human MIP1α and human CD80.

Example 5: Production of EnAd Viruses Expressing the T Cell Activating Antigen CD80, the Chemokine MIP1α and Flt3 Ligand The plasmid pEnAd2.4 was used to generate the plasmids pNG-346 by direct insertion of a cassette encoding the human T cell activating antigen CD80 (SEQ ID NO 11), the human macrophage Inflammatory Protein 1a (MIP1α, SEQ ID NO. 14) and the human Flt3 Ligand (SEQ ID NO: 13). The pNG-346 cassette contains; a 5' short splice acceptor sequence CAGG; human IFNα cDNA; a high efficiency self-cleavable P2A peptide sequence (SEQ ID NO: 7); human MIP1α cDNA (isoform LD78β); a high efficiency self-cleavable T2A peptide sequence (SEQ ID NO: 10); human Flt3 Ligand cDNA sequence and a 3' polyadenylation sequence (SEQ ID NO: 5). A schematic of the inserted transgene cassette is shown in FIG. 3E. Construction of the plasmid is confirmed by DNA sequencing.

Virus Production and Characterisation

The plasmid pNG-346 is linearised by restriction digest with the enzyme AscI to produce the virus genome NG-346 (SEQ ID NO: 19). The virus NG-346 is amplified and purified according to methods detailed in Example 1

Example 6: Production of EnAd Viruses Expressing the T Cell Activating Antigen CD80, the Chemokine MIP1α and the Cytokine IFNα

Figure 3F:
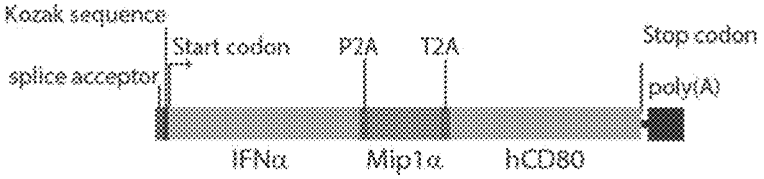
FIG. 3F shows a schematic for a virus co-expressing human IFNα, human MIP1α and human CD80.

The plasmid pEnAd2.4 was used to generate the plasmids pNG-347 by direct insertion of a cassette encoding the human T cell activating antigen CD80 (SEQ ID NO: 11), the human macrophage Inflammatory Protein 1α (MIP1α, SEQ ID NO. 14) and the human cytokine interferon α (IFNα, SEQ ID NO: 12). The pNG-347 cassette contains; a 5' short splice acceptor sequence CAGG; human IFNα cDNA; a high efficiency self-cleavable P2A peptide sequence (SEQ ID NO: 7); human MIP1α cDNA (isoform LD78β); a high efficiency self-cleavable T2A peptide sequence (SEQ ID NO: 10); human CD80 cDNA sequence and a 3' polyadenylation sequence (SEQ ID NO: 5). A Schematic of the inserted transgene cassette is shown in FIG. 3F. Construction of the plasmid is confirmed by DNA sequencing.

Virus Production and Characterisation

The plasmid pNG-347 is linearised by restriction digest with the enzyme AscI to produce the virus genome NG-347 (SEQ ID NO: 20). The virus NG-347 is amplified and purified according to methods detailed in Example 1.

Example 7: Production of EnAd Viruses Expressing the T Cell Activating Antigen CD80 and a Membrane-Anchored Single Chain Fv Fragment Antibody to the ε Chain of the Human CD3 Complex (CD3ε)

The plasmid pEnAd2.4 was used to generate the plasmids pNG-348 by direct insertion of a cassette encoding the human T cell activating antigen CD80 (SEQ ID NO: 11) and a membrane-anchored chimeric form of the single chain Fv anti-human CD3e (SEQ ID NO: 15). The pNG-348 cassette contains; a 5' short splice acceptor sequence CAGG; membrane-anchored anti-human CD3e scFv cDNA; a high efficiency self-cleavable P2A peptide sequence (SEQ ID NO: 7); human CD80 cDNA sequence and a 3' polyadenylation sequence (SEQ ID NO: 5). A Schematic of the inserted transgene cassette is shown in FIG. 3C. Construction of the plasmid is confirmed by DNA sequencing.

Virus Production and Characterisation

The plasmid pNG-348 is linearised by restriction digest with the enzyme AscI to produce the virus genome NG-348 (SEQ ID NO: 96). The virus NG-348 is amplified and purified according to methods detailed in Example 1.

Example 8: Activity of EnAd Virus, NG-343, Expressing Two Transgenes; the T Cell Activating Antigen CD80 and the Cytokine IFNα

Characterisation of NG-343 Virus Activity Compared to EnAd in Carcinoma Cell Lines NG-343 or EnAd virus replication (assessed by qPCR), CD80 transgene expression (assessed by flow cytometry) or IFNα transgene expression (assessed by ELISA) was compared in the colon carcinoma cell line, HT-29 or the lung carcinoma cell line, A549. NG-343 is a virus derived from EnAd that contains a transgene cassette encoding the human T cell activating antigen, CD80 as well as the human cytokine Interferon alpha 2b located after the EnAd late gene, L5 (Fibre). A schematic of the inserted cassette is shown in FIG. 3B. Production of NG-343 virus is detailed in Example 3. A549 or HT-29 carcinoma cell lines were seeded in 12 well plates at cell densities of $7.5\times10^5$ cells/well for A549 cells or $1.4\times10^6$ cells/well for HT-29 cells. Plates were incubated for 18 hrs, 37° C., 5% $CO_2$, before cells were either infected with EnAd or NG-343 at 100 virus particles per cell (ppc) or were left uninfected. Assays were carried out 24, 48 or 72 hrs post infection.

Virus Replication Assessed by qPCR

HT-29 cells infected for 24, 48 or 72 hrs with 100 ppc EnAd or NG-343 or left uninfected were used for quantification of viral DNA by qPCR. Cell supernatants were collected and clarified by centrifuging for 5 mins, 1200 rpm. DNA was extracted from 10 μl of supernatant using the Sigma Genelute DNA extraction Kit, according to the manufacturer's protocol. A standard curve using EnAd virus particles ($2.5\times10^{10}$ to $2.5\times10^5$ vp) was also prepared and extracted using the Sigma Genelute Kit. Each extracted sample or standard was analysed by qPCR using an EnAd E3 gene specific primer-probe set.

Figure 7A:
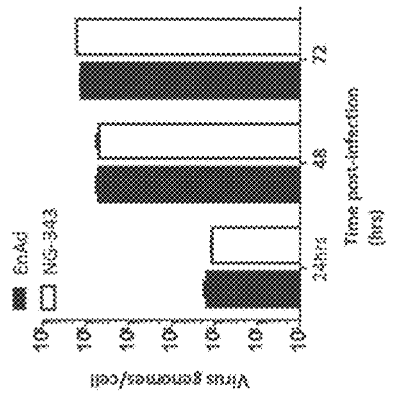
FIG. 7A shows comparable oncolytic potency of EnAd and the CD80+IFNα expressing NG-343 virus.

Quantification of the number of detected virus genomes per cell demonstrated that NG-343 and EnAd virus replication was comparable at all time points analysed (FIG. 7A). No virus genomes could be detected in uninfected cells (data not shown).

Analysis of IFNα Expression by ELISA

Supernatants of HT-29 or A549 cell lines infected for 24, 48 or 72 hrs with 10 ppc of EnAd or NG-343 or left uninfected were analysed for expression of secreted IFNα by ELISA.

Culture supernatants were removed from each well and centrifuged for 5 mins, 1200 rpm to remove cell debris. Supernatants were diluted into 5% BSA/PBS assay buffer (1:2 or 1:50 or 1:100) and ELISA was carried out using the Verikine Human IFN alpha Kit (Pbl assay science) according to the manufacturer's protocol.

Figure 7B:
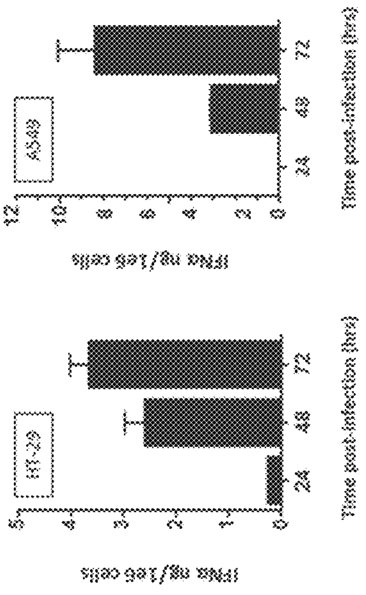
FIG. 7B shows secretion of IFNα by NG-343 infected HT-29 and A549 tumour cells over a period of up to 72 hours.

The concentrations of secreted IFNα were determined by interpolating from the standard curves. IFNα expression which increased in the cellular supernatants over the course of infection was detected in both HT-29 and A549 cells lines (FIG. 7B)

CD80 Cell Surface Expression Assessed by Flow Cytometry

Figures 8A, 8B, 8C, 8D:
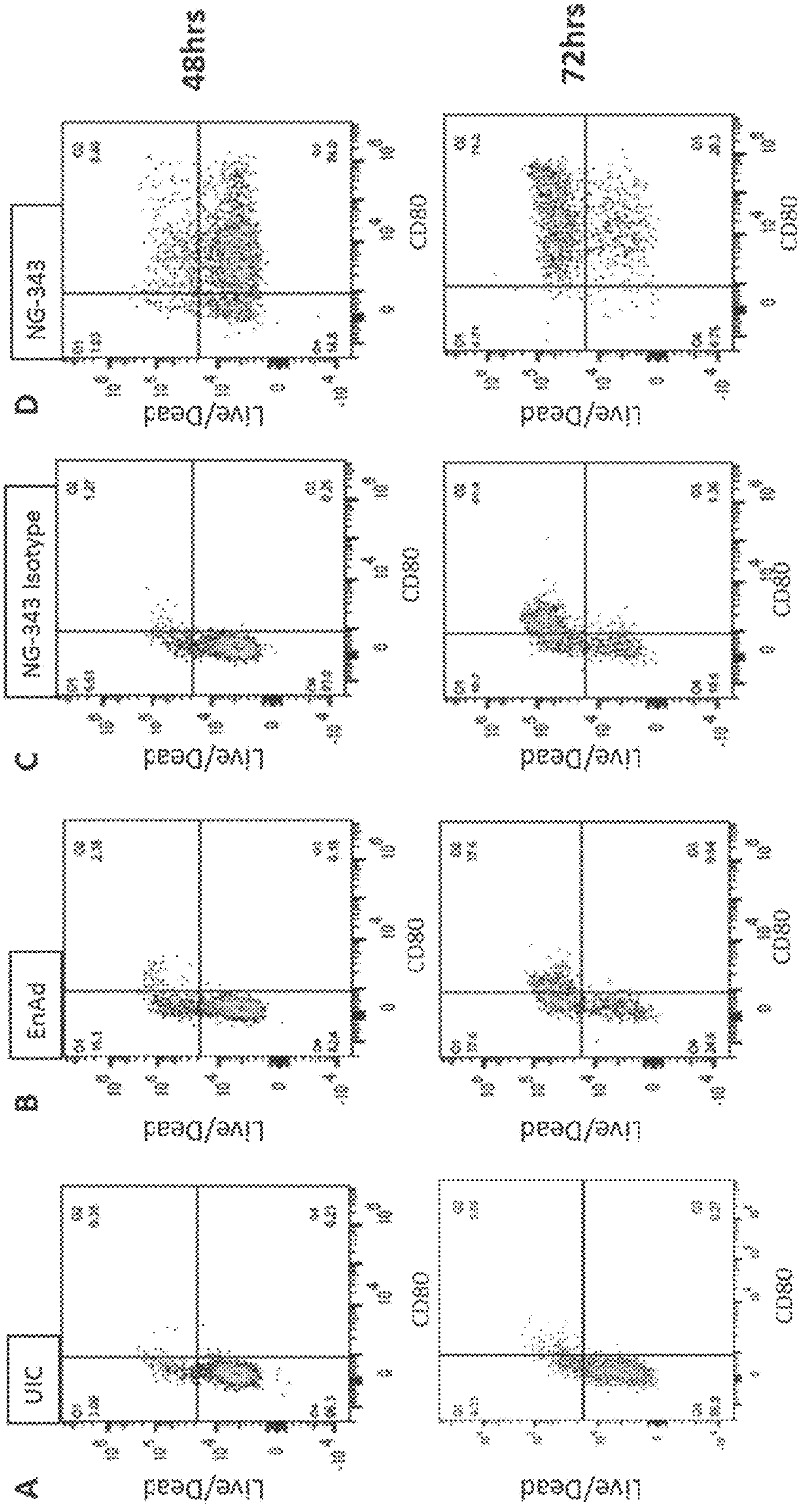
FIG. 8A shows expression of CD80 and tumour cell killing at 48 or 72 hours post infection by FACS analysis using anti-CD80 immunostaining together with a cell viability stain in uninfected control (UIC) A549 tumour cells.
FIG. 8B shows expression of CD80 and tumour cell killing at 48 or 72 hours post infection by FACS analysis using anti-CD80 immunostaining together with a cell viability stain in A549 tumour cells infected with EnAd.
FIG. 8C shows expression of CD80 and tumour cell killing at 48 or 72 hours post infection by FACS analysis using anti-CD80 immunostaining together with a cell viability stain in A549 tumour cells infected with NG-343 Isotype.
FIG. 8D shows expression of CD80 and tumour cell killing at 48 or 72 hours post infection by FACS analysis using anti-CD80 immunostaining together with a cell viability stain in A549 tumour cells infected with NG-343. CD80 could be detected at the cell surface of both live and dead NG-343 treated cells but not EnAd or uninfected control (UIC) A549 tumour cells (FIGS. 8A-D).
Figure 3E:
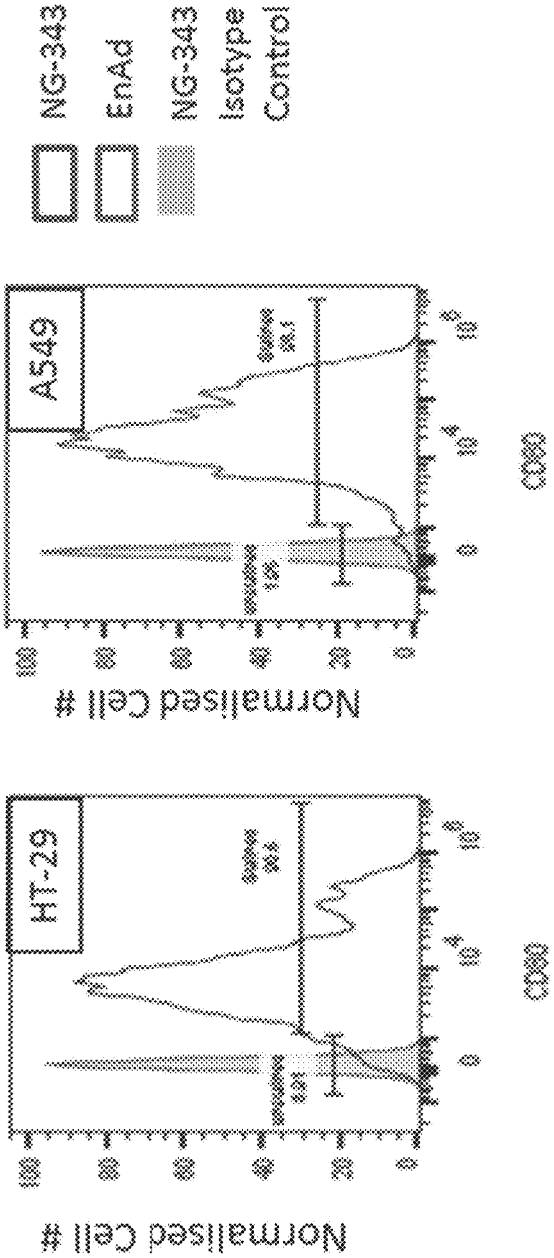

A549 cells lines infected for 48 or 72 hrs with 10 ppc EnAd or NG-343 or left uninfected were used for analysis of CD80 transgene expression on the cell surface. At the appropriate time point post-infection A549 cells were removed from the plate surface by treatment with trypsin, centrifuged and then resuspended in 1% BSA/PBS. Samples were then either incubated at 5° C. for 1 hr with buffer, mouse isotype control antibody conjugated to Cy5 or anti-human CD80 antibody conjugated to Cy5 (clone 2D10). All samples were also co-stained with Zombie Aqua live/dead to differentiate viable cells. Samples were washed 3 times with 1% BSA/PBS before analysis by flow cytometry (FACS, Attune) for cell viability and CD80 protein expression on the cell surface. Analysis of CD80 expression vs Live/dead staining showed that at both 48 and 72 hrs post infection CD80 could be detected at the cell surface of NG-343 treated cells but not EnAd or uninfected control (UIC) cells (FIG. 8). Cell viability at 72 hrs post virus treatment was not sufficient to carry out comprehensive CD80 expression analysis, however high levels of CD80 could be detected on both live and dying cells treated with NG-343 at this time point (FIG. 8D, lower panel).

CD80 protein expression was then compared in HT-29 and A549 cells at 48 hrs post-infection with 100 ppc. Samples were harvested and stained as above before analysis of cell viability and CD80 protein expression on the cell surface. Analysis of CD80 expression at this time point on only cells stained as live cells showed CD80 could be detected on the surface of ~91% of NG-343 treated HT-29 cells and ~98% of NG-343 treated A549 cells but not on EnAd treated controls.

Example 9: Selectivity of NG-343 Virus Activity and Transgene Expression in Carcinoma, Stromal Fibroblast and Epithelial Cell Lines To show that the IFNα and CD80 transgenes encoded in the NG-343 virus are selectively expressed only in cells permissive to NG-343 or EnAd infection, virus replication (assessed by qPCR), IFNα expression (assessed by ELISA) and CD80 expression (assessed by flow cytometry) were measured in cancer cells (HT-29) known to be permissive to EnAd infection, fibroblast cell lines (WI-38 and MRC-5) previously characterised to be non-permissive and a bronchial epithelial cell line (BE) which shows only limited permissivity to EnAd infection. Briefly, cells were seeded in 12 well plates and infected 18 hrs post-seeding with 100 ppc NG-343 or EnAd virus for WI38, MRC5 or BE cells or 10 ppc NG-343 or EnAd virus for HT-29 cells. Cells were incubated with virus particles for 4 hrs before the infection media was removed from the cells and replaced with fresh culture media. At 1 hr or 72 hrs post the 4 hr infection period, cell supernatants were harvested for qPCR or ELISA analysis and the cells were treated with trypsin to remove them from the plates for analysis by flow cytometry.

NG-343 and EnAd Selective Virus Replication

For qPCR, cell supernatants were collected and clarified by centrifuging for 5 mins, 1200 rpm. DNA was extracted from 10 μl of supernatant using the Sigma Genelute DNA extraction Kit, according to the manufacturer's protocol. A standard curve using EnAd virus particles ($2.5\times10^{10}$ to $2.5\times10^{5}$ vp) was also prepared and extracted using the Sigma Genelute Kit. Each extracted sample or standard was analysed by qPCR using an EnAd E3 gene specific primer-probe set.

Figure 9B:
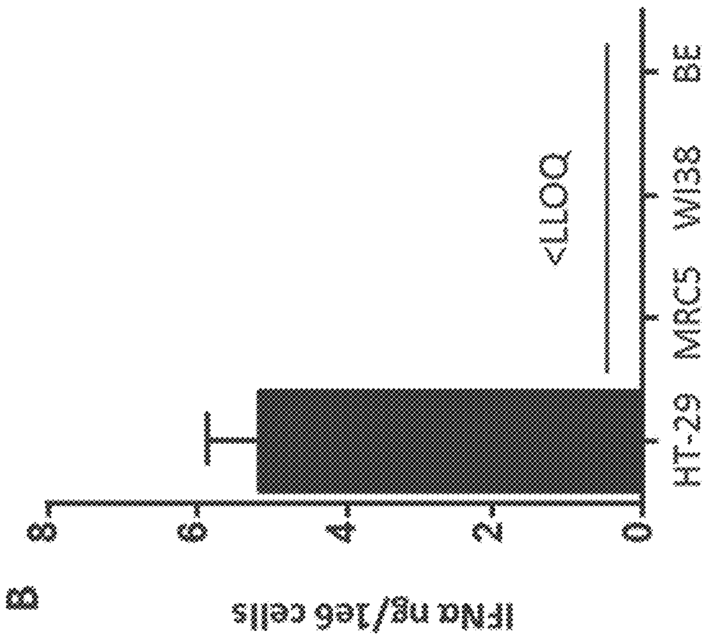
FIG. 9B shows IFNα secretion following infection.
Figure 9A:
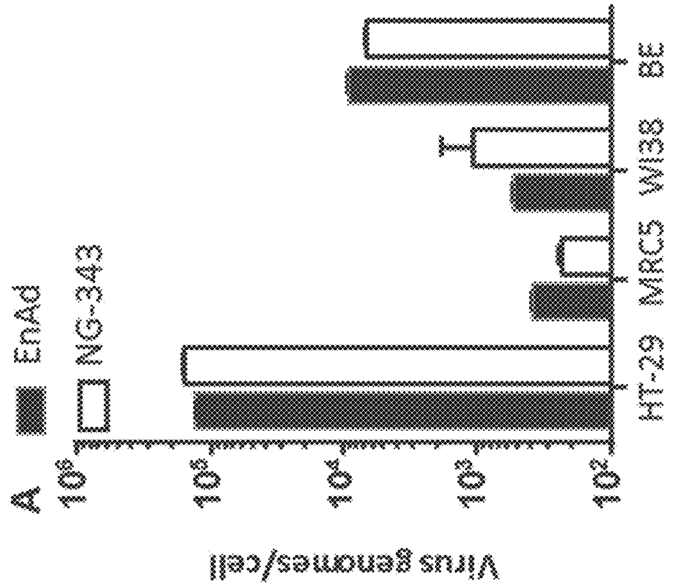
FIG. 9A shows virus replication with EnAd and NG-343 in tumour (HT-29) and non-tumour (MRC5, WI38 and bronchial epthelial cells) cells.

Quantification of the number of detected virus genomes per cell demonstrated that NG-343 and EnAd virus replication was comparable in all cell lines analysed (FIG. 9A).

NG-343 Selective Transgene Expression

For detection of IFNα expression, cell supernatants were collected and clarified by centrifuging for 5 mins, 1200 rpm. Supernatants were diluted into 5% BSA/PBS assay buffer (1:2 or 1:50 or 1:100) and ELISA was carried out using the Verikine Human IFN alpha Kit (PH assay science) according to the manufacturer's protocol.

The concentrations of secreted IFNα were determined by interpolating from the standard curve. IFNα expression could only be detected in the supernatants of NG-343 infected HT-29 cells and was not detectable (less than the lower limit of quantitation [<LLOQ]) in either of the fibroblast cell lines, or the bronchial epithelial cell line (FIG. 9B).

Figure 9C:
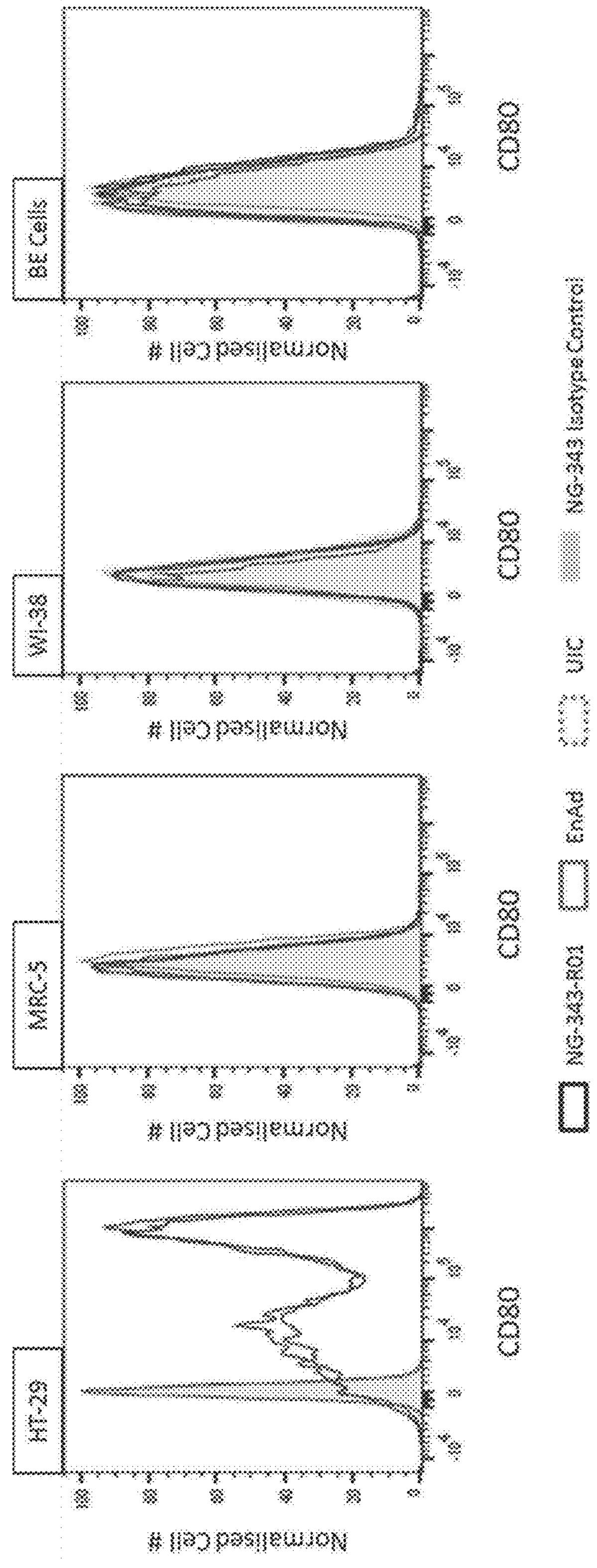
FIG. 9C shows CD80 expression following infection.

For CD80 cell surface expression, cells were then either incubated at 5° C. for 1 hr with buffer, mouse isotype control antibody conjugated to Cy5 or anti-human CD80 antibody conjugated to Cy5 (clone 2D10). All samples were also co-stained with Zombie Aqua live/dead to differentiate viable cells. Samples were washed 3 times with 1% BSA/PBS before analysis by flow cytometry (FACS, Attune) for cell viability and CD80 protein expression on the cell surface. In keeping with the IFNα expression data, CD80 expression could only be detected on HT-29 cells, with no detectable expression on either the fibroblast or bronchial epithelial cell lines (FIG. 9C).

Taken together these data demonstrated that both IFNα and CD80 transgenes are selectively expressed in cells permissive to EnAd virus infection i.e. carcinoma cells, and the encoding of transgenes does not alter the selectivity of the NG-343 virus when compared to the parental EnAd virus.

Example 10: Activity of NG-343 Transgene Expression on Immune Cell Activation

Figure 10:
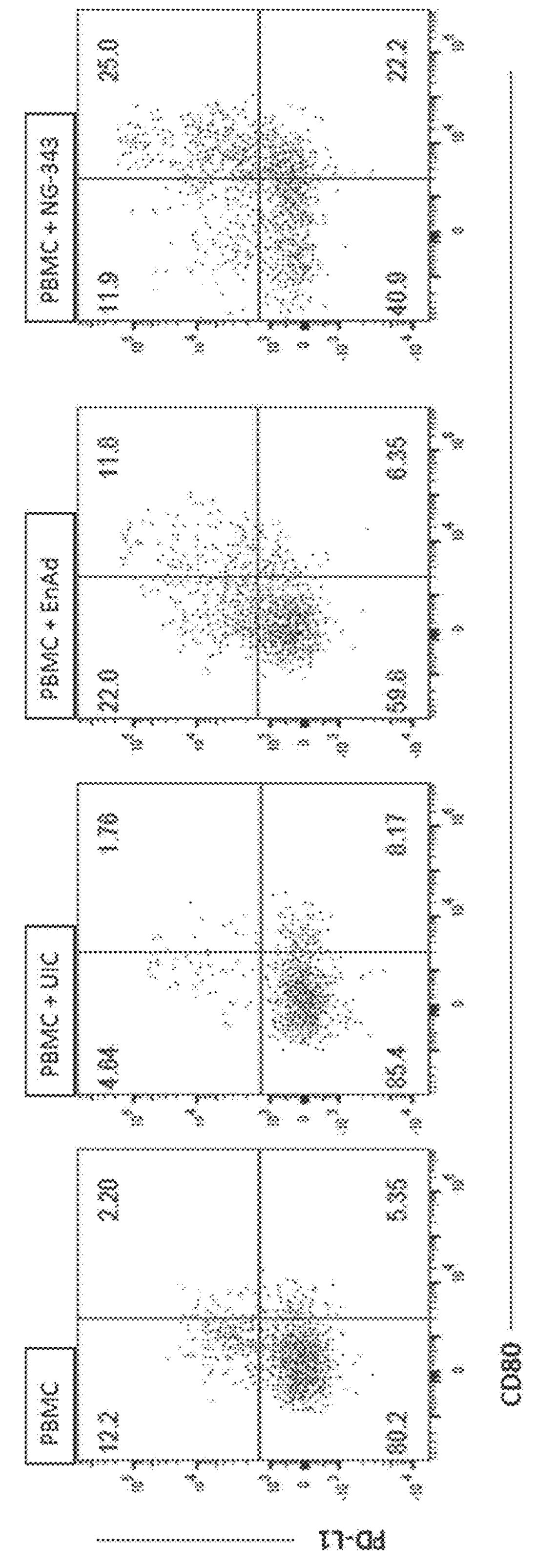
FIG. 10 shows that A549 tumour cells infected with NG-343 can induce increased surface levels of both CD80 and PD-L1 on the surface of DCs in PBMC co-cultures when compared to EnAd infected or uninfected tumour cell culture.

To determine if treatment of tumour cells with NG-343 virus could lead to enhanced innate immune cell responses compared to no treatment or to EnAd treatment, freshly isolated peripheral blood mononuclear cells (PBMCs) were co-cultured with tumour cells either infected with NG-343 or EnAd or left uninfected. Immune cell activation was assessed by flow cytometry analysis of innate immune cell populations or ELISA analysis of co-culture supernatants. Briefly, A549 lung carcinoma cells were seeded in 12 well plates at a density of $4\times10^{5}$ cells/well. After 20 hrs cells were infected with 10 ppc of EnAd or NG-343 virus or left uninfected and then incubated for 24 hrs, 37 degrees, 5% $CO_2$. PBMCs isolated from a healthy human donor by density gradient centrifugation were then added to the A549 culture wells at a ratio of 5 PBMCs to 1 A549 cell. At 48 hrs post addition of PBMCs co-culture supernatants were harvested from the plates. To analyse dendritic cell activation at this point, cells were incubated at 5° C. for 1 hr with buffer, mouse isotype control antibodies conjugated to Alexa Fluor 488, PE, PerCP/Cy5.5, BV605 or BV412, anti-CD14 antibody conjugated to Alexa Fluor 488, anti-CD80 antibody conjugated to PE, anti-HLA-DR conjugated to PerCP.Cy5.5, anti-CD3 conjugated to BV605 or anti-PD-L1 antibody conjugated to BV421. All samples were also co-stained with Zombie Aqua live/dead to differentiate viable cells. Samples were washed 3 times with 1% BSA/PBS before analysis by flow cytometry (FACS, Attune). Viable cells that stained negative for both CD14 and CD3 but positive for HLA-DR were defined as the dendritic cell population. Expression of the DC activation marker, CD80 and PD-L1 was compared on this population (FIG. 10). These analyses revealed that tumour cells infected with NG-343 could induce increased surface levels of both CD80 and PD-L1 on the surface of DCs when compared to EnAd infected or uninfected tumour cell culture.

Example 11: Activity of EnAd Virus, NG-347, Expressing Three Transgenes; the T Cell Activating Antigen CD80, the Chemokine MIP1α and the Cytokine IFNα

Characterisation of NG-347 Virus Activity Compared to EnAd in Carcinoma Cell Lines CD80 transgene expression (assessed by flow cytometry) and IFNα or MIP1α (CCL3) transgene expression (assessed by ELISA) was compared in NG-347 and EnAd treated colon carcinoma cell line, HT-29 or lung carcinoma cell line, A549. NG-347 is a virus derived from EnAd that contains a transgene cassette encoding the human T cell activating antigen, CD80, the human cytokine Interferon alpha 2b and the human chemokine MIP1α (LD78β isoform). Transgene expression is under the control of the virus endogenous major late promoter. A schematic of the inserted cassette is shown in FIG. 3F. Production of NG-347 virus is detailed in Example 6. A549 or HT-29 carcinoma cell lines were seeded in 12 well plates at cell densities of $7.5\times10^5$ cells/well for A549 cells or $1.4\times10^6$ cells/well for HT-29 cells. Plates were incubated for 18 hrs, 37° C., 5% $CO_2$, before cells were either infected with 100 EnAd or NG-347 virus particles per cell (ppc) or were left uninfected. Assays were carried out 24, 48 or 72 hrs post infection.

Analysis of IFNα or MIP1α Expression by ELISA

Supernatants of HT-29 or A549 cells lines infected for 24, 48 or 72 hrs with 100 ppc of EnAd or NG-347 or left uninfected were analysed for expression of secreted IFNα or secreted MIP1α by ELISA.

Culture supernatants were prepared according to the methods detailed in Example 9. IFNα ELISA was carried out using the Verikine Human IFN alpha Kit (Pbl assay science) and MIP1α ELISA was carried out using the Human CCL3 Quantikine ELISA kit (R & D systems). Both assays were carried out according to the manufacturers' protocol.

Figure 11B:
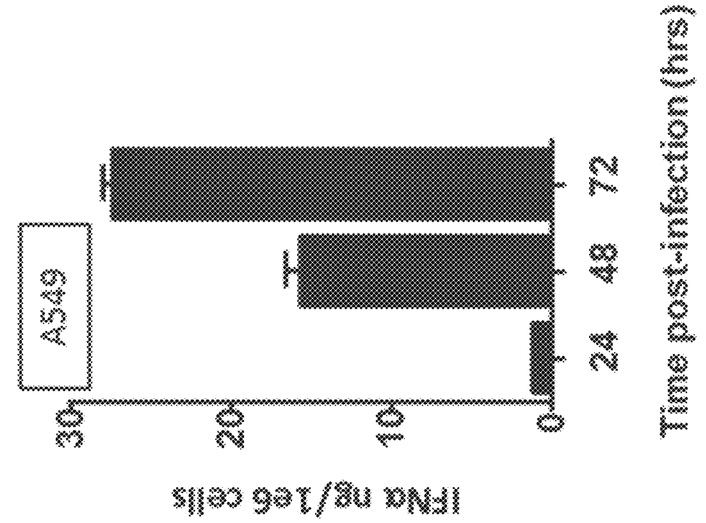
FIG. 11B shows expression of IFNα by A549 tumour cells infected with NG-347 virus.
Figure 11A:
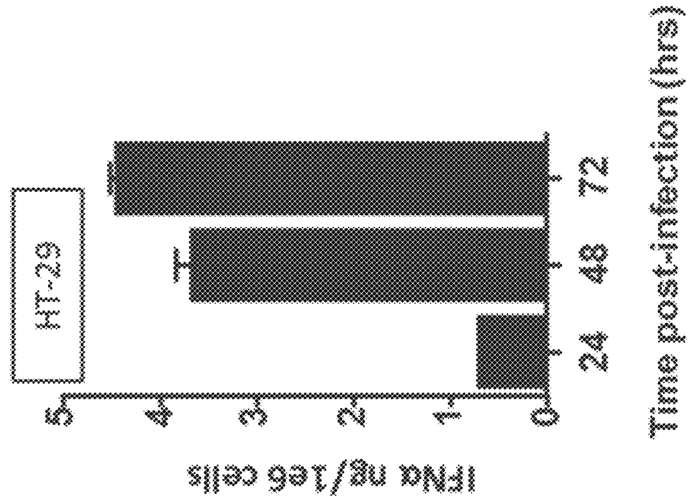
FIG. 11A shows expression of IFNα by HT-29 tumor cells infected with NG-347 virus.

The concentrations of secreted IFNα or MIPα were determined by interpolating from the standard curves. IFNα and MIP1α expression increased in the cellular supernatants over the course of infection and was detected for both HT-29 and A549 cells lines (FIG. 11A and FIG. 11B).

Analysis of CD80 Expression by Flow Cytometry

Figure 11C:
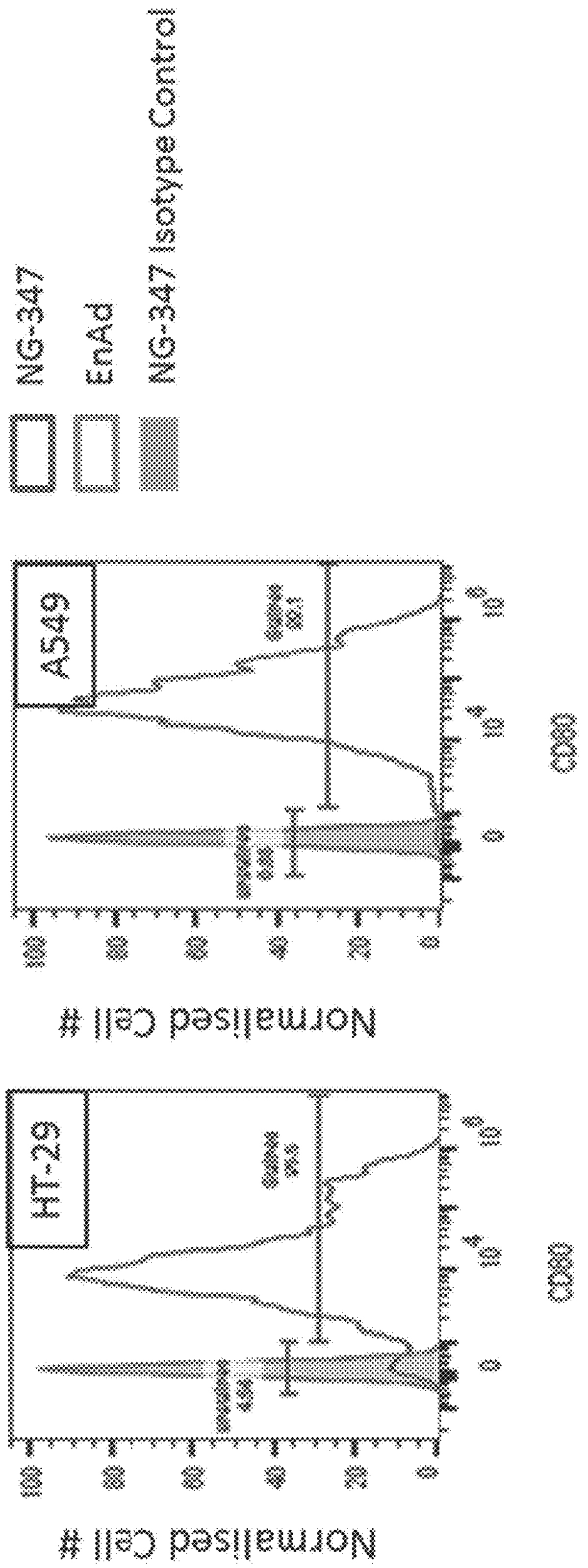
FIG. 11C shows CD80 expression by HT-29 and A549 tumour cells infected with NG-347, EnAd or NG-347 Isotype Control.

CD80 protein expression was compared on the surface of HT-29 and A549 cells at 48 hrs post-infection. Cells were harvested and stained according to methods detailed in example 9. Cells were analysed for cell viability and CD80 protein expression on the cell surface by flow cytometry. Analysis of CD80 expression at this time point on live cells showed CD80 could be detected on the surface of ~96% of NG-347 treated HT-29 cells and ~99% of NG-347 treated A549 cells but no staining was detected on EnAd treated controls (FIG. 11C).

Example 12: Activity of EnAd Virus, NG-345, Expressing Three Transgenes; the Cytokine Flt3 Ligand, the Chemokine Mip1α and the Cytokine IFNα

Characterisation of NG-345 Virus Activity Compared to EnAd in Carcinoma Cell Lines Flt3 Ligand, IFNα and MIP1α transgene expression (assessed by ELISA) was compared in NG-345 and EnAd treated colon carcinoma cell line, HT-29 or lung carcinoma cell line, A549. NG-345 is a virus derived from EnAd that contains a transgene cassette encoding a soluble variant of human Flt-3 ligand, the human cytokine Interferon alpha 2b and the human chemokine MIP1α (LD78β isoform). Transgene expression is under the control of the virus endogenous major late promoter. A schematic of the inserted cassette is shown in FIG. 3D. Production of NG-345 virus is detailed in Example 4. A549 or HT-29 carcinoma cell lines were seeded in 12 well plates at cell densities of $7.5\times10^5$ cells/well for A549 cells or $1.4\times10^6$ cells/well for HT-29 cells. Plates were incubated for 18 hrs, 37° C., 5% $CO_2$, before cells were either infected with 100 EnAd or NG-345 virus particles per cell (ppc) or were left uninfected. Assays were carried out 24, 48 or 72 hrs post infection.

Analysis of FLt-3 Ligand, IFNα or MIP1α Expression by ELISA

Supernatants of HT-29 or A549 cells lines infected for 24, 48 or 72 hrs with 100 ppc of EnAd or NG-345 or left uninfected were analysed for expression of secreted Flt3-Ligand, secreted IFNα or secreted MIP1α by ELISA.

Culture supernatants were prepared according to the methods detailed in Example 9. IFNα ELISA was carried out using the Verikine Human IFN alpha Kit (Pbl assay science), MIP1α ELISA was carried out using the Human CCL3 Quantikine ELISA kit (R & D systems) and Flt3L ELISA was carried out using the Flt3L human ELISA kit (Abcam). All assays were carried out according to the manufacturers' protocol.

Figure 12C:
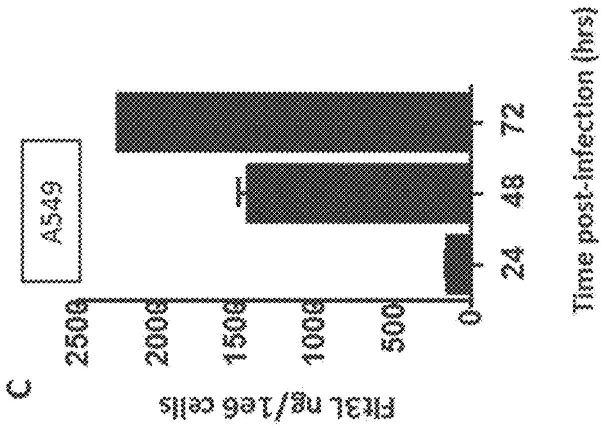
FIG. 12C shows expression of Flt3L by A549 tumour cells infected with NG-345 virus.
Figure 12B:
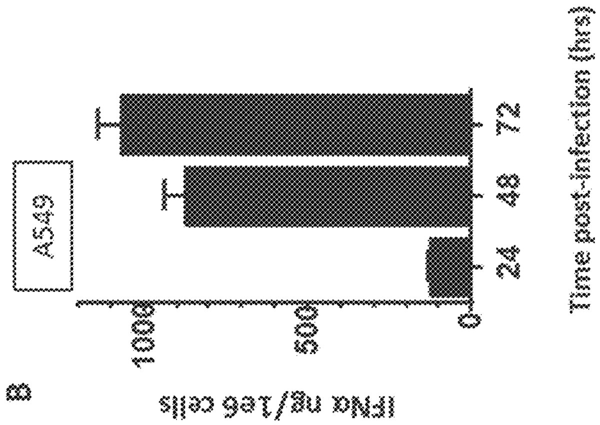
FIG. 12B shows IFNα expression by A549 tumour cells infected with NG-345 virus.
Figure 12A:
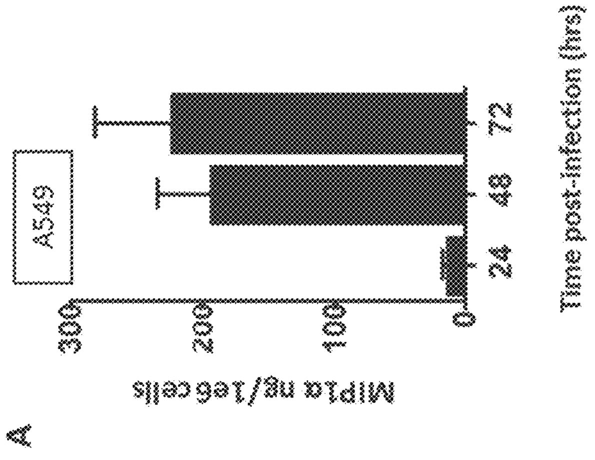
FIG. 12A shows expression of MIP1α by A549 tumour cells infected with NG-345 virus.

The concentrations of secreted IFNα, MIPα or FLt3L were determined by interpolating from the standard curves. IFNα, MIP1α and Flt3 L expression increased in the cellular supernatants over the course of infection and was detected in both HT-29 and A549 cells lines (FIG. 12A-C).

Figures 13A, 13B:
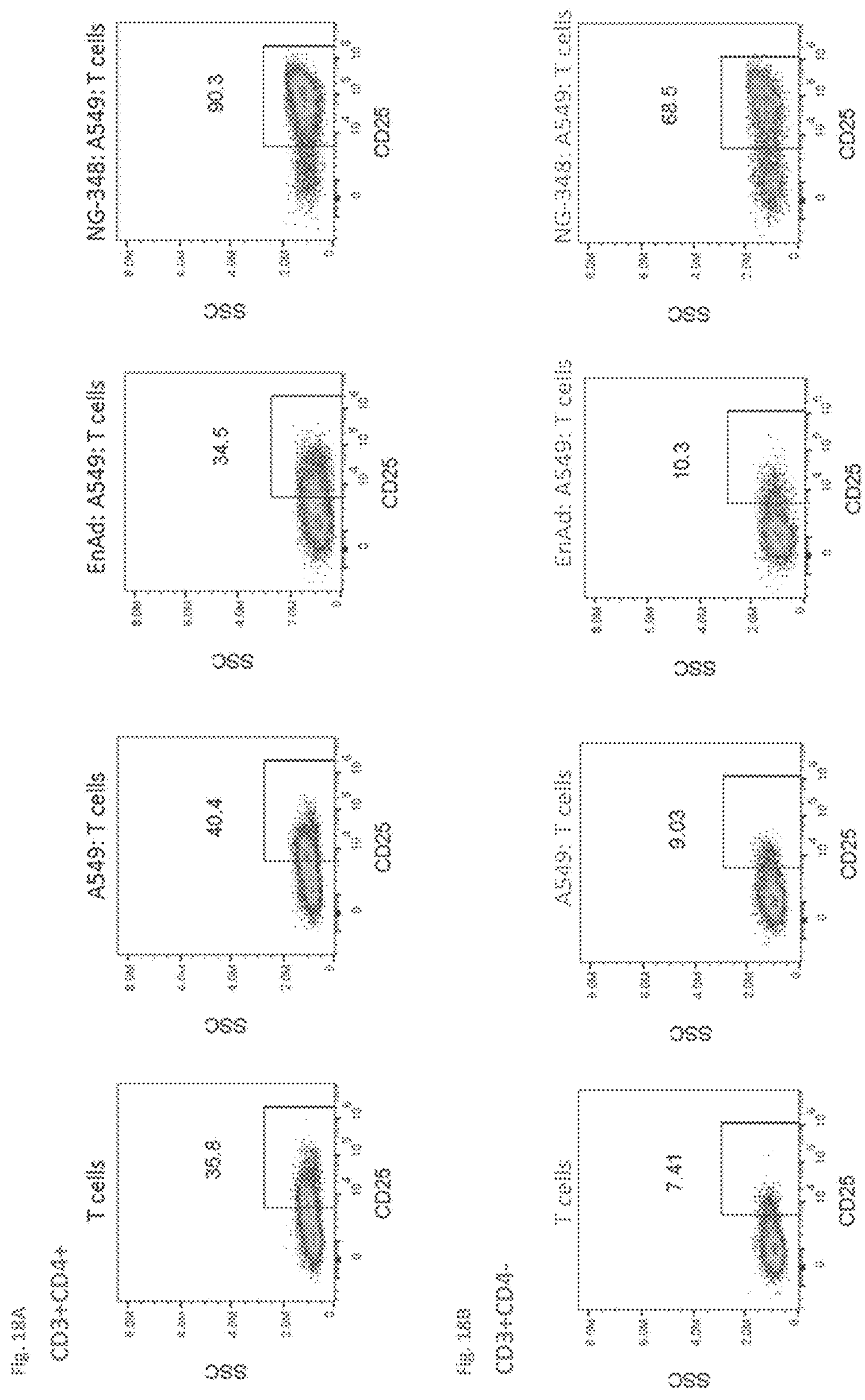
FIG. 13A shows oncolytic potency of EnAd and NG-347 viruses in an HT-29 cytotoxicity assay.
FIG. 13B shows oncolytic potency of EnAd and NG-348 viruses in an HT-29 cytotoxicity assay. NG-347 and NG-348 oncolytic potency was comparable to EnAd.

Example 13. Oncolytic Activity and Infectivity of NG-347 and NG-348 Viruses in Colon Carcinoma Cells Virus Oncolytic Potency HT-29 colon carcinoma cells were seeded in 96 well plates at a cell density of 2.5e4 cells/well. Plates were incubated for 4 hrs, 37° C., 5% $CO_2$, before cells were either infected with EnAd, NG-347 or NG-348 virus particles at an infection density range of 100-0.39 particles per cell (ppc). HT-29 cell viability was assessed using Cell Titre 96 MTS Reagent (Promega: G3581) 72 hrs post infection. Quantification of the % cell survival at each infection density demonstrated that NG-347 and NG-348 oncolytic potency was comparable to EnAd (FIGS. 13A and 13B).

Viral Particle Infectivity

HT-29 colon carcinoma cells were seeded in 12 well plates at a cell density of 4e5 cells/well. Plates were incubated for 24 hrs, 37° C., 5% $CO_2$, before cells were either infected with EnAd, NG-347 or NG-348 virus particles at an infection density range of 1.6e7-2e6 vp/mL. Infection of HT-29 cells was detected by antibody staining of the virus protein hexon. Stained cells were quantified by manual counting of 6 fields of view per well, across 6 replicate wells for each dilution tested. The particle to infectivity ratio (P:I) was calculated for each virus from the viral titre and demonstrated both NG-347 and NG-348 have similar infectivity ratios to EnAd reference controls (FIG. 13C).

Figure 14A:
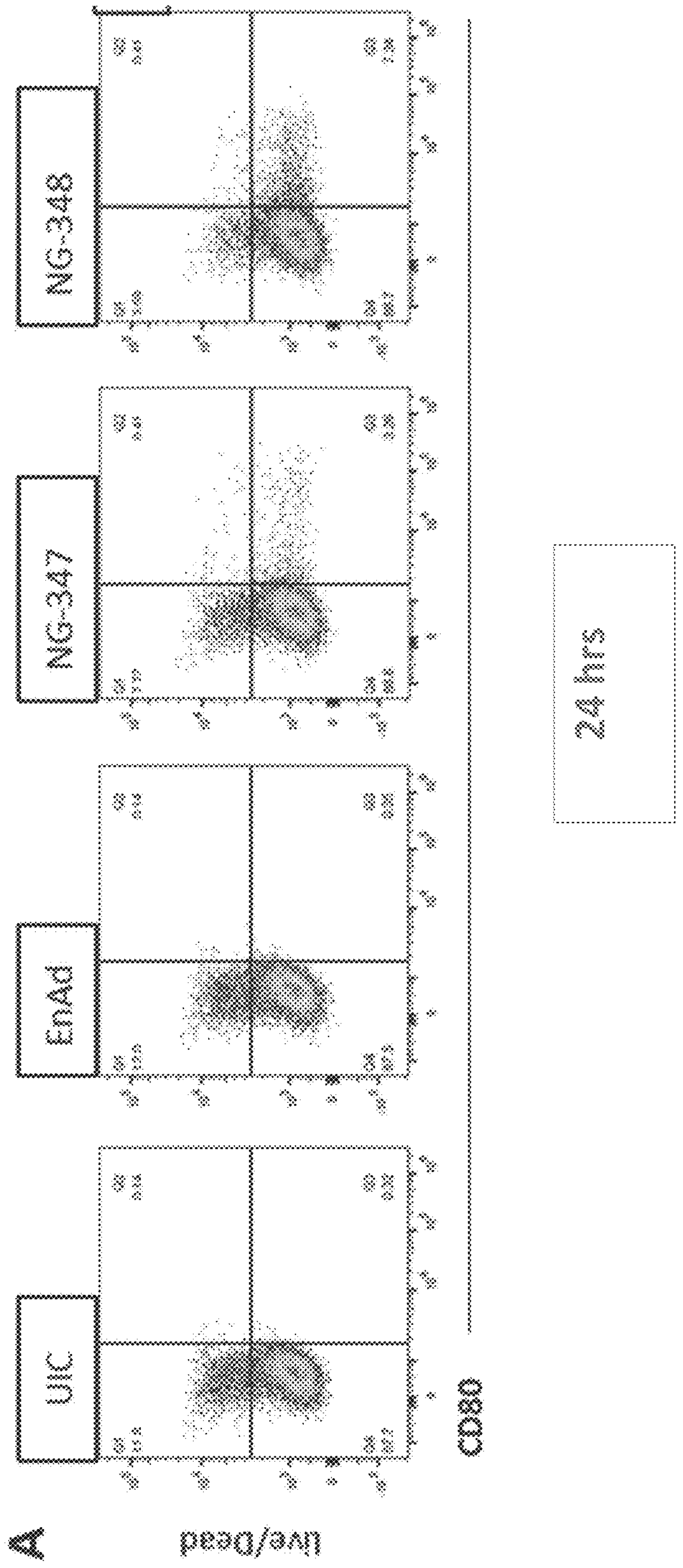
FIG. 14A shows high CD80 expression by 48 hours on the cell surface of A549 tumour cells infected with either NG-347 or NG-348 viruses but little or no CD80 expression following EnAd infection.
Figure 14B:
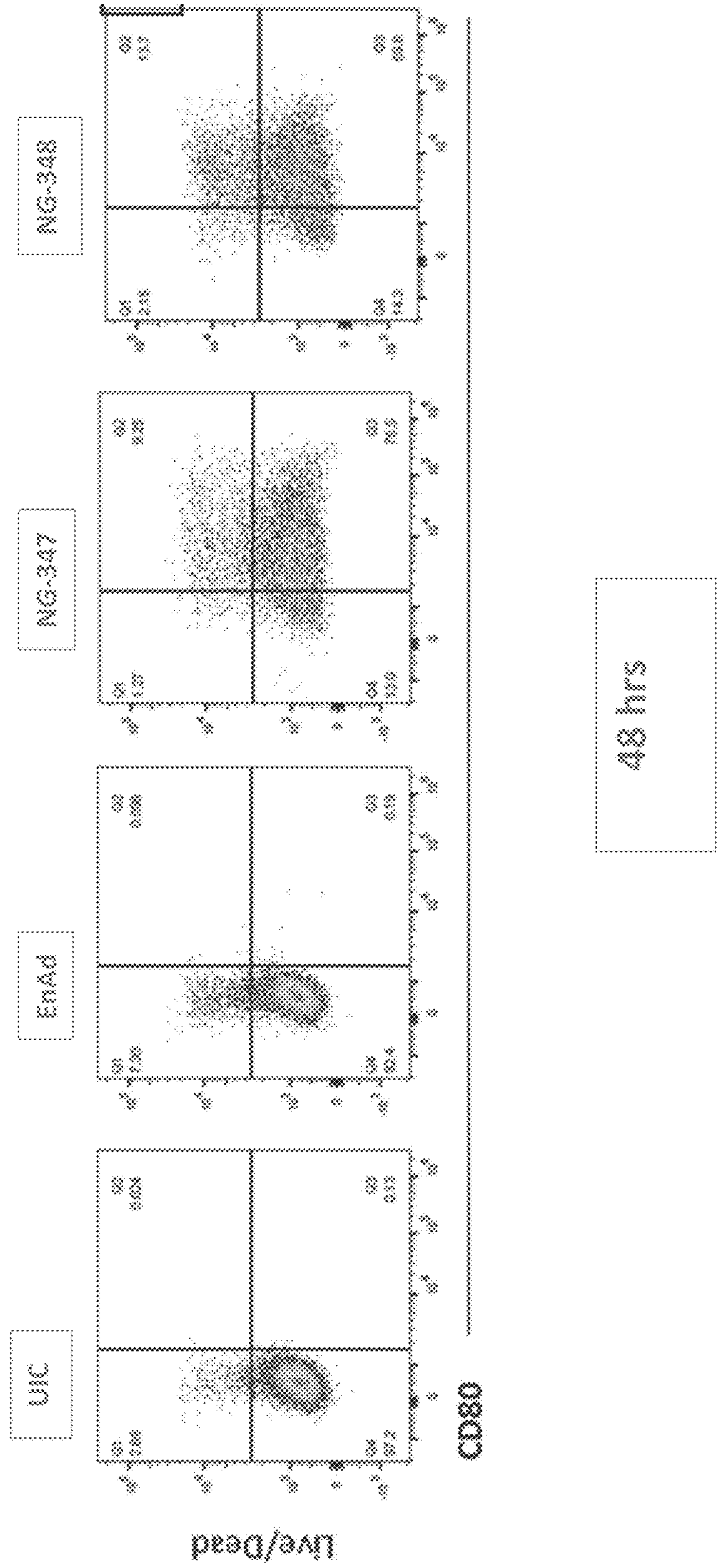
FIG. 14B shows CD80 expression levels on the cell surface of A549 tumour cells 72 hours after infection with NG-347, NG-348 or EnAd.
Figure 14C:
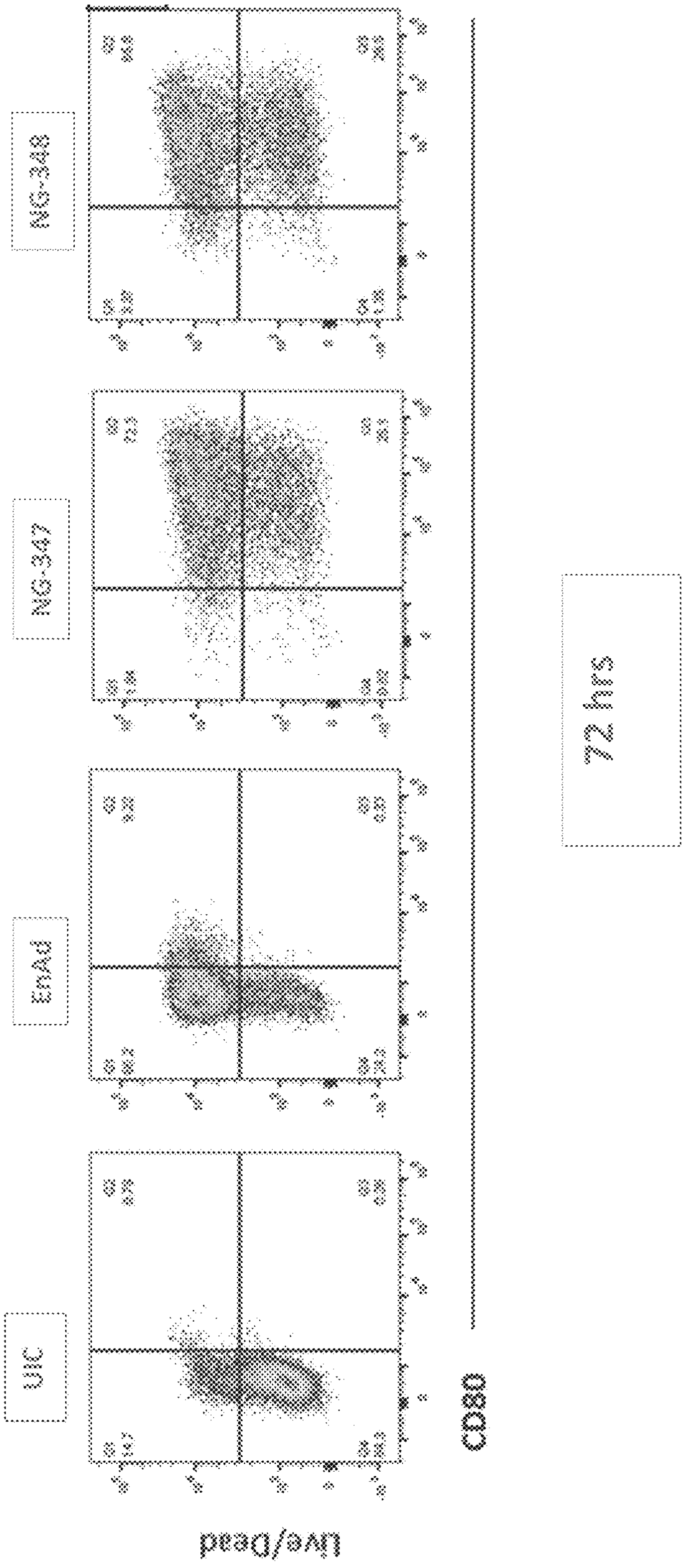
FIG. 14C shows CD80 expression levels on the cell surface of A549 tumour cells 96 hours after infection with NG-347, NG-348 or EnAd.
Figure 14D:
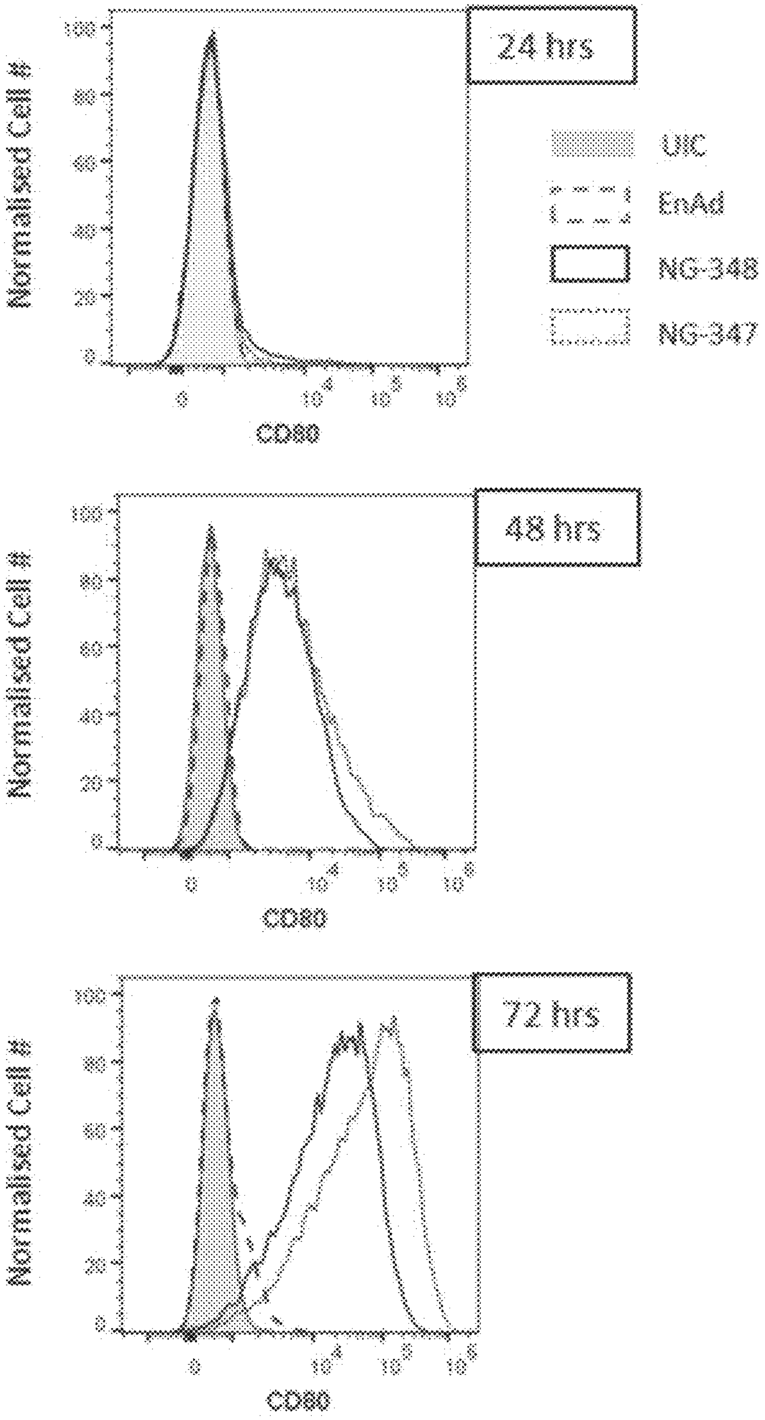
FIG. 14D shows high CD80 expression by 48 hours on the cell surface of A549 tumour cells infected with either NG-347 or NG-348 viruses but little or no CD80 expression following EnAd infection.
Figure 15A:
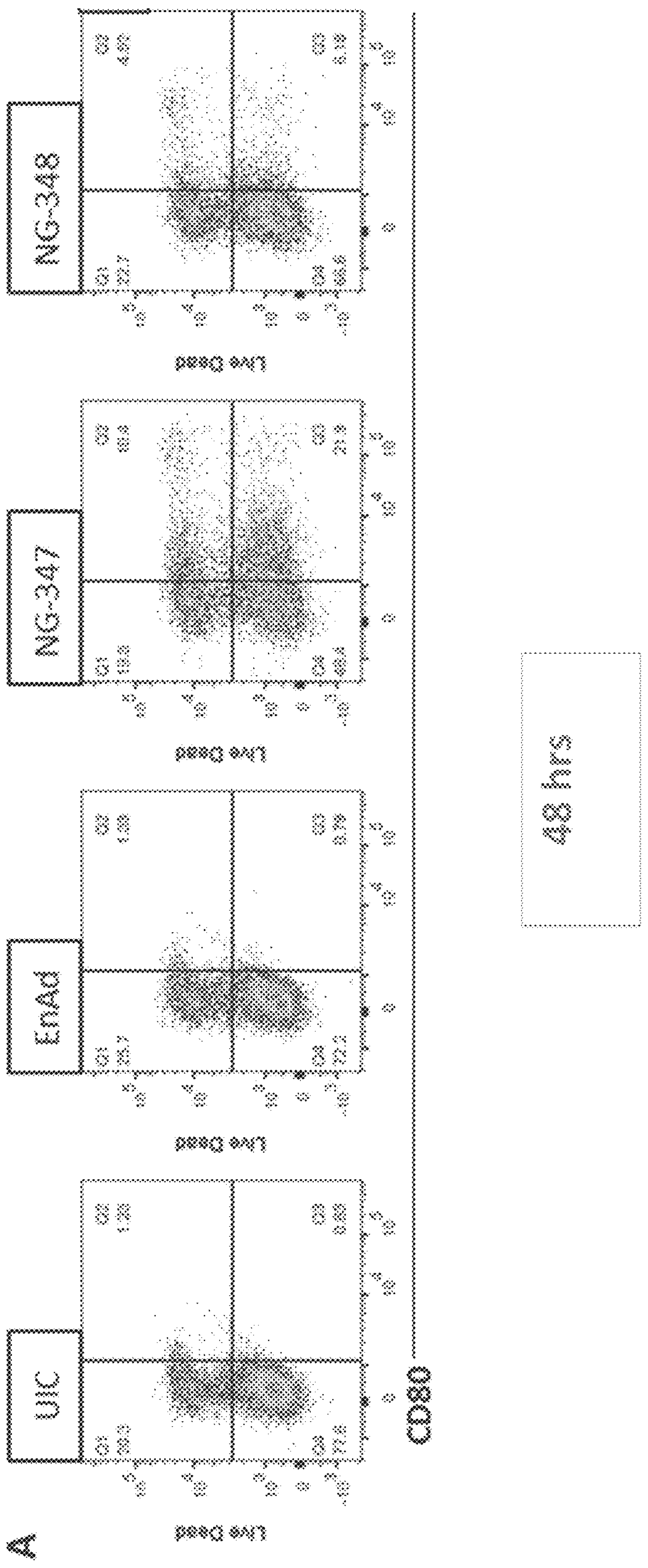
FIG. 15A shows high CD80 expression by 48 hours on the cell surface of DLD-1 tumour cells infected with either NG-347 or NG-348 viruses but little or no CD80 expression following EnAd infection.
Figure 15B:
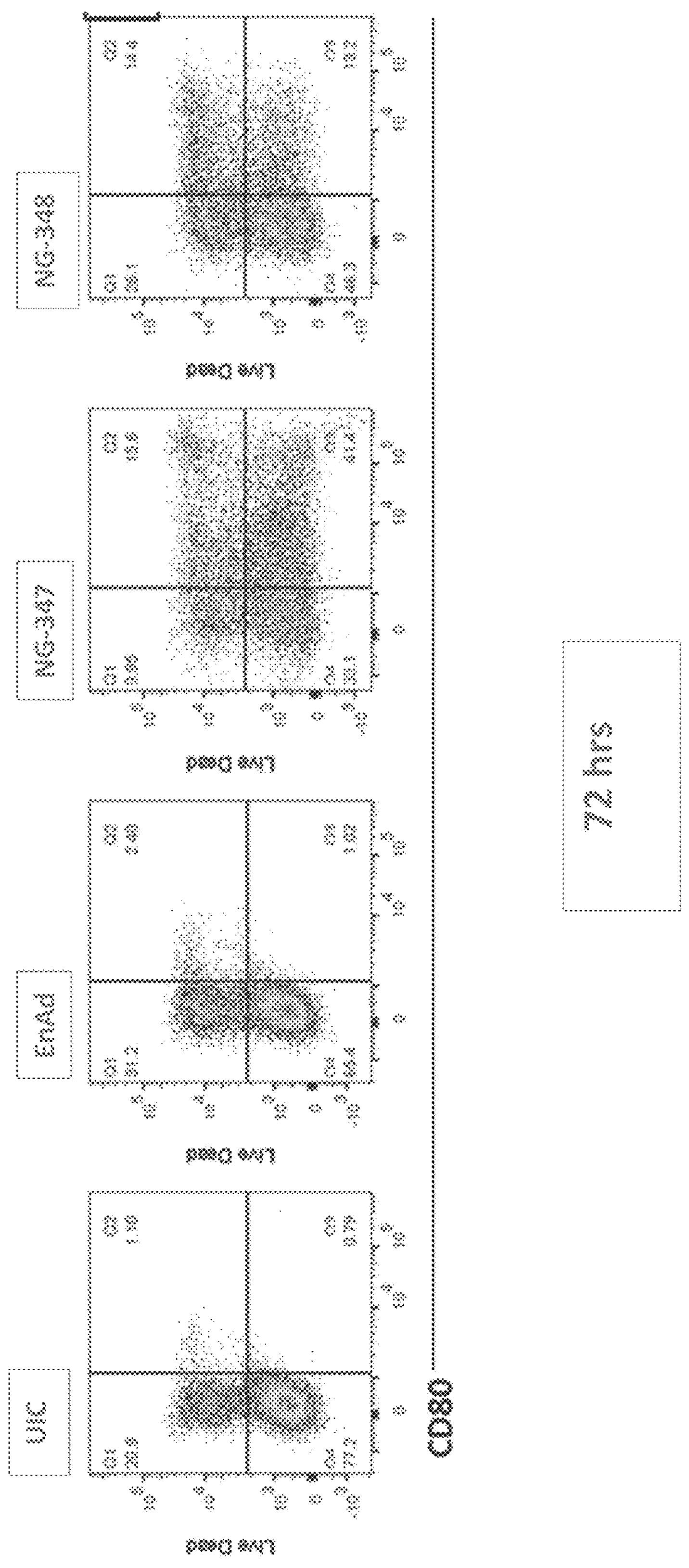
FIG. 15B shows CD80 expression levels on the cell surface of DLD-1 tumour cells 72 hours after infection with NG-347, NG-348 or EnAd.
Figure 15C:
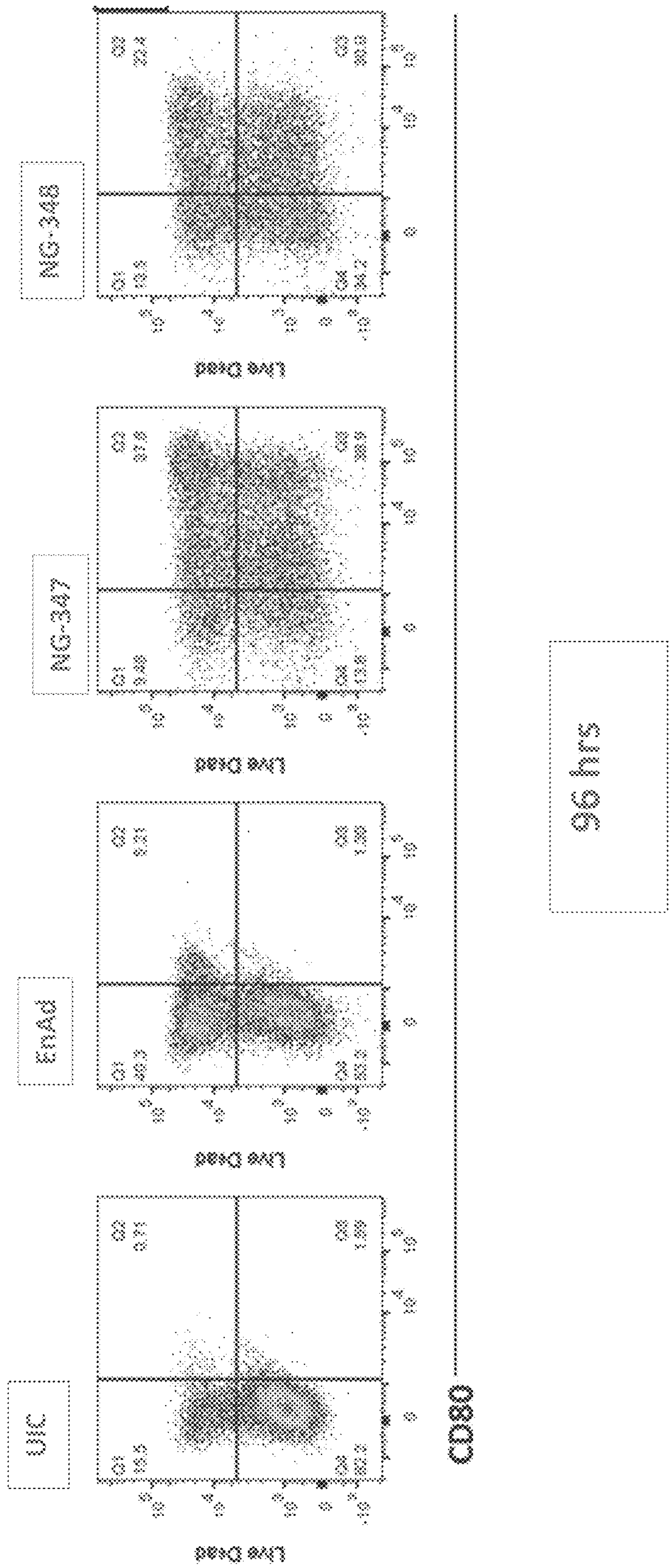
FIG. 15C shows CD80 expression levels on the cell surface of DLD-1 tumour cells 96 hours after infection with NG-347, NG-348 or EnAd.
Figure 15D:
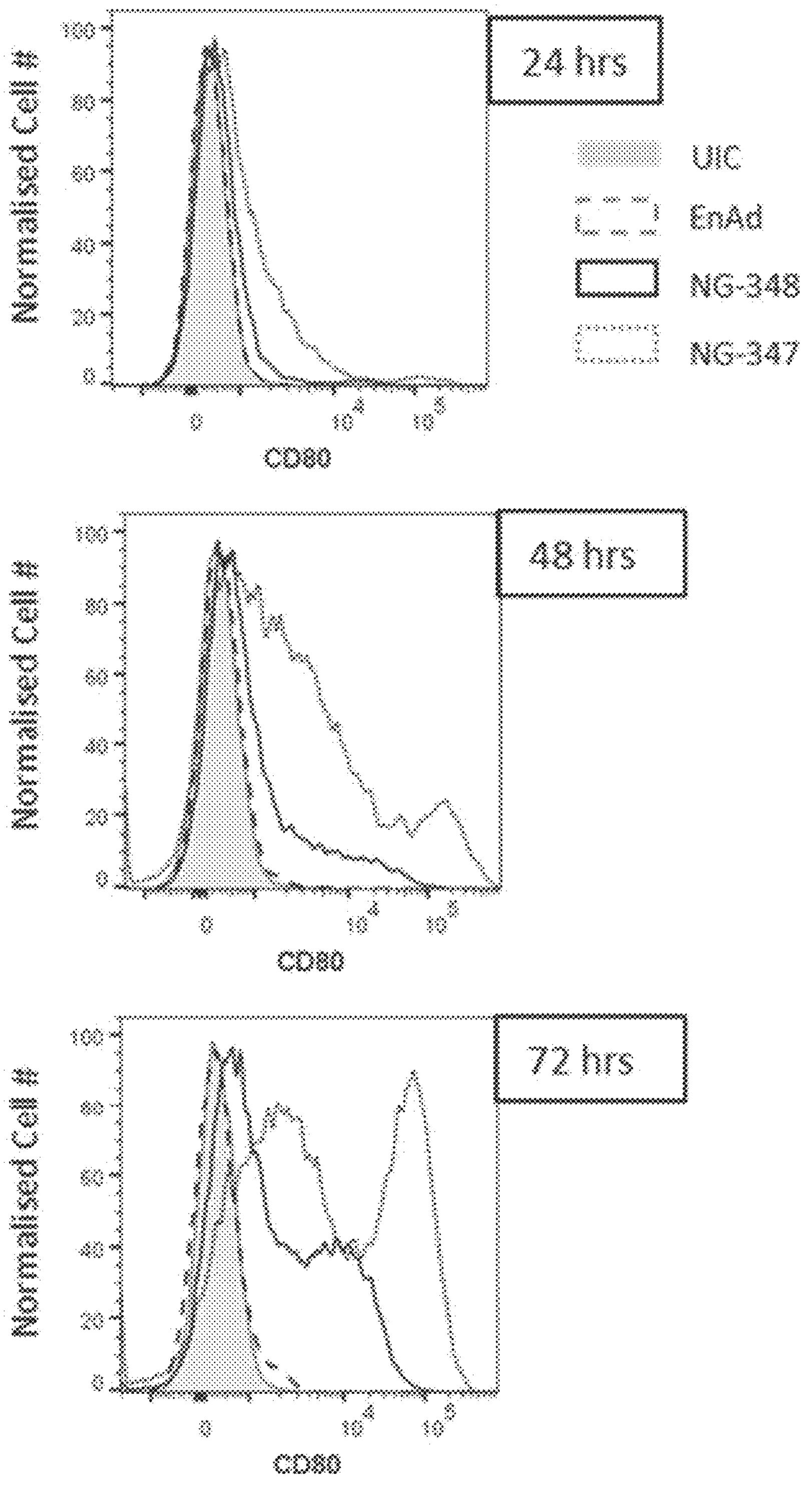
FIG. 15D shows high CD80 expression by 48 hours on the cell surface of DLD-1 tumour cells infected with either NG-347 or NG-348 viruses but little or no CD80 expression following EnAd infection.

Example 14. Cell Surface Expression of the T Cell Activating Antigen, CD80, in NG-347 and NG-348 Infected Carcinoma Cell Lines CD80 transgene expression (assessed by flow cytometry) was compared in NG-347, NG-348 and EnAd treated colon carcinoma cell line, DLD-1 or lung carcinoma cell line, A549. A549 or DLD-1 carcinoma cell lines were seeded in 12 well plates at cell densities of 7.5e5 cells/well. Plates were incubated for 18 hrs, 37° C., 5% $CO_2$, before cells were either infected with, 10 EnAd, NG-348 or NG-347 virus particles per cell (ppc) or were left uninfected. CD80 protein expression was compared on the surface of A549 or DLD-1 cells at 24, 48, 72 or 96 hrs post-infection. At each time point cells were harvested and stained according to methods detailed in example 9. Cells were analysed for cell viability and CD80 protein expression at the cell surface by flow cytometry. Analysis of CD80 expression at 72 hrs post infection in A549 cells showed CD80 could be detected on the surface of >95% of NG-347 or NG-348 treated cells (FIGS. 14A and 14B). At 96 hrs post infection the virus treatments had lysed the majority of A549 cells therefore FACs analysis was not carried out. For DLD-1 cells expression could be detected on >50% of cells by 96 hrs post-treatment with NG-348 and >70% of cells following NG-347 treatment (FIGS. 15A and 15B). Staining was not detected on EnAd or untreated controls.

Example 15. T Cell Activation and Degranulation Mediated by NG-348 Infected Carcinoma Cell Lines A549 lung carcinoma cells, either infected with NG-348 or EnAd virus particles or left uninfected, were co-cultured with T cells isolated from human PBMC donors. The selectivity of expression of NG-348 virus encoded CD80 was assessed on the surface of both A549 and T cells by flow cytometry. T cell activation was assessed by analysing cell surface activation markers (by Flow cytometry), CD107a cell surface expression as a marker for degranulation (by Flow cytometry) and secretion of stimulatory cytokines, IL-2 and IFNγ (by ELISA).

A549 cells were seeded into 12 well plates at a density of 5e5 cells/well. Plates were incubated for 18 hrs, 37° C., 5% $CO_2$, before cells were either infected with 10 EnAd or NG-348 virus particles per cell (ppc) or were left uninfected. At 48 hrs post-infection $CD3^+$ T cells, isolated by negative selection from PBMCs (MACs) were added to the A549 cell monolayers at a ratio of 8 T cells:1 tumour cell. The co-culture was carried out for 16 hrs, after which point cellular supernatants were collected for ELISA analysis and tumour cells and T cells harvested for Flow cytometry analysis.

Culture media containing non-adherent cells was removed from co-culture wells and centrifuged (300×g). The supernatant was carefully removed, diluted 1 in 2 with PBS 5% BSA and stored for ELISA analysis. The adherent cell monolayers were washed once with PBS and then detached using trypsin. The trypsin was inactivated using complete media and the cells were added to the cell pellets that had been collected from the culture supernatants. The cells were centrifuged (300×g), the supernatant discarded and the cell pellet washed in 200 μL of PBS. The cells were centrifuged again then resuspended in 5 μl of FACs buffer (5% BSA PBS) containing Live/Dead Aqua (Life tech) for 15 minutes at RT. The cells were washed once in FACs buffer before staining with panels of directly conjugated antibodies: anti-CD3 conjugated to BV605; anti-CD25 conjugated to BV421; anti-CD107a conjugated to FITC; anti-EpCam conjugated to PE or anti-CD4 conjugated to PE; and either anti-CD80 conjugated to PE/Cy5 or anti-HLA-DR conjugated to PE/Cy5. A sample of cells from each co-culture condition was also stained with relevant isotype control antibodies. All staining was carried out in FACs buffer in a total volume of 50 μL/well for 15 minutes, 4° C. Cells were then washed with FACs buffer (200 μL) before resuspension in 200 μL of FACs buffer and analysis by Flow cytometry (Attune).

Selective Expression of CD80

Figure 16:
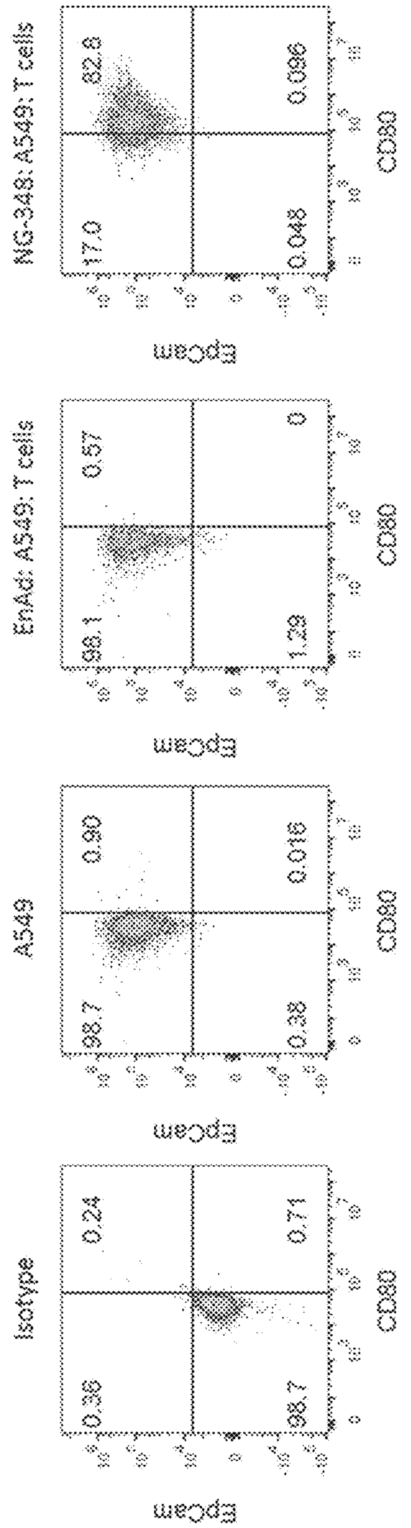
FIG. 16 shows CD80 expression on EpCam$^+$ A549 cells infected with NG-348 and co-cultured with human CD3$^+$ T-cells, but not when infection was with EnAd.

Similar to results shown in example 14, CD80 expression was detectable at the surface of >80% of NG-348 infected $EpCam^+$ A549 cells but not EnAd infected or uninfected control cells (FIG. 16). In contrast $CD3^+$ T cells showed no detectable expression of CD80 at the cell surface indicating, at least under these experimental conditions, transgene expression is selective for tumour cells in the co-culture.

Upregulation of T Cell Activation Markers

Figure 17A:
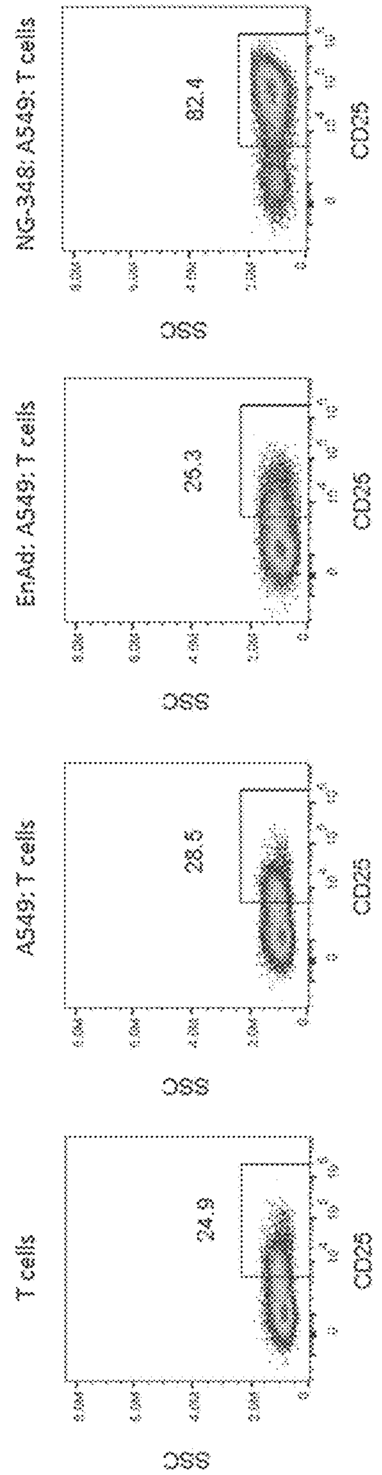
FIG. 17A shows CD25 is upregulated on human CD3$^+$ T-cells following co-culture with NG-348 infected A549 cells, but not when infection was with EnAd.
Figure 17C:
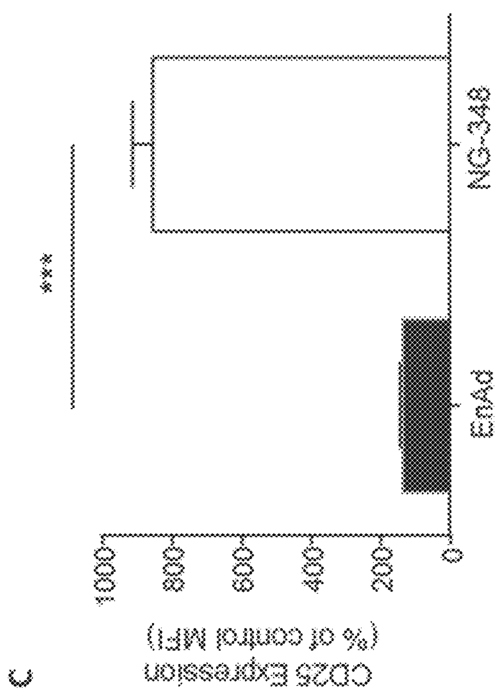
FIG. 17C shows the level of CD25 expression per cell was increased.
Figure 17B:
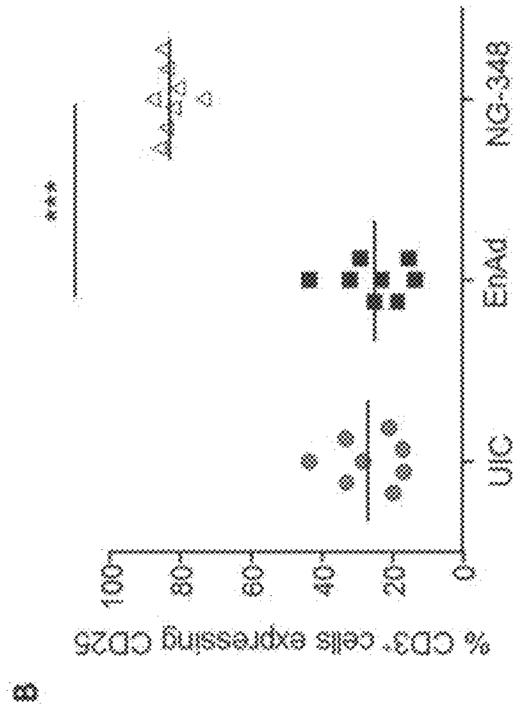
FIG. 17B shows the percentage of $CD25^+$ cells was increased.
Figure 18D:
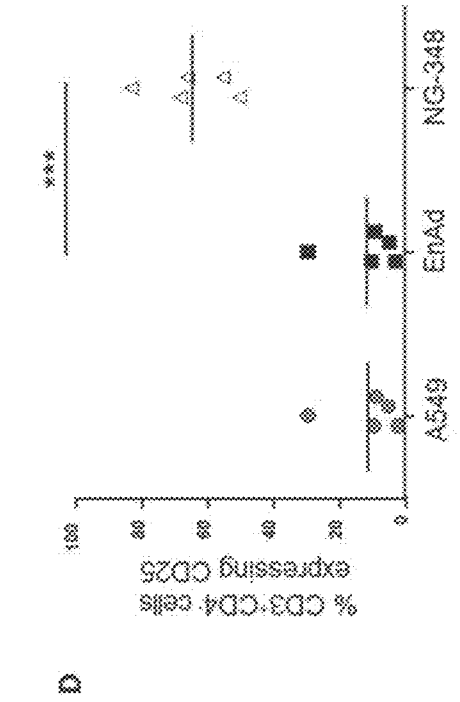
FIG. 18D shows the percentage of $CD3^+$ $CD4^+$ T-cells expressing CD25 co-cultured with uninfected A549 cells or A549 cells infected with EnAd or NG-348.
Figure 18C:
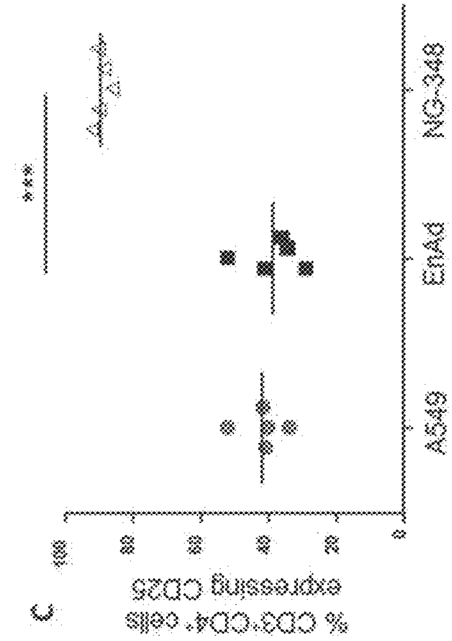
FIG. 18C shows the percentage of $CD3^+$ $CD4^+$ T-cells expressing CD25 co-cultured with uninfected A549 cells or A549 cells infected with EnAd or NG-348.

Flow cytometry analysis of T cell activation was assessed by expression of the T cell activation markers CD25 and HLA-DR on live, $CD3^+$, single cells. These data showed that both the number of T cells expressing CD25 (FIGS. 17A and 17B) and the average level of CD25 expression on the T cell surface (FIG. 17C) were significantly higher for T cells cultured with NG-348 infected A549 cells than EnAd or uninfected controls. Specifically, there was no difference in T cell activation status when comparing untreated controls to EnAd (26.9%±3.4% and 25.3±3.5% of T cells expressing CD25, respectively) whereas CD25 was upregulated on the majority of cells co-cultured with NG-348 (83.2±1.5%). CD25 expression was also analysed on CD4 and CD8 T cell subsets by gating the $CD3^+$ T cells based on their expression of CD4. These analyses showed that CD25 expression is significantly upregulated on both $CD4^+$ and CD4− T cell subsets in NG-348 treated co-cultures compared to EnAd and uninfected controls (FIG. 18).

Figure 19B:
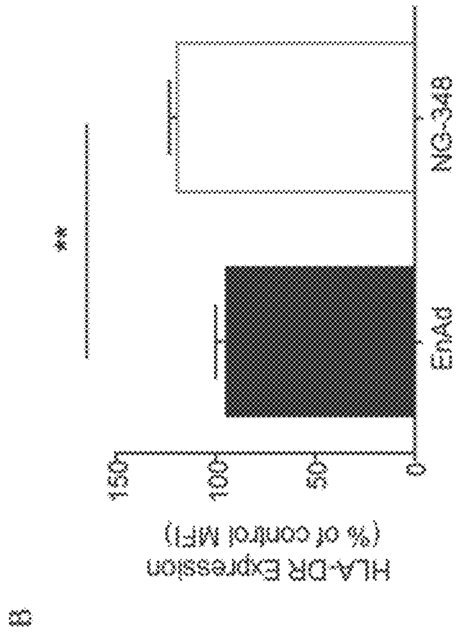
FIG. 19B shows the HLA-DR expression of $CD3^+$ cells after co-culture with A549 cells infected with EnAd or NG-348 compared to controls.
Figure 19A:
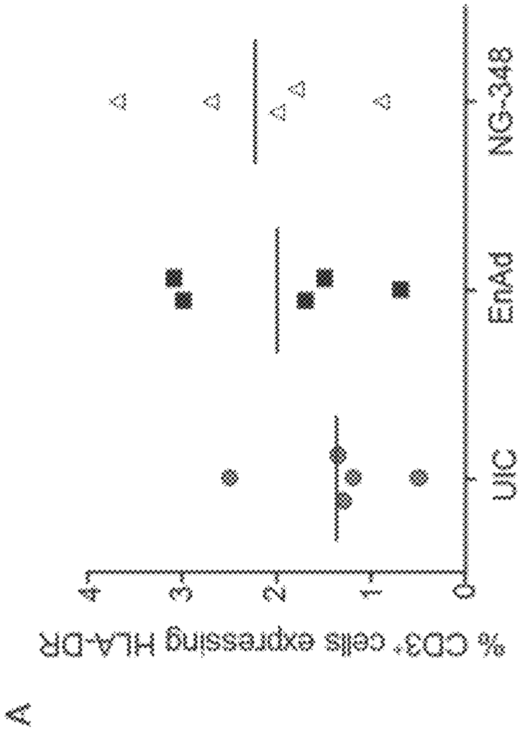
FIG. 19A shows the percentage of $CD3^+$ cells expressing HLA-DR after co-culture with unifected A549 cells (UIC) or A549 cells infected with EnAd or NG348.

In contrast to CD25 the number of cells expressing HLA-DR was low, <5%, for all conditions tested (FIG. 19A). This is likely due to the early time point after co-culture at which flow cytometry analysis was carried out. However, there was a slight but significant increase in the mean fluorescence intensity of HLA-DR staining $CD3^+$ $HLA\text{-}DR^+$ cells from NG-348 treated co-cultures compared to controls (FIG. 19B).

Stimulation of T Cell Degranulation

Figures 20A, 20B:
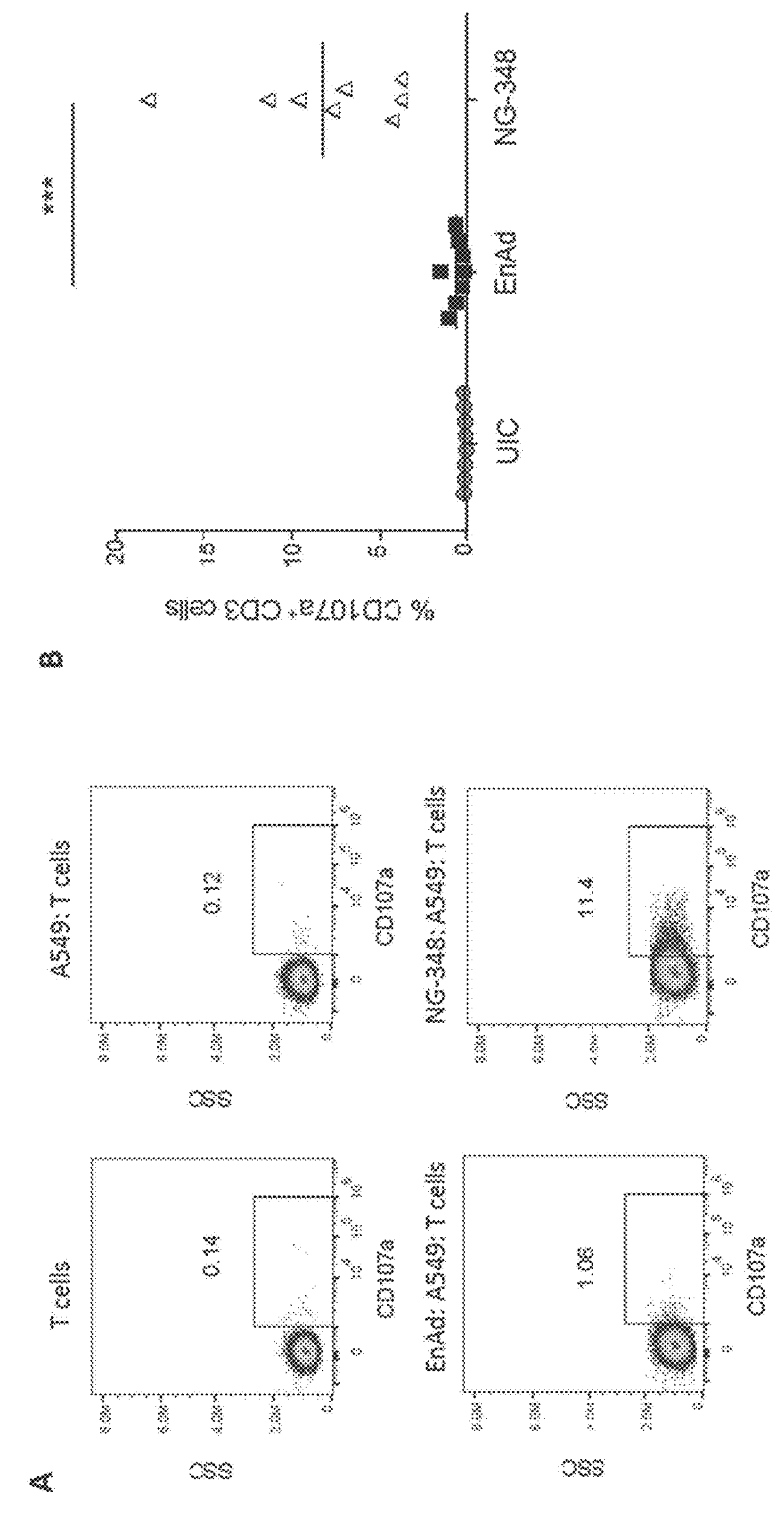
FIG. 20A shows upregulation of CD107a expression on the surface of live, $CD3^+$ T cells following co-culture with NG-348 infected A549 cells, but not when co-cultured with A549 cells infected with EnAd or uninfected A549 cells.
FIG. 20B shows the percentage of CD3 cells expressing $CD107a^+$ after co-culture with unifected A549 cells or A549 cells infected with EnAd or NG-348.
Figures 21A, 21B:
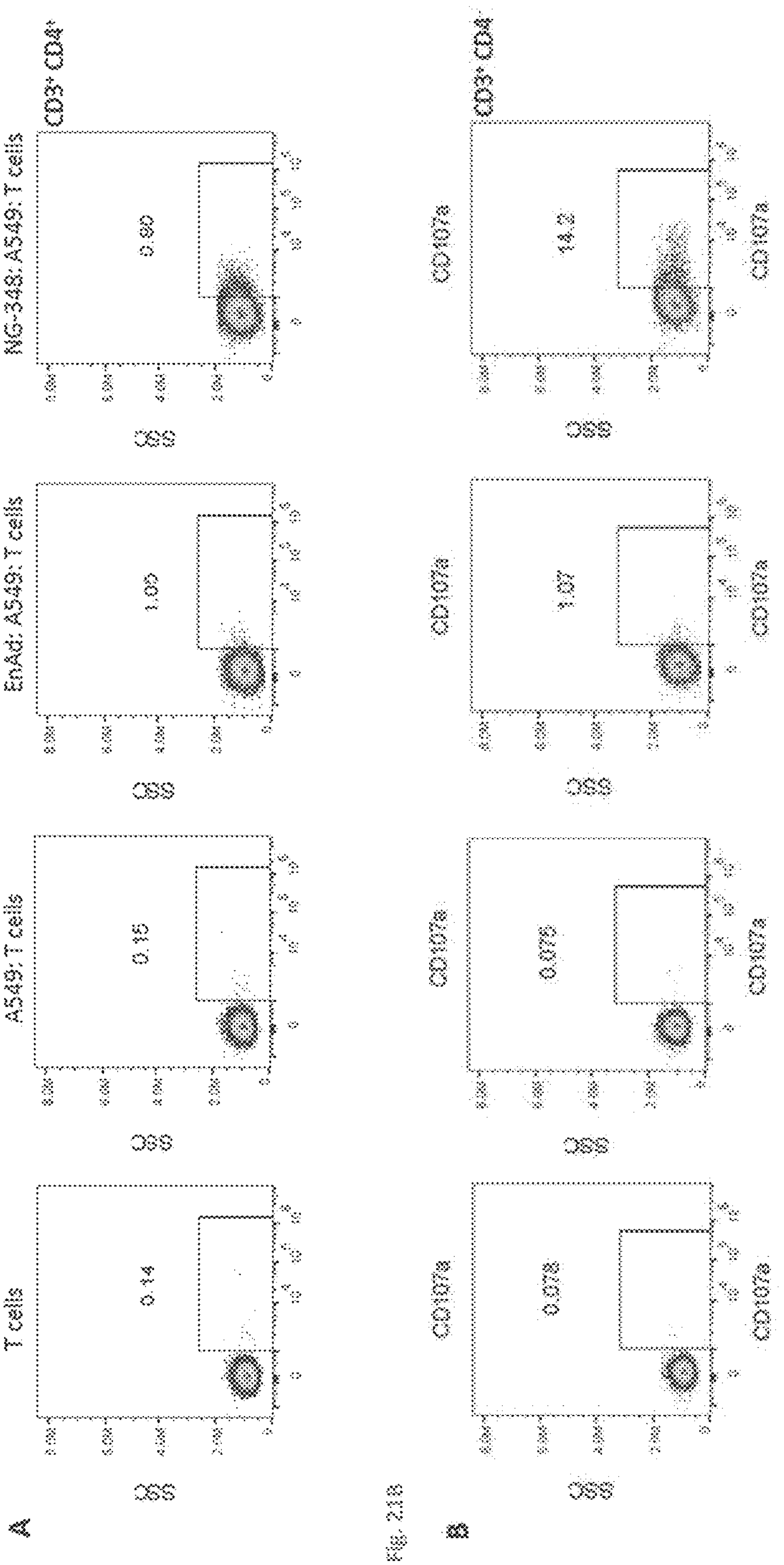
FIG. 21A shows CD107a is upregulated on human $CD3^+$ $CD4^+$ T-cells following co-culture with NG-348 infected A549 cells but is not upregulated when co-cultured with A549 cells infected with EnAd.
FIG. 21B shows CD107a is upregulated on human $CD3^+$ $CD4^+$ T-cells following co-culture with NG-348 infected A549 cells but is not upregulated when co-cultured with A549 cells infected with EnAd.
Figure 21D:
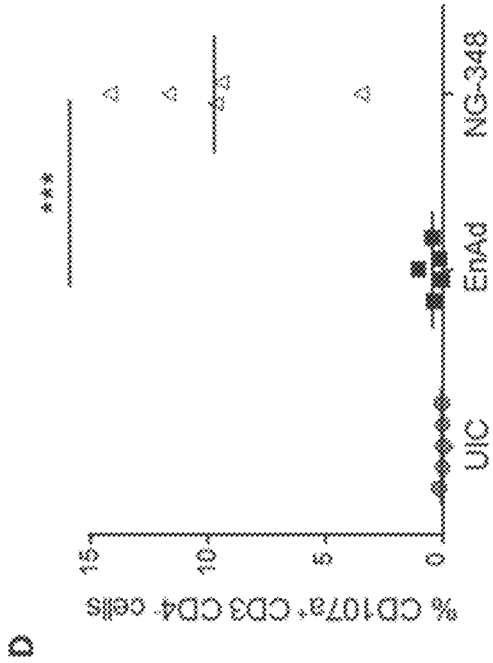
FIG. 21D shows the percentage of $CD3^+$ $CD4^+$ T-cells expressing CD107a following co-culture with uninfected A549 cells (UIC), or A549 cells infected with EnAd or NG-348.
Figure 21C:
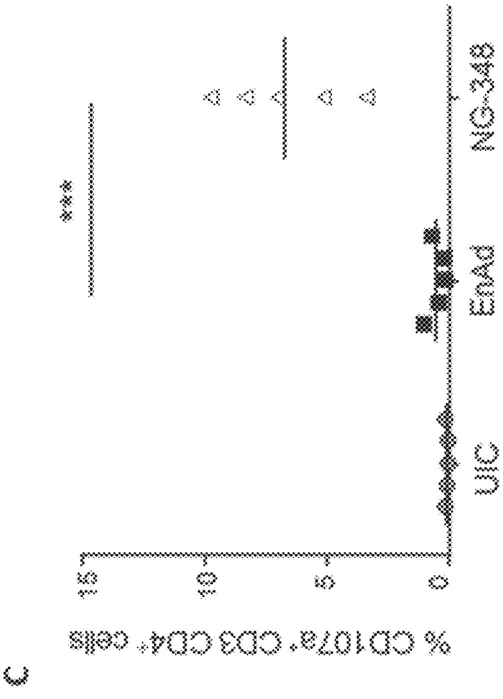
FIG. 21C shows the percentage of CD107a expressing $CD3^+$ $CD4^+$ T-cells following co-culture with uninfected A549 cells (UIC), A549 infected with EnAd or NG-348.

Analysis of CD107a expression on the surface of live, $CD3^+$ T cells showed a significant increase in the number of T cells which had degranulated and were therefore stained with CD107a, when A549 cells were infected with NG-348 (8.3%±1.7% of cells) compared to either EnAd (0.6%±0.2% of cells) or untreated controls (0.1%±0.02% of cells) (FIG. 20). Similar to CD25 upregulation, both $CD4^+$ and CD4− T cell subsets showed significantly increased CD107a expression compared to EnAd or A549 controls (FIG. 21).

Secretion of the Stimulatory Cytokines IL-2 and IFNγ

For detection of IL-2 or IFNγ expression, co-culture supernatants were diluted into 5% BSA/PBS assay buffer (in a range of 1:100 to 1:1000) and ELISA was carried out using the Human IL-2 Ready Set go Kit (Affymetrix) or Human IFN gamma Ready set go kit (Affymetrix) according to the manufacturer's protocol.

Figure 22B:
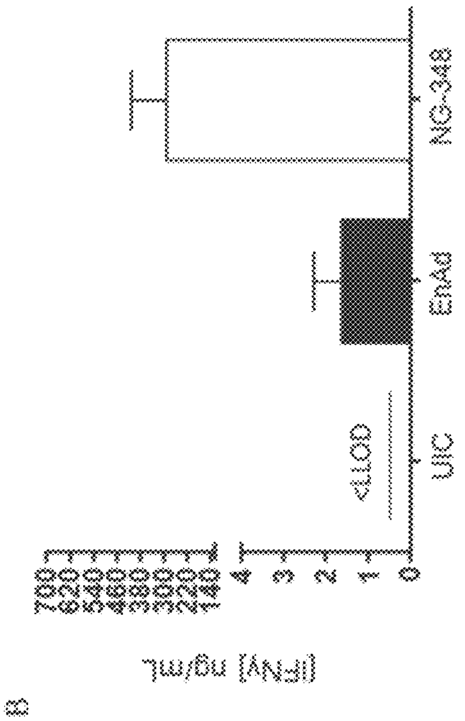
FIG. 22B shows induction of IFNγ production by $CD3^+$ T cells following co-culture with NG-348 infected A549 cells, but no IL-2 and only low levels of IFNγ when infection was with EnAd.
Figure 22A:
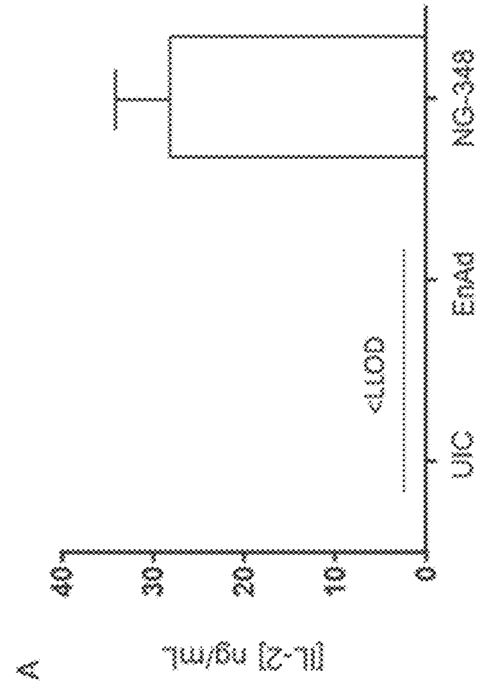
FIG. 22A shows induction of IL-2 production by $CD3^+$ T cells following co-culture with NG-348 infected A549 cells, but no IL-2 and only low levels of IFNγ when infection was with EnAd.

The concentrations of secreted IL-2 or IFNγ were determined by interpolating from the standard curves. Expression of IL-2 could only be detected in the supernatants of co-cultures using NG-348 infected A549 cells and was not detectable in either the EnAd, or untreated controls (FIG. 22A). Expression of IFNγ could also be detected, at very high levels (>300 ng/mL) in supernatants of co-cultures from NG-348 infected A549 cells, which was significantly higher that either EnAd or untreated controls (FIG. 22B).

Example 16. T Cell Activation of CD4 and CD8 T Cells can be Independently Mediated by NG-348 Infected Carcinoma Cell Lines A549 lung carcinoma cells infected with NG-348 or EnAd virus particles or left uninfected, were co-cultured with either $CD4^+$ T cells or $CD8^+$ T cells isolated from human PBMC donors. T cell activation was assessed by the secretion of the stimulatory cytokine IFNγ into culture supernatants.

A549 cells were seeded and infected with NG-348 or EnAd virus particles or left uninfected according to the methods detailed in Example 14. 48 hrs post infection $CD4^+$ T cells or $CD8^+$ T cells isolated by negative selection from a PBMC donor were added to the A549 cell monolayer at a ratio of 8 T cells to 1 tumour cells. After 16 hrs of co-culture supernatants were harvested and assessed for IFNγ according to the methods detailed in Example 14.

Figure 23B:
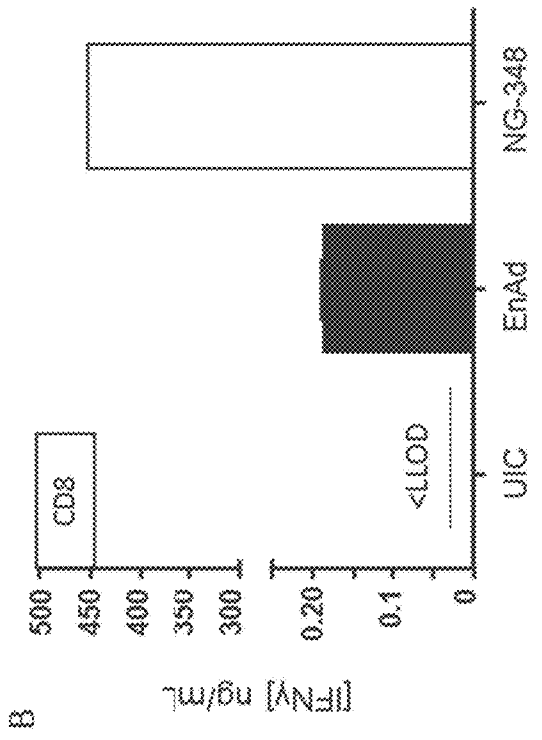
FIG. 23B shows induction of IFNγ production by $CD8^+$ $CD3^+$ T cells following co-culture with NG-348 infected A549 cells, but low IFNγ when infection was with EnAd.
Figure 23A:
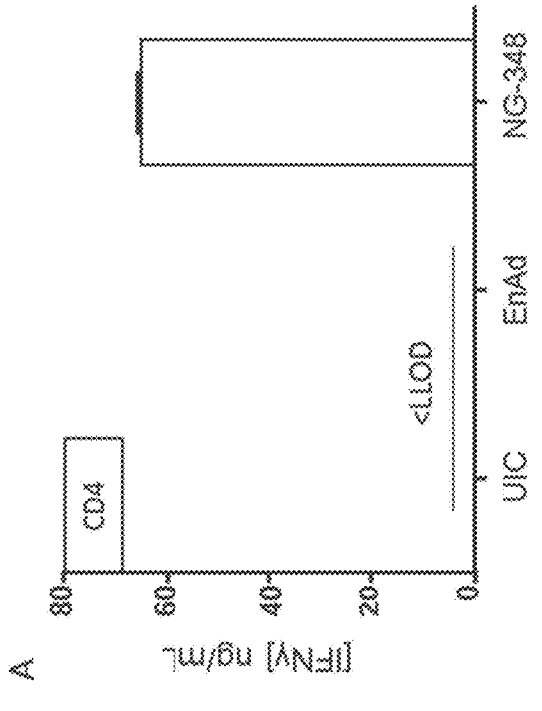
FIG. 23A shows induction of IFNγ production by $CD4^+$ $CD3^+$ T cells following co-culture with NG-348 infected A549 cells, but no IFNγ when infection was with EnAd.

For $CD4^+$ T cells Expression of IFNγ was only detected in supernatants of co-cultures from NG-348 infected A549 cells and was not detectable in either the EnAd or untreated controls (FIG. 23A). For $CD8^+$ T cells expression of IFNγ was detected at significantly higher levels for NG-348 infected A549 cells than for EnAd or untreated controls (FIG. 23B), demonstrating that both CD8 and CD4 cells can be activated to secret IFNγ by NG-348 virus activity in tumour cell lines.

Example 17. T Cell Activation Mediated by NG-347 Infected Carcinoma Cell Lines A549 lung carcinoma cells, either infected with NG-347 or EnAd virus particles or left uninfected, were co-cultured with T cells isolated from human PBMC donors. T cell activation was assessed by analysing cell surface activation markers (by Flow cytometry) and secretion of the stimulatory cytokine, IFNγ (by ELISA analysis of cellular supernatants).

A549 cells were seeded into 12 well plates at a density of 5e5 cells/well. Plates were incubated for 18 hrs, 37° C., 5% $CO_2$, before cells were either infected with 10 EnAd or NG-347 virus particles per cell (ppc) or were left uninfected. At 24 hrs post-infection $CD3^+$ T cells, isolated by negative selection from PBMCs (MACs) were added to the A549 cell monolayers at a ratio of 5 T cells:1 tumour cell. The co-culture was carried out for 48 hrs, before cellular supernatants were collected for ELISA analysis and tumour cells and T cells harvested for Flow cytometry analysis according to the methods detailed in EG 15.

The harvested cells were stained with directly conjugated antibodies: anti-CD3 conjugated to BV605 and anti-CD69 conjugated to BV421. A sample of cells from each co-culture condition was also stained with relevant isotype control antibodies. All staining was carried out in FACs buffer in a total volume of 50 μL/well for 15 minutes, 4° C. Cells were then washed with FACs buffer (200 μL) before resuspension in 20 μL of FACs buffer and analysis by Flow cytometry (Attune).

Upregulation of T Cell Activation Marker, CD69

Figure 24A:
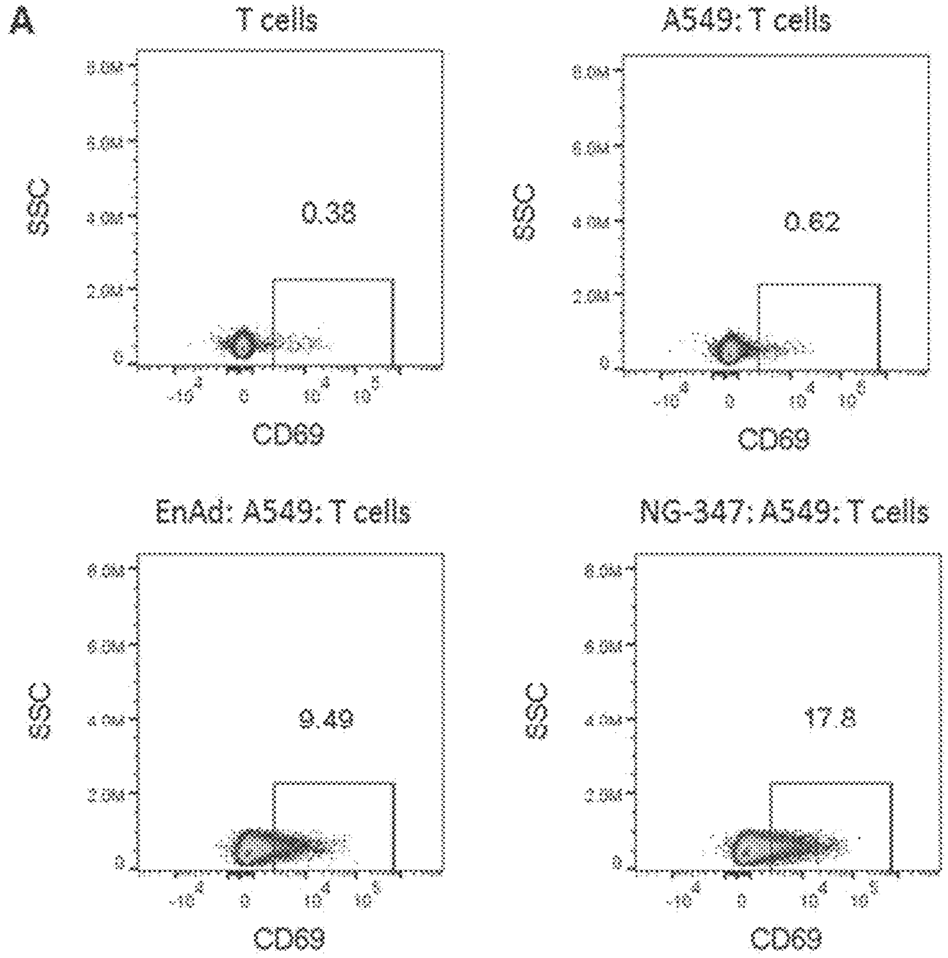
FIG. 24A shows CD69 expression $CD3^+$ T-cells following co-culture with unifected A549 cells, and A549 cells infected with EnAd or NG-347.
Figure 24B:
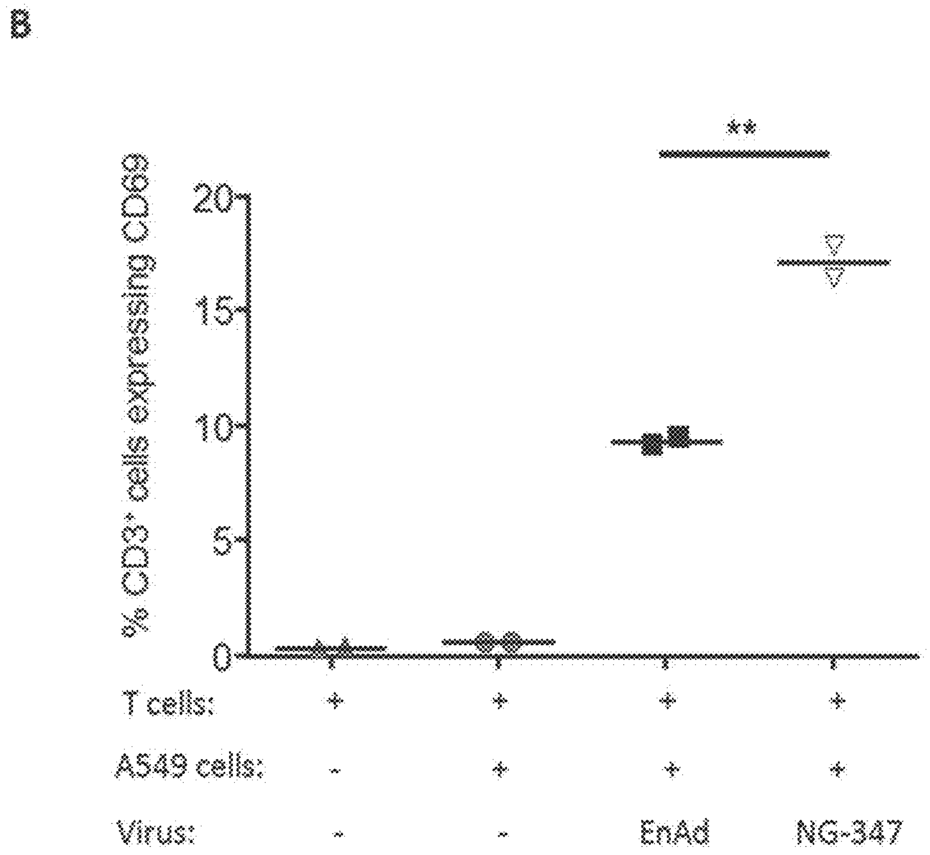
FIG. 24B shows the percentage of $CD3^+$ T-cells expressing CD69 after co-culture with unifected A549 cells, and A549 cells infected with EnAd or NG-347.

Flow cytometry analysis of T cell activation was assessed by expression of the T cell activation marker CD69 on live, $CD3^+$, single cells. These data showed that the number of T cells expressing CD69 was significantly higher for T cells cultured with NG-347 infected A549 cells than EnAd or uninfected controls (FIG. 24).

Secretion of the Stimulatory Cytokine IFNγ

For detection of IL-2 or IFNγ expression, co-culture supernatants were diluted into 5% BSA/PBS assay buffer (in a range of 1:100 to 1:1000) and ELISA was carried out using the Human IFN gamma Ready set go kit (Affymetrix) according to the manufacturer's protocol.

Figure 25:
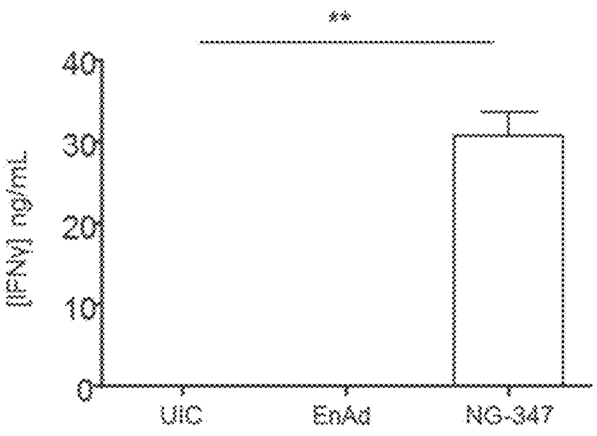
FIG. 25 shows induction of IFNγ production by human $CD3^+$ T cells following co-culture with NG-347 infected A549 cells, but not when infection was with EnAd

The concentration of secreted IFNγ was determined by interpolating from the standard curve. Expression of IFNγ could only be detected in the supernatants of co-cultures using NG-347 infected A549 cells and was not detectable in either the EnAd, or untreated controls (FIG. 25).

Example 18: Production of EnAd Viruses Expressing the T Cell Activating Antigen CD80 and a Membrane-Anchored Single Chain Fv Fragment Antibody to the ε Chain of the Human CD3 Complex (CD3ε)

Figure 26A:
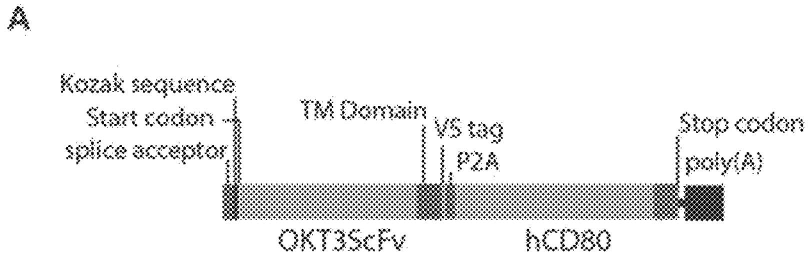
FIG. 26A shows a schematic of the NG-348A transgene cassette.

The plasmid pEnAd2.4 was used to generate the plasmids pNG-348A by direct insertion of a cassette encoding the human T cell activating antigen CD80 (SEQ ID NO 11) and a membrane-anchored chimeric form of the single chain Fv anti-human CD3e with a C-terminal V5 tag (SEQ ID NO: 99). The pNG-348 cassette contains; a 5' short splice acceptor sequence (SEQ ID NO. 2); membrane-anchored anti-human CD3e ScFv cDNA; a C-terminal V5 tag (SEQ ID NO: 100); a high efficiency self-cleavable P2A peptide sequence (SEQ ID NO: 7); human CD80 cDNA sequence and a 3' polyadenylation sequence (SEQ ID NO: 5). A Schematic of the NG-348A transgene cassettes is shown in FIG. 26A. Construction of the plasmid is confirmed by DNA sequencing.

Virus Production and Characterisation

The plasmid pNG-348A is linearised by restriction digest with the enzyme AscI to produce the virus genome NG-348A (SEQ ID NO: 101). The virus NG-348A is amplified and purified according to methods detailed in Example 1.

Example 19: Production of EnAd Viruses a Membrane-Anchored Single Chain Fv Fragment Antibody to the ε Chain of the Human CD3 Complex (CD3ε)

Figure 26B:
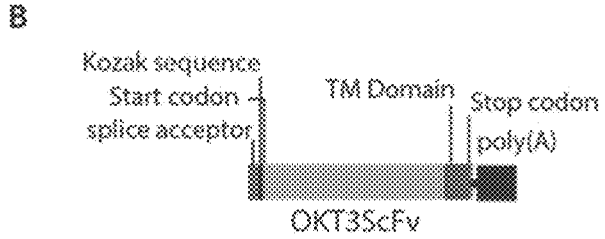
FIG. 26B shows a schematic of the NG-420 transgene cassette.
Figure 26C:
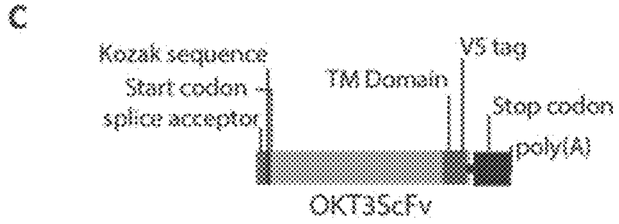
FIG. 26C shows a schematic of the NG-420A transgene cassette.

The plasmid pEnAd2.4 was used to generate the plasmids pNG-420 and pNG-420A by direct insertion of a cassettes encoding a membrane-anchored chimeric form of the single chain Fv anti-human CD3e with a C-terminal V5 tag (SEQ ID NO: 99) or without a V5 tag (SEQ ID NO: 15). The pNG-420 cassette contains; a 5' short splice acceptor sequence CAGG; membrane-anchored anti-human CD3e scFv cDNA and a 3' polyadenylation sequence (SEQ ID NO: 5). The pNG-420A cassette contains; a 5' short splice acceptor sequence cagg; membrane-anchored anti-human CD3e ScFv cDNA; a C-terminal V5 tag (SEQ ID NO: 100) and a 3' polyadenylation sequence (SEQ ID NO: 5). Schematics of the NG-420 and NG-420A transgene cassettes are shown in FIGS. 26B and 26C. Construction of each plasmid is confirmed by DNA sequencing.

Virus Production and Characterisation

The plasmids pNG-420 and pNG-420A are linearised by restriction digest with the enzyme AscI to produce the virus genomes NG-420 (SEQ ID NO: 102) and NG-420A (SEQ ID NO: 103). The viruses NG-420 and NG-420A are amplified and purified according to methods detailed in Example 1.

Example 20

A549 human lung carcinoma cells and MRC5 human fibroblast cells were cultured with EnAd, NG-347 or NG-348 viruses (at 10 ppc) to compare virus genome replication, virus hexon and transgene expression by these cell types. After 72 hours culture, cells were either stained for FACS analyses of surface markers or supernatants and cell lysates prepared for virus genome replication (qPCR) or mRNA (RT-qPCR) analyses of hexon or transgene expression.

Figure 27:
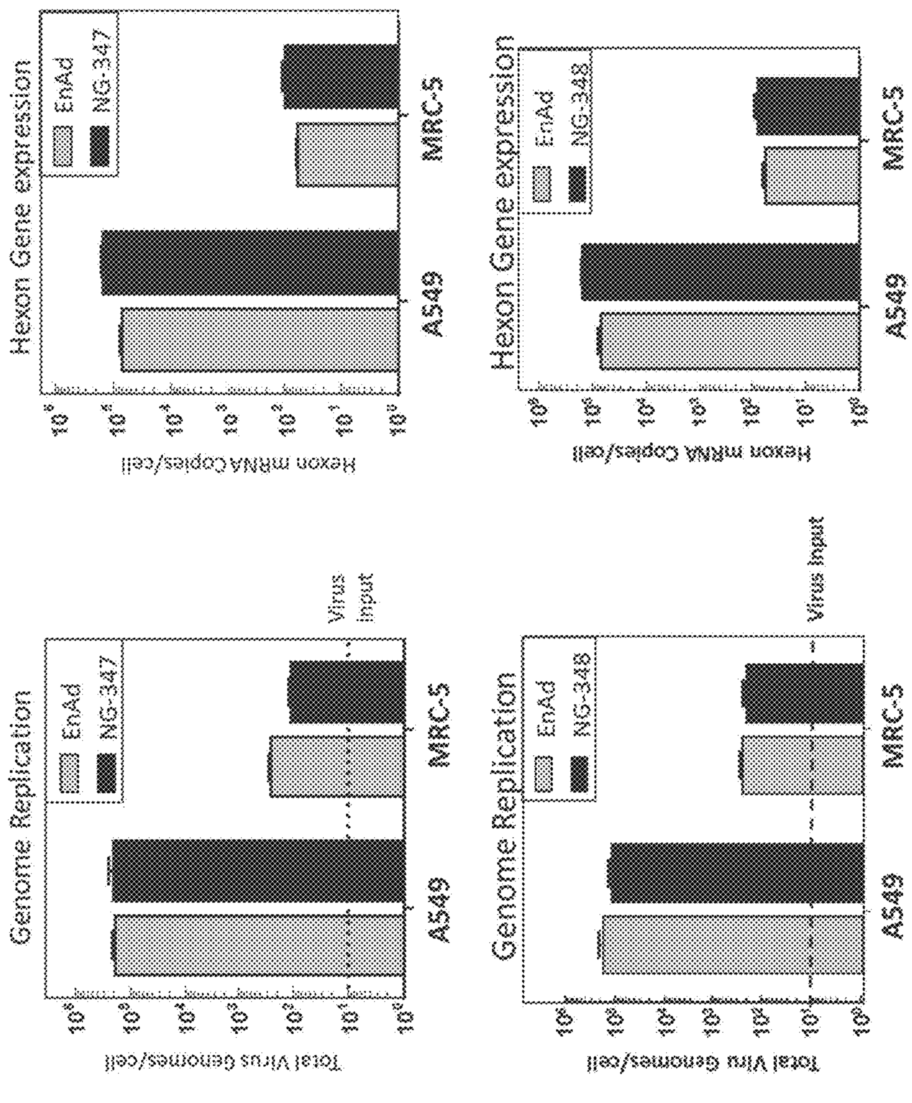
FIG. 27 shows genome replication and hexon gene expression (mRNA levels) for EnAd, NG-347, and NG-348 in MRC-5 fibroblast cells compared to A549 tumour cells
Figure 28:
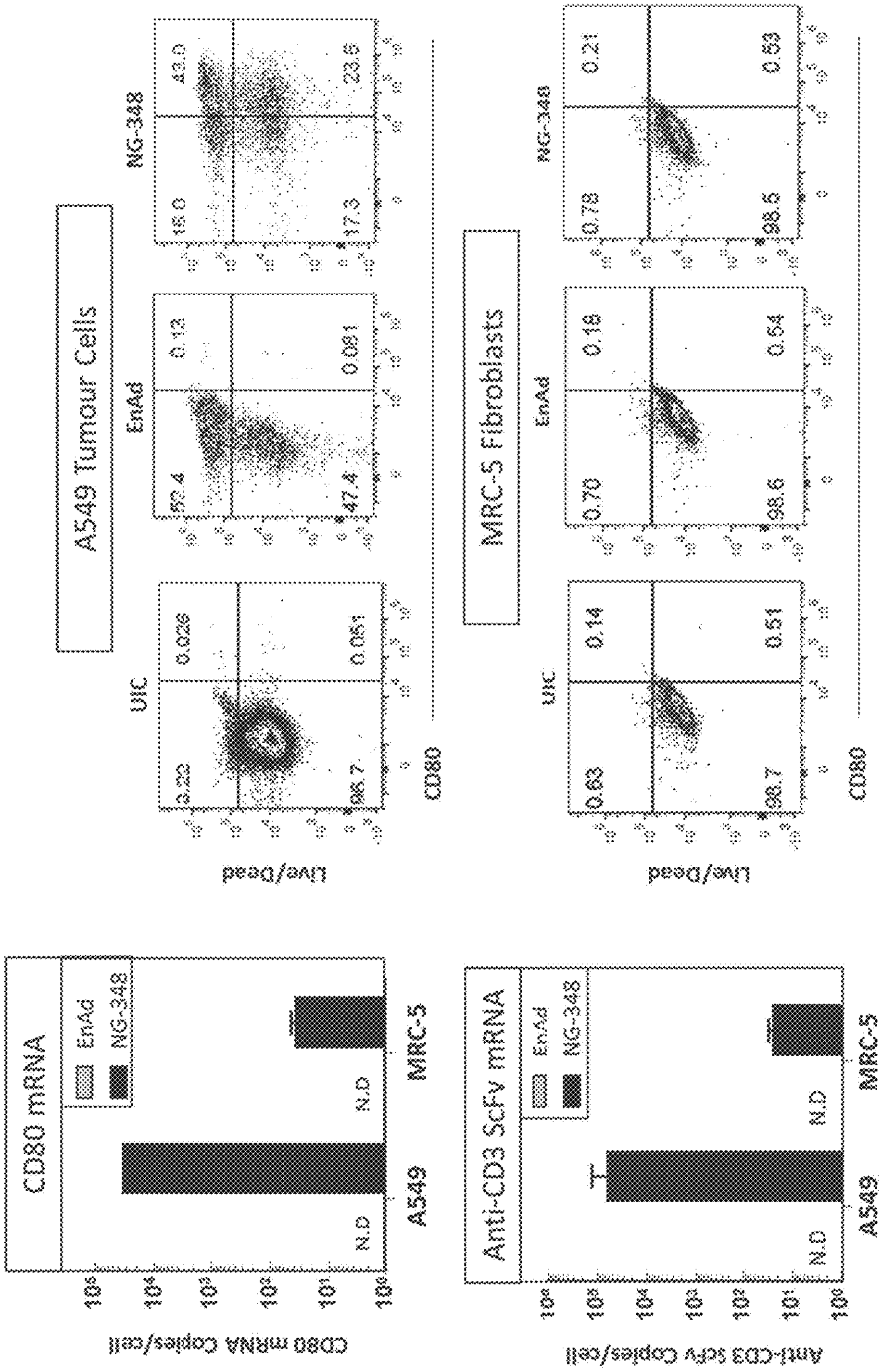
FIG. 28 shows CD80 and anti-CD3-scFv transgene mRNA and CD80 transgene protein (flow cytometry) expression for virus NG-348 in MRC-5 fibroblast cells compared to A549 tumour cells.
Figure 29:
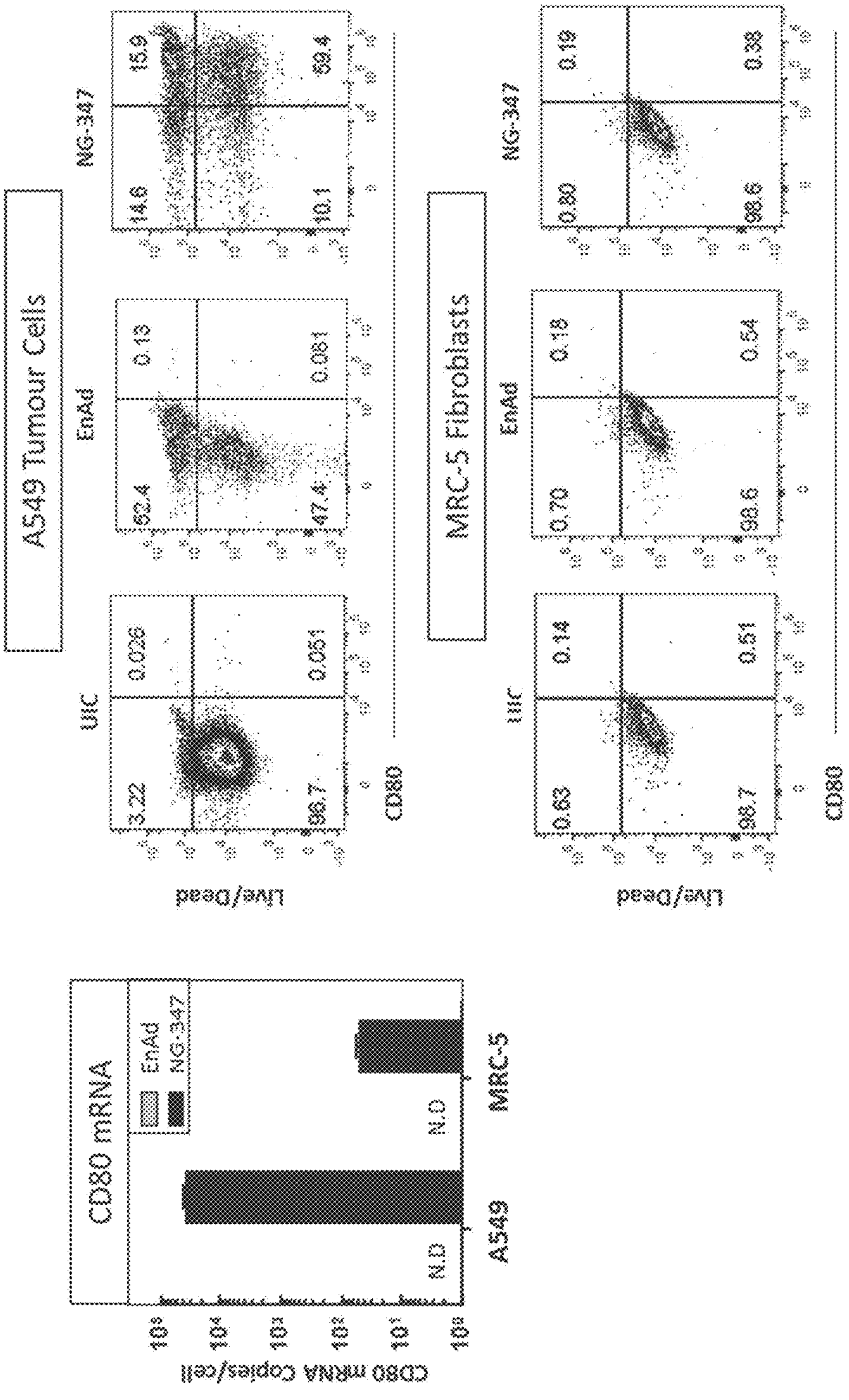
FIG. 29 shows CD80 transgene mRNA and CD80 transgene protein for virus NG-347 in MRC-5 fibroblast cells compared to A549 tumour cells.

Virus genome replication and hexon mRNA expression for the two transgene bearing viruses, NG-347 and NG-348 were equivalent to those for the parental virus, EnAd (FIG. 27). For NG-348 (FIG. 28), CD80 and anti-human CD3-scFv transgene mRNA expression levels were high with A549 tumour cells, with only a low level signal for the non-tumour MRC5 cells. CD80 protein expression on the surface of cells assessed by FACS was detected on the majority of NG-348 treated A549 cells but was not detectable on MRC5 cells, with no CD80 detected on either cell type left untreated or treated with EnAd. Similarly, CD80 transgene mRNA and protein expression following NG-347 treatment was selectively detected in A549 tumour cells not MRC5 cells (FIG. 29).

Figure 30:
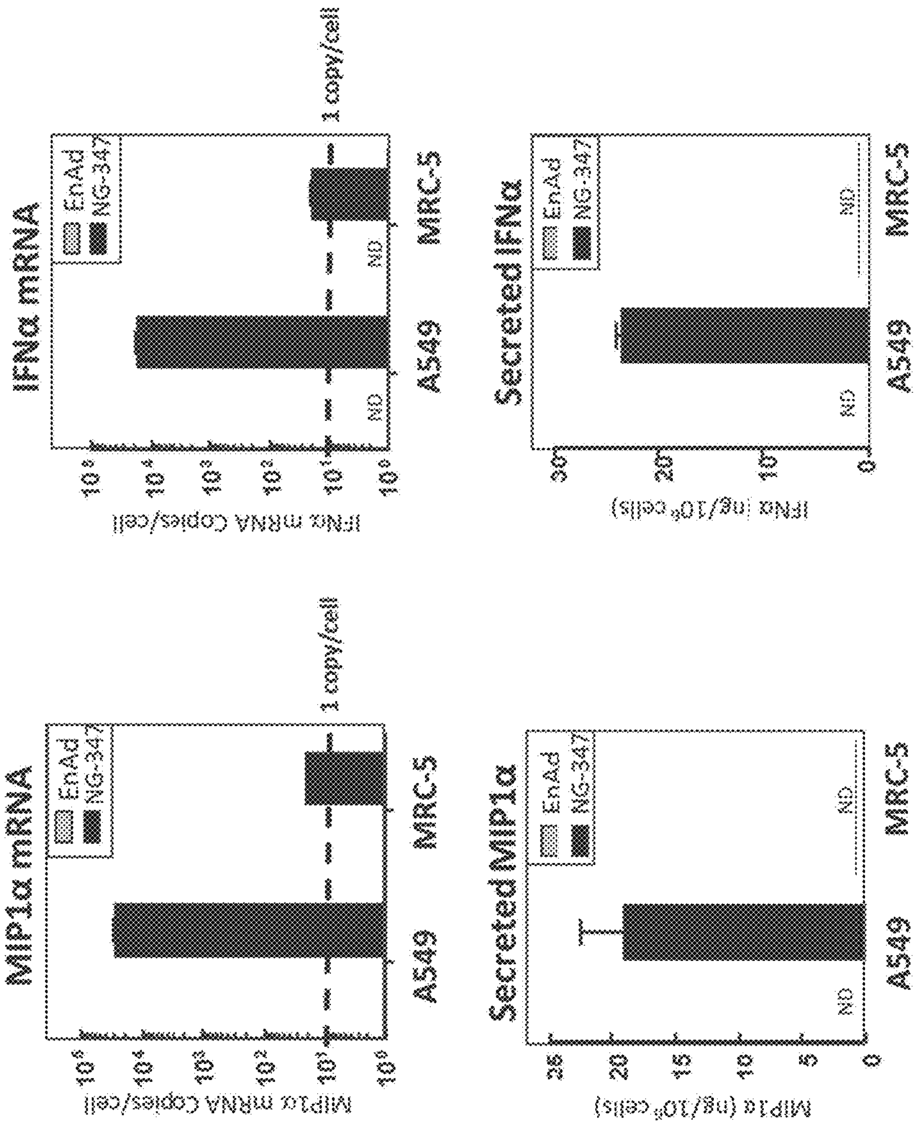
FIG. 30 shows mRNA and secreted protein levels of MIP1α and IFNα generated by virus NG-347 in MRC-5 fibroblast cells compared to A549 tumour cells.

For EnAd and NG-347 treated cell cultures, levels of MIP1α and IFNα mRNA in cell lysates and secreted proteins in supernatants were measured by RT-qPCR and specific ELISAs, respectively. Data (FIG. 30) show selective expression of both transgenes by A549 tumour cells, with no detectable MIP1α chemokine or IFNα cytokine in MRC5 supernatants.

Example 21

The selectivity/activity of EnAd, NG-347 and NG-348 viruses with human T-cells was evaluated by culturing isolated $CD3^+$ T cells for 3 days with either 500 ppc or 5000 ppc of each virus. Selectivity/activity was assessed by a) flow cytometry analysis of T cells stained with antibodies targeting CD69, CD4, CD80, CD25 and CD3, b) ELISA analysis of human MIP1α, IFNα and IFNγ protein secretion, c) qPCR analysis of virus replication and d) RT-qPCR analysis of gene expression.

Figure 31:
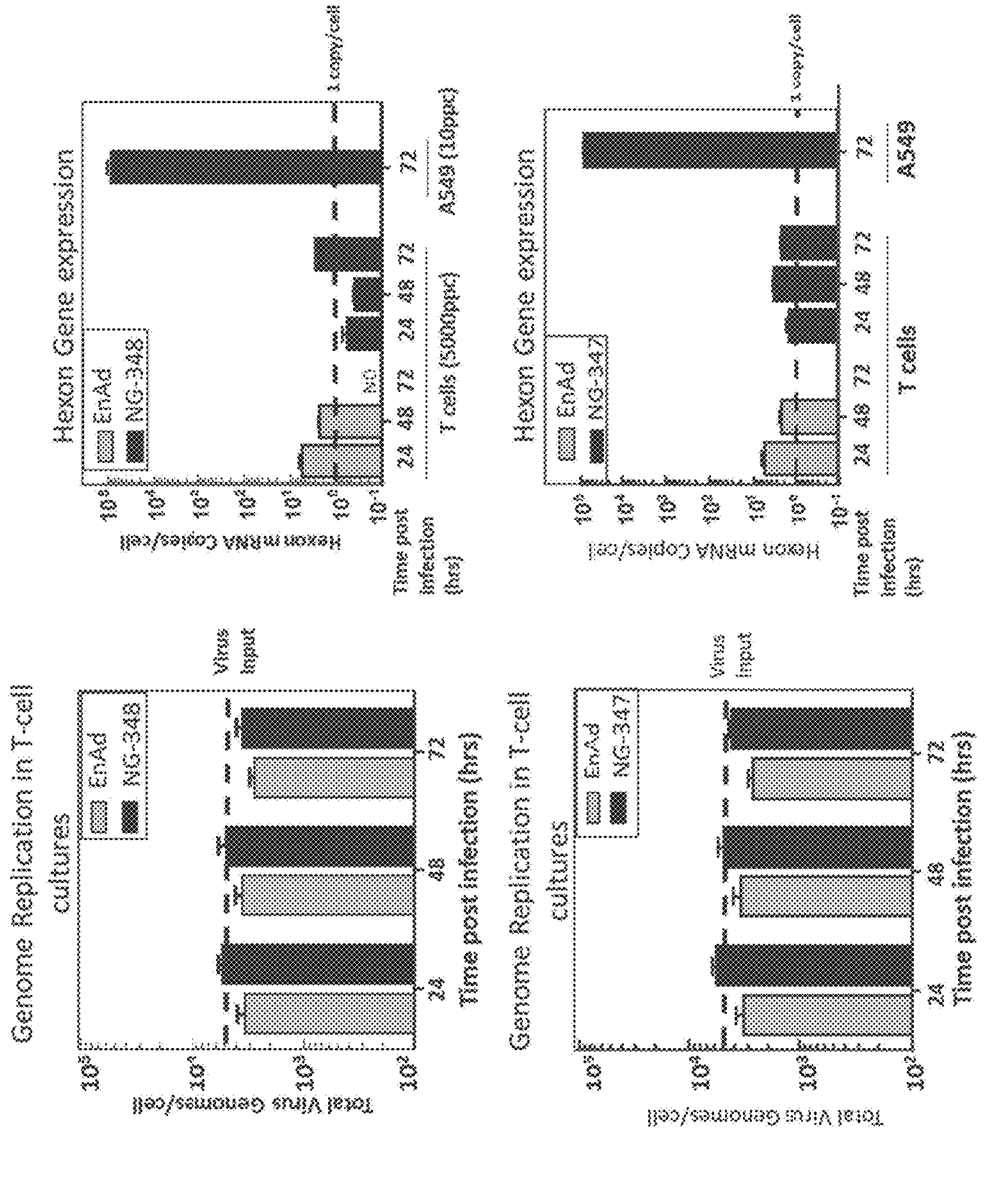
FIG. 31 shows genome replication and hexon gene expression (mRNA levels) for EnAd, NG-347, and NG-348 in purified human T-cell cultures.
Figure 32:
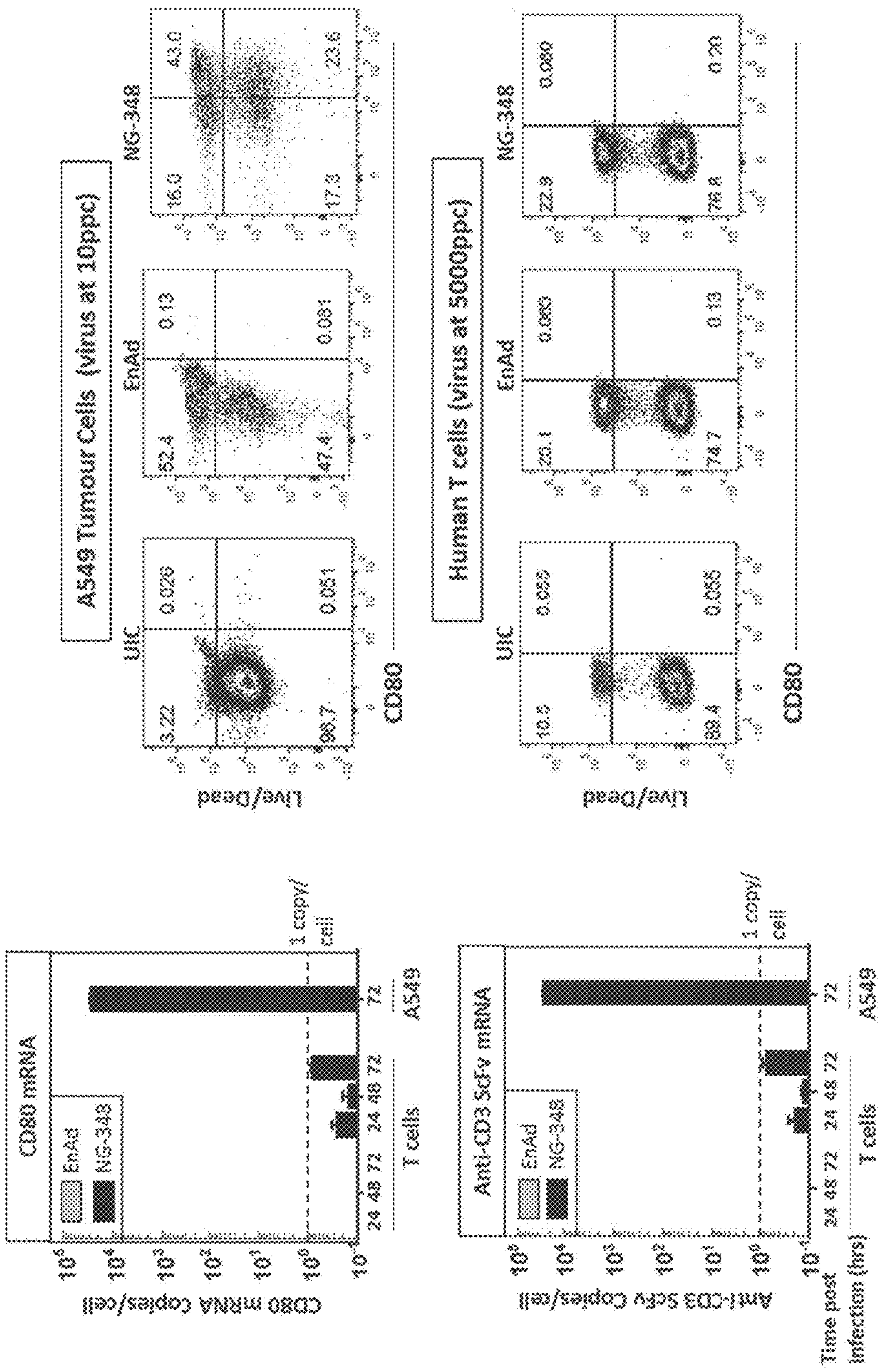
FIG. 32 shows CD80 and anti-CD3 scFv transgene mRNA and CD80 protein expression (flow cytometry) for virus NG-348 in human T-cells compared to A549 tumour cells
Figure 33:
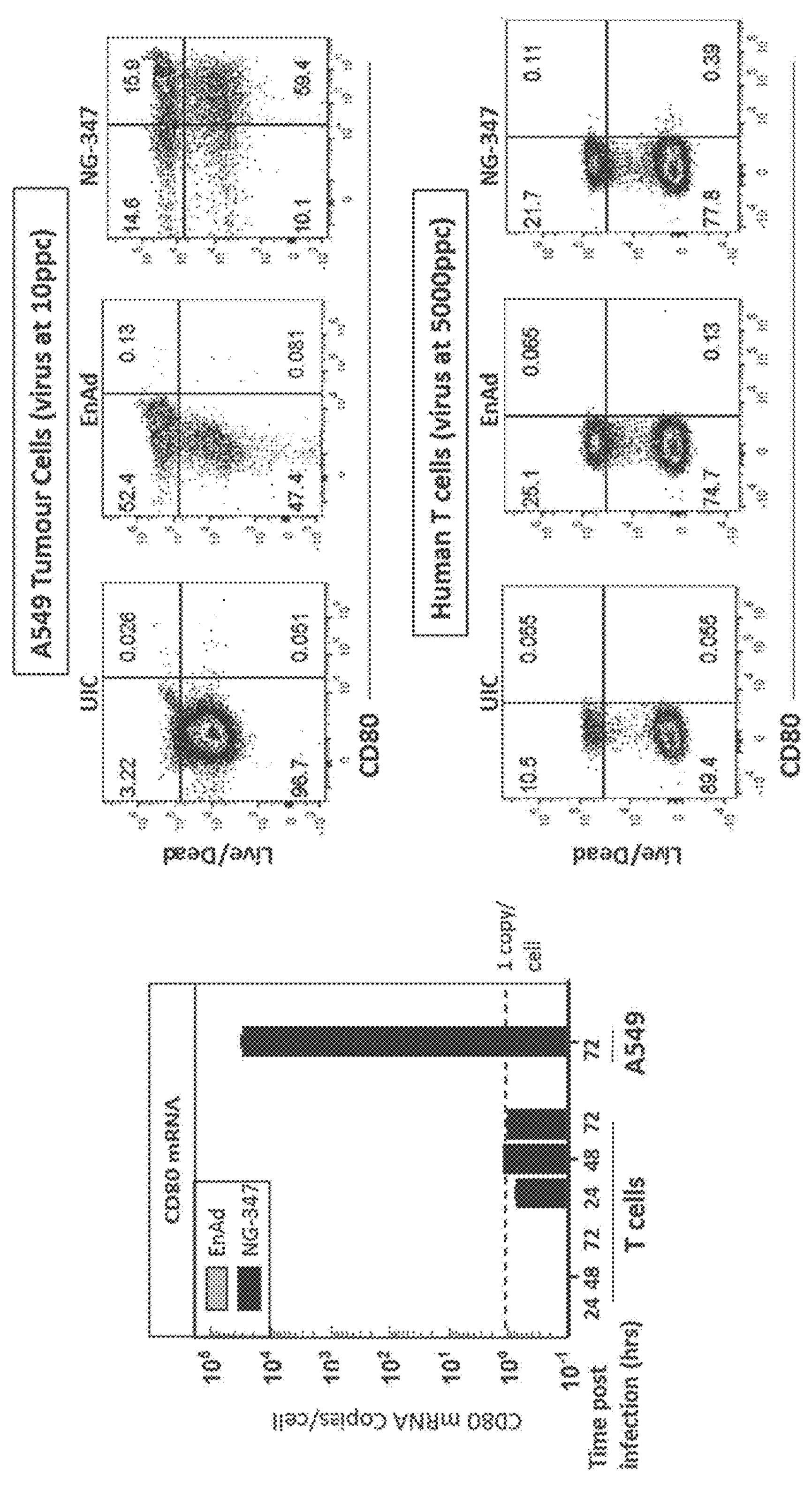
FIG. 33 shows CD80 transgene mRNA and CD80 transgene protein for virus NG-347 in purified human T-cells compared to A549 tumour cells.
Figure 34:
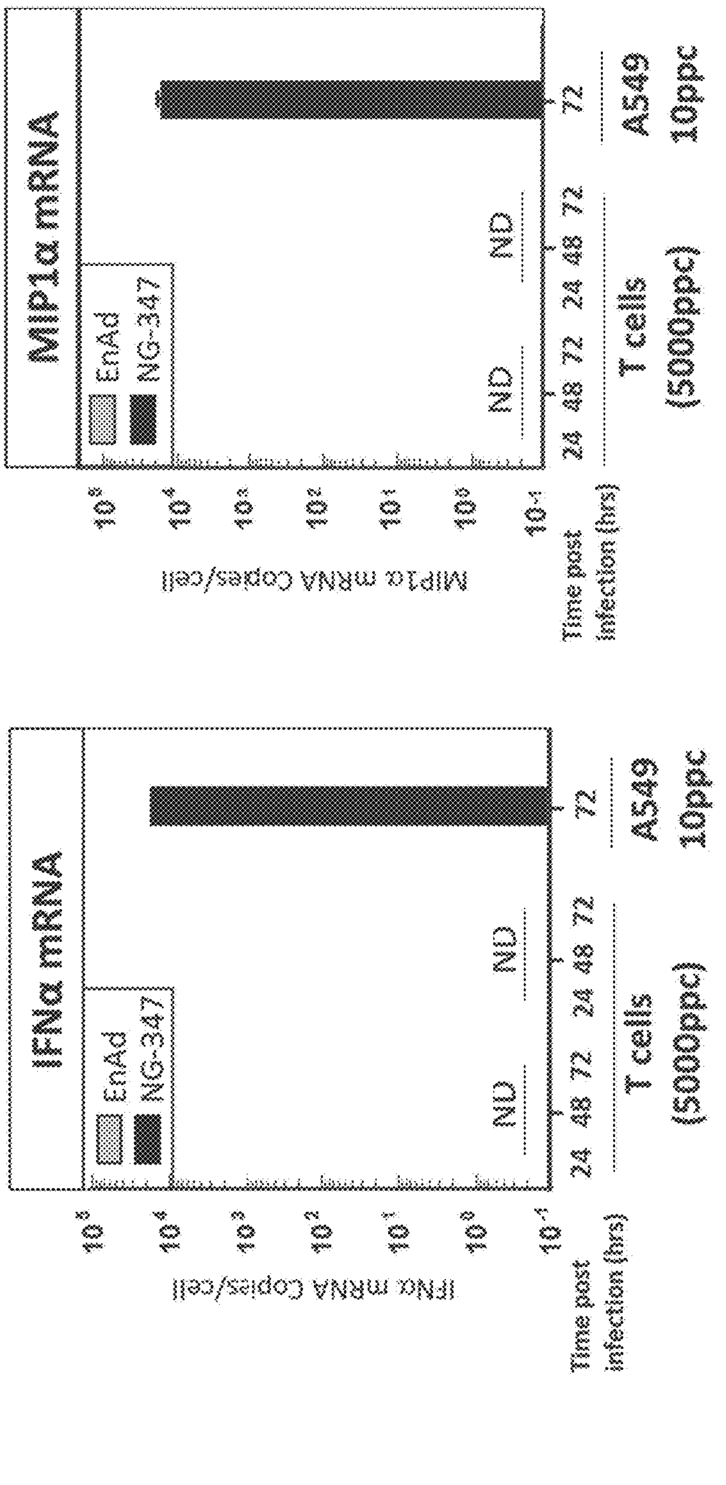
FIG. 34 shows IFNα and MIP1α transgene mRNA generated by virus NG-347 in T cells compared to A549 tumour cells.

As shown in FIG. 31, T-cells were not supportive of virus genome replication for any of the viruses tested with only background signals in the virus hexon RT-qPCR assay. A549 tumour cells supported high levels of hexon mRNA expression. RT-qPCR analyses for transgene mRNA expression by T-cells showed only background signals (<1 copy/cell) for CD80 by both NG-347 and NG-348, and a similar lack of significant expression of anti-CD3-ScFv mRNA by NG-348, despite the high virus exposure (5000 ppc). High levels of expression of both transgenes were detected with treated (10 ppc) A549 tumour cells (FIGS. 32 & 33). Expression of IFNα and MIP1α transgene mRNA was also selectively detected by NG-347 (not EnAd) treated A549 tumour cells (at 10 ppc) and not by T-cells treated with 5000 ppc (FIG. 34). In addition, CD80 cell surface protein expression was only detectable with A549 cells not T-cells for both NG-347 and NG-348 (FIGS. 32 & 33). EnAd treatment did not lead to CD80 expression by either cell type, and A549 cell death (as assessed by dye uptake) was similarly high for all three viruses; a low level of non-specific T-cell death was induced by all viruses due to the very high levels of virus particles used in the experiment (FIGS. 32 & 33). Similar transgene mRNA and protein expression data were obtained when viruses were used at 500 ppc (data not shown).

In the absence of tumour cells, purified human T-cells were not activated to upregulate activation markers CD25 or CD69 when cultured with any of the viruses (Table 5).

TABLE 5

Lack of expression of activation markers CD25 and CD69 by purified human $CD3^+$ T-cells treated with 5000 ppc of different viruses

| | Untreated | EnAd | NG-347 | NG-348 |
|---|---|---|---|---|
| $CD25^+$ CD4 T-cells | 30.7 | 24.6 | 23.4 | 23.3 |
| $CD69^+$ CD4 T-cells | 0.1 | 0.4 | 0.3 | 0.7 |
| $CD25^+$ CD8 T-cells | 5.9 | 4.7 | 4.1 | 4.1 |
| $CD69^+$ CD8 T-cells | 0.5 | 1.0 | 0.9 | 1.3 |

Example 22

Figure 35:
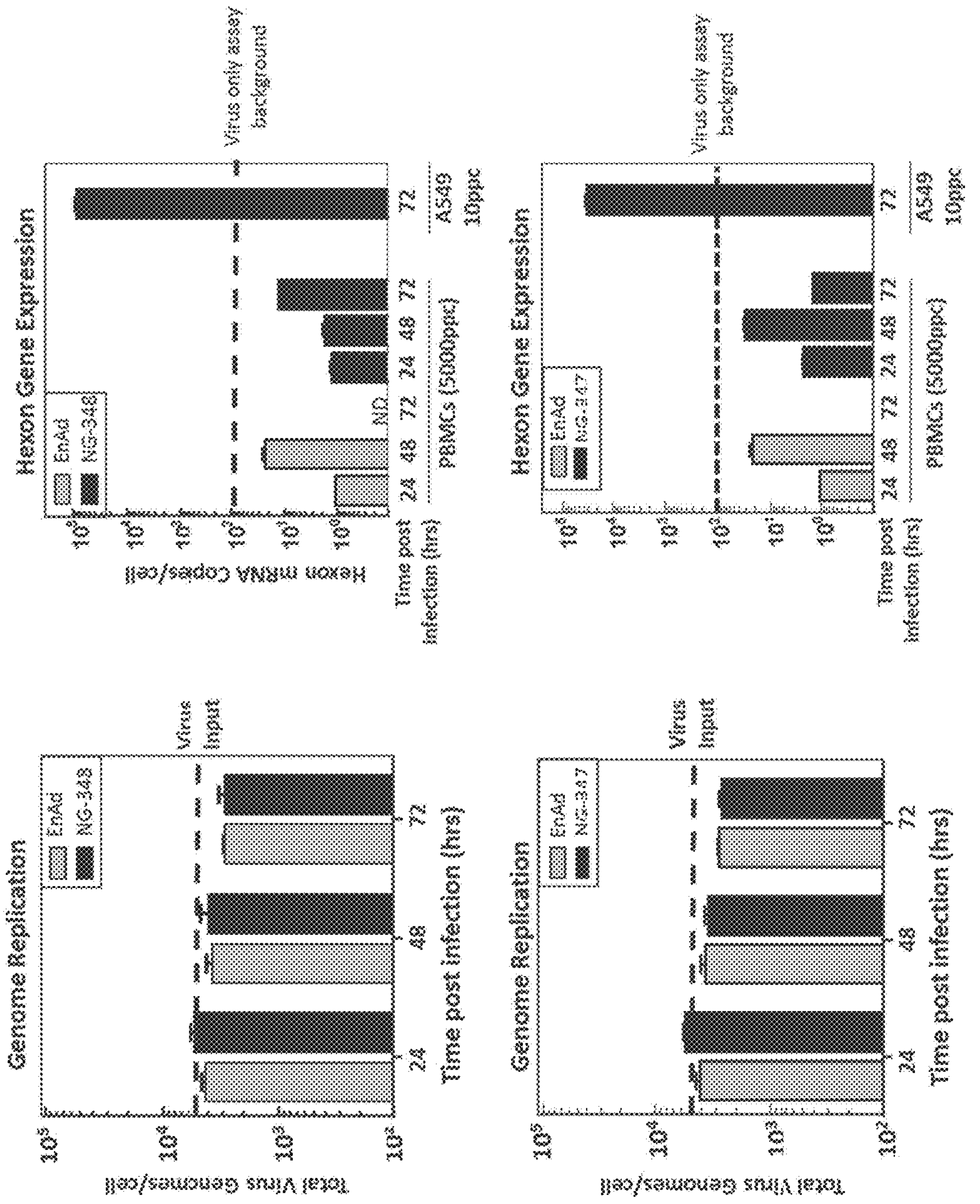
FIG. 35 shows NG-347 and NG-348 genome replication and hexon gene expression by human PBMCs compared to A549 tumour cells.
Figure 36:
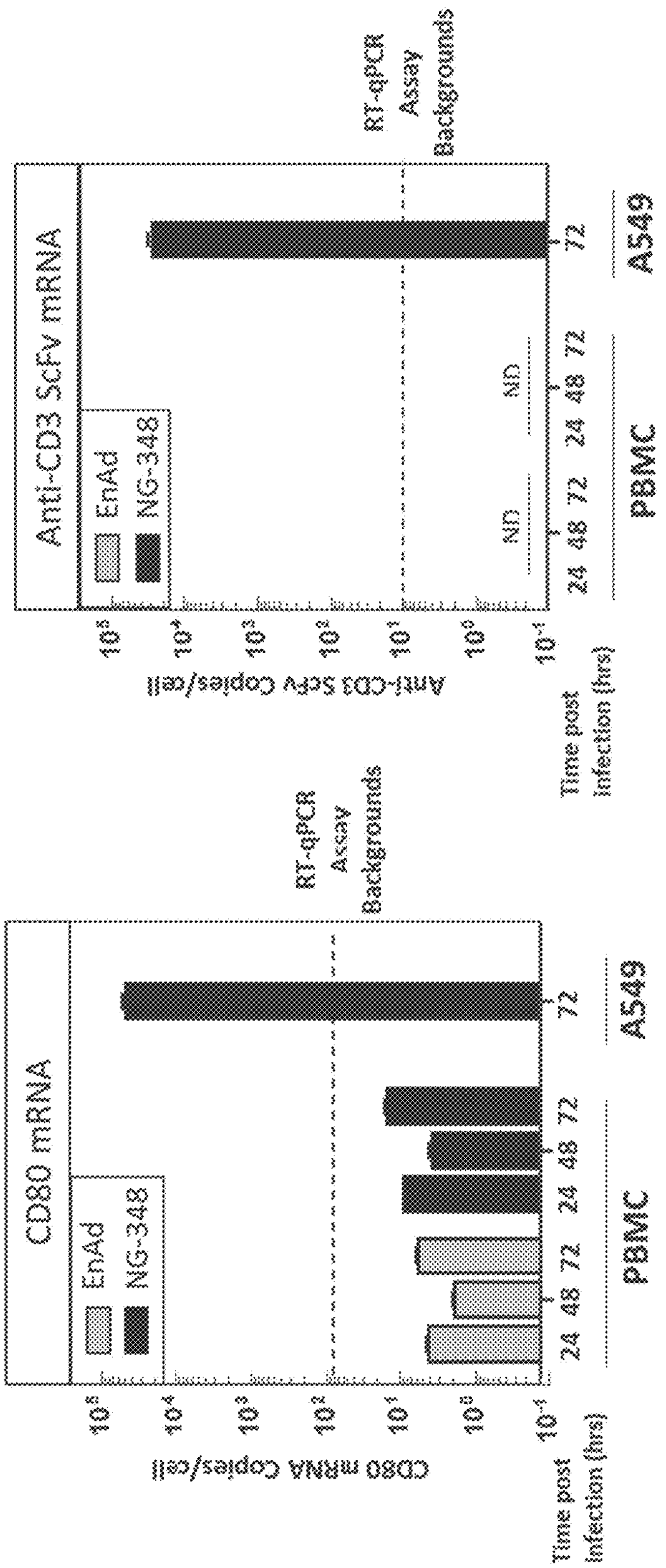
FIG. 36 shows CD80 and anti-CD3 scFv mRNA generated by virus NG-348 by PBMCs compared to A549 tumour cells.
Figure 37:
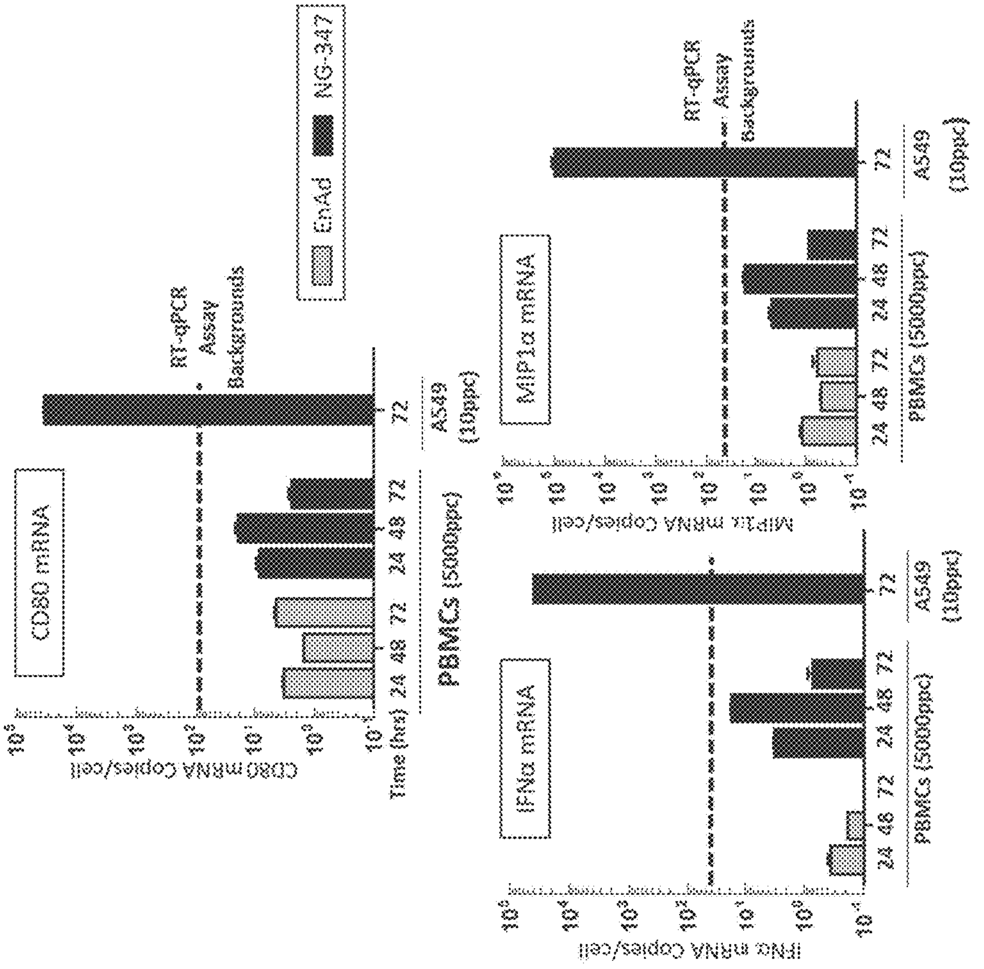
FIG. 37 shows CD80, IFNα and MIP1α mRNA generated by virus NG-347 by PBMCs compared to A549 tumour cells.

A similar virus selectivity experiment to that described in Example 21 was carried out using unseparated human PBMCs rather than purified T-cells, including making the same activity assessments. As with human T-cells in example 21, the data from this study collectively demonstrate lack of virus replication and transgene expression by human PBMCs. FIGS. 35-37 show data using 5000 ppc of EnAd, NG-347 or NG-348, but similar data was generated using 500 ppc (not shown). FIG. 35 shows virus genome replication and hexon mRNA expression and FIGS. 36 & 37 show transgene mRNA expression. Assay backgrounds were set according to signals generated in the assay with the respective virus spiked into culture media and then processed in the same way as for the cell lysate samples. There was no detectable expression of CD80 transgene on CD3+ T-cells or CD40+ cells (primarily B-cells) in these PBMC cultures with any of the viruses (not shown).

Figure 38A:
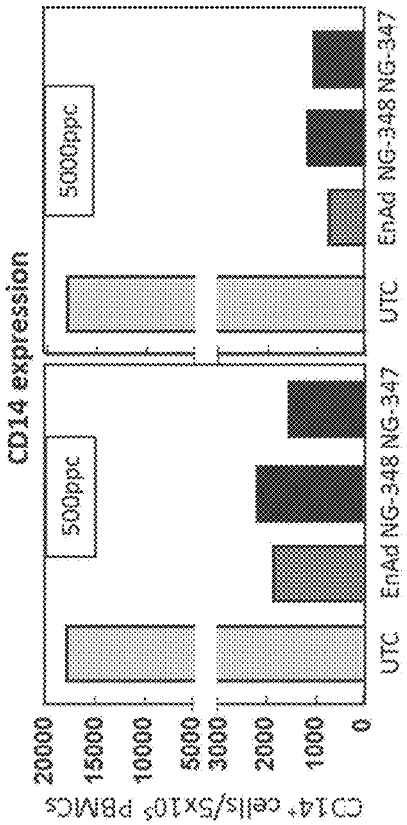
FIG. 38A shows the similar activation of human dendritic cells by EnAd, NG-347 and NG-348 virus particles, as measured by down-regulation of CD14 expression.
Figure 38B:
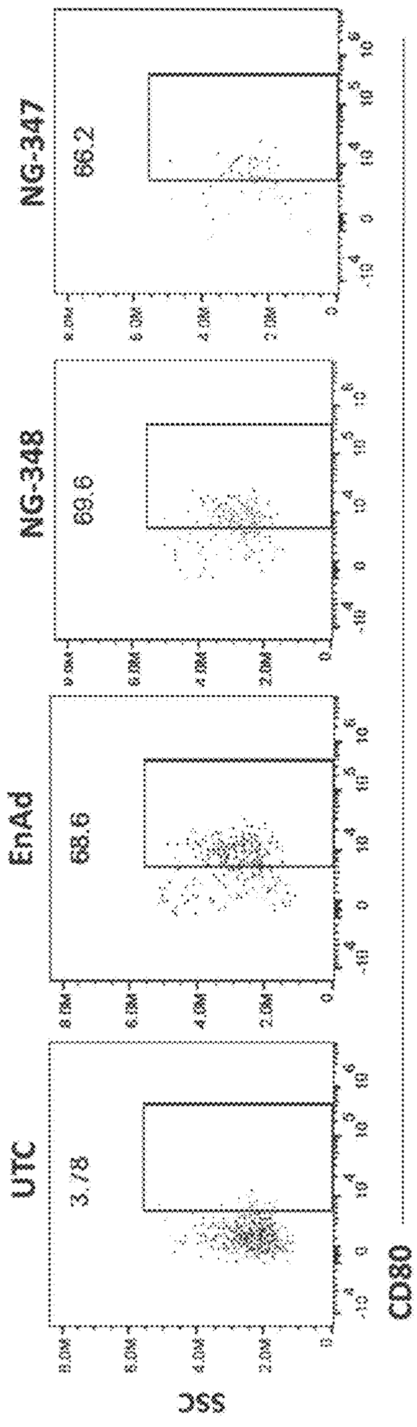
FIG. 38B shows the similar activation of human dendritic cells by EnAd, NG-347 and NG-348 virus particles, as measured by upregulation of CD80 on cell surface.
Figure 39A:
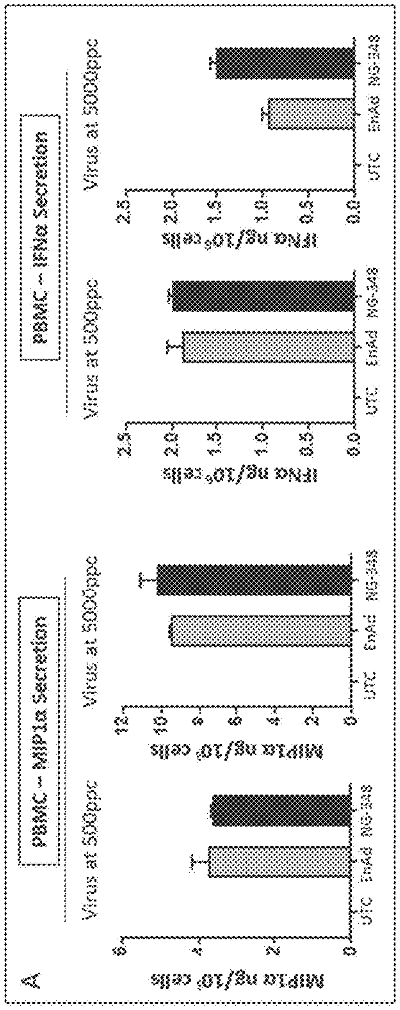
FIG. 39A shows similar particle-mediated MIP1α and IFNα protein secretion from PBMCs cultured with NG-348 compared to EnAd.
Figure 39B:
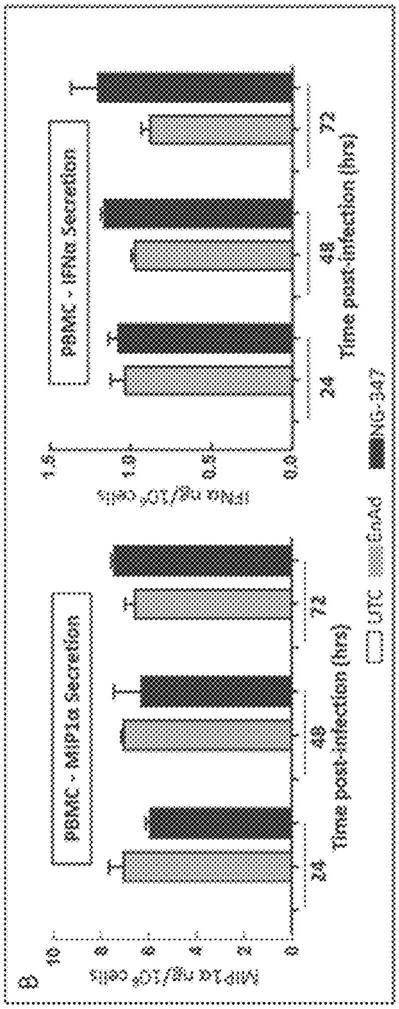
FIG. 39B shows similar particle-mediated MIP1α and IFNα protein secretion from PBMCs cultured with NG-347 compared to EnAd.

NG-347 and NG-348 virus particle-mediated activation of innate immune cells (monocytes, DCs) in the PBMC cultures were similar to those of EnAd, as shown in FIGS. 38 and 39 for downregulation of CD14 expression and upregulation of HLA-DR and endogenous cell surface CD80, as well as secretion of MIP1α and IFNα (note that despite NG-347 encoding both of these molecules in its genome there was no increase in production levels over those for EnAd and NG-348 which do not encode the transgenes).

Example 23

This example is similar in design to experiments in examples 15-17, 21 and 22 but in these studies, the human PBMCs or purified T-cells were co-cultured with virus pre-treated (48 hours) A549 tumour cells or MRC5 fibroblasts. A549 or MRC5 cells were treated with 10 ppc of EnAd, NG-347, NG-348 or left untreated (UTC) and cultured for 48 hours to allow sufficient time for virus replication and any transgene expression. PBMCs or T-cells were then added to the cultures and left for 24 or 48 hours to evaluate the ability of virus treated cells to activate T-cells.

Figure 40:
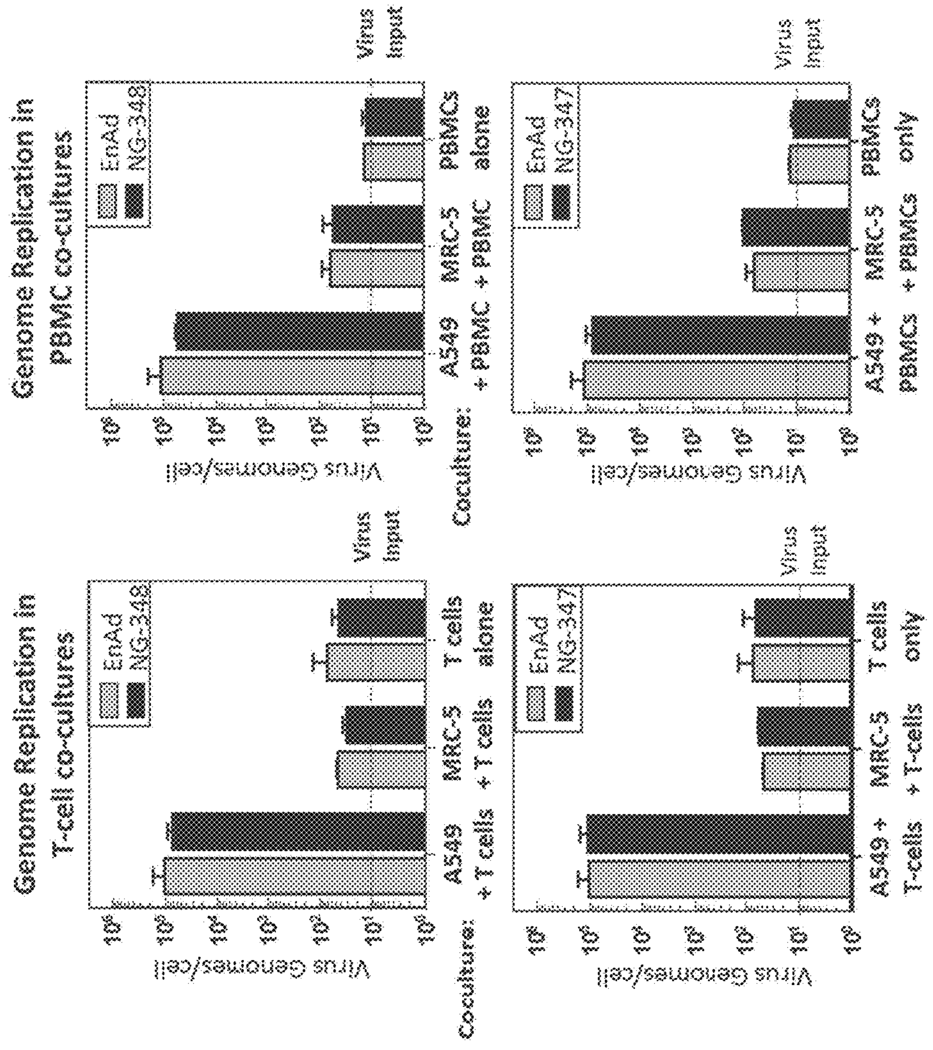
FIG. 40 shows NG-347 or NG-348 genome replication in co-cultures or T-cells or PBMCs with MRC-5 fibroblast cells compared to co-cultures with A549 tumour cells.

FIG. 40 shows virus genome replication data showing comparable replication of the three viruses in PBMC or T-cell co-cultures with both cell types, replication levels being high with A549 tumour cells and low with MRC5 fibroblasts.

T-cell activation as measured by upregulation of CD25 surface expression and CD8 effector T-cell degranulation, as measured by upregulation of CD107a on the cell surface, and IFNγ production measured by intracellular cytokine staining were all selectively stimulated by NG-348 treated A549 cells compared to EnAd, with no stimulation mediated with MRC co-cultures (Table 6).

TABLE 6

Flow cytometry analyses of activation of human CD3+ T-cells in T-cell and PBMC co-cultures with viruses

| Cells | Treatment | % $CD25^+$ | % $CD8^+CD107a^+$ | % $IFN\gamma^+$ |
|---|---|---|---|---|
| A549 + T-cells | Untreated | 37.5 | 0.1 | 0.1 |
| A549 + T-cells | EnAd | 38.4 | 0.1 | 0.2 |
| A549 + T-cells | NG-348 | 88.2 | 17.9 | 12.0 |
| MRC5 + T-cells | Untreated | 38.8 | 0.3 | 0.4 |
| MRC5 + T-cells | EnAd | 38.9 | 0.2 | 0.4 |
| MRC5 + T-cells | NG-348 | 39.1 | 0.3 | 0.3 |
| A549 + PBMCs | Untreated | 28.3 | ND | ND |
| A549 + PBMCs | EnAd | 29.4 | ND | ND |
| A549 + PBMCs | NG-348 | 73.7 | ND | ND |
| MRC5 + PBMCs | Untreated | 23.0 | ND | ND |

TABLE 6-continued

| Flow cytometry analyses of activation of human CD3+ T-cells in T-cell and PBMC co-cultures with viruses | | | | |
|---|---|---|---|---|
| Cells | Treatment | % CD25$^+$ | % CD8$^+$CD107a$^+$ | % IFNγ$^+$ |
| MRC5 + PBMCs | EnAd | 23.3 | ND | ND |
| MRC5 + PBMCs | NG-348 | 21.7 | ND | ND |

ND = Not determined

Figure 41:
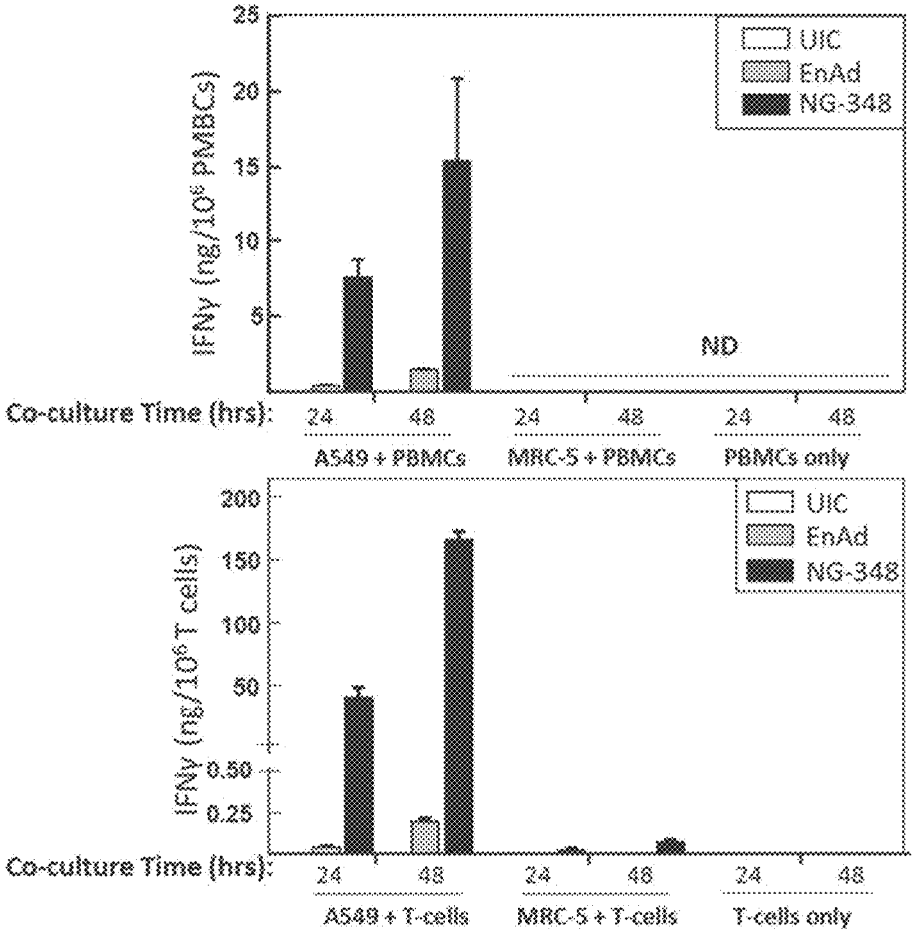
FIG. 41 shows INFγ secreted by PBMCs or T-cells co-cultured with MRC-5 fibroblast cells compared to A549 tumour cells, and treated with EnAd or virus NG-348.

IFNγ secretion into co-culture supernatants was also quantified by ELISA. The data (FIG. 41) similarly demonstrate selective activation of T-cells co-cultured with NG-348 treated A549 tumour cells not MRC5 fibroblasts, with either purified T-cells or PBMCs used in the assays.

Ability of NG-347 to activate T-cells was also assessed by measuring CD69 levels on T-cells from co-cultures of either purified T-cells or PBMCs with A549 tumour cells or MRC5 fibroblasts. As shown in Table Z, a small enhancement in CD69 positive T-cells was seen with NG-347 treatment of A549 tumour cells compared to EnAd, which itself leads to upregulation of this early activation marker. These effects were not seen in MRC5 co-cultures. No CD80 expression was detected on the T-cells (not shown).

TABLE 7

| CD69 expression on T-cells from NG-347 or EnAd treated co-cultures | | |
|---|---|---|
| Cells | Treatment | % CD69+ |
| A549 + T-cells | Untreated | 2.1 |
| A549 + T-cells | EnAd | 18.7 |
| A549 + T-cells | NG-348 | 35.0 |
| MRC5 + T-cells | Untreated | 3.8 |
| MRC5 + T-cells | EnAd | 3.6 |
| MRC5 + T-cells | NG-348 | 4.4 |
| A549 + PBMCs | Untreated | 1.2 |
| A549 + PBMCs | EnAd | 19.1 |
| A549 + PBMCs | NG-348 | 28.7 |
| MRC5 + PBMCs | Untreated | 2.6 |
| MRC5 + PBMCs | EnAd | 2.7 |
| MRC5 + PBMCs | NG-348 | 3.9 |

In a separate experiment, A549 cells treated with NG-347 and co-cultured with human CD3+ T-cells led to upregulation of CD69 activation marker on the T-cells and secretion of IFNγ (see FIGS. 24 & 25).

Example 24

Figure 42:
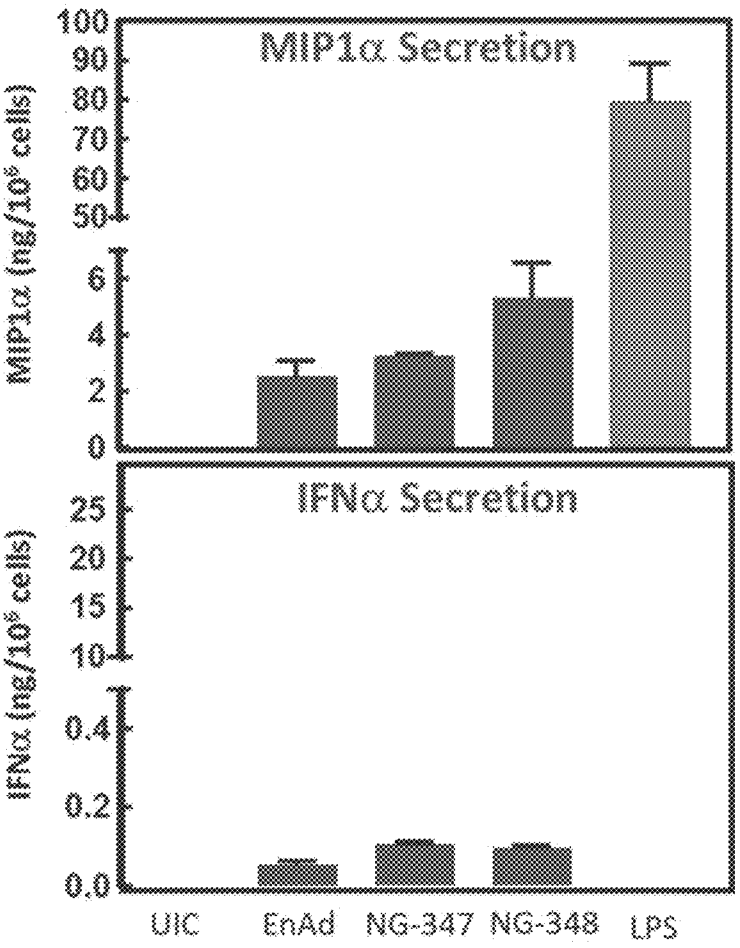
FIG. 42 shows similar MIP1α and IFNα secreted by human dendritic cells treated with EnAd, NG-347 or NG-348 virus particles.

CD14+ monocytic cells were isolated from PBMCs by antibody coated magnetic bead separation and cultured with human IL-4 and GM-CSF to differentiate them into dendritic cells. After 3 days of culture, the cells were treated with EnAd, NG-347 or NG-348 at 5000 ppc or left untreated. As a positive activation control, some cells were stimulated with LPS. Two days later supernatants were taken for cytokine ELISAs and cells were stained for surface activation marker expression and analysed by flow cytometry. As shown in table 8 all viruses induced upregulation of the costimulatory molecules CD80 and CD86, indicating that this previously identified particle-mediated innate immune cell activation effect was not altered by the transgene incorporation into the genomes of NG-347 and NG-348. All viruses also stimulated secretion of similar levels of MIP1α and IFNγ (FIG. 42).

TABLE 8

| Particle-mediated activation of human dendritic cells by EnAd, NG-347 and NG-348 | | |
|---|---|---|
| DC treatment | % CD80$^+$ | % CD86$^+$ |
| Untreated | 3.0 | 10.4 |
| EnAd | 81.6 | 99.3 |
| NG-347 | 82.1 | 99.4 |
| NG-348 | 62.5 | 99.5 |
| LPS positive control | 97.5 | 98.5 |

Example 25

Figure 43:
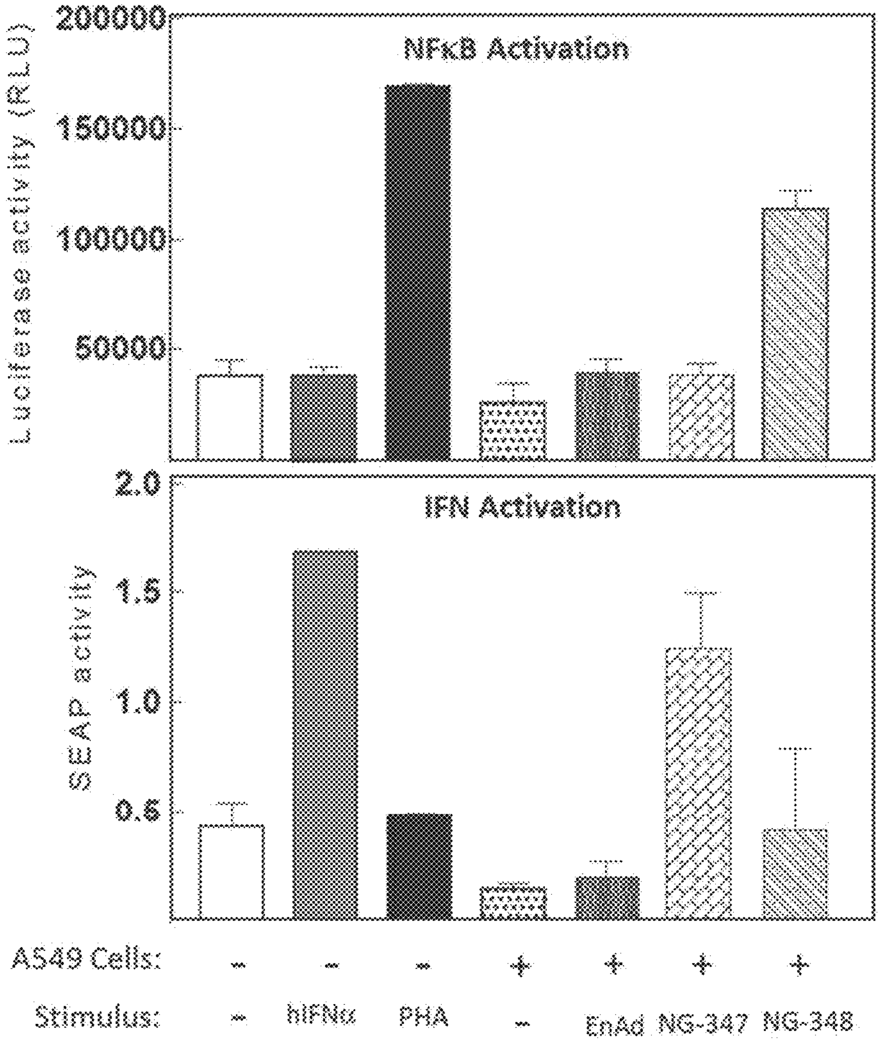
FIG. 43 shows NFκB (luciferase) and IFN (SEAP) reporter gene activation in JurkatDual reporter T-cells co-cultured with EnAd, NG-347 or NG-348 infected A549 tumour cells.

In a set of experiments, JurkatDual cells were used in co-cultures with tumour cells as a T-cell activation reporter assay for assessing functionality of transgene expression by NG-347, NG-348 and NG-420 viruses, with EnAd serving as a negative control. JurkatDual cells stably express two different reporter genes: an NFκB reporter gene producing a secreted form of luciferase which is responsive to signalling via the T-cell receptor complex and an IFNα-responsive secreted alkaline phosphatase (SEAP) reporter gene. A549 cells were pre-cultured with viruses at '10 ppc for two days, and then JurkatDual cells were added for overnight co-culture (18-24 h) and then supernatants collected for assay of luciferase and SEAP activities. As shown in FIG. 43, NG-347 infected A549 cells selectively induced SEAP production, which aligns with their production of IFNα (see FIG. 11) but did not induce luciferase activity. In contrast, NG-348 which expresses the membrane anti-CD3-ScFv to activate the T-cell receptor complex induced luciferase but not SEAP.

Figure 44:
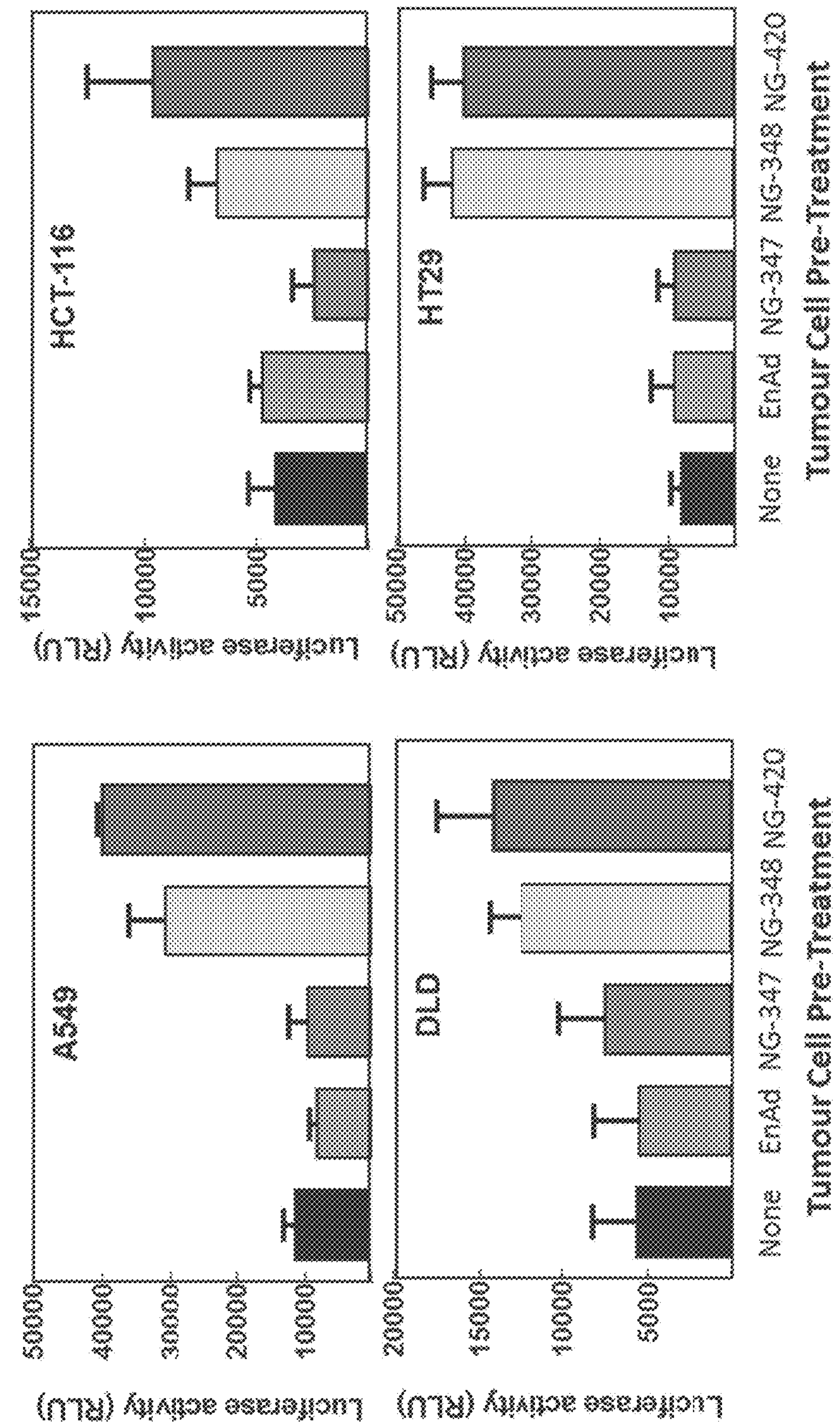
FIG. 44 shows NF-κB-luciferase reporter activity generated by JurkatDual reporter T-cells co-cultured with EnAd, NG-347, NG-348 or NG-420 treated A549 HCT-116, DLD and HT29 tumour cells.

In another experiment A549 lung carcinoma cells and HCT-116, HT-29 & DLD colon carcinoma cells were pre-cultured for 48 hours with 10 ppc of EnAd, NG-347, NG-348 or NG-420 viruses before co-culturing with JurkatDual cells overnight, with supernatants tested for levels of luciferase to indicate level of activation induced. As shown in FIG. 44, all four tumour cell types cultured with NG-348 or NG-420 viruses, which encode cell surface anti-CD3-ScFv, activated the JurkatDual cells whereas EnAd and NG-347 did not, with levels of luciferase similar to that of uninfected tumour cell controls (UIC).

Figure 45:
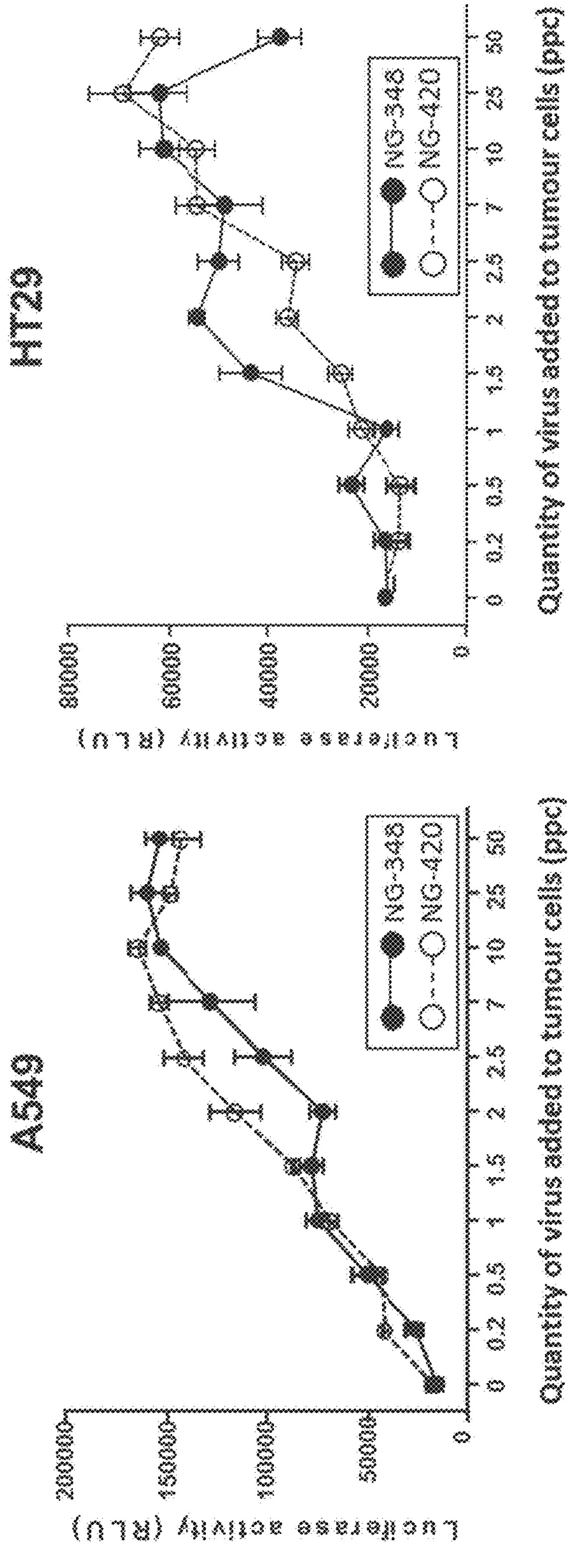
FIG. 45 shows NF-κB-luciferase reporter activity generated by JurkatDual cells co-cultured with either A549 or HT29 tumour cells infected with virus NG-348 or virus NG-420 as a function of virus particles added.

In another experiment, A549 or HT-29 tumour cells were pre-cultured with different amounts of either NG-348 or NG-420 before adding the JurkatDual cells and measuring their luciferase secretion. The data in FIG. 45 show that activation of the NFκB activity in JurkatDual cells is dependent on the dose of virus used to treat the tumour cells with.

Example 26

Figure 46:
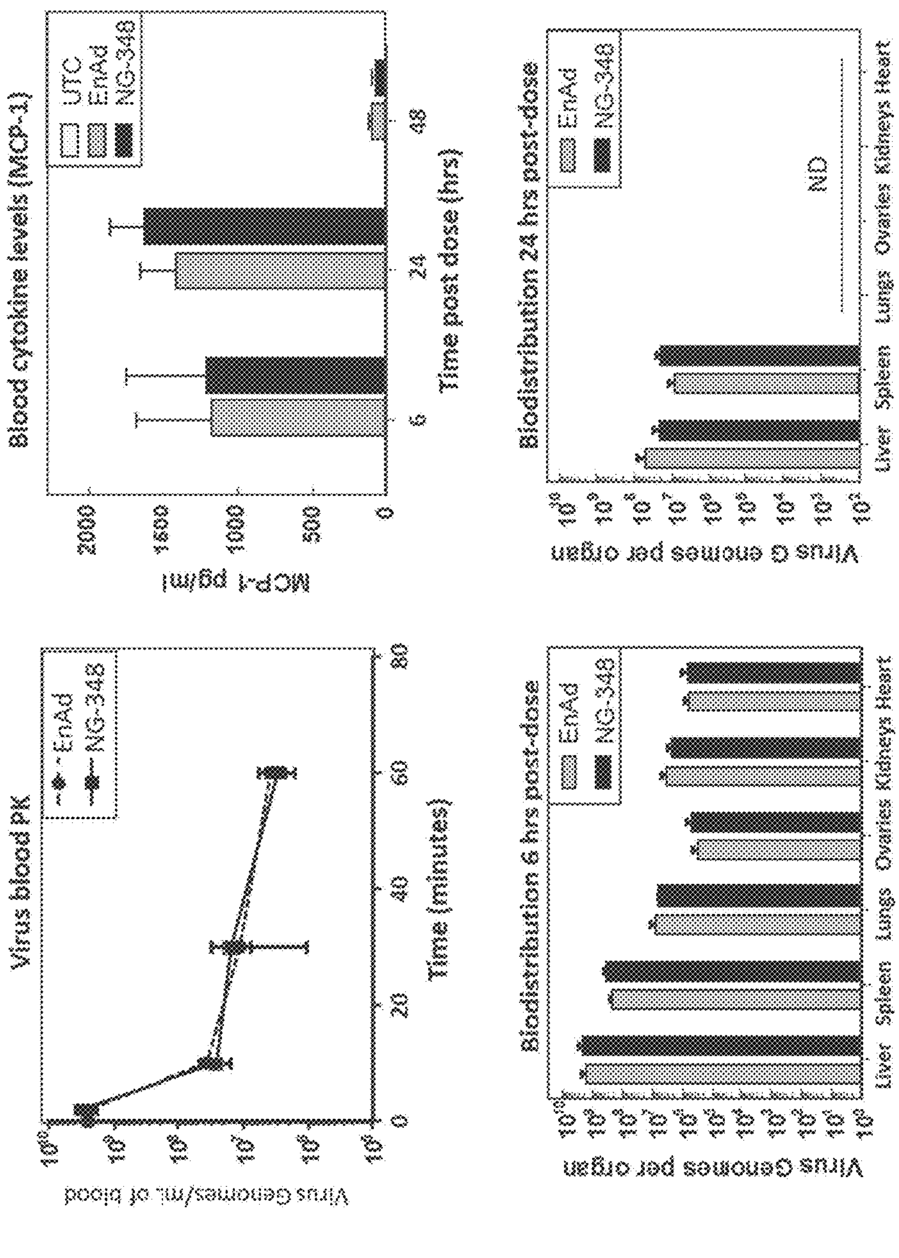
FIG. 46 shows the pharmacokinetics of EnAd and virus NG-348 in blood; blood cytokine levels after exposure to EnAd or virus NG-348; tissue biodistribution of EnAd or NG-348 viruses 6 or 24 hours after IV administration to CD1 mice.

The in vivo pharmacokinetic, biodistribution and particle-mediated systemic cytokine induction activities of EnAd and NG-348 following IV dosing in immunocompetent CD1 mice were compared, Mice were dosed intravenously with $5\times10^9$ particles of either EnAd or NG-348 and bled 2, 10, 30, 60 and 120 minutes post dosing. Whole blood was DNA extracted and analysed by qPCR for levels of virus genome (FIG. 46). Clearance of both viruses from the blood followed similar kinetics. Similarly, the induction of MCP-1 cytokine response (a measure of particle-mediated activation of innate immune such as liver Kupffer cells) was also similar for both viruses, as were the tissue biodistribution patterns (FIG. 46).

Example 27

Figure 47:
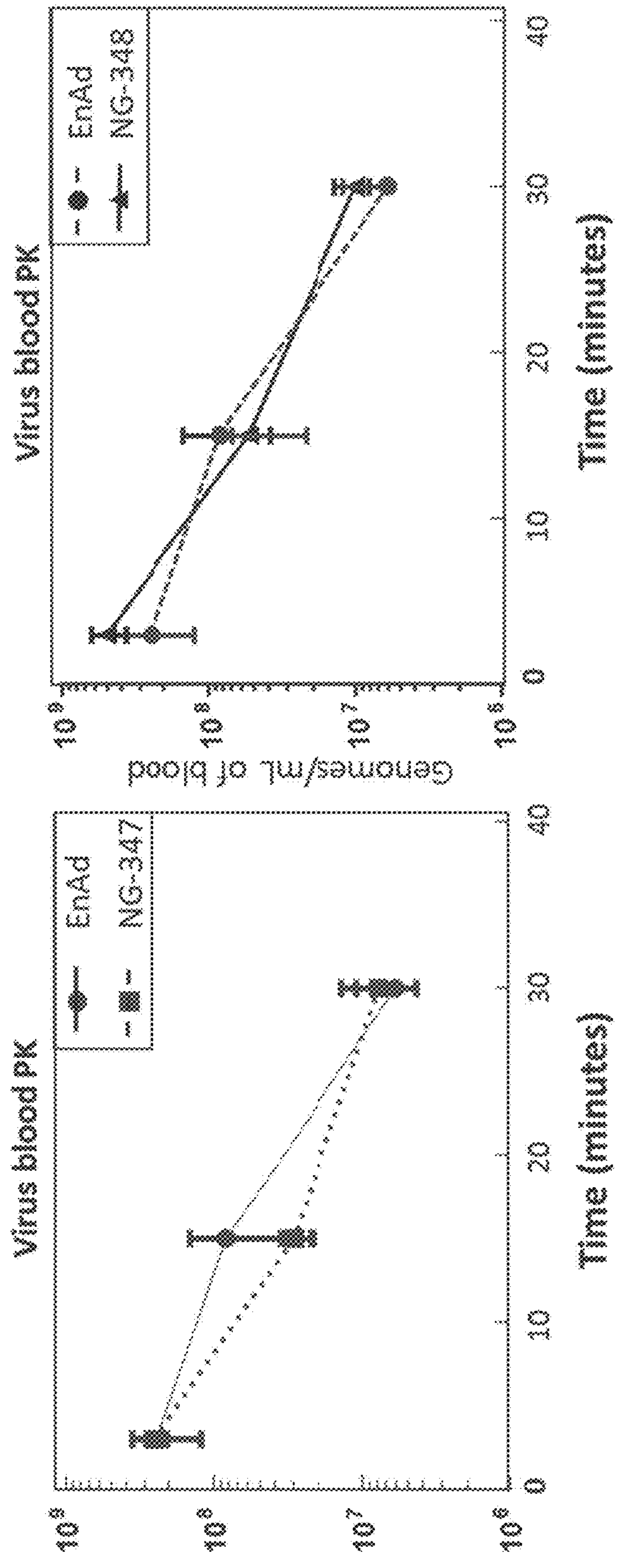
FIG. 47 shows the pharmacokinetics in blood of EnAd, NG-347 and NG-348 viruses following IV administration to CB17-SCID mice bearing a subcutaenous HCT-116 tumour xenograft.
Figure 48A:
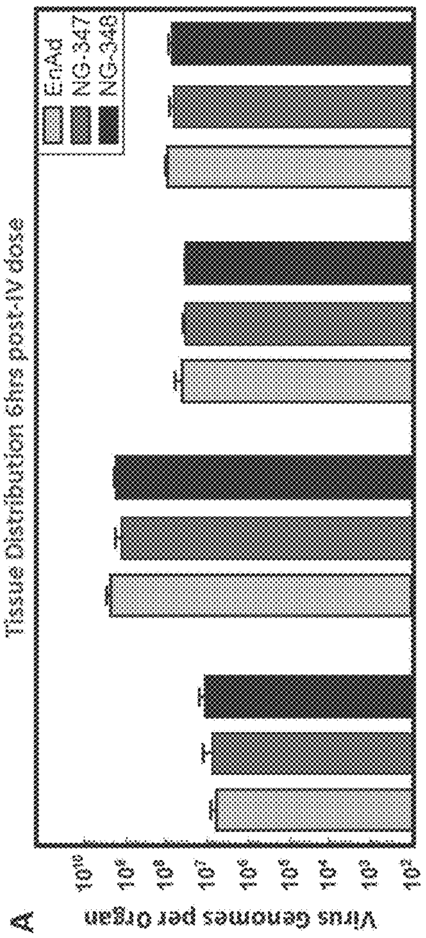
FIG. 48A shows the tissue distribution of EnAd, NG-347 and NG-348 viruses 6 hours post intravenous dosing in tumour-bearing CB17-SCID mice.
Figure 48B:
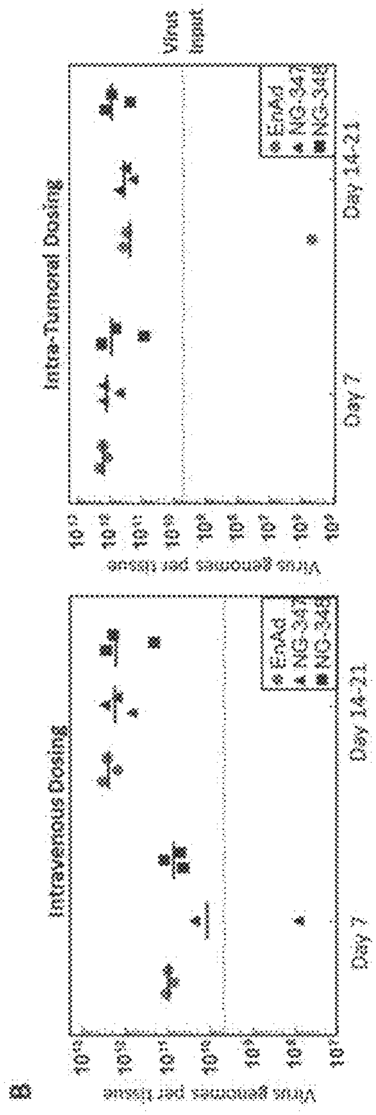
FIG. 48B shows virus genomes in HCT-116 tumour xenografts at day 7 and day 14-21 following intravenous or intra-tumoral dosing of EnAd, NG-347 or NG-348.

CB17 SCID mice were implanted subcutaneously with HCT116 cells and injected intratumourally (IT) or intravenously (IV) with EnAd, NG-347 or NG-348 viruses ($5\times10^9$ virus particles), or control, once tumours were greater than 70 $mm^3$. For the IV dosed mice, blood samples were taken from three mice from each group 3, 15 and 30 minutes after IV dosing, DNA extracted and the level of virus genomes in the blood assessed by qPCR (pharmacokinetics [PK] analysis). Data (FIG. 47) show that NG-347 and NG-348 have similar PK to EnAd (and to each other). After 6 hours, tumours, livers, lungs and spleens were resected from 3 mice from each group. Homogenised tissues were DNA extracted and analysed for level of virus genomes by qPCR (biodistribution analysis). Data (FIG. 48A) show similar tissue biodistribution for the three viruses. After 7 days or 14-21 days, tumours were excised from three mice from each group and homogenized to produce a tumour lysate which was used to prepare both DNA and RNA. Level of virus genomes in the tumours at the two time points were measured by qPCR analyses of the extracted DNA. Data (FIG. 48B) show that tumours from both IV and IT dosed mice have levels of virus genomes higher than the amount of virus dosed, indicating virus replication in the tissue, with IT dosing giving higher genome levels than IV at day 7, but both being similarly high at the 14-21 day timeframe. All three viruses replicated to similar levels.

Figure 49:
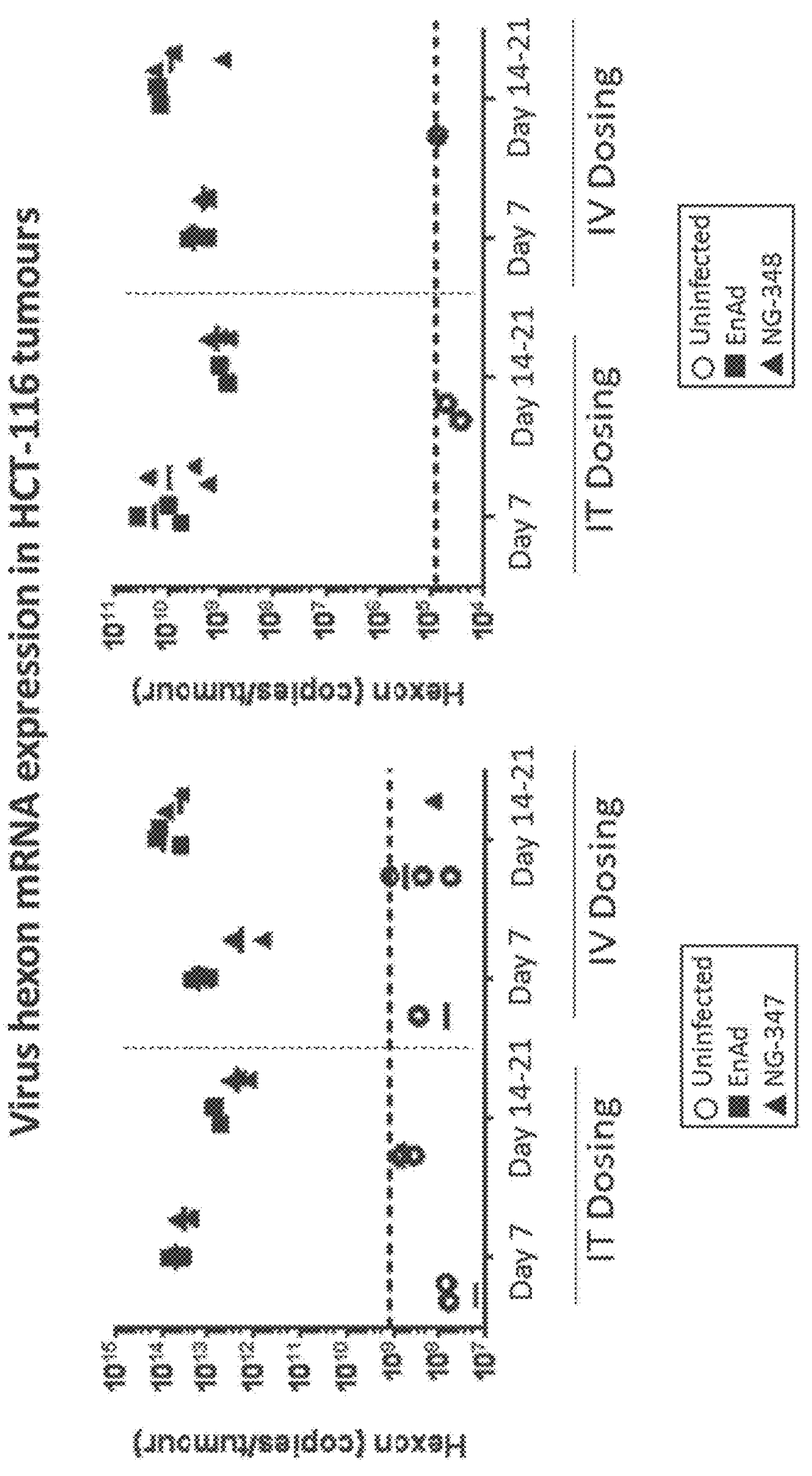
FIG. 49 shows virus hexon mRNA generated in HCT-116 tumour xenografts by EnAd, NG-347 or NG-348 viruses on day 7 or 14-21 following intravenous or intra-tumoral dosing.
Figure 50:
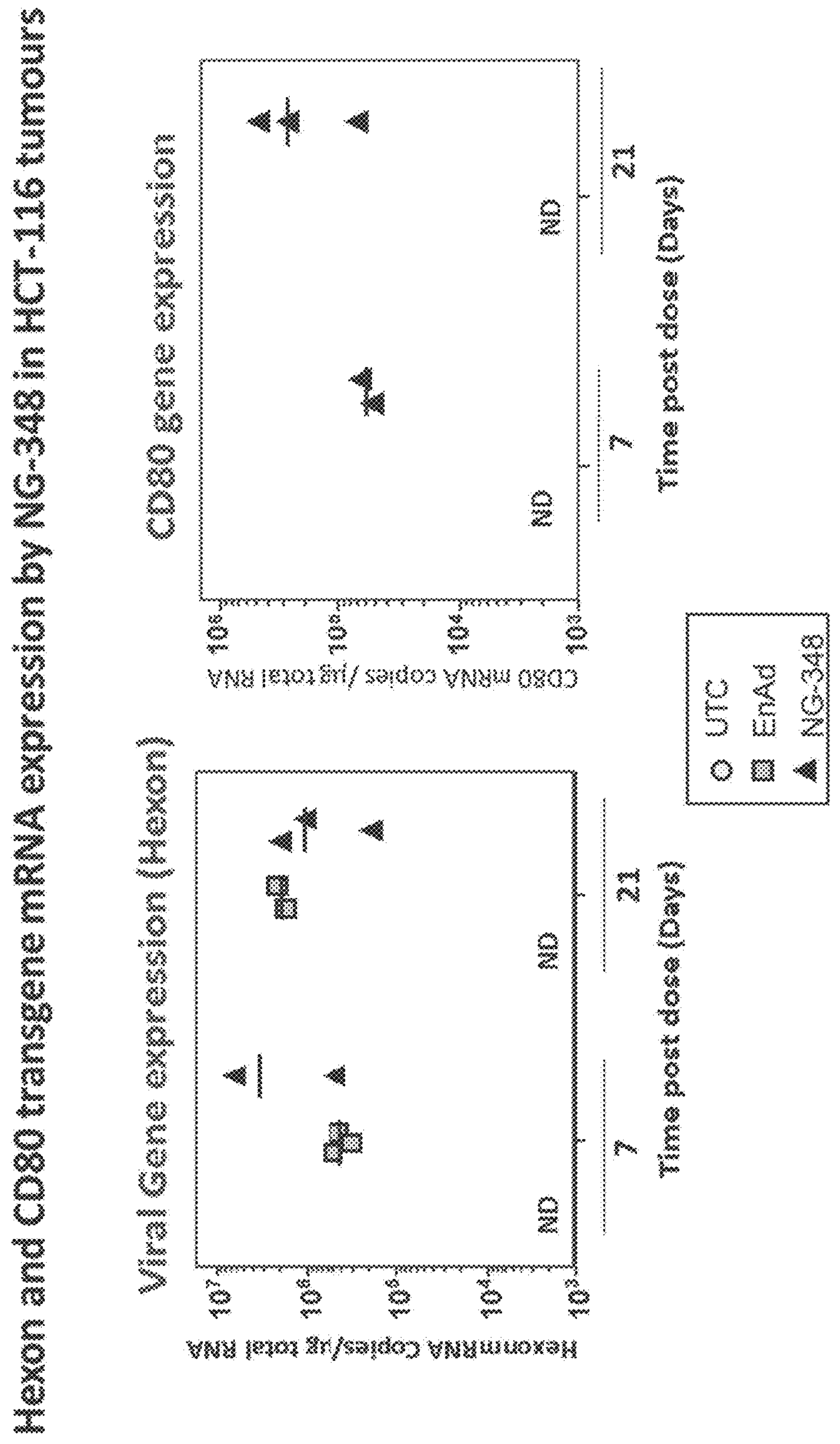
FIG. 50 shows mRNA levels for hexon and CD80 transgene in HCT-116 tumour xenografts 7 or 21 days following intravenous dosing with virus NG-348 or EnAd.
Figure 51:
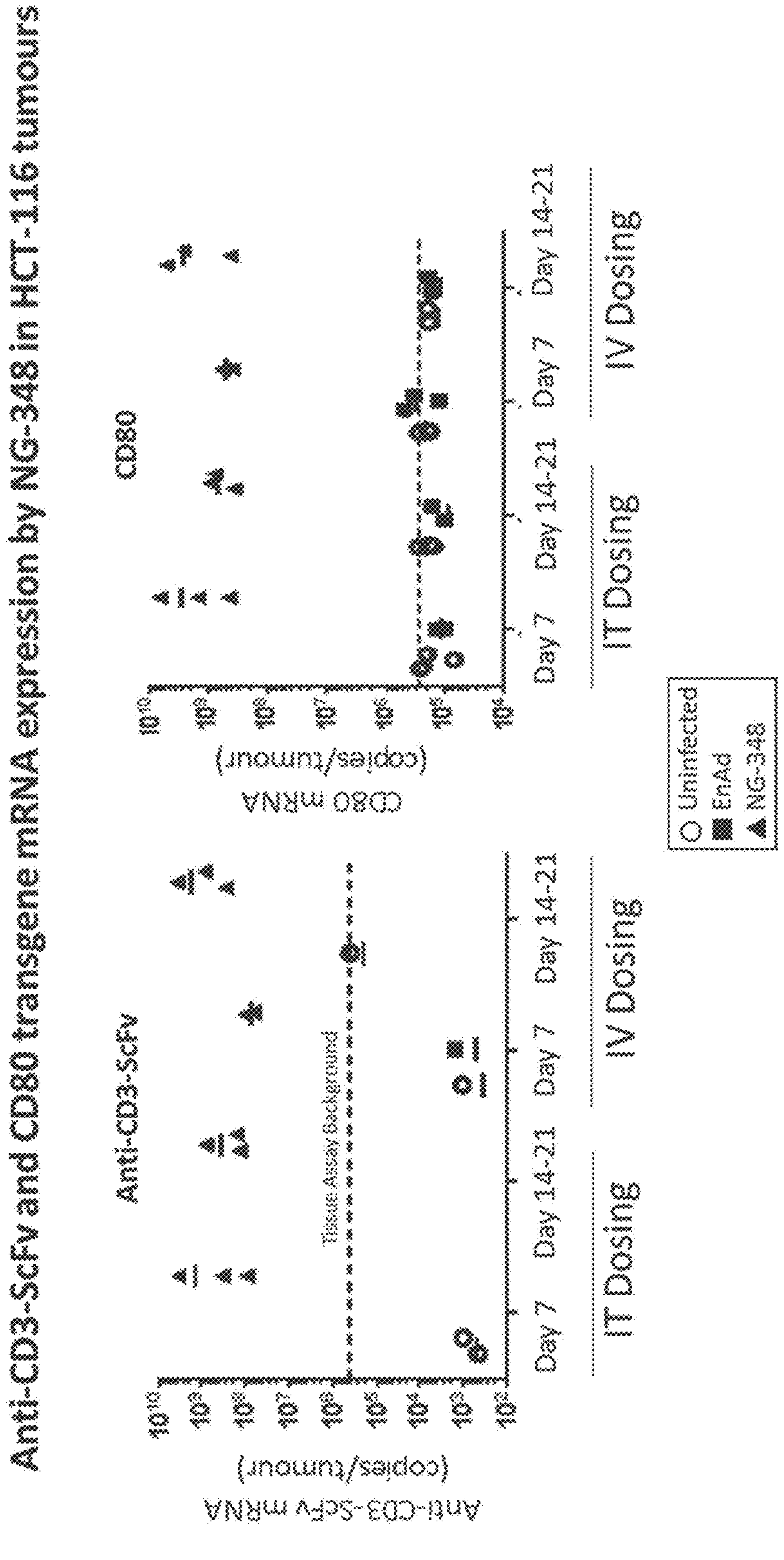
FIG. 51 shows mRNA levels for a transgenes encoding anti-CD3 ScFv and CD80 in HCT-116 tumour xenografts 7 or 14-21 days following IV dosing with virus NG-348 or EnAd.
Figure 52:
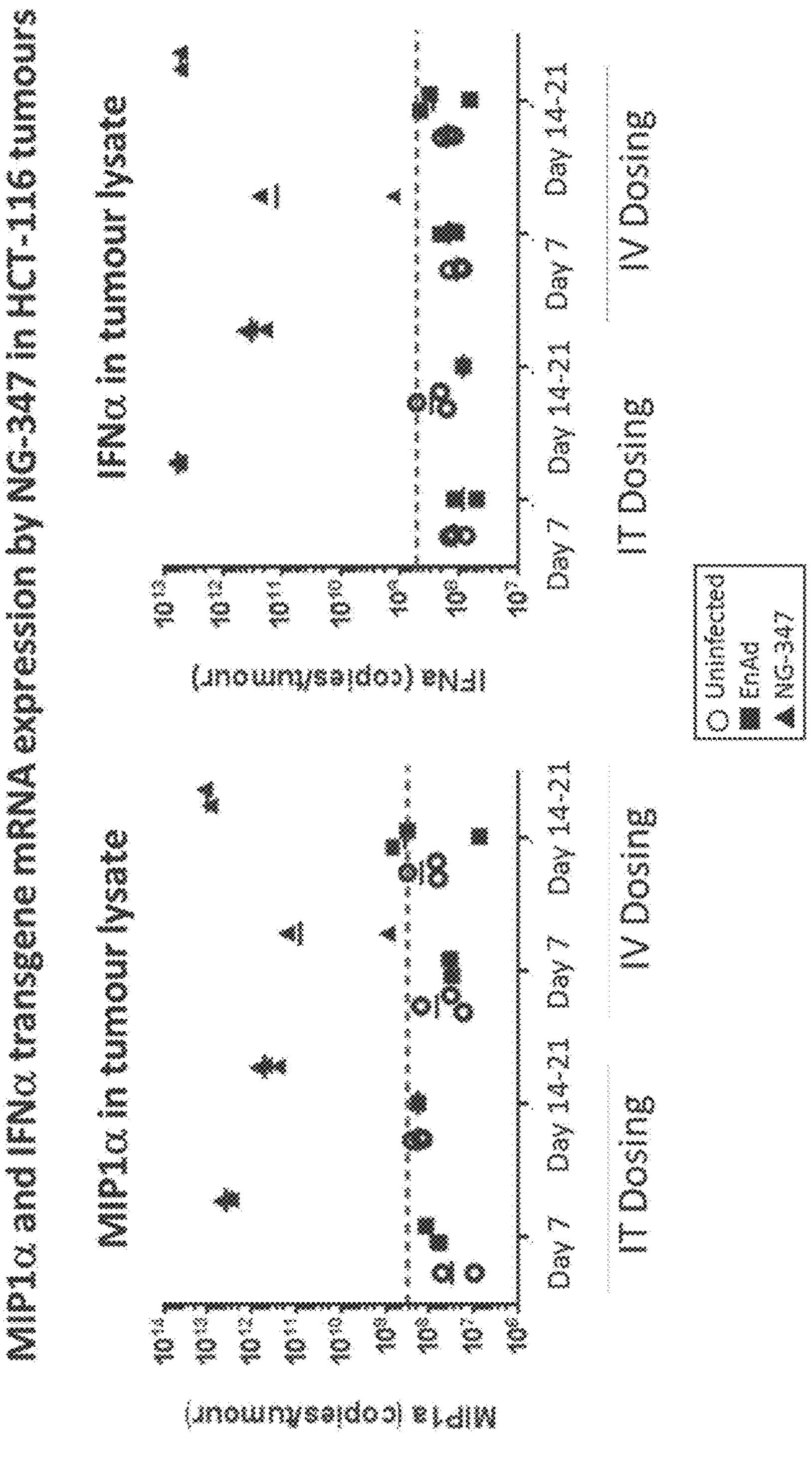
FIG. 52 shows mRNA levels of MIP1α and IFNα transgenes in HCT-116 tumour xenografts 7 or 14-21 days following intravenous dosing with virus NG-347 or EnAd.

Similarly, levels of virus hexon mRNA in tumour lysates detected by RT-qPCR were comparable between EnAd, NG-347 and NG-348 at both time points tested (FIGS. 49 and 50). Similar levels of anti-CD3-ScFv and CD80 mRNA were detected at both time points and both dosing routes for NG-348 treatment, with only assay background readings with EnAd dosing (FIGS. 50 & 51). MIP1α and IFNα mRNA levels were also selectively detected following NG-347 dosing, either IT or IV (FIG. 52).

Figure 53:
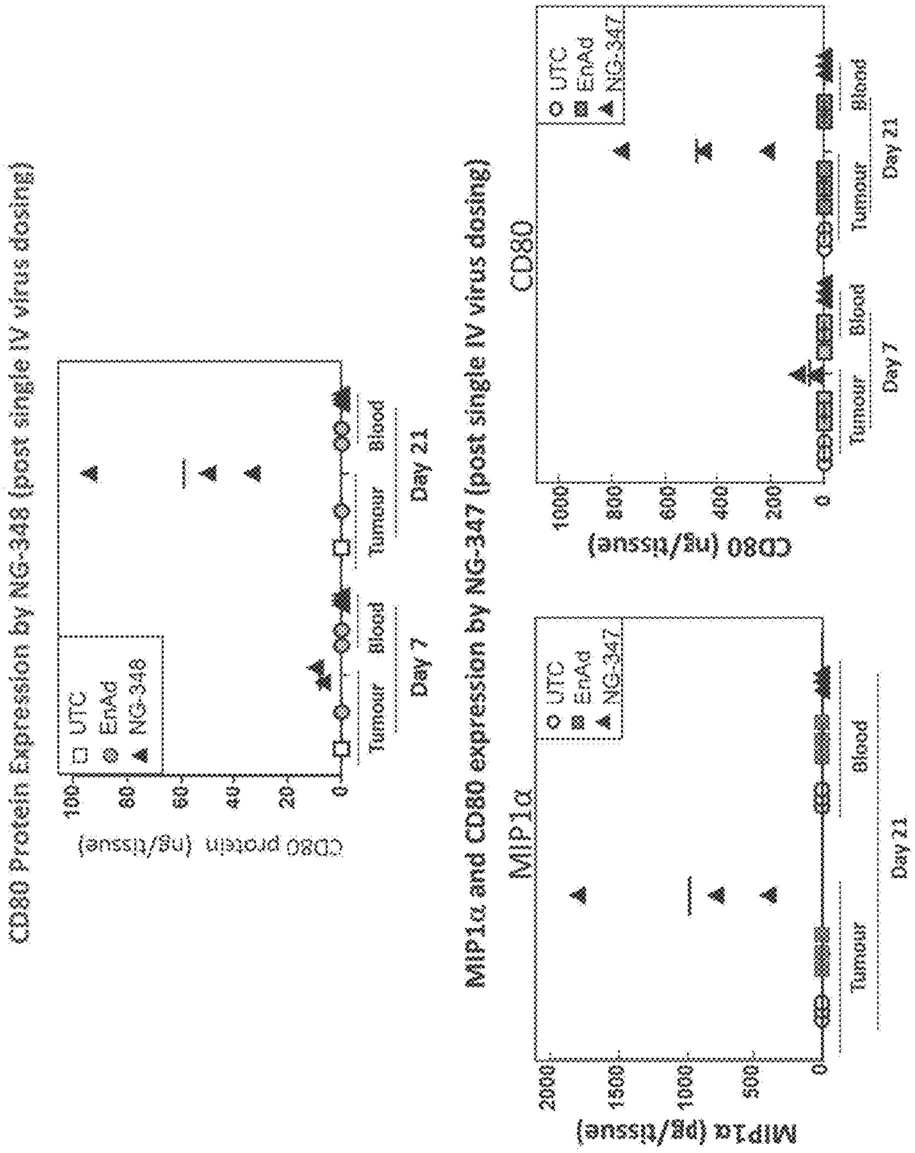
FIG. 53 shows CD80 protein expression in HCT-116 tumour xenografts 7 and 21 days following an intravenous dose of virus NG-348; and shows MIP1α and CD80 protein expression in HCT-116 tumours following an intravenous dose of virus NG-347 or EnAd.

Levels of CD80 protein encoded by both NG-347 and NG-348, and MIP1α protein encoded by NG-347 were measured in tumour lysates using specific ELISAs. The data in FIG. 53 show that following the single IV virus dose, both proteins could also be detected selectively in tumour extracts. Neither protein was detected in blood samples from the same mice.

Example 28

To evaluate the activity and tumour cell dependency of NG-348 virus in vivo, different combination of human PBMCs ($5\times10^7$ cells), A549 human tumour cells ($5\times10^6$) and either EnAd or NG-348 (at $5\times10^9$ ppc) were injected into the peritoneum of immune-deficient SCID-beige mice, with viruses or control (saline) being dosed within 15 minutes after injection of the cells. After 3 days, the peritoneal cavity was lavaged with 5 mL of saline and recovered cells were analysed by flow cytometric analyses with a panel of T-cell activation markers (CD25, CD69 and HLA-DR) to assess levels of T-cell activation, following gating on the CD3+ T-cell population. Data from two separate experiments (Table 9) demonstrate that NG-348 selectively leads to human T-cell activation in vivo in a tumour cell dependent manner.

TABLE 9

In vivo activation of human T-cells in A549 tumour bearing mice by NG-348

| Group | Virus | Tumour | N | % $CD25^+$ | % $CD69^+$ | % $DR^+$ | % $CD25^+$, $CD69^+$ | % $CD25^+$, $DR^+$ |
|---|---|---|---|---|---|---|---|---|
| | | | | Experiment 1 | | | | |
| 1 | EnAd | Saline | 2 | 1.9, 2.3 | 1.6, 3.0 | 7.7, 9.1 | 0.2, 0.5 | 0.3, 0.6 |
| 2 | EnAd | $5\times10^6$ A549 cells | 2 | 4.2, 2.9 | 6.2, 5.5 | 8.4, 8.4 | 0.8, 0.3 | 1.4, 0.4 |
| 3 | NG-348 | Saline | 1 | 3.4 | 2.6 | 9.2 | 0.5 | 0.8 |
| 4 | NG-348 | $5\times10^6$ A549 cells | 2 | 35.8, 36.6 | 50.4, 42.2 | 26.3, 19.2 | 22.4, 18.0 | 16.4, 12.2 |
| | | | | Experiment 2 | | | | |
| 1 | Saline | Saline | 1 | 25.6 | 37.3 | 14.8 | 14.1 | 7.08 |
| 2 | EnAd | Saline | 2 | 6.5, 7.3 | 17.8, 18.2 | 5.50, 6.1 | 3.58, 3.46 | 1.01, 1.49 |
| 3 | NG-348 | Saline | 2 | 10.2, 6.5 | 26.7, 18.3 | 7.7, 6.0 | 6.73, 3.61 | 2.16, 1.44 |
| 4 | Saline | $5\times10^6$ A549 cells | 2 | 28.4, 22.7 | 54.4, 51.1 | 13.3 15.0 | 22.3 17.5 | 8.54, 7.72 |
| 5 | EnAd | $5\times10^6$ A549 cells | 1 | 13.2 | 29.4 | 5.1 | 7.84 | 1.62 |
| 6 | NG-348 | $5\times10^6$ A549 cells | 3 | 34.4, 29.6, 56.4 | 58.9, 59.2, 85.0 | 12.5 9.8, 17.0 | 27.2, 23.3, 52.7 | 9.07 7.5, 14.2 |

Example 29 Assessment of Human Naive T Cell Activation

Study Overview

Figure 54:
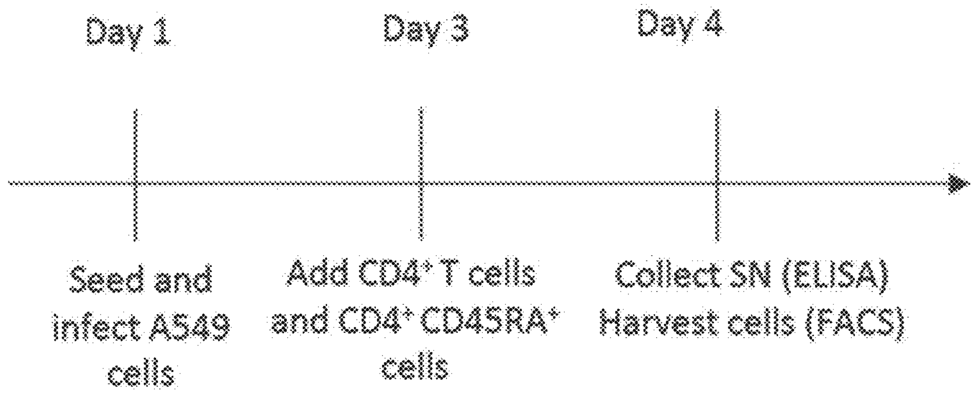
FIG. 54 shows the experimental design for studies depicted in FIGS. 55 and 56 (example 29).

The aim of this study was to assess the ability of NG-348-PSI-01 or EnAd to mediate naïve T cell activation after treatment of A549 cells. This was assessed by:

1. Flow cytometry analysis of markers of T cell activation
2. ELISA analysis of Interferon γ (IFN-γ) and IL-2 cytokine secretion A549 cells were treated for 48 hrs with either EnAd or NG-348-PSI-01 at 1 or 10 ppc. They were then co-cultured for 16 h (overnight) with purified CD3+ T cells, CD4+ T cells and naive CD4+ T cells isolated by negative selection from human PBMCs. The study schematic below gives an overview of the experiment design (FIG. 54).

Results Summary

Figure 55:
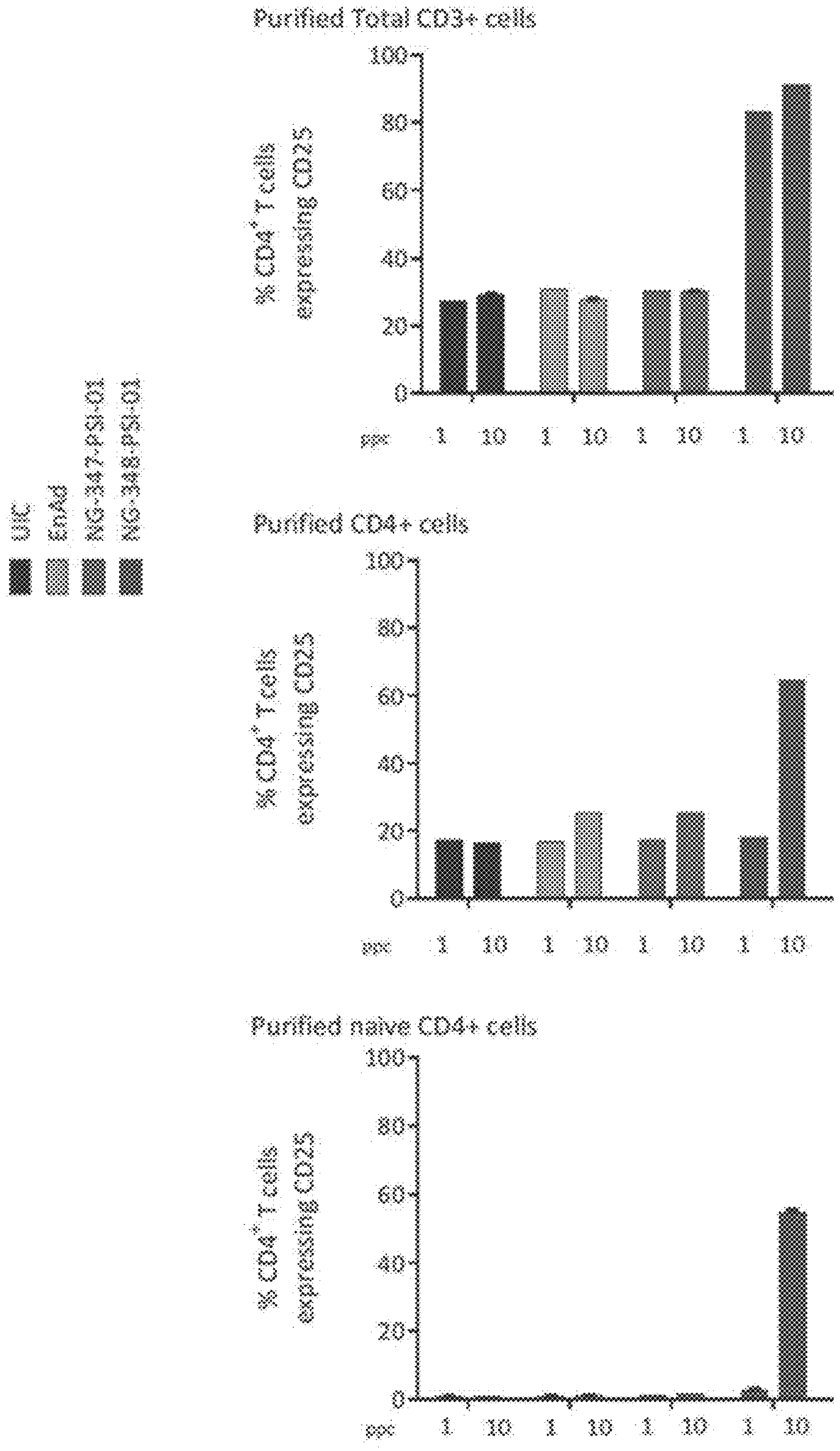
FIG. 55 shows CD25 expression on the surface of CD4$^+$ T-cells. A549 were infected with EnAd or NextGen viruses at 1 or 10 ppc. After 48 hrs, total CD3$^+$ T cells (top panel), CD3$^+$ CD4$^+$ T cells (middle panel) or naïve CD3$^+$ CD4$^+$ T cells (bottom panel) were added. Cells were harvested 16 h post coculture and stained with antibodies to CD25. Cells were gated on single live CD4$^+$ cells in the lymphocyte population.
Figure 56:
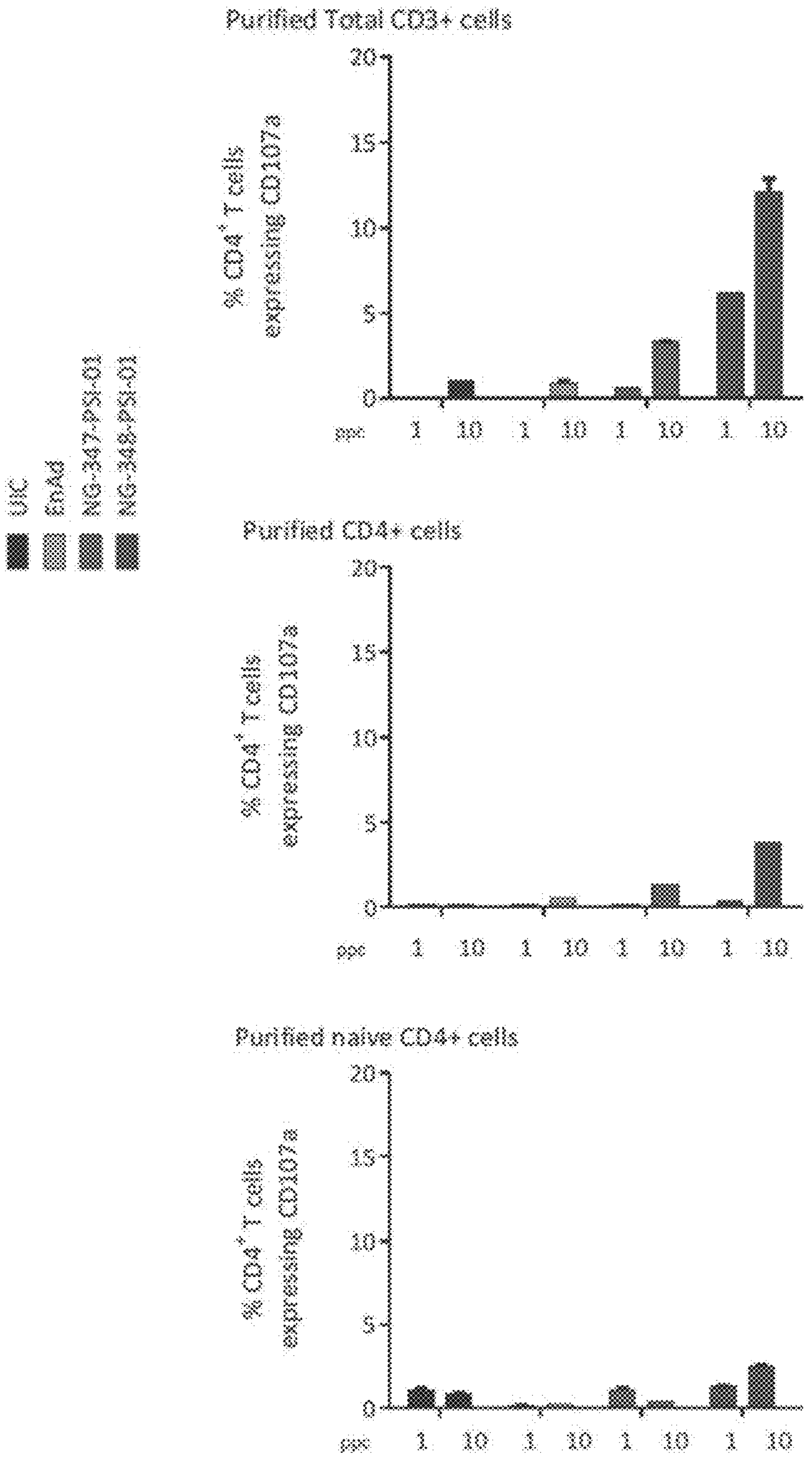
FIG. 56 shows CD107a staining on the surface of CD4$^+$ T-cells. A549 were infected with EnAd or NextGen viruses at 1 or 10 ppc. After 48 hrs, total CD3$^+$ T cells (top panel), CD3$^+$ CD4$^+$ T cells (middle panel) and naïve CD3$^+$ CD4$^+$ T cells (bottom panel) were added. Cells were harvested 16 h post coculture and stained with antibodies to CD107a. Cells were gated on single live CD4$^+$ cells in the lymphocyte population.
Figure 57A:
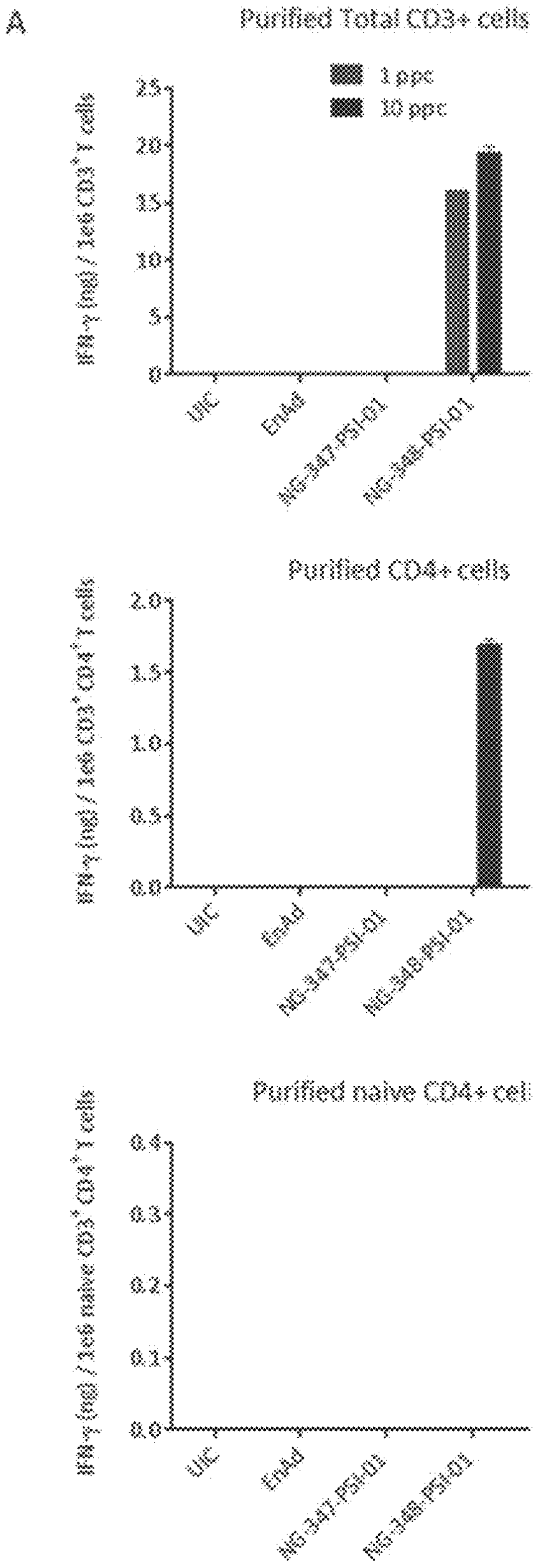
FIG. 57A shows IFN-γ secretion by T-cells after 16 h co-culture with virus-infected A549 cells. A549 were infected with EnAd or NextGen viruses at 1 or 10 ppc. After 48 hrs, total CD3$^+$ T cells (top panel), CD3$^+$ CD4$^+$ T cells (middle panel) and naïve CD3$^+$ CD4$^+$ T cells (bottom panel) were added. Supernatants were harvested 16 h post coculture and used for IFN-γ ELISA. Error bars represent SEM from two biological replicates.
Figure 57B:
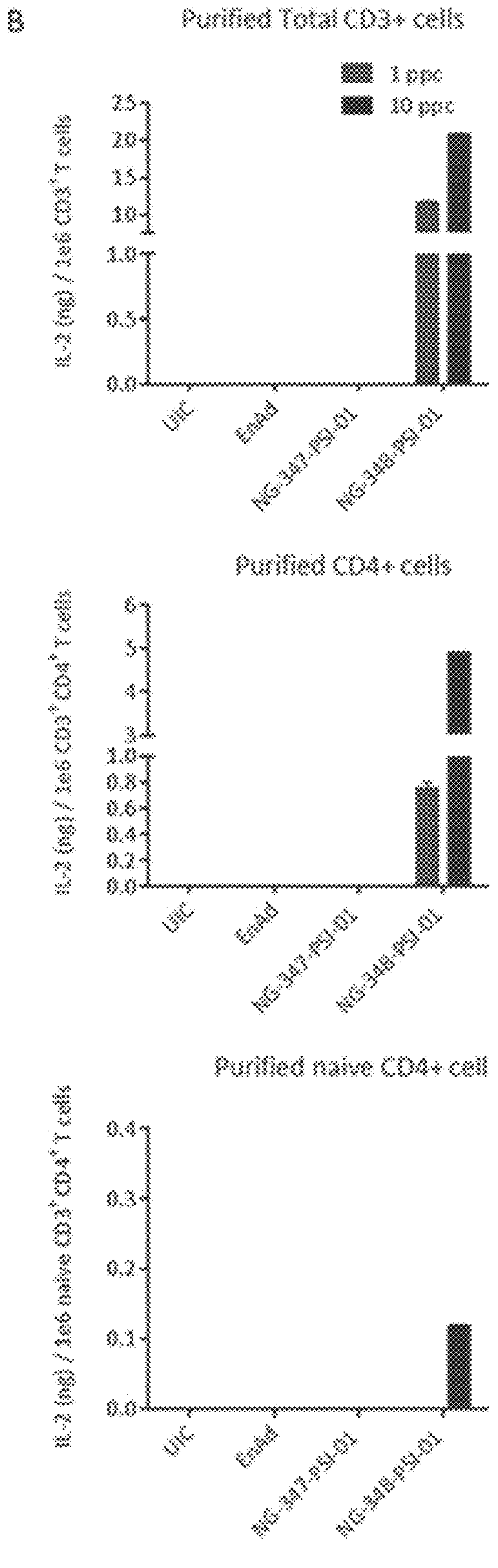
FIG. 57B shows IL-γ secretion by T-cells after 16 h co-culture with virus-infected A549 cells. A549 were infected with EnAd or NextGen viruses at 1 or 10 ppc. After 48 hrs, total CD3$^+$ T cells (top panel), CD3$^+$ CD4$^+$ T cells (middle panel) and naïve CD3$^+$ CD4$^+$ T cells (bottom panel) were added. Supernatants were harvested 16 h post coculture and used for IL-2 ELISA. Error bars represent SEM from two biological replicates.

Co-culture of total CD3+ cells with A549 cells infected by either 1 or 10 ppc of NG-348-PSI-01 led to high percentage of activated CD4+ T cells, based on CD25 and CD107a (FIGS. 55 and 56, top panel) as well as IFN-γ and IL-2 secretion (FIG. 57).

The invention claimed is:

1. A replication competent oncolytic adenovirus comprising SEQ ID NO: 96.

2. A pharmaceutical formulation of an adenovirus according to claim 1, and a diluent or carrier.

3. A pharmaceutical formulation according to claim 2, wherein the formulation is for parenteral administration.

4. A pharmaceutical formulation according to claim 3, wherein the formulation comprises $2\times10^{12}$ viral particle/mL.

5. A pharmaceutical formulation according to claim 4, wherein the viral particles are formulated in 5 mM HEPES, 20% glycerol with a final pH of 7.8.

6. A method of treatment comprising administering a therapeutically effective amount of a replication competent oncolytic adenovirus comprising SEQ ID NO: 96.

7. A method of treatment according to claim 6, for the treatment of cancer.

8. A method of treatment according to claim 7, wherein the cancer is selected from the group comprising: colorectal cancer, hepatoma, prostate cancer, pancreatic cancer, breast cancer, ovarian cancer, thyroid cancer, renal cancer, bladder cancer, head and neck cancer and lung cancer.

9. A method of treatment comprising administering a therapeutically effective amount of a pharmaceutical formulation comprising a replication competent oncolytic adenovirus comprising SEQ ID NO: 96 and a diluent or carrier.

10. A method of treatment according to claim 9, wherein the pharmaceutical formulation is administered parenterally.

11. A method according to claim 10, wherein the dose per administration is in the range of $1\times10^{10}$ to $1\times10^{14}$ virus particles.

12. A method of treatment according to claim 11, for the treatment of cancer.

13. A method of treatment according to claim 12 wherein the cancer is selected from the group comprising: colorectal cancer, hepatoma, prostate cancer, pancreatic cancer, breast cancer, ovarian cancer, thyroid cancer, renal cancer, bladder cancer, head and neck cancer and lung cancer.

14. The replication competent oncolytic adenovirus of claim 1, wherein the virus comprises SEQ ID NO: 101.

15. A pharmaceutical formulation of an adenovirus according to claim 14, and a diluent or carrier.

16. A pharmaceutical formulation according to claim 15, wherein the formulation is for parenteral administration.

17. A pharmaceutical formulation according to claim 16, wherein the formulation comprises $2\times10^{12}$ viral particle/mL.

18. A pharmaceutical formulation according to claim 17, wherein the viral particles are formulated in 5 mM HEPES, 20% glycerol with a final pH of 7.8.

* * * * *

SEQUENCE LISTING

<160> NUMBER OF SEQ ID NOS: 109

<210> SEQ ID NO 1
<211> LENGTH: 35
<212> TYPE: DNA
<213> ORGANISM: Artificial Sequence
<220> FEATURE:
<223> OTHER INFORMATION: By DNA sequence corresponding to and including bp 29345-29379 of the EnAd genome.

<400> SEQUENCE: 1
caaataaagt ttaacttgtt tatttgaaaa tcaat 35

<210> SEQ ID NO 2
<211> LENGTH: 48
<212> TYPE: PRT
<213> ORGANISM: Artificial Sequence
<220> FEATURE:
<223> OTHER INFORMATION: PDGF TM domain

<400> SEQUENCE: 2

Ala Val Gly Gln Asp Thr Gln Glu Val Ile Val Val Pro His Ser Leu
1 5 10 15

Pro Phe Lys Val Val Val Ile Ser Ala Ile Leu Ala Leu Val Val Leu
20 25 30

Thr Ile Ile Ser Leu Ile Ile Leu Ile Met Leu Trp Gln Lys Pro Arg
35 40 45

<210> SEQ ID NO 3
<211> LENGTH: 14
<212> TYPE: DNA
<213> ORGANISM: Artificial Sequence
<220> FEATURE:
<223> OTHER INFORMATION: SPLICE ACCEPTOR SEQUENCE

<400> SEQUENCE: 3
tttctctctt cagg 14

<210> SEQ ID NO 4
<211> LENGTH: 26
<212> TYPE: DNA
<213> ORGANISM: Artificial Sequence
<220> FEATURE:
<223> OTHER INFORMATION: SPLICE ACCEPTOR SEQUENCE

<400> SEQUENCE: 4
tgctaatctt cctttctctc ttcagg 26

<210> SEQ ID NO 5
<211> LENGTH: 192
<212> TYPE: DNA
<213> ORGANISM: Artificial Sequence
<220> FEATURE:
<223> OTHER INFORMATION: poly adenylation sequence (SV40 late polyA sequence)

<400> SEQUENCE: 5
cagacatgat aagatacatt gatgagtttg gacaaaccac aactagaatg cagtgaaaaa 60
aatgctttat ttgtgaaatt tgtgatgcta ttgctttatt tgtaaccatt ataagctgca 120
ataaacaagt taacaacaac aattgcattc attttatgtt tcaggttcag ggggaggtgt 180
gggaggtttt tt 192

<210> SEQ ID NO 6

-continued

<211> LENGTH: 551
<212> TYPE: DNA
<213> ORGANISM: Artificial Sequence
<220> FEATURE:
<223> OTHER INFORMATION: Internal Ribosome Entry Sequence (IRES)

<400> SEQUENCE: 6

```
cgttactggc cgaagccgct tggaataagg ccggtgtgcg tttgtctata tgttattttc     60

caccatattg ccgtcttttg gcaatgtgag ggcccggaaa cctggccctg tcttcttgac    120

gagcattcct aggggtcttt cccctctcgc caaaggaatg caaggtctgt tgaatgtcgt    180

gaaggaagca gttcctctgg aagcttcttg aagacaaaca acgtctgtag cgaccctttg    240

caggcagcgg aaccccccac ctggcgacag gtgcctctgc ggccaaaagc cacgtgtata    300

agatacacct gcaaaggcgg cacaacccca gtgccacgtt gtgagttgga tagttgtgga    360

aagagtcaaa tggctcccct caagcgtatt caacaagggg ctgaaggatg cccagaaggt    420

accccattgt atgggatctg atctggggcc tcggtgcaca tgcttttcat gtgtttagtc    480

gaggttaaaa aacgtctagg ccccccgaac cacggggacg tggttttcct ttgaaaaaca    540

cgatgataat a                                                         551
```

<210> SEQ ID NO 7
<211> LENGTH: 22
<212> TYPE: PRT
<213> ORGANISM: Artificial Sequence
<220> FEATURE:
<223> OTHER INFORMATION: High efficiency self-cleavable P2A peptide sequence

<400> SEQUENCE: 7

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 8
<211> LENGTH: 21
<212> TYPE: PRT
<213> ORGANISM: Artificial Sequence
<220> FEATURE:
<223> OTHER INFORMATION: High efficiency self-cleavable F2A peptide sequence

<400> SEQUENCE: 8

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 9
<211> LENGTH: 23
<212> TYPE: PRT
<213> ORGANISM: Artificial Sequence
<220> FEATURE:
<223> OTHER INFORMATION: High efficiency self-cleavable E2A peptide sequence

<400> SEQUENCE: 9

```
Gly Ser Gly Gln Cys Thr Asn Tyr Ala Leu Leu Lys Leu Ala Gly Asp
1               5                   10                  15

Val Glu Ser Asn Pro Gly Pro
            20
```

<210> SEQ ID NO 10
<211> LENGTH: 25
<212> TYPE: PRT
<213> ORGANISM: Artificial Sequence
<220> FEATURE:
<223> OTHER INFORMATION: High efficiency self-cleavable T2A peptide sequence

<400> SEQUENCE: 10

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 11
<211> LENGTH: 288
<212> TYPE: PRT
<213> ORGANISM: Artificial Sequence
<220> FEATURE:
<223> OTHER INFORMATION: Human CD80 amino acid sequence

<400> SEQUENCE: 11

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
```

275 280 285

<210> SEQ ID NO 12
<211> LENGTH: 188
<212> TYPE: PRT
<213> ORGANISM: Artificial Sequence
<220> FEATURE:
<223> OTHER INFORMATION: Human Interferona amino acid sequence

<400> SEQUENCE: 12

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185
```

<210> SEQ ID NO 13
<211> LENGTH: 179
<212> TYPE: PRT
<213> ORGANISM: Artificial Sequence
<220> FEATURE:
<223> OTHER INFORMATION: Human soluble Flt3 ligand amino acid sequence

<400> SEQUENCE: 13

```
Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110
```

-continued

```
Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro


<210> SEQ ID NO 14
<211> LENGTH: 93
<212> TYPE: PRT
<213> ORGANISM: Artificial Sequence
<220> FEATURE:
<223> OTHER INFORMATION: Human Macrophage Inflammatory protein 1a amino
      acid sequence (LD78b isoform)

<400> SEQUENCE: 14

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90


<210> SEQ ID NO 15
<211> LENGTH: 322
<212> TYPE: PRT
<213> ORGANISM: Artificial Sequence
<220> FEATURE:
<223> OTHER INFORMATION: Membrane anchored form of the anti-human CD3
      single chain Fv

<400> SEQUENCE: 15

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
```

130 135 140

Gly Gly Gly Ser Gly Gly Gly Gly Ser Asp Ile Val Leu Thr Gln Ser
145 150 155 160

Pro Ala Ile Met Ser Ala Ser Pro Gly Glu Lys Val Thr Met Thr Cys
165 170 175

Ser Ala Ser Ser Ser Val Ser Tyr Met Asn Trp Tyr Gln Gln Lys Ser
180 185 190

Gly Thr Ser Pro Lys Arg Trp Ile Tyr Asp Thr Ser Lys Leu Ala Ser
195 200 205

Gly Val Pro Ala His Phe Arg Gly Ser Gly Ser Gly Thr Ser Tyr Ser
210 215 220

Leu Thr Ile Ser Gly Met Glu Ala Glu Asp Ala Ala Thr Tyr Tyr Cys
225 230 235 240

Gln Gln Trp Ser Ser Asn Pro Phe Thr Phe Gly Ser Gly Thr Lys Leu
245 250 255

Glu Ile Asn Arg Gly Ser Glu Gln Lys Leu Ile Ser Glu Glu Asp Leu
260 265 270

Asn Ala Val Gly Gln Asp Thr Gln Glu Val Ile Val Val Pro His Ser
275 280 285

Leu Pro Phe Lys Val Val Val Ile Ser Ala Ile Leu Ala Leu Val Val
290 295 300

Leu Thr Ile Ile Ser Leu Ile Ile Leu Ile Met Leu Trp Gln Lys Lys
305 310 315 320

Pro Arg

<210> SEQ ID NO 16
<211> LENGTH: 33493
<212> TYPE: DNA
<213> ORGANISM: Artificial Sequence
<220> FEATURE:
<223> OTHER INFORMATION: NG-330 virus genome sequence comprising the EnAd genome with a transgene cassette that encodes the T lymphocyte activation antigen, CD80, inserted in the region By. The transgene cassette contains a 5' SSA, human CD80 cDNA sequence and a 3' poly(A)

<400> SEQUENCE: 16
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540
tctgcgccgg cagtttaata ataaaaaaat gagagatttg cgatttctgc ctcaggaaat 600
aatctctgct gagactggaa atgaaatatt ggagcttgtg gtgcacgccc tgatgggaga 660
cgatccggag ccacctgtgc agctttttga gcctcctacg cttcaggaac tgtatgattt 720
agaggtagag ggatcggagg attctaatga ggaagctgta aatggctttt ttaccgattc 780
tatgctttta gctgctaatg aagggttaga attagatccg cctttggaca cttttgatac 840

-continued

```
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
tttgatcac aatgtgatga cgaagtgtac catgcatgca ggtgggcgta gaggaatgtt    3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
```

-continued

```
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaacttttct  3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg ggtcaaaaa caagttttcc gccatatttt ttgatgcgtt tcttaccttt    5580
```

-continued

```
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tgggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
```

-continued

```
gcgttgcacg ggttgtatct cgtgaatgag ttgtacctgg cttcccttga cgagaaattt    8040
cagtgggaag ccgaggcctg gcgattgtat ctcgtgcttt actatgttgt ctgcatcggc    8100
ctgttcatct tctgtctcga tggtggtcat gctgacgagc cctcgcggga ggcaagtcca    8160
gacctcggcg cggcaggggc ggagctcgag gacgagagcg cgcaggctgg agctgtccag    8220
ggtcctgaga cgctgcggac tcaggttagt aggcagtgtc aggagattaa cttgcatgat    8280
cttttggagg gcgtgcggga ggttcagata gtacttgatc tcaacgggtc cgttggtgga    8340
gatgtcgatg gcttgcaggg ttccgtgtcc cttgggcgct accaccgtgc ccttgttttt    8400
cattttggac ggcggtggct ctgttgcttc ttgcatgttt agaagcggtg tcgagggcgc    8460
gcaccgggcg gcaggggcgg ctcgggaccc ggcggcatgg ctggcagtgg tacgtcggcg    8520
ccgcgcgcgg gtaggttctg gtactgcgcc ctgagaagac tcgcatgcgc gacgacgcgg    8580
cggttgacat cctggatctg acgcctctgg gtgaaagcta ccggccccgt gagcttgaac    8640
ctgaaagaga gttcaacaga atcaatctcg gtatcgttga cggcggcttg cctaaggatt    8700
tcttgcacgt caccagagtt gtcctggtag gcgatctccg ccatgaactg ctcgatctct    8760
tcctcttgaa gatctccgcg gcccgctctc tcgacggtgg ccgcgaggtc gttggagatg    8820
cgcccaatga gttgagagaa tgcattcatg cccgcctcgt tccagacgcg gctgtagacc    8880
acggccccca cgggatctct cgcgcgcatg accacctggg cgaggttgag ctccacgtgg    8940
cgggtgaaga ccgcatagtt gcataggcgc tggaaaaggt agttgagtgt ggtggcgatg    9000
tgctcggtga cgaagaaata catgatccat cgtctcagcg gcatctcgct gacatcgccc    9060
agagcttcca agcgctccat ggcctcgtag aagtccacgg caaaattaaa aaactgggag    9120
tttcgcgcgg acacggtcaa ctcctcttcc agaagacgga taagttcggc gatggtggtg    9180
cgcacctcgc gctcgaaagc ccctgggatt tcttcctcaa tctcttcttc ttccactaac    9240
atctcttcct cttcaggtgg ggctgcagga ggagggggaa cgcggcgacg ccggcggcgc    9300
acgggcagac ggtcgatgaa tctttcaatg acctctccgc ggcggcggcg catggtttca    9360
gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540
aacctttcga cgaaagcgtc taaccagtca cagtcacaag gtaggctgag tacggcttct    9600
tgtgggcggg ggtggttatg tgttcggtct gggtcttctg tttcttcttc atctcgggaa    9660
ggtgagacga tgctgctggt gatgaaatta aagtaggcag ttctaagacg gcggatggtg    9720
gcgaggagca ccaggtcttt gggtccggct tgctggatac gcaggcgatt ggccattccc    9780
caagcattat cctgacatct agcaagatct ttgtagtagt cttgcatgag ccgttctacg    9840
ggcacttctt cctcacccgt tctgccatgc atacgtgtga gtccaaatcc gcgcattggt    9900
tgtaccagtg ccaagtcagc tacgactctt tcggcgagga tggcttgctg tacttgggta    9960
agggtggctt gaaagtcatc aaaatccaca aagcggtggt aagctcctgt attaatggtg   10020
taagcacagt tggccatgac tgaccagtta actgtctggt gaccagggcg cacgagctcg   10080
gtgtatttaa ggcgcgaata ggcgcgggtg tcaaagatgt aatcgttgca ggtgcgcacc   10140
agatactggt accctataag aaaatgcggc ggtggttggc ggtagagagg ccatcgttct   10200
gtagctggag cgccaggggc gaggtcttcc aacataaggc ggtgatagcc gtagatgtac   10260
ctggacatcc aggtgattcc tgcggcggta gtagaagccc gaggaaactc gcgtacgcgg   10320
```

-continued

```
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat ccccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
```

-continued

```
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgccccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
```

-continued

```
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg ggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
```

-continued

```
ctggagcgac atcggcacga gccaactgaa cgggggcgcc ttcaattgga gcagtatctg  17520
gagcgggctt aaaaattttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
```

-continued

```
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
```

-continued

```
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
```

-continued

```
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
```

-continued

```
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa atttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
cccctttata aacccagggt ttatttcccc aaatggcttc acacaaagcc caaacggagt  28500
tcttacttta aaatgtttaa ccccactaac aaccacaggc ggatctctac agctaaaagt  28560
gggagggga cttacagtgg atgacaccaa cggtttttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
```

-continued

```
aacctctgct acaaccctag tcacctcccc atttaccttt tactacatca gagaagacga  29340
ctgacaaata aagtttgcga tcgccaggcc caccatgggc cacacacgga ggcagggaac  29400
atcaccatcc aagtgtccat acctcaattt ctttcagctc ttggtgctgg ctggtctttc  29460
tcacttctgt tcaggtgtta tccacgtgac caaggaagtg aaagaagtgg caacgctgtc  29520
ctgtggtcac aatgtttctg ttgaagagct ggcacaaact cgcatctact ggcaaaagga  29580
gaagaaaatg gtgctgacta tgatgtctgg ggacatgaat atatggcccg agtacaagaa  29640
ccggaccatc tttgatatca ctaataacct ctccattgtg atcctggctc tgcgcccatc  29700
tgacgagggc acatacgagt gtgttgttct gaagtatgaa aaagacgctt tcaagcggga  29760
acacctggct gaagtgacgt tatcagtcaa agctgacttc cctacaccta gtatatctga  29820
ctttgaaatt ccaacttcta atattagaag gataatttgc tcaacctctg gaggttttcc  29880
agagcctcac ctctcctggt tggaaaatgg agaagaatta aatgccatca acacaacagt  29940
ttcccaagat cctgaaactg agctctatgc tgttagcagc aaactggatt tcaatatgac  30000
aaccaaccac agcttcatgt gtctcatcaa gtatggacat ttaagagtga atcagacctt  30060
caactggaat acaaccaagc aagagcattt tcctgataac ctgctcccat cctgggccat  30120
taccttaatc tcagtaaatg gaatttttgt gatatgctgc ctgacctact gctttgcccc  30180
aagatgcaga gagagaagga ggaatgagag attgagaagg gaaagtgtac gccctgtata  30240
agctagcttg actgactgag atacagcgta ccttcagctc acagacatga taagatacat  30300
tgatgagttt ggacaaacca caactagaat gcagtgaaaa aaatgcttta tttgtgaaat  30360
ttgtgatgct attgctttat ttgtaaccat tataagctgc aataaacaag ttaacaacaa  30420
caattgcatt cattttatgt ttcaggttca gggggaggtg tgggaggttt tttaaagcaa  30480
gtaaaacctc tacaaatgtg gtagtcgtca gctatcctgc aggaacttgt ttatttgaaa  30540
atcaattcac aaaatccgag tagttatttt gcctccccct tcccatttaa cagaatacac  30600
caatctctcc ccacgcacag ctttaaacat ttggatacca ttagatatag acatggtttt  30660
agattccaca ttccaaacag tttcagagcg agccaatctg ggtcagtga tagataaaaa  30720
tccatcggga tagtctttta aagcgctttc acagtccaac tgctgcggat gcgactccgg  30780
agtctggatc acggtcatct ggaagaagaa cgatgggaat cataatccga aaacggtatc  30840
ggacgattgt gtctcatcaa acccacaagc agccgctgtc tgcgtcgctc cgtgcgactg  30900
ctgtttatgg gatcagggtc cacagtgtcc tgaagcatga ttttaatagc ccttaacatc  30960
aactttctgg tgcgatgcgc gcagcaacgc attctgattt cactcaaatc tttgcagtag  31020
gtacaacaca ttattacaat attgtttaat aaaccataat taaaagcgct ccagccaaaa  31080
ctcatatctg atataatcgc ccctgcatga ccatcatacc aaagtttaat ataaattaaa  31140
tgacgttccc tcaaaaacac actacccaca tacatgatct cttttggcat gtgcatatta  31200
acaatctgtc tgtaccatgg acaacgttgg ttaatcatgc aacccaatat aaccttccgg  31260
aaccacactg ccaacaccgc tcccccagcc atgcattgaa gtgaaccctg ctgattacaa  31320
tgacaatgaa gaacccaatt ctctcgaccg tgaatcactt gagaatgaaa aatatctata  31380
gtggcacaac atagacataa atgcatgcat cttctcataa tttttaactc ctcaggattt  31440
agaaacatat cccagggaat aggaagctct tgcagaacag taaagctggc agaacaagga  31500
agaccacgaa cacaacttac actatgcata gtcatagtat cacaatctgg caacagcggg  31560
tggtcttcag tcatagaagc tcgggtttca ttttcctcac aacgtggtaa ctgggctctg  31620
gtgtaagggt gatgtctggc gcatgatgtc gagcgtgcgc gcaaccttgt cataatggag  31680
```

ttgcttcctg acattctcgt attttgtata gcaaaacgcg gccctggcag aacacactct 31740
tcttcgcctt ctatcctgcc gcttagcgtg ttccgtgtga tagttcaagt acaaccacac 31800
tcttaagttg gtcaaaagaa tgctggcttc agttgtaatc aaaactccat cgcatctaat 31860
cgttctgagg aaatcatcca agcaatgcaa ctggattgtg tttcaagcag gagaggagag 31920
ggaagagacg gaagaaccat gttaattttt attccaaacg atctcgcagt acttcaaatt 31980
gtagatcgcg cagatggcat ctctcgcccc cactgtgttg gtgaaaaagc acagctagat 32040
caaaagaaat gcgattttca aggtgctcaa cggtggcttc cagcaaagcc tccacgcgca 32100
catccaagaa caaaagaata ccaaaagaag gagcattttc taactcctca atcatcatat 32160
tacattcctg caccattccc agataatttt cagctttcca gccttgaatt attcgtgtca 32220
gttcttgtgg taaatccaat ccacacatta caaacaggtc ccggagggcg ccctccacca 32280
ccattcttaa acacaccctc ataatgacaa aatatcttgc tcctgtgtca cctgtagcga 32340
attgagaatg gcaacatcaa ttgacatgcc cttggctcta agttcttctt taagttctag 32400
ttgtaaaaac tctctcatat tatcaccaaa ctgcttagcc agaagccccc cgggaacaag 32460
agcaggggac gctacagtgc agtacaagcg cagacctccc caattggctc cagcaaaaac 32520
aagattggaa taagcatatt gggaaccgcc agtaatatca tcgaagttgc tggaaatata 32580
atcaggcaga gtttcttgta aaaattgaat aaaagaaaaa tttgccaaaa aaacattcaa 32640
aacctctggg atgcaaatgc aataggttac cgcgctgcgc tccaacattg ttagttttga 32700
attagtctgc aaaaataaaa aaaaaaacaa gcgtcatatc atagtagcct gacgaacaga 32760
tggataaatc agtctttcca tcacaagaca agccacaggg tctccagctc gaccctcgta 32820
aaacctgtca tcatgattaa acaacagcac cgaaagttcc tcgcggtgac cagcatgaat 32880
aattcttgat gaagcataca atccagacat gttagcatca gttaacgaga aaaaacagcc 32940
aacatagcct ttgggtataa ttatgcttaa tcgtaagtat agcaaagcca cccctcgcgg 33000
atacaaagta aaaggcacag gagaataaaa aatataatta tttctctgct gctgttcagg 33060
caacgtcgcc cccggtccct ctaaatacac atacaaagcc tcatcagcca tggcttacca 33120
gacaaagtac agcgggcaca caaagcacaa gctctaaagt gactctccaa cctctccaca 33180
atatatatat acacaagccc taaactgacg taatgggagt aaagtgtaaa aaatcccgcc 33240
aaacccaaca cacaccccga aactgcgtca ccagggaaaa gtacagtttc acttccgcaa 33300
tcccaacagg cgtaacttcc tctttctcac ggtacgtgat atcccactaa cttgcaacgt 33360
cattttccca cggtcgcacc gccccttta gccgttaacc ccacagccaa tcaccacacg 33420
atccacactt tttaaaatca cctcatttac atattggcac cattccatct ataaggtata 33480
ttatatagat aga 33493

<210> SEQ ID NO 17
<211> LENGTH: 34119
<212> TYPE: DNA
<213> ORGANISM: Artificial Sequence
<220> FEATURE:
<223> OTHER INFORMATION: NG-343 virus genome sequence comprising the EnAd genome with a transgene cassette that encodes IFNa, and CD80, inserted in the region By. The transgene cassette contains a 5' SSA, IFNa cDNA sequence, P2A peptide, CD80 cDNA sequence and a 3' poly(A)

<400> SEQUENCE: 17
tctatctata taatatacct tatagatgga atggtgccaa tatgtaaatg aggtgatttt 60

-continued

```
aaaaagtgtg gatcgtgtgg tgattggctg tggggttaac ggctaaaagg ggcggtgcga    120
ccgtgggaaa atgacgtttt gtgggggtgg agtttttttg caagttgtcg cgggaaatgt    180
gacgcataaa aaggcttttt tctcacggaa ctacttagtt ttcccacggt atttaacagg    240
aaatgaggta gttttgaccg gatgcaagtg aaaattgttg attttcgcgc gaaaactgaa    300
tgaggaagtg tttttctgaa taatgtggta tttatggcag ggtggagtat ttgttcaggg    360
ccaggtagac tttgacccat tacgtggagg tttcgattac cgtgtttttt acctgaattt    420
ccgcgtaccg tgtcaaagtc ttctgttttt acgtaggtgt cagctgatcg ctagggtatt    480
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
```

acagtataag attactagac ggattaatat ccggaatgct tgttacatat ctggaaatgg 2520
ggctgaggtg gtaatagata ctcaagacaa ggcagttatt agatgctgca tgatggatat 2580
gtggcctggg gtagtcggta tggaagcagt aacttttgta aatgttaagt ttaggggaga 2640
tggttataat ggaatagtgt ttatggccaa taccaaactt atattgcatg gttgtagctt 2700
ttttggtttc aacaatacct gtgtagatgc ctggggacag gttagtgtac ggggatgtag 2760
tttctatgcg tgttggattg ccacagctgg cagaaccaag agtcaattgt ctctgaagaa 2820
atgcatattt caaagatgta acctgggcat tctgaatgaa ggcgaagcaa gggtccgcca 2880
ctgcgcttct acagatactg gatgttttat tttgattaag ggaaatgcca gcgtaaagca 2940
taacatgatt tgcggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgatga cgaagtgtac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tttttgacat gaacatgcaa atctggaaga tcctgaggta 3240
tgatgatacg agatcgaggg tacgcgcatg cgaatgcgga ggcaagcatg ccaggttcca 3300
gccggtgtgt gtagatgtga ctgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctg tcttgcagct 3480
gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaacttttct 3840
cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800

-continued cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg ggtccccgc 5880 tggggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060
tttcatgagg ttttcgtcca tctggtcaga aaacacaatt tttttattgt caagtttggt 6120
ggcaaatgat ccatacaggg cgttggataa aagtttggca atggatcgca tggtttggtt 6180
cttttccttg tccgcgcgct ctttggcggc gatgttgagt tggacatact cgcgtgccag 6240
gcacttccat tcggggaaga tagttgttaa ttcatctggc acgattctca cttgccaccc 6300
tcgattatgc aaggtaatta aatccacact ggtggccacc tcgcctcgaa ggggttcatt 6360
ggtccaacag agcctacctc ctttcctaga acagaaaggg ggaagtgggt ctagcataag 6420
ttcatcggga gggtctgcat ccatggtaaa gattcccgga agtaaatcct tatcaaaata 6480
gctgatggga gtggggtcat ctaaggccat ttgccattct cgagctgcca gtgcgcgctc 6540
atatgggtta aggggactgc cccatggcat gggatgggtg agtgcagagg catacatgcc 6600
acagatgtca tagacgtaga tgggatcctc aaagatgcct atgtaggttg gatagcatcg 6660 ccccccctctg atacttgctc gcacatagtc atatagttca tgtgatggcg ctagcagccc 6720
cggacccaag ttggtgcgat tgggtttttc tgttctgtag acgatctggc gaaagatggc 6780
gtgagaattg gaagagatgg tgggtctttg aaaaatgttg aaatgggcat gaggtagacc 6840
tacagagtct ctgacaaagt gggcataaga ttcttgaagc ttggttacca gttcggcggt 6900
gacaagtacg tctagggcgc agtagtcaag tgtttcttga atgatgtcat aacctggttg 6960
gtttttcttt tcccacagtt cgcggttgag aaggtattct tcgcgatcct tccagtactc 7020
ttctagcgga aacccgtctt tgtctgcacg gtaagatcct agcatgtaga actgattaac 7080
tgccttgtaa gggcagcagc ccttctctac gggtagagag tatgcttgag cagcttttcg 7140
tagcgaagcg tgagtaaggg caaaggtgtc tctgaccatg actttgagga attggtattt 7200

```
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
```

-continued

```
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
```

-continued

```
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgccccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
```

ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccccctc gcacttagaa 15960
gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg gggtacaaa ctgtagacat taagattccc actgaaagta tggaagtgca 16680

-continued

```
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
```

-continued

```
atcagaaagt cgaatatgat atcgacatgg agtttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
```

agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760

-continued

```
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
```

accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
cccctttata aacccagggt ttatttcccc aaatggcttc acacaaagcc caaacggagt 28500

-continued

```
tcttacttta aaatgtttaa ccccactaac aaccacaggc ggatctctac agctaaaagt  28560
gggaggggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc accatggcct tgacctttgc tttactggtg  29400
gccctcctgg tgctcagctg caagtcaagc tgctctgtgg gctgtgatct gcctcaaacc  29460
cacagcctgg gtagcaggag gaccttgatg ctcctggcac agatgaggag aatctctctt  29520
ttctcctgct tgaaggacag acatgacttt ggatttcccc aggaggagtt tggcaaccag  29580
ttccaaaagg ctgaaaccat ccctgtcctc catgagatga tccagcagat cttcaatctc  29640
ttcagcacaa aggactcatc tgctgcttgg gatgagaccc tcctagacaa attctacact  29700
gaactctacc agcagctgaa tgacctggaa gcctgtgtga tacagggggt gggggtgaca  29760
gagactcccc tgatgaagga ggactccatt ctggctgtga ggaaatactt ccaaagaatc  29820
actctctatc tgaaagagaa gaaatacagc ccttgtgcct gggaggttgt cagagcagaa  29880
atcatgagat ctttttcttt gtcaacaaac ttgcaagaaa gtttaagaag taaggaagga  29940
agcggagcta ctaacttcag cctgctgaag caggctggag acgtggagga gaaccctgga  30000
cctggccaca cacggaggca gggaacatca ccatccaagt gtccatacct caatttcttt  30060
cagctcttgg tgctggctgg tctttctcac ttctgttcag gtgttatcca cgtgaccaag  30120
gaagtgaaag aagtggcaac gctgtcctgt ggtcacaatg tttctgttga agagctggca  30180
caaactcgca tctactggca aaaggagaag aaaatggtgc tgactatgat gtctggggac  30240
atgaatatat ggcccgagta caagaaccgg accatctttg atatcactaa taacctctcc  30300
attgtgatcc tggctctgcg cccatctgac gagggcacat acgagtgtgt tgttctgaag  30360
tatgaaaaag acgctttcaa gcgggaacac ctggctgaag tgacgttatc agtcaaagct  30420
gacttcccta cacctagtat atctgacttt gaaattccaa cttctaatat tagaaggata  30480
atttgctcaa cctctggagg ttttccagag cctcacctct cctggttgga aaatggagaa  30540
gaattaaatg ccatcaacac aacagtttcc caagatcctg aaactgagct ctatgctgtt  30600
agcagcaaac tggatttcaa tatgacaacc aaccacagct tcatgtgtct catcaagtat  30660
ggacatttaa gagtgaatca gaccttcaac tggaatacaa ccaagcaaga gcattttcct  30720
gataacctgc tcccatcctg ggccattacc ttaatctcag taaatggaat ttttgtgata  30780
tgctgcctga cctactgctt tgccccaaga tgcagagaga gaaggaggaa tgagagattg  30840
agaagggaaa gtgtacgccc tgtataagct agcttgactg actgagatac agcgtacctt  30900
```

```
cagctcacag acatgataag atacattgat gagtttggac aaaccacaac tagaatgcag  30960
tgaaaaaaat gctttatttg tgaaatttgt gatgctattg ctttatttgt aaccattata  31020
agctgcaata aacaagttaa caacaacaat tgcattcatt ttatgtttca ggttcagggg  31080
gaggtgtggg aggtttttta aagcaagtaa aacctctaca aatgtggtag tcgtcagcta  31140
tcctgcagga acttgtttat ttgaaaatca attcacaaaa tccgagtagt tattttgcct  31200
ccccccttccc atttaacaga atacaccaat ctctccccac gcacagcttt aaacatttgg  31260
ataccattag atatagacat ggttttagat tccacattcc aaacagtttc agagcgagcc  31320
aatctggggt cagtgataga taaaaatcca tcgggatagt cttttaaagc gctttcacag  31380
tccaactgct gcggatgcga ctccggagtc tggatcacgg tcatctggaa gaagaacgat  31440
gggaatcata atccgaaaac ggtatcggac gattgtgtct catcaaaccc acaagcagcc  31500
gctgtctgcg tcgctccgtg cgactgctgt ttatgggatc agggtccaca gtgtcctgaa  31560
gcatgatttt aatagccctt aacatcaact ttctggtgcg atgcgcgcag caacgcattc  31620
tgatttcact caaatctttg cagtaggtac aacacattat tacaatattg tttaataaac  31680
cataattaaa agcgctccag ccaaaactca tatctgatat aatcgcccct gcatgaccat  31740
cataccaaag tttaatataa attaaatgac gttccctcaa aaacacacta cccacataca  31800
tgatctcttt tggcatgtgc atattaacaa tctgtctgta ccatggacaa cgttggttaa  31860
tcatgcaacc caatataacc ttccggaacc acactgccaa caccgctccc ccagccatgc  31920
attgaagtga accctgctga ttacaatgac aatgaagaac ccaattctct cgaccgtgaa  31980
tcacttgaga atgaaaaata tctatagtgg cacaacatag acataaatgc atgcatcttc  32040
tcataatttt taactcctca ggatttagaa acatatccca gggaatagga agctcttgca  32100
gaacagtaaa gctggcagaa caaggaagac cacgaacaca acttacacta tgcatagtca  32160
tagtatcaca atctggcaac agcgggtggt cttcagtcat agaagctcgg gtttcatttt  32220
cctcacaacg tggtaactgg gctctggtgt aagggtgatg tctggcgcat gatgtcgagc  32280
gtgcgcgcaa ccttgtcata atggagttgc ttcctgacat tctcgtattt tgtatagcaa  32340
aacgcggccc tggcagaaca cactcttctt cgccttctat cctgccgctt agcgtgttcc  32400
gtgtgatagt tcaagtacaa ccacactctt aagttggtca aaagaatgct ggcttcagtt  32460
gtaatcaaaa ctccatcgca tctaatcgtt ctgaggaaat catccaagca atgcaactgg  32520
attgtgtttc aagcaggaga ggagagggaa gagacggaag aaccatgtta atttttattc  32580
caaacgatct cgcagtactt caaattgtag atcgcgcaga tggcatctct cgcccccact  32640
gtgttggtga aaaagcacag ctagatcaaa agaaatgcga ttttcaaggt gctcaacggt  32700
ggcttccagc aaagcctcca cgcgcacatc caagaacaaa agaataccaa aagaaggagc  32760
attttctaac tcctcaatca tcatattaca ttcctgcacc attcccagat aattttcagc  32820
tttccagcct tgaattattc gtgtcagttc ttgtggtaaa tccaatccac acattacaaa  32880
caggtcccgg agggcgccct ccaccaccat tcttaaacac accctcataa tgacaaaata  32940
tcttgctcct gtgtcacctg tagcgaattg agaatggcaa catcaattga catgcccttg  33000
gctctaagtt cttctttaag ttctagttgt aaaaactctc tcatattatc accaaactgc  33060
ttagccagaa gcccccccggg aacaagagca ggggacgcta cagtgcagta caagcgcaga  33120
cctccccaat tggctccagc aaaaacaaga ttggaataag catattggga accgccagta  33180
atatcatcga agttgctgga aatataatca ggcagagttt cttgtaaaaa ttgaataaaa  33240
```

```
gaaaaatttg ccaaaaaaac attcaaaacc tctgggatgc aaatgcaata ggttaccgcg  33300

ctgcgctcca acattgttag ttttgaatta gtctgcaaaa ataaaaaaaa aaacaagcgt  33360

catatcatag tagcctgacg aacagatgga taaatcagtc tttccatcac aagacaagcc  33420

acagggtctc cagctcgacc ctcgtaaaac ctgtcatcat gattaaacaa cagcaccgaa  33480

agttcctcgc ggtgaccagc atgaataatt cttgatgaag catacaatcc agacatgtta  33540

gcatcagtta acgagaaaaa acagccaaca tagcctttgg gtataattat gcttaatcgt  33600

aagtatagca aagccacccc tcgcggatac aaagtaaaag gcacaggaga ataaaaaata  33660

taattatttc tctgctgctg ttcaggcaac gtcgcccccg gtccctctaa atacacatac  33720

aaagcctcat cagccatggc ttaccagaca aagtacagcg ggcacacaaa gcacaagctc  33780

taaagtgact ctccaacctc tccacaatat atatatacac aagccctaaa ctgacgtaat  33840

gggagtaaag tgtaaaaaat cccgccaaac ccaacacaca ccccgaaact gcgtcaccag  33900

ggaaaagtac agtttcactt ccgcaatccc aacaggcgta acttcctctt tctcacggta  33960

cgtgatatcc cactaacttg caacgtcatt ttcccacggt cgcaccgccc cttttagccg  34020

ttaaccccac agccaatcac cacacgatcc acacttttta aaatcacctc atttacatat  34080

tggcaccatt ccatctataa ggtatattat atagataga                         34119


<210> SEQ ID NO 18
<211> LENGTH: 34131
<212> TYPE: DNA
<213> ORGANISM: Artificial Sequence
<220> FEATURE:
<223> OTHER INFORMATION: NG-345 virus genome sequence comprising the
      EnAd genome with a transgene cassette that encodes Flt3 Ligand,
      MIP1a and IFNa, inserted in the region BY. The transgene cassette
      contains a 5' SSA, Flt3 Ligand cDNA , P2A peptide sequence, MIP1a
      cDNA sequence

<400> SEQUENCE: 18

tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540

tctgcgccgg cagtttaata ataaaaaaat gagagatttg cgatttctgc ctcaggaaat    600

aatctctgct gagactggaa atgaaatatt ggagcttgtg gtgcacgccc tgatgggaga    660

cgatccggag ccacctgtgc agctttttga gcctcctacg cttcaggaac tgtatgattt    720

agaggtagag ggatcggagg attctaatga ggaagctgta aatggctttt ttaccgattc    780

tatgctttta gctgctaatg aagggttaga attagatccg cctttggaca cttttgatac    840

tccaggggta attgtggaaa gcggtacagg tgtaagaaaa ttacctgatt tgagttccgt    900

ggactgtgat ttgcactgct atgaagacgg gtttcctccg agtgatgagg aggaccatga    960

aaaggagcag tccatgcaga ctgcagcggg tgagggagtg aaggctgcca atgttggttt   1020

tcagttggat tgcccggagc ttcctggaca tggctgtaag tcttgtgaat ttcacaggaa   1080
```

-continued

```
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg atagggggcgt  2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
```

-continued

```
tggggtggga ttttcagatg gacagattga gtaaaaattt gtttttctg tcttgcagct   3480

gtcatgagtg gaaacgcttc ttttaagggg ggagtcttca gcccttatct gacagggcgt   3540

ctcccatcct gggcaggagt tcgtcagaat gttatgggat ctactgtgga tggaagaccc   3600

gtccaacccg ccaattcttc aacgctgacc tatgctactt taagttcttc acctttggac   3660

gcagctgcag ctgccgccgc cgcttctgtt gccgctaaca ctgtgcttgg aatgggttac   3720

tatggaagca tcatggctaa ttccacttcc tctaataacc cttctaccct gactcaggac   3780

aagttacttg tccttttggc ccagctggag gctttgaccc aacgtctggg tgaacttttct   3840

cagcaggtgg tcgagttgcg agtacaaact gagtctgctg tcggcacggc aaagtctaaa   3900

taaaaaaatc ccagaatcaa tgaataaata aacaagcttg ttgttgattt aaaatcaagt   3960

gtttttattt catttttcgc gcacggtatg ccctagacca ccgatctcta tcattgagaa   4020

ctcggtggat tttttccagg atcctataga ggtgggattg aatgtttaga tacatgggca   4080

ttaggccgtc tttggggtgg agatagctcc attgaaggga ttcatgctcc ggggtagtgt   4140

tgtaaatcac ccagtcataa caaggtcgca gtgcatggtg ttgcacaata tcttttagaa   4200

gtaggctgat tgccacagat aagcccttgg tgtaggtgtt tacaaaccgg ttgagctggg   4260

atgggtgcat tcggggtgaa attatgtgca ttttggattg gatttttaag ttggcaatat   4320

tgccgccaag atcccgtctt gggttcatgt tatgaaggac caccaagacg gtgtatccgg   4380

tacatttagg aaatttatcg tgcagcttgg atggaaaagc gtggaaaaat ttggagacac   4440

ccttgtgtcc tccaagattt tccatgcact catccatgat aatagcaatg gggccgtggg   4500

cagcggcgcg ggcaaacacg ttccgtgggt ctgacacatc atagttatgt tcctgagtta   4560

aatcatcata agccatttta atgaatttgg ggcggagagt accagattgg ggtatgaatg   4620

ttccttcggg ccccggagca tagttcccct cacagatttg catttcccaa gctttcagtt   4680

ccgagggtgg aatcatgtcc acctgggggg ctatgaaaaa caccgtttct ggggcggggg   4740

tgattaattg tgatgatagc aaatttctga gcaattgaga tttgccacat ccggtggggc   4800

cataaatgat tccgattacg ggttgcaggt ggtagtttag ggaacggcaa ctgccgtctt   4860

ctcgaagcaa gggggccacc tcgttcatca tttcccttac atgcatattt tcccgcacca   4920

aatccattag gaggcgctct cctcctagtg atagaagttc ttgtagtgag gaaaagtttt   4980

tcagcggttt cagaccgtca gccatgggca ttttggagag agtttgctgc aaaagttcta   5040

gtctgttcca cagttcagtg atgtgttcta tggcatctcg atccagcaga cctcctcgtt   5100

tcgcgggttt ggacggctcc tggaataggg tatgagacga tgggcgtcca gcgctgccag   5160

ggttcggtcc ttccagggtc tcagtgttcg agtcagggtt gtttccgtca cagtgaaggg   5220

gtgtgcgcct gcttgggcgc ttgccagggt gcgcttcaga ctcatcctgc tggtcgaaaa   5280

cttctgtcgc ttggcgccct gtatgtcggc caagtagcag tttaccatga gttcgtagtt   5340

gagcgcctcg gctgcgtggc ctttggcgcg gagcttacct ttggaagttt tcttgcatac   5400

cgggcagtat aggcatttca gcgcatacaa cttgggcgca aggaaaacgg attctgggga   5460

gtatgcatct gcgccgcagg aggcgcaaac agtttcacat tccaccagcc aggttaaatc   5520

cggttcattg gggtcaaaaa caagttttcc gccatatttt ttgatgcgtt tcttaccttt   5580

ggtctccatg agttcgtgtc ctcgttgagt gacaaacagg ctgtccgtgt ccccgtagac   5640

tgattttaca ggcctcttct ccagtggagt gcctcggtct tcttcgtaca ggaactctga   5700

ccactctgat acaaaggcgc gcgtccaggc cagcacaaag gaggctatgt gggaggggta   5760

gcgatcgttg tcaaccaggg ggtccacctt ttccaaagta tgcaaacaca tgtcaccctc   5820
```

-continued

```
ttcaacatcc aggaatgtga ttggcttgta ggtgtatttc acgtgacctg ggtccccgc   5880
tgggggggta taaaaggggg cggttctttg ctcttcctca ctgtcttccg gatcgctgtc  5940
caggaacgtc agctgttggg gtaggtattc cctctcgaag gcgggcatga cctctgcact  6000
caggttgtca gtttctaaga acgaggagga tttgatattg acagtgccgg ttgagatgcc  6060
tttcatgagg ttttcgtcca tctggtcaga aaacacaatt tttttattgt caagtttggt  6120
ggcaaatgat ccatacaggg cgttggataa aagtttggca atggatcgca tggtttggtt  6180
cttttccttg tccgcgcgct ctttggcggc gatgttgagt tggacatact cgcgtgccag  6240
gcacttccat tcggggaaga tagttgttaa ttcatctggc acgattctca cttgccaccc  6300
tcgattatgc aaggtaatta aatccacact ggtggccacc tcgcctcgaa ggggttcatt  6360
ggtccaacag agcctacctc ctttcctaga acagaaaggg ggaagtgggt ctagcataag  6420
ttcatcggga gggtctgcat ccatggtaaa gattcccgga agtaaatcct tatcaaaata  6480
gctgatggga gtggggtcat ctaaggccat ttgccattct cgagctgcca gtgcgcgctc  6540
atatgggtta aggggactgc cccatggcat gggatgggtg agtgcagagg catacatgcc  6600
acagatgtca tagacgtaga tgggatcctc aaagatgcct atgtaggttg gatagcatcg  6660
ccccctctg atacttgctc gcacatagtc atatagttca tgtgatggcg ctagcagccc   6720
cggacccaag ttggtgcgat tgggtttttc tgttctgtag acgatctggc gaaagatggc  6780
gtgagaattg gaagagatgg tgggtctttg aaaaatgttg aaatgggcat gaggtagacc  6840
tacagagtct ctgacaaagt gggcataaga ttcttgaagc ttggttacca gttcggcggt  6900
gacaagtacg tctagggcgc agtagtcaag tgtttcttga atgatgtcat aacctggttg  6960
gtttttcttt tcccacagtt cgcggttgag aaggtattct tcgcgatcct tccagtactc  7020
ttctagcgga aacccgtctt tgtctgcacg gtaagatcct agcatgtaga actgattaac  7080
tgccttgtaa gggcagcagc ccttctctac gggtagagag tatgcttgag cagcttttcg  7140
tagcgaagcg tgagtaaggg caaaggtgtc tctgaccatg actttgagga attggtattt  7200
gaagtcgatg tcgtcacagg ctccctgttc ccagagttgg aagtctaccc gtttcttgta  7260
ggcggggttg ggcaaagcga aagtaacatc attgaagaga atcttgccgg ccctgggcat  7320
gaaattgcga gtgatgcgaa aaggctgtgg tacttccgct cggttattga taacctgggc  7380
agctaggacg atctcgtcga aaccgttgat gttgtgtcct acgatgtata attctatgaa  7440
acgcggcgtg cctctgacgt gaggtagctt actgagctca tcaaaggtta ggtctgtggg  7500
gtcagataag gcgtagtgtt cgagagccca ttcgtgcagg tgaggattcg ctttaaggaa  7560
ggaggaccag aggtccactg ccagtgctgt ttgtaactgg tcccggtact gacgaaaatg  7620
ccgtccgact gccatttttt ctggggtgac gcaatagaag gtttgggggt cctgccgcca  7680
gcgatcccac ttgagtttta tggcgaggtc ataggcgatg ttgacgagcc gctggtctcc  7740
agagagtttc atgaccagca tgaaggggat tagctgcttg ccaaaggacc ccatccaggt  7800
gtaggtttcc acatcgtagg tgagaaagag cctttctgtg cgaggatgag agccaatcgg  7860
gaagaactgg atctcctgcc accagttgga ggaatggctg ttgatgtgat ggaagtagaa  7920
ctccctgcga cgcgccgagc attcatgctt gtgcttgtac agacggccgc agtagtcgca  7980
gcgttgcacg ggttgtatct cgtgaatgag ttgtacctgg cttcccttga cgagaaattt  8040
cagtgggaag ccgaggcctg gcgattgtat ctcgtgcttt actatgttgt ctgcatcggc  8100
ctgttcatct tctgtctcga tggtggtcat gctgacgagc cctcgcggga ggcaagtcca  8160
```

-continued

```
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
```

acaaaaatcc aggatacgga atcgagtcgt tttgctggtt tccgaatggc agggaagtga 10620
gtcctatttt tttttttgc cgctcagatg catcccgtgc tgcgacagat gcgcccccaa 10680
caacagcccc cctcgcagca gcagcagcag caatcacaaa aggctgtccc tgcaactact 10740
gcaactgccg ccgtgagcgg tgcgggacag cccgcctatg atctggactt ggaagagggc 10800
gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900

-continued

```
catgtatgcc agtaaccgac ctttcattaa caaactgctg gactacttgc acagagctgc  12960
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
```

cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg ggcgaagag ccatgcttag 15780 ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtccccctc gcacttagaa 15960
gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg gggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220
gttttttacc agccttaatt ccaattatcg ctgctgcaat tggcgcgata ccaggcatag 17280
cttccgtggc ggttcaggcc tcgcaacgac attgacattg gaaaaaaacg tataaataaa 17340
aaaaaaaaaa tacaatggac tctgacactc ctggtcctgt gactatgttt tcttagagat 17400
ggaagacatc aatttttcat ccttggctcc gcgacacggc acgaagccgt acatgggcac 17460
ctggagcgac atcggcacga gccaactgaa cgggggcgcc ttcaattgga gcagtatctg 17520
gagcgggctt aaaaatttgg gctcaaccat aaaaacatac gggaacaaag cttggaacag 17580
cagtacagga caggcgctta gaaataaact taaagaccag aacttccaac aaaaagtagt 17640

-continued

```
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
```

```
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac cctactttg   20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
```

caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa actttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac caccccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aacccccgctc gggcggaatc gggaccgttc 27060
aatttgtgga ggagtttact ccctctgtct acttcaaccc cttctccgga tctcctgggc 27120

-continued attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa atttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
cccctttata aacccagggt ttatttcccc aaatggcttc acacaaagcc caaacggagt 28500
tcttacttta aaatgtttaa ccccactaac aaccacaggc ggatctctac agctaaaagt 28560
gggagggga cttacagtgg atgacaccaa cggtttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct ttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc accatgacag tgctggcgcc agcctggagc 29400
ccaacaacct atctcctcct gctgctgctg ctgagctcgg gactcagtgg gacccaggac 29460
tgctccttcc aacacagccc catctcctcc gacttcgctg tcaaaatccg tgagctgtct 29520

-continued

```
gactacctgc ttcaagatta cccagtcacc gtggcctcca acctccagga cgaggagctc  29580
tgcgggggcc tctggcggct ggtcctggca cagcgctgga tggagcggct caagactgtc  29640
gctgggtcca agatgcaagg cttgctggag cgcgtgaaca cggagataca ctttgtcacc  29700
aaatgtgcct ttcagccccc ccccagctgt cttcgcttcg tccagaccaa catctcccgc  29760
ctcctacagg agacctccga gcagctggtg gcgctgaagc cctggatcac tcgccagaac  29820
ttctcccggt gcctggagct gcagtgtcag cccgactcct caaccctgcc acccccatgg  29880
agtccccggc ccctggaggc cacagccccg ggaagcggag ctactaactt cagcctgctg  29940
aagcaggctg gagacgtgga ggagaaccct ggacctcagg tctccactgc tgcccttgcc  30000
gtcctcctct gcaccatggc tctctgcaac caggtcctct ctgcaccact tgctgctgac  30060
acgccgaccg cctgctgctt cagctacacc tcccgacaga ttccacagaa tttcatagct  30120
gactactttg agacgagcag ccagtgctcc aagcccagtg tcatcttcct aaccaagaga  30180
ggccggcagg tctgtgctga ccccagtgag gagtgggtcc agaaatacgt cagtgacctg  30240
gagctgagtg ccggaagcgg agagggcaga ggaagtctgc taacatgcgg tgacgtcgag  30300
gagaatcctg gacctgcctt gacctttgct ttactggtgg ccctcctggt gctcagctgc  30360
aagtcaagct gctctgtggg ctgtgatctg cctcaaaccc acagcctggg tagcaggagg  30420
accttgatgc tcctggcaca gatgaggaga atctctcttt tctcctgctt gaaggacaga  30480
catgactttg gatttcccca ggaggagttt ggcaaccagt tccaaaaggc tgaaaccatc  30540
cctgtcctcc atgagatgat ccagcagatc ttcaatctct tcagcacaaa ggactcatct  30600
gctgcttggg atgagaccct cctagacaaa ttctacactg aactctacca gcagctgaat  30660
gacctggaag cctgtgtgat acaggggggtg ggggtgacag agactcccct gatgaaggag  30720
gactccattc tggctgtgag gaaatacttc caaagaatca ctctctatct gaaagagaag  30780
aaatacagcc cttgtgcctg ggaggttgtc agagcagaaa tcatgagatc tttttctttg  30840
tcaacaaact tgcaagaaag tttaagaagt aaggaataag ctagcttgac tgactgagat  30900
acagcgtacc ttcagctcac agacatgata agatacattg atgagtttgg acaaaccaca  30960
actagaatgc agtgaaaaaa atgctttatt tgtgaaattt gtgatgctat tgctttattt  31020
gtaaccatta taagctgcaa taaacaagtt aacaacaaca attgcattca ttttatgttt  31080
caggttcagg gggaggtgtg ggaggttttt taaagcaagt aaaacctcta caaatgtggt  31140
agtcgtcagc tatcctgcag gaacttgttt atttgaaaat caattcacaa aatccgagta  31200
gttattttgc ctcccccttc ccatttaaca gaatacacca atctctcccc acgcacagct  31260
ttaaacattt ggataccatt agatatagac atggttttag attccacatt ccaaacagtt  31320
tcagagcgag ccaatctggg gtcagtgata gataaaaatc catcgggata gtcttttaaa  31380
gcgctttcac agtccaactg ctgcggatgc gactccggag tctggatcac ggtcatctgg  31440
aagaagaacg atgggaatca taatccgaaa acggtatcgg acgattgtgt ctcatcaaac  31500
ccacaagcag ccgctgtctg cgtcgctccg tgcgactgct gtttatggga tcagggtcca  31560
cagtgtcctg aagcatgatt ttaatagccc ttaacatcaa ctttctggtg cgatgcgcgc  31620
agcaacgcat tctgatttca ctcaaatctt tgcagtaggt acaacacatt attacaatat  31680
tgtttaataa accataatta aaagcgctcc agccaaaact catatctgat ataatcgccc  31740
ctgcatgacc atcataccaa agtttaatat aaattaaatg acgttccctc aaaaacacac  31800
tacccacata catgatctct tttggcatgt gcatattaac aatctgtctg taccatggac  31860
```

-continued

```
aacgttggtt aatcatgcaa cccaatataa ccttccggaa ccacactgcc aacaccgctc  31920
ccccagccat gcattgaagt gaaccctgct gattacaatg acaatgaaga acccaattct  31980
ctcgaccgtg aatcacttga gaatgaaaaa tatctatagt ggcacaacat agacataaat  32040
gcatgcatct tctcataatt tttaactcct caggatttag aaacatatcc cagggaatag  32100
gaagctcttg cagaacagta aagctggcag aacaaggaag accacgaaca caacttacac  32160
tatgcatagt catagtatca caatctggca acagcgggtg gtcttcagtc atagaagctc  32220
gggtttcatt ttcctcacaa cgtggtaact gggctctggt gtaagggtga tgtctggcgc  32280
atgatgtcga gcgtgcgcgc aaccttgtca taatggagtt gcttcctgac attctcgtat  32340
tttgtatagc aaaacgcggc cctggcagaa cacactcttc ttcgccttct atcctgccgc  32400
ttagcgtgtt ccgtgtgata gttcaagtac aaccacactc ttaagttggt caaaagaatg  32460
ctggcttcag ttgtaatcaa aactccatcg catctaatcg ttctgaggaa atcatccaag  32520
caatgcaact ggattgtgtt tcaagcagga gaggagaggg aagagacgga agaaccatgt  32580
taatttttat tccaaacgat ctcgcagtac ttcaaattgt agatcgcgca gatggcatct  32640
ctcgcccccca ctgtgttggt gaaaaagcac agctagatca aaagaaatgc gattttcaag  32700
gtgctcaacg gtggcttcca gcaaagcctc cacgcgcaca tccaagaaca aaagaatacc  32760
aaaagaagga gcattttcta actcctcaat catcatatta cattcctgca ccattcccag  32820
ataattttca gctttccagc cttgaattat tcgtgtcagt tcttgtggta aatccaatcc  32880
acacattaca aacaggtccc ggagggcgcc ctccaccacc attcttaaac acaccctcat  32940
aatgacaaaa tatcttgctc ctgtgtcacc tgtagcgaat tgagaatggc aacatcaatt  33000
gacatgccct tggctctaag ttcttcttta agttctagtt gtaaaaactc tctcatatta  33060
tcaccaaact gcttagccag aagccccccg ggaacaagag caggggacgc tacagtgcag  33120
tacaagcgca gacctcccca attggctcca gcaaaaacaa gattggaata agcatattgg  33180
gaaccgccag taatatcatc gaagttgctg gaaatataat caggcagagt ttcttgtaaa  33240
aattgaataa aagaaaaatt tgccaaaaaa acattcaaaa cctctgggat gcaaatgcaa  33300
taggttaccg cgctgcgctc caacattgtt agttttgaat tagtctgcaa aaataaaaaa  33360
aaaaacaagc gtcatatcat agtagcctga cgaacagatg gataaatcag tctttccatc  33420
acaagacaag ccacagggtc tccagctcga ccctcgtaaa acctgtcatc atgattaaac  33480
aacagcaccg aaagttcctc gcggtgacca gcatgaataa ttcttgatga agcatacaat  33540
ccagacatgt tagcatcagt taacgagaaa aaacagccaa catagccttt gggtataatt  33600
atgcttaatc gtaagtatag caaagccacc cctcgcggat acaaagtaaa aggcacagga  33660
gaataaaaaa tataattatt tctctgctgc tgttcaggca acgtcgcccc cggtccctct  33720
aaatacacat acaaagcctc atcagccatg gcttaccaga caaagtacag cgggcacaca  33780
aagcacaagc tctaaagtga ctctccaacc tctccacaat atatatatac acaagcccta  33840
aactgacgta atgggagtaa agtgtaaaaa atcccgccaa acccaacaca caccccgaaa  33900
ctgcgtcacc agggaaaagt acagtttcac ttccgcaatc ccaacaggcg taacttcctc  33960
tttctcacgg tacgtgatat cccactaact tgcaacgtca ttttcccacg gtcgcaccgc  34020
cccttttagc cgttaacccc acagccaatc accacacgat ccacactttt taaaatcacc  34080
tcatttacat attggcacca ttccatctat aaggtatatt atatagatag a           34131
```

<210> SEQ ID NO 19
<211> LENGTH: 34432

```
<212> TYPE: DNA
<213> ORGANISM: Artificial Sequence
<220> FEATURE:
<223> OTHER INFORMATION: NG-346 virus genome sequence comprising a
      transgene cassette that encodes Flt3 Ligand, MIP1a and CD80,
      employing SSA and P2A sequence, inserted in the region BY

<400> SEQUENCE: 19

tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540

tctgcgccgg cagtttaata ataaaaaaat gagagatttg cgatttctgc ctcaggaaat    600

aatctctgct gagactggaa atgaaatatt ggagcttgtg gtgcacgccc tgatgggaga    660

cgatccggag ccacctgtgc agctttttga gcctcctacg cttcaggaac tgtatgattt    720

agaggtagag ggatcggagg attctaatga ggaagctgta aatggctttt ttaccgattc    780

tatgctttta gctgctaatg aagggttaga attagatccg cctttggaca cttttgatac    840

tccaggggta attgtggaaa gcggtacagg tgtaagaaaa ttacctgatt tgagttccgt    900

ggactgtgat ttgcactgct atgaagacgg gtttcctccg agtgatgagg aggaccatga    960

aaaggagcag tccatgcaga ctgcagcggg tgagggagtg aaggctgcca atgttggttt   1020

tcagttggat tgcccggagc ttcctggaca tggctgtaag tcttgtgaat ttcacaggaa   1080

aaatactgga gtaaaggaac tgttatgttc gctttgttat atgagaacgc actgccactt   1140

tatttacagt aagtgtgttt aagttaaaat ttaaaggaat atgctgtttt tcacatgtat   1200

attgagtgtg agttttgtgc ttcttattat aggtcctgtg tctgatgctg atgaatcacc   1260

atctcctgat tctactacct cacctcctga gattcaagca cctgttcctg tggacgtgcg   1320

caagcccatt cctgtgaagc ttaagcctgg gaaacgtcca gcagtggaaa aacttgagga   1380

cttgttacag ggtggggacg gacctttgga cttgagtaca cggaaacgtc caagacaata   1440

agtgttccat atccgtgttt acttaaggtg acgtcaatat ttgtgtgaca gtgcaatgta   1500

ataaaaatat gttaactgtt cactggtttt tattgctttt tgggcgggga ctcaggtata   1560

taagtagaag cagacctgtg tggttagctc ataggagctg gctttcatcc atggaggttt   1620

gggccatttt ggaagacctt aggaagacta ggcaactgtt agagaacgct tcggacggag   1680

tctccggttt ttggagattc tggttcgcta gtgaattagc tagggtagtt tttaggataa   1740

aacaggacta taaacaagaa tttgaaaagt tgttggtaga ttgcccagga ctttttgaag   1800

ctcttaattt gggccatcag gttcacttta aagaaaaagt tttatcagtt ttagactttt   1860

caaccccagg tagaactgct gctgctgtgg cttttcttac ttttatatta gataaatgga   1920

tcccgcagac tcatttcagc aggggatacg ttttggattt catagccaca gcattgtgga   1980

gaacatggaa ggttcgcaag atgaggacaa tcttaggtta ctggccagtg cagcctttgg   2040

gtgtagcggg aatcctgagg catccaccgg tcatgccagc ggttctggag gaggaacagc   2100
```

-continued

```
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaacttttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat ttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg ggccgtggg   4500
```

```
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tggggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
```

-continued

```
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
```

-continued

```
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
```

-continued

```
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgccccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
```

-continued

```
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg gggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
```

-continued

```
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
```

ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agtttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg gggtgctgg ctggtcaagc gtctcagtta aatgcagtgg 19320
ttgacttgca ggacagaaac acagaacttt cttaccaact cttgcttgac tctctgggcg 19380
acagaaccag atactttagc atgtggaatc aggctgtgga cagttatgat cctgatgtac 19440
gtgttattga aaatcatggt gtggaagatg aacttcccaa ctactgtttt ccactggacg 19500
gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220
caaccaatat tcccatttcc attccttctc gcaactgggc ggctttcaga ggctggtcat 20280
ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060

-continued

```
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat ttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttcttttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
```

cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac cacccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800

-continued

```
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
```

-continued

```
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
ccccttata aacccagggt ttatttcccc aaatggcttc acacaaagcc caaacggagt  28500
tcttacttta aaatgtttaa ccccactaac aaccacaggc ggatctctac agctaaaagt  28560
gggaggggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc accatgacag tgctggcgcc agcctggagc  29400
ccaacaacct atctcctcct gctgctgctg ctgagctcgg gactcagtgg gacccaggac  29460
tgctccttcc aacacagccc catctcctcc gacttcgctg tcaaaatccg tgagctgtct  29520
gactacctgc ttcaagatta cccagtcacc gtggcctcca acctccagga cgaggagctc  29580
tgcgggggcc tctggcggct ggtcctggca cagcgctgga tggagcggct caagactgtc  29640
gctgggtcca agatgcaagg cttgctggag cgcgtgaaca cggagataca ctttgtcacc  29700
aaatgtgcct ttcagccccc cccagctgt cttcgcttcg tccagaccaa catctcccgc  29760
ctcctacagg agacctccga gcagctggtg gcgctgaagc cctggatcac tcgccagaac  29820
ttctcccggt gcctggagct gcagtgtcag cccgactcct caaccctgcc acccccatgg  29880
agtccccggc ccctggaggc cacagccccg ggaagcggag ctactaactt cagcctgctg  29940
aagcaggctg gagacgtgga ggagaaccct ggacctcagg tctccactgc tgcccttgcc  30000
gtcctcctct gcaccatggc tctctgcaac caggtcctct ctgcaccact tgctgctgac  30060
acgccgaccg cctgctgctt cagctacacc tcccgacaga ttccacagaa tttcatagct  30120
gactactttg agacgagcag ccagtgctcc aagcccagtg tcatcttcct aaccaagaga  30180
ggccggcagg tctgtgctga ccccagtgag gagtgggtcc agaaatacgt cagtgacctg  30240
gagctgagtg ccggaagcgg agagggcaga ggaagtctgc taacatgcgg tgacgtcgag  30300
gagaatcctg gacctggcca cacacggagg cagggaacat caccatccaa gtgtccatac  30360
ctcaatttct ttcagctctt ggtgctggct ggtctttctc acttctgttc aggtgttatc  30420
cacgtgacca aggaagtgaa agaagtggca acgctgtcct gtggtcacaa tgtttctgtt  30480
gaagagctgg cacaaactcg catctactgg caaaaggaga agaaaatggt gctgactatg  30540
```

-continued

```
atgtctgggg acatgaatat atggcccgag tacaagaacc ggaccatctt tgatatcact  30600
aataacctct ccattgtgat cctggctctg cgcccatctg acgagggcac atacgagtgt  30660
gttgttctga agtatgaaaa agacgctttc aagcgggaac acctggctga agtgacgtta  30720
tcagtcaaag ctgacttccc tacacctagt atatctgact ttgaaattcc aacttctaat  30780
attagaagga taatttgctc aacctctgga ggttttccag agcctcacct ctcctggttg  30840
gaaaatggag aagaattaaa tgccatcaac acaacagttt cccaagatcc tgaaactgag  30900
ctctatgctg ttagcagcaa actggatttc aatatgacaa ccaaccacag cttcatgtgt  30960
ctcatcaagt atggacattt aagagtgaat cagaccttca actggaatac aaccaagcaa  31020
gagcattttc ctgataacct gctcccatcc tgggccatta ccttaatctc agtaaatgga  31080
atttttgtga tatgctgcct gacctactgc tttgccccaa gatgcagaga gagaaggagg  31140
aatgagagat tgagaaggga aagtgtacgc cctgtataag ctagcttgac tgactgagat  31200
acagcgtacc ttcagctcac agacatgata agatacattg atgagtttgg acaaaccaca  31260
actagaatgc agtgaaaaaa atgctttatt tgtgaaattt gtgatgctat tgctttattt  31320
gtaaccatta taagctgcaa taaacaagtt aacaacaaca attgcattca ttttatgttt  31380
caggttcagg gggaggtgtg ggaggttttt taaagcaagt aaaacctcta caaatgtggt  31440
agtcgtcagc tatcctgcag gaacttgttt atttgaaaat caattcacaa aatccgagta  31500
gttattttgc ctcccccttc ccatttaaca gaatacacca atctctcccc acgcacagct  31560
ttaaacattt ggataccatt agatatagac atggttttag attccacatt ccaaacagtt  31620
tcagagcgag ccaatctggg gtcagtgata gataaaaatc catcgggata gtcttttaaa  31680
gcgctttcac agtccaactg ctgcggatgc gactccggag tctggatcac ggtcatctgg  31740
aagaagaacg atgggaatca taatccgaaa acggtatcgg acgattgtgt ctcatcaaac  31800
ccacaagcag ccgctgtctg cgtcgctccg tgcgactgct gtttatggga tcagggtcca  31860
cagtgtcctg aagcatgatt ttaatagccc ttaacatcaa ctttctggtg cgatgcgcgc  31920
agcaacgcat tctgatttca ctcaaatctt tgcagtaggt acaacacatt attacaatat  31980
tgtttaataa accataatta aaagcgctcc agccaaaact catatctgat ataatcgccc  32040
ctgcatgacc atcataccaa agtttaatat aaattaaatg acgttccctc aaaaacacac  32100
tacccacata catgatctct tttggcatgt gcatattaac aatctgtctg taccatggac  32160
aacgttggtt aatcatgcaa cccaatataa ccttccggaa ccacactgcc aacaccgctc  32220
ccccagccat gcattgaagt gaaccctgct gattacaatg acaatgaaga acccaattct  32280
ctcgaccgtg aatcacttga gaatgaaaaa tatctatagt ggcacaacat agacataaat  32340
gcatgcatct tctcataatt tttaactcct caggatttag aaacatatcc cagggaatag  32400
gaagctcttg cagaacagta aagctggcag aacaaggaag accacgaaca caacttacac  32460
tatgcatagt catagtatca caatctggca acagcgggtg gtcttcagtc atagaagctc  32520
gggtttcatt ttcctcacaa cgtggtaact gggctctggt gtaagggtga tgtctggcgc  32580
atgatgtcga gcgtgcgcgc aaccttgtca taatggagtt gcttcctgac attctcgtat  32640
tttgtatagc aaaacgcggc cctggcagaa cacactcttc ttcgccttct atcctgccgc  32700
ttagcgtgtt ccgtgtgata gttcaagtac aaccacactc ttaagttggt caaaagaatg  32760
ctggcttcag ttgtaatcaa aactccatcg catctaatcg ttctgaggaa atcatccaag  32820
caatgcaact ggattgtgtt tcaagcagga gaggagaggg aagagacgga agaaccatgt  32880
taatttttat tccaaacgat ctcgcagtac ttcaaattgt agatcgcgca gatggcatct  32940
```

```
ctcgccccca ctgtgttggt gaaaaagcac agctagatca aaagaaatgc gattttcaag  33000

gtgctcaacg gtggcttcca gcaaagcctc cacgcgcaca tccaagaaca aaagaatacc  33060

aaaagaagga gcattttcta actcctcaat catcatatta cattcctgca ccattcccag  33120

ataattttca gctttccagc cttgaattat tcgtgtcagt tcttgtggta aatccaatcc  33180

acacattaca aacaggtccc ggagggcgcc ctccaccacc attcttaaac acaccctcat  33240

aatgacaaaa tatcttgctc ctgtgtcacc tgtagcgaat tgagaatggc aacatcaatt  33300

gacatgccct tggctctaag ttcttcttta agttctagtt gtaaaaactc tctcatatta  33360

tcaccaaact gcttagccag aagccccccg ggaacaagag caggggacgc tacagtgcag  33420

tacaagcgca gacctcccca attggctcca gcaaaaacaa gattggaata agcatattgg  33480

gaaccgccag taatatcatc gaagttgctg gaaatataat caggcagagt ttcttgtaaa  33540

aattgaataa aagaaaaatt tgccaaaaaa acattcaaaa cctctgggat gcaaatgcaa  33600

taggttaccg cgctgcgctc caacattgtt agttttgaat tagtctgcaa aaataaaaaa  33660

aaaaacaagc gtcatatcat agtagcctga cgaacagatg gataaatcag tctttccatc  33720

acaagacaag ccacagggtc tccagctcga ccctcgtaaa acctgtcatc atgattaaac  33780

aacagcaccg aaagttcctc gcggtgacca gcatgaataa ttcttgatga agcatacaat  33840

ccagacatgt tagcatcagt taacgagaaa aaacagccaa catagccttt gggtataatt  33900

atgcttaatc gtaagtatag caaagccacc cctcgcggat acaaagtaaa aggcacagga  33960

gaataaaaaa tataattatt tctctgctgc tgttcaggca acgtcgcccc cggtccctct  34020

aaatacacat acaaagcctc atcagccatg gcttaccaga caaagtacag cgggcacaca  34080

aagcacaagc tctaaagtga ctctccaacc tctccacaat atatatatac acaagcccta  34140

aactgacgta atgggagtaa agtgtaaaaa atcccgccaa acccaacaca caccccgaaa  34200

ctgcgtcacc agggaaaagt acagtttcac ttccgcaatc ccaacaggcg taacttcctc  34260

tttctcacgg tacgtgatat cccactaact tgcaacgtca ttttcccacg gtcgcaccgc  34320

cccttttagc cgttaacccc acagccaatc accacacgat ccacactttt taaaatcacc  34380

tcatttacat attggcacca ttccatctat aaggtatatt atatagatag ga          34432
```

<210> SEQ ID NO 20
<211> LENGTH: 34458
<212> TYPE: DNA
<213> ORGANISM: Artificial Sequence
<220> FEATURE:
<223> OTHER INFORMATION: NG-347 virus genome sequence comprising a transgene cassette encoding IFNa, MIP1a and CD80, employing SSA and a P2A sequence, inserted in the region BY

<400> SEQUENCE: 20

```
tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480
```

-continued

```
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
```

-continued

```
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
```

-continued

```
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tggggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
```

-continued ccgtccgact gccatttttt ctggggtgac gcaatagaag gtttgggggt cctgccgcca 7680
gcgatcccac ttgagtttta tggcgaggtc ataggcgatg ttgacgagcc gctggtctcc 7740
agagagtttc atgaccagca tgaaggggat tagctgcttg ccaaaggacc ccatccaggt 7800
gtaggtttcc acatcgtagg tgagaaagag cctttctgtg cgaggatgag agccaatcgg 7860
gaagaactgg atctcctgcc accagttgga ggaatggctg ttgatgtgat ggaagtagaa 7920
ctccctgcga cgcgccgagc attcatgctt gtgcttgtac agacggccgc agtagtcgca 7980
gcgttgcacg ggttgtatct cgtgaatgag ttgtacctgg cttcccttga cgagaaattt 8040
cagtgggaag ccgaggcctg gcgattgtat ctcgtgcttt actatgttgt ctgcatcggc 8100
ctgttcatct tctgtctcga tggtggtcat gctgacgagc cctcgcggga ggcaagtcca 8160
gacctcggcg cggcaggggc ggagctcgag gacgagagcg cgcaggctgg agctgtccag 8220
ggtcctgaga cgctgcggac tcaggttagt aggcagtgtc aggagattaa cttgcatgat 8280
cttttggagg gcgtgcggga ggttcagata gtacttgatc tcaacgggtc cgttggtgga 8340
gatgtcgatg gcttgcaggg ttccgtgtcc cttgggcgct accaccgtgc ccttgttttt 8400
cattttggac ggcggtggct ctgttgcttc ttgcatgttt agaagcggtg tcgagggcgc 8460
gcaccgggcg gcaggggcgg ctcgggaccc ggcggcatgg ctggcagtgg tacgtcggcg 8520
ccgcgcgcgg gtaggttctg gtactgcgcc ctgagaagac tcgcatgcgc gacgacgcgg 8580
cggttgacat cctggatctg acgcctctgg gtgaaagcta ccggccccgt gagcttgaac 8640
ctgaaagaga gttcaacaga atcaatctcg gtatcgttga cggcggcttg cctaaggatt 8700
tcttgcacgt caccagagtt gtcctggtag gcgatctccg ccatgaactg ctcgatctct 8760
tcctcttgaa gatctccgcg gcccgctctc tcgacggtgg ccgcgaggtc gttggagatg 8820
cgcccaatga gttgagagaa tgcattcatg cccgcctcgt tccagacgcg gctgtagacc 8880
acggccccca cgggatctct cgcgcgcatg accacctggg cgaggttgag ctccacgtgg 8940
cgggtgaaga ccgcatagtt gcataggcgc tggaaaaggt agttgagtgt ggtggcgatg 9000
tgctcggtga cgaagaaata catgatccat cgtctcagcg gcatctcgct gacatcgccc 9060
agagcttcca agcgctccat ggcctcgtag aagtccacgg caaaattaaa aaactgggag 9120
tttcgcgcgg acacggtcaa ctcctcttcc agaagacgga taagttcggc gatggtggtg 9180
cgcacctcgc gctcgaaagc ccctgggatt tcttcctcaa tctcttcttc ttccactaac 9240
atctcttcct cttcaggtgg ggctgcagga ggagggggaa cgcggcgacg ccggcggcgc 9300
acgggcagac ggtcgatgaa tctttcaatg acctctccgc ggcggcggcg catggtttca 9360
gtgacggcgc ggccgttctc gcgcggtcgc agagtaaaaa caccgccgcg catctcctta 9420
aagtggtgac tgggaggttc tccgtttggg agggagaggg cgctgattat acattttatt 9480
aattggcccg tagggactgc acgcagagat ctgatcgtgt caagatccac gggatctgaa 9540
aacctttcga cgaaagcgtc taaccagtca cagtcacaag gtaggctgag tacggcttct 9600
tgtgggcggg ggtggttatg tgttcggtct gggtcttctg tttcttcttc atctcgggaa 9660
ggtgagacga tgctgctggt gatgaaatta aagtaggcag ttctaagacg gcggatggtg 9720
gcgaggagca ccaggtcttt gggtccggct tgctggatac gcaggcgatt ggccattccc 9780
caagcattat cctgacatct agcaagatct ttgtagtagt cttgcatgag ccgttctacg 9840
ggcacttctt cctcacccgt tctgccatgc atacgtgtga gtccaaatcc gcgcattggt 9900
tgtaccagtg ccaagtcagc tacgactctt tcggcgagga tggcttgctg tacttgggta 9960

-continued

```
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
```

-continued agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700

-continued

```
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg gggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
```

```
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
```

-continued

```
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg actttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
```

tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180

-continued caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg cccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac cacccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580

```
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
cccctttata aacccagggt ttatttcccc aaatggcttc acacaaagcc caaacggagt  28500
tcttacttta aaatgtttaa ccccactaac aaccacaggc ggatctctac agctaaaagt  28560
gggaggggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
```

-continued

```
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc accatggcct tgacctttgc tttactggtg  29400
gccctcctgg tgctcagctg caagtcaagc tgctctgtgg gctgtgatct gcctcaaacc  29460
cacagcctgg gtagcaggag gaccttgatg ctcctggcac agatgaggag aatctctctt  29520
ttctcctgct tgaaggacag acatgacttt ggatttcccc aggaggagtt tggcaaccag  29580
ttccaaaagg ctgaaaccat ccctgtcctc catgagatga tccagcagat cttcaatctc  29640
ttcagcacaa aggactcatc tgctgcttgg gatgagaccc tcctagacaa attctacact  29700
gaactctacc agcagctgaa tgacctggaa gcctgtgtga tacagggggt gggggtgaca  29760
gagactcccc tgatgaagga ggactccatt ctggctgtga ggaaatactt ccaaagaatc  29820
actctctatc tgaaagagaa gaaatacagc ccttgtgcct gggaggttgt cagagcagaa  29880
atcatgagat ctttttcttt gtcaacaaac ttgcaagaaa gtttaagaag taaggaagga  29940
agcggagcta ctaacttcag cctgctgaag caggctggag acgtggagga gaaccctgga  30000
cctcaggtct ccactgctgc ccttgccgtc ctcctctgca ccatggctct ctgcaaccag  30060
gtcctctctg caccacttgc tgctgacacg ccgaccgcct gctgcttcag ctacacctcc  30120
cgacagattc cacagaattt catagctgac tactttgaga cgagcagcca gtgctccaag  30180
cccagtgtca tcttcctaac caagagaggc cggcaggtct gtgctgaccc cagtgaggag  30240
tgggtccaga aatacgtcag tgacctggag ctgagtgccg gaagcggaga gggcagagga  30300
agtctgctaa catgcggtga cgtcgaggag aatcctggac ctggccacac acggaggcag  30360
ggaacatcac catccaagtg tccatacctc aatttctttc agctcttggt gctggctggt  30420
ctttctcact tctgttcagg tgttatccac gtgaccaagg aagtgaaaga agtggcaacg  30480
ctgtcctgtg gtcacaatgt ttctgttgaa gagctggcac aaactcgcat ctactggcaa  30540
aaggagaaga aaatggtgct gactatgatg tctggggaca tgaatatatg gcccgagtac  30600
aagaaccgga ccatctttga tatcactaat aacctctcca ttgtgatcct ggctctgcgc  30660
ccatctgacg agggcacata cgagtgtgtt gttctgaagt atgaaaaaga cgctttcaag  30720
cgggaacacc tggctgaagt gacgttatca gtcaaagctg acttccctac acctagtata  30780
tctgactttg aaattccaac ttctaatatt agaaggataa tttgctcaac ctctggaggt  30840
tttccagagc ctcacctctc ctggttggaa aatggagaag aattaaatgc catcaacaca  30900
acagtttccc aagatcctga aactgagctc tatgctgtta gcagcaaact ggatttcaat  30960
atgacaacca accacagctt catgtgtctc atcaagtatg gacatttaag agtgaatcag  31020
accttcaact ggaatacaac caagcaagag cattttcctg ataacctgct cccatcctgg  31080
gccattacct taatctcagt aaatggaatt tttgtgatat gctgcctgac ctactgcttt  31140
gccccaagat gcagagagag aaggaggaat gagagattga gaagggaaag tgtacgccct  31200
gtataagcta gcttgactga ctgagataca gcgtaccttc agctcacaga catgataaga  31260
tacattgatg agtttggaca aaccacaact agaatgcagt gaaaaaaatg ctttatttgt  31320
```

gaaatttgtg atgctattgc tttatttgta accattataa gctgcaataa acaagttaac 31380
aacaacaatt gcattcattt tatgtttcag gttcaggggg aggtgtggga ggttttttaa 31440
agcaagtaaa acctctacaa atgtggtagt cgtcagctat cctgcaggaa cttgtttatt 31500
tgaaaatcaa ttcacaaaat ccgagtagtt attttgcctc cccttccca tttaacagaa 31560
tacaccaatc tctccccacg cacagcttta aacatttgga taccattaga tatagacatg 31620
gttttagatt ccacattcca aacagtttca gagcgagcca atctggggtc agtgatagat 31680
aaaaatccat cgggatagtc ttttaaagcg ctttcacagt ccaactgctg cggatgcgac 31740
tccggagtct ggatcacggt catctggaag aagaacgatg ggaatcataa tccgaaaacg 31800
gtatcggacg attgtgtctc atcaaaccca caagcagccg ctgtctgcgt cgctccgtgc 31860
gactgctgtt tatgggatca gggtccacag tgtcctgaag catgatttta atagccctta 31920
acatcaactt tctggtgcga tgcgcgcagc aacgcattct gatttcactc aaatctttgc 31980
agtaggtaca acacattatt acaatattgt ttaataaacc ataattaaaa gcgctccagc 32040
caaaactcat atctgatata atcgcccctg catgaccatc ataccaaagt ttaatataaa 32100
ttaaatgacg ttccctcaaa aacacactac ccacatacat gatctctttt ggcatgtgca 32160
tattaacaat ctgtctgtac catggacaac gttggttaat catgcaaccc aatataacct 32220
tccggaacca cactgccaac accgctcccc cagccatgca ttgaagtgaa ccctgctgat 32280
tacaatgaca atgaagaacc caattctctc gaccgtgaat cacttgagaa tgaaaaatat 32340
ctatagtggc acaacataga cataaatgca tgcatcttct cataattttt aactcctcag 32400
gatttagaaa catatcccag ggaataggaa gctcttgcag aacagtaaag ctggcagaac 32460
aaggaagacc acgaacacaa cttacactat gcatagtcat agtatcacaa tctggcaaca 32520
gcgggtggtc ttcagtcata gaagctcggg tttcattttc ctcacaacgt ggtaactggg 32580
ctctggtgta agggtgatgt ctggcgcatg atgtcgagcg tgcgcgcaac cttgtcataa 32640
tggagttgct tcctgacatt ctcgtatttt gtatagcaaa acgcggccct ggcagaacac 32700
actcttcttc gccttctatc ctgccgctta gcgtgttccg tgtgatagtt caagtacaac 32760
cacactctta agttggtcaa aagaatgctg gcttcagttg taatcaaaac tccatcgcat 32820
ctaatcgttc tgaggaaatc atccaagcaa tgcaactgga ttgtgtttca agcaggagag 32880
gagagggaag agacggaaga accatgttaa tttttattcc aaacgatctc gcagtacttc 32940
aaattgtaga tcgcgcagat ggcatctctc gcccccactg tgttggtgaa aaagcacagc 33000
tagatcaaaa gaaatgcgat ttcaaggtg ctcaacggtg gcttccagca aagcctccac 33060
gcgcacatcc aagaacaaaa gaataccaaa agaaggagca ttttctaact cctcaatcat 33120
catattacat tcctgcacca ttcccagata attttcagct ttccagcctt gaattattcg 33180
tgtcagttct tgtggtaaat ccaatccaca cattacaaac aggtcccgga gggcgccctc 33240
caccaccatt cttaaacaca ccctcataat gacaaaatat cttgctcctg tgtcacctgt 33300
agcgaattga gaatggcaac atcaattgac atgcccttgg ctctaagttc ttctttaagt 33360
tctagttgta aaaactctct catattatca ccaaactgct tagccagaag cccccggga 33420
acaagagcag ggacgctac agtgcagtac aagcgcagac ctccccaatt ggctccagca 33480
aaaacaagat tggaataagc atattgggaa ccgccagtaa tatcatcgaa gttgctggaa 33540
atataatcag gcagagtttc ttgtaaaaat tgaataaaag aaaaatttgc caaaaaaaca 33600
ttcaaaacct ctgggatgca aatgcaatag gttaccgcgc tgcgctccaa cattgttagt 33660
tttgaattag tctgcaaaaa taaaaaaaaa aacaagcgtc atatcatagt agcctgacga 33720
acagatggat aaatcagtct ttccatcaca agacaagcca cagggtctcc agctcgaccc 33780
tcgtaaaacc tgtcatcatg attaaacaac agcaccgaaa gttcctcgcg gtgaccagca 33840
tgaataattc ttgatgaagc atacaatcca gacatgttag catcagttaa cgagaaaaaa 33900
cagccaacat agcctttggg tataattatg cttaatcgta agtatagcaa agccacccct 33960
cgcggataca aagtaaaagg cacaggagaa taaaaaatat aattatttct ctgctgctgt 34020
tcaggcaacg tcgcccccgg tccctctaaa tacacataca aagcctcatc agccatggct 34080
taccagacaa agtacagcgg gcacacaaag cacaagctct aaagtgactc tccaacctct 34140
ccacaatata tatatacaca agccctaaac tgacgtaatg ggagtaaagt gtaaaaaatc 34200
ccgccaaacc caacacacac cccgaaactg cgtcaccagg gaaaagtaca gtttcacttc 34260
cgcaatccca acaggcgtaa cttcctcttt ctcacggtac gtgatatccc actaacttgc 34320
aacgtcattt tcccacggtc gcaccgcccc ttttagccgt taaccccaca gccaatcacc 34380
acacgatcca cactttttaa aatcacctca tttacatatt ggcaccattc catctataag 34440
gtatattata tagataga 34458

<210> SEQ ID NO 21
<211> LENGTH: 32326
<212> TYPE: DNA
<213> ORGANISM: Artificial Sequence
<220> FEATURE:
<223> OTHER INFORMATION: EnAd Genome

<400> SEQUENCE: 21
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540
tctgcgccgg cagtttaata ataaaaaaat gagagatttg cgatttctgc ctcaggaaat 600
aatctctgct gagactggaa atgaaatatt ggagcttgtg gtgcacgccc tgatgggaga 660
cgatccggag ccacctgtgc agctttttga gcctcctacg cttcaggaac tgtatgattt 720
agaggtagag ggatcggagg attctaatga ggaagctgta aatggctttt ttaccgattc 780
tatgctttta gctgctaatg aagggttaga attagatccg cctttggaca cttttgatac 840
tccaggggta attgtggaaa gcggtacagg tgtaagaaaa ttacctgatt tgagttccgt 900
ggactgtgat ttgcactgct atgaagacgg gtttcctccg agtgatgagg aggaccatga 960
aaaggagcag tccatgcaga ctgcagcggg tgagggagtg aaggctgcca atgttggttt 1020
tcagttggat tgcccggagc ttcctggaca tggctgtaag tcttgtgaat ttcacaggaa 1080
aaatactgga gtaaaggaac tgttatgttc gctttgttat atgagaacgc actgccactt 1140
tatttacagt aagtgtgttt aagttaaaat ttaaaggaat atgctgtttt tcacatgtat 1200
attgagtgtg agttttgtgc ttcttattat aggtcctgtg tctgatgctg atgaatcacc 1260

-continued

```
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
```

-continued gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaacttttct 3840 cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg gggtccccgc 5880 tggggggggta taaaaggggg cggttctttg ctcttcctca ctgtcttccg gatcgctgtc 5940
caggaacgtc agctgttggg gtaggtattc cctctcgaag gcgggcatga cctctgcact 6000

-continued

```
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
```

-continued

```
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
```

-continued gcaactgccg ccgtgagcgg tgcgggacag cccgcctatg atctggactt ggaagagggc 10800
gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgccccccacc 13020 tggtttctac acgggcgaat atgacatgcc cgaccctaat gacggatttc tgtgggacga 13080

-continued

```
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
```

```
ccgtgttcgc ggacattttc gcgctccatg gggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
```

gctggtgacg cgcgtagatg aaccgccttc ttatgaggaa gcaacgaagc ttggaatgcc 17880
caccactaga ccgatagccc caatggccac cggggtgatg aaaccttctc agttgcatcg 17940
acccgtcacc ttggatttgc cccctccccc tgctgctact gctgtacccg cttctaagcc 18000
tgtcgctgcc ccgaaaccag tcgccgtagc caggtcacgt cccgggggcg ctcctcgtcc 18060
aaatgcgcac tggcaaaata ctctgaacag catcgtgggt ctaggcgtgc aaagtgtaaa 18120
acgccgtcgc tgcttttaat taaatatgga gtagcgctta acttgcctat ctgtgtatat 18180
gtgtcattac acgccgtcac agcagcagag gaaaaaagga agaggtcgtg cgtcgacgct 18240
gagttacttt caagatggcc accccatcga tgctgcccca atgggcatac atgcacatcg 18300
ccggacagga tgcttcggag tacctgagtc cgggtctggt gcagttcgcc cgcgccacag 18360
acacctactt caatctggga aataagttta gaaatcccac cgtagcgccg acccacgatg 18420
tgaccaccga ccgtagccag cggctcatgt tgcgcttcgt gcccgttgac cgggaggaca 18480
atacatactc ttacaaagtg cggtacaccc tggccgtggg cgacaacaga gtgctggata 18540
tggccagcac gttctttgac attaggggtg tgttggacag aggtcccagt ttcaaaccct 18600
attctggtac ggcttacaac tccctggctc ctaaaggcgc tccaaataca tctcagtgga 18660
ttgcagaagg tgtaaaaaat acaactggtg aggaacacgt aacagaagag gaaaccaata 18720
ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agtttttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg ggggtgctgg ctggtcaagc gtctcagtta aatgcagtgg 19320
ttgacttgca ggacagaaac acagaacttt cttaccaact cttgcttgac tctctgggcg 19380
acagaaccag atactttagc atgtggaatc aggctgtgga cagttatgat cctgatgtac 19440
gtgttattga aaatcatggt gtggaagatg aacttcccaa ctactgtttt ccactggacg 19500
gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220

-continued caaccaatat tcccatttcc attccttctc gcaactgggc ggctttcaga ggctggtcat 20280
ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560

-continued

```
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
```

-continued

```
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac caccccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
```

-continued

```
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
ccccttata aacccagggt ttatttcccc aaatggcttc acacaaagcc caaacggagt  28500
tcttacttta aaatgtttaa ccccactaac aaccacaggc ggatctctac agctaaaagt  28560
gggagggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttaact tgtttatttg aaaatcaatt cacaaaatcc gagtagttat  29400
tttgcctccc ccttcccatt taacagaata caccaatctc tccccacgca cagctttaaa  29460
catttggata ccattagata tagacatggt tttagattcc acattccaaa cagtttcaga  29520
gcgagccaat ctggggtcag tgatagataa aaatccatcg ggatagtctt ttaaagcgct  29580
ttcacagtcc aactgctgcg gatgcgactc cggagtctgg atcacggtca tctggaagaa  29640
gaacgatggg aatcataatc cgaaaacggt atcggacgat tgtgtctcat caaacccaca  29700
```

-continued

```
agcagccgct gtctgcgtcg ctccgtgcga ctgctgttta tgggatcagg gtccacagtg  29760
tcctgaagca tgattttaat agcccttaac atcaactttc tggtgcgatg cgcgcagcaa  29820
cgcattctga tttcactcaa atctttgcag taggtacaac acattattac aatattgttt  29880
aataaaccat aattaaaagc gctccagcca aaactcatat ctgatataat cgcccctgca  29940
tgaccatcat accaaagttt aatataaatt aaatgacgtt ccctcaaaaa cacactaccc  30000
acatacatga tctcttttgg catgtgcata ttaacaatct gtctgtacca tggacaacgt  30060
tggttaatca tgcaacccaa tataaccttc cggaaccaca ctgccaacac cgctccccca  30120
gccatgcatt gaagtgaacc ctgctgatta caatgacaat gaagaaccca attctctcga  30180
ccgtgaatca cttgagaatg aaaaatatct atagtggcac aacatagaca taaatgcatg  30240
catcttctca taatttttaa ctcctcagga tttagaaaca tatcccaggg aataggaagc  30300
tcttgcagaa cagtaaagct ggcagaacaa ggaagaccac gaacacaact tacactatgc  30360
atagtcatag tatcacaatc tggcaacagc gggtggtctt cagtcataga agctcgggtt  30420
tcattttcct cacaacgtgg taactgggct ctggtgtaag ggtgatgtct ggcgcatgat  30480
gtcgagcgtg cgcgcaacct tgtcataatg gagttgcttc ctgacattct cgtattttgt  30540
atagcaaaac gcggccctgg cagaacacac tcttcttcgc cttctatcct gccgcttagc  30600
gtgttccgtg tgatagttca agtacaacca cactcttaag ttggtcaaaa gaatgctggc  30660
ttcagttgta atcaaaactc catcgcatct aatcgttctg aggaaatcat ccaagcaatg  30720
caactggatt gtgtttcaag caggagagga gagggaagag acggaagaac catgttaatt  30780
tttattccaa acgatctcgc agtacttcaa attgtagatc gcgcagatgg catctctcgc  30840
ccccactgtg ttggtgaaaa agcacagcta gatcaaaaga aatgcgattt tcaaggtgct  30900
caacggtggc ttccagcaaa gcctccacgc gcacatccaa gaacaaaaga ataccaaaag  30960
aaggagcatt ttctaactcc tcaatcatca tattacattc ctgcaccatt cccagataat  31020
tttcagcttt ccagccttga attattcgtg tcagttcttg tggtaaatcc aatccacaca  31080
ttacaaacag gtcccggagg gcgccctcca ccaccattct taaacacacc ctcataatga  31140
caaaatatct tgctcctgtg tcacctgtag cgaattgaga atggcaacat caattgacat  31200
gcccttggct ctaagttctt ctttaagttc tagttgtaaa aactctctca tattatcacc  31260
aaactgctta gccagaagcc ccccgggaac aagagcaggg gacgctacag tgcagtacaa  31320
gcgcagacct ccccaattgg ctccagcaaa aacaagattg gaataagcat attgggaacc  31380
gccagtaata tcatcgaagt tgctggaaat ataatcaggc agagtttctt gtaaaaattg  31440
aataaaagaa aaatttgcca aaaaaacatt caaaacctct gggatgcaaa tgcaataggt  31500
taccgcgctg cgctccaaca ttgttagttt tgaattagtc tgcaaaaata aaaaaaaaaa  31560
caagcgtcat atcatagtag cctgacgaac agatggataa atcagtcttt ccatcacaag  31620
acaagccaca gggtctccag ctcgaccctc gtaaaacctg tcatcatgat taaacaacag  31680
caccgaaagt tcctcgcggt gaccagcatg aataattctt gatgaagcat acaatccaga  31740
catgttagca tcagttaacg agaaaaaaca gccaacatag cctttgggta taattatgct  31800
taatcgtaag tatagcaaag ccacccctcg cggatacaaa gtaaaaggca caggagaata  31860
aaaaatataa ttatttctct gctgctgttc aggcaacgtc gcccccggtc cctctaaata  31920
cacatacaaa gcctcatcag ccatggctta ccagacaaag tacagcgggc acacaaagca  31980
caagctctaa agtgactctc caacctctcc acaatatata tatacacaag ccctaaactg  32040
```

acgtaatggg agtaaagtgt aaaaaatccc gccaaaccca acacacaccc cgaaactgcg 32100
tcaccaggga aaagtacagt ttcacttccg caatcccaac aggcgtaact tcctctttct 32160
cacggtacgt gatatcccac taacttgcaa cgtcattttc ccacggtcgc accgcccctt 32220
ttagccgtta accccacagc caatcaccac acgatccaca ctttttaaaa tcacctcatt 32280
tacatattgg caccattcca tctataaggt atattatata gataga 32326

<210> SEQ ID NO 22
<211> LENGTH: 5288
<212> TYPE: DNA
<213> ORGANISM: Artificial Sequence
<220> FEATURE:
<223> OTHER INFORMATION: DNA SEQUENCE CORRESPONDING TO E2B REGION OF THE
ENAD GENOME (BP 10355-5068)

<400> SEQUENCE: 22
ctatggcatc tcgatccagc agacctcctc gtttcgcggg tttggacggc tcctggaata 60
gggtatgaga cgatgggcgt ccagcgctgc cagggttcgg tccttccagg gtctcagtgt 120
tcgagtcagg gttgtttccg tcacagtgaa ggggtgtgcg cctgcttggg cgcttgccag 180
ggtgcgcttc agactcatcc tgctggtcga aaacttctgt cgcttggcgc cctgtatgtc 240
ggccaagtag cagtttacca tgagttcgta gttgagcgcc tcggctgcgt ggcctttggc 300
gcggagctta cctttggaag ttttcttgca taccgggcag tataggcatt tcagcgcata 360
caacttgggc gcaaggaaaa cggattctgg ggagtatgca tctgcgccgc aggaggcgca 420
aacagtttca cattccacca gccaggttaa atccggttca ttggggtcaa aaacaagttt 480
tccgccatat tttttgatgc gtttcttacc tttggtctcc atgagttcgt gtcctcgttg 540
agtgacaaac aggctgtccg tgtccccgta gactgatttt acaggcctct tctccagtgg 600
agtgcctcgg tcttcttcgt acaggaactc tgaccactct gatacaaagg cgcgcgtcca 660
ggccagcaca aaggaggcta tgtgggaggg gtagcgatcg ttgtcaacca gggggtccac 720
cttttccaaa gtatgcaaac acatgtcacc ctcttcaaca tccaggaatg tgattggctt 780
gtaggtgtat ttcacgtgac ctggggtccc cgctgggggg gtataaaagg gggcggttct 840
ttgctcttcc tcactgtctt ccggatcgct gtccaggaac gtcagctgtt ggggtaggta 900
ttccctctcg aaggcgggca tgacctctgc actcaggttg tcagtttcta agaacgagga 960
ggatttgata ttgacagtgc cggttgagat gcctttcatg aggttttcgt ccatctggtc 1020
agaaaacaca atttttttat tgtcaagttt ggtggcaaat gatccataca gggcgttgga 1080
taaaagtttg gcaatggatc gcatggtttg gttcttttcc ttgtccgcgc gctctttggc 1140
ggcgatgttg agttggacat actcgcgtgc caggcacttc cattcgggga agatagttgt 1200
taattcatct ggcacgattc tcacttgcca ccctcgatta tgcaaggtaa ttaaatccac 1260
actggtggcc acctcgcctc gaaggggttc attggtccaa cagagcctac ctcctttcct 1320
agaacagaaa gggggaagtg ggtctagcat aagttcatcg ggagggtctg catccatggt 1380
aaagattccc ggaagtaaat ccttatcaaa atagctgatg ggagtggggt catctaaggc 1440
catttgccat tctcgagctg ccagtgcgcg ctcatatggg ttaaggggac tgccccatgg 1500
catgggatgg gtgagtgcag aggcatacat gccacagatg tcatagacgt agatgggatc 1560
ctcaaagatg cctatgtagg ttggatagca tcgcccccct ctgatacttg ctcgcacata 1620
gtcatatagt tcatgtgatg gcgctagcag ccccggaccc aagttggtgc gattgggttt 1680
ttctgttctg tagacgatct ggcgaaagat ggcgtgagaa ttggaagaga tggtgggtct 1740

-continued ttgaaaaatg ttgaaatggg catgaggtag acctacagag tctctgacaa agtgggcata 1800
agattcttga agcttggtta ccagttcggc ggtgacaagt acgtctaggg cgcagtagtc 1860
aagtgtttct tgaatgatgt cataacctgg ttggttttc ttttcccaca gttcgcggtt 1920
gagaaggtat tcttcgcgat ccttccagta ctcttctagc ggaaacccgt ctttgtctgc 1980
acggtaagat cctagcatgt agaactgatt aactgccttg taagggcagc agcccttctc 2040
tacgggtaga gagtatgctt gagcagcttt tcgtagcgaa gcgtgagtaa gggcaaaggt 2100
gtctctgacc atgactttga ggaattggta tttgaagtcg atgtcgtcac aggctccctg 2160
ttcccagagt tggaagtcta cccgtttctt gtaggcgggg ttgggcaaag cgaaagtaac 2220
atcattgaag agaatcttgc cggccctggg catgaaattg cgagtgatgc gaaaaggctg 2280
tggtacttcc gctcggttat tgataacctg ggcagctagg acgatctcgt cgaaaccgtt 2340
gatgttgtgt cctacgatgt ataattctat gaaacgcggc gtgcctctga cgtgaggtag 2400
cttactgagc tcatcaaagg ttaggtctgt ggggtcagat aaggcgtagt gttcgagagc 2460
ccattcgtgc aggtgaggat tcgctttaag gaaggaggac cagaggtcca ctgccagtgc 2520
tgtttgtaac tggtcccggt actgacgaaa atgccgtccg actgccattt tttctggggt 2580
gacgcaatag aaggtttggg ggtcctgccg ccagcgatcc cacttgagtt ttatggcgag 2640
gtcataggcg atgttgacga gccgctggtc tccagagagt ttcatgacca gcatgaaggg 2700
gattagctgc ttgccaaagg accccatcca ggtgtaggtt tccacatcgt aggtgagaaa 2760
gagcctttct gtgcgaggat gagagccaat cgggaagaac tggatctcct gccaccagtt 2820
ggaggaatgg ctgttgatgt gatggaagta gaactccctg cgacgcgccg agcattcatg 2880
cttgtgcttg tacagacggc cgcagtagtc gcagcgttgc acgggttgta tctcgtgaat 2940
gagttgtacc tggcttccct tgacgagaaa tttcagtggg aagccgaggc ctggcgattg 3000
tatctcgtgc tttactatgt tgtctgcatc ggcctgttca tcttctgtct cgatggtggt 3060
catgctgacg agccctcgcg ggaggcaagt ccagacctcg gcgcggcagg ggcggagctc 3120
gaggacgaga gcgcgcaggc tggagctgtc cagggtcctg agacgctgcg gactcaggtt 3180
agtaggcagt gtcaggagat taacttgcat gatcttttgg agggcgtgcg ggaggttcag 3240
atagtacttg atctcaacgg gtccgttggt ggagatgtcg atggcttgca gggttccgtg 3300
tcccttgggc gctaccaccg tgcccttgtt tttcattttg gacggcggtg gctctgttgc 3360
ttcttgcatg tttagaagcg gtgtcgaggg cgcgcaccgg gcggcagggg cggctcggga 3420
cccggcggca tggctggcag tggtacgtcg gcgccgcgcg cgggtaggtt ctggtactgc 3480
gccctgagaa gactcgcatg cgcgacgacg cggcggttga catcctggat ctgacgcctc 3540
tgggtgaaag ctaccggccc cgtgagcttg aacctgaaag agagttcaac agaatcaatc 3600
tcggtatcgt tgacggcggc ttgcctaagg atttcttgca cgtcaccaga gttgtcctgg 3660
taggcgatct ccgccatgaa ctgctcgatc tcttcctctt gaagatctcc gcggcccgct 3720
ctctcgacgg tggccgcgag gtcgttggag atgcgcccaa tgagttgaga gaatgcattc 3780
atgcccgcct cgttccagac gcggctgtag accacggccc ccacgggatc tctcgcgcgc 3840
atgaccacct gggcgaggtt gagctccacg tggcgggtga agaccgcata gttgcatagg 3900
cgctggaaaa ggtagttgag tgtggtggcg atgtgctcgg tgacgaagaa atacatgatc 3960
catcgtctca gcggcatctc gctgacatcg cccagagctt ccaagcgctc catggcctcg 4020
tagaagtcca cggcaaaatt aaaaaactgg gagtttcgcg cggacacggt caactcctct 4080
tccagaagac ggataagttc ggcgatggtg gtgcgcacct cgcgctcgaa agcccctggg 4140
atttcttcct caatctcttc ttcttccact aacatctctt cctcttcagg tggggctgca 4200
ggaggagggg gaacgcggcg acgccggcgg cgcacgggca gacggtcgat gaatctttca 4260
atgacctctc cgcggcggcg gcgcatggtt tcagtgacgg cgcggccgtt ctcgcgcggt 4320
cgcagagtaa aaacaccgcc gcgcatctcc ttaaagtggt gactgggagg ttctccgttt 4380
gggagggaga gggcgctgat tatacatttt attaattggc ccgtagggac tgcacgcaga 4440
gatctgatcg tgtcaagatc cacgggatct gaaaaccttt cgacgaaagc gtctaaccag 4500
tcacagtcac aaggtaggct gagtacggct tcttgtgggc gggggtggtt atgtgttcgg 4560
tctgggtctt ctgtttcttc ttcatctcgg gaaggtgaga cgatgctgct ggtgatgaaa 4620
ttaaagtagg cagttctaag acggcggatg gtggcgagga gcaccaggtc tttgggtccg 4680
gcttgctgga tacgcaggcg attggccatt ccccaagcat tatcctgaca tctagcaaga 4740
tctttgtagt agtcttgcat gagccgttct acgggcactt cttcctcacc cgttctgcca 4800
tgcatacgtg tgagtccaaa tccgcgcatt ggttgtacca gtgccaagtc agctacgact 4860
ctttcggcga ggatggcttg ctgtacttgg gtaagggtgg cttgaaagtc atcaaaatcc 4920
acaaagcggt ggtaagctcc tgtattaatg gtgtaagcac agttggccat gactgaccag 4980
ttaactgtct ggtgaccagg gcgcacgagc tcggtgtatt taaggcgcga ataggcgcgg 5040
gtgtcaaaga tgtaatcgtt gcaggtgcgc accagatact ggtaccctat aagaaaatgc 5100
ggcggtggtt ggcggtagag aggccatcgt tctgtagctg gagcgccagg ggcgaggtct 5160
tccaacataa ggcggtgata gccgtagatg tacctggaca tccaggtgat tcctgcggcg 5220
gtagtagaag cccgaggaaa ctcgcgtacg cggttccaaa tgttgcgtag cggcatgaag 5280
tagttcat 5288

<210> SEQ ID NO 23
<211> LENGTH: 981
<212> TYPE: DNA
<213> ORGANISM: Artificial Sequence
<220> FEATURE:
<223> OTHER INFORMATION: E3 REGION FROM ENAD

<400> SEQUENCE: 23
atgtctggtg acgcggctga gctatctcgg ctgcgacatc tagaccactg ccgccgcttt 60
cgctgctttg cccgggaact cattgagttc atctacttcg aactccccaa ggatcaccct 120
caaggtccgg cccacggagt gcggatttct atcgaaggca aaatagactc tcgcctgcaa 180
cgaattttct cccagcggcc cgtgctgatc gagcgagacc agggaaacac cacggtttcc 240
atctactgca tttgtaatca ccccggattg catgaaagcc tttgctgtct tatgtgtact 300
gagtttaata aaaactgaat taagactctc ctacggactg ccgcttcttc aacccggatt 360
ttacaaccag aagaacgaaa cttttcctgt cgtccaggac tctgttaact tcacctttcc 420
tactcacaaa ctagaagctc aacgactaca ccgcttttcc agaagcattt tccctactaa 480
tactactttc aaaaccggag gtgagctcca aggtcttcct acagaaaacc cttgggtgga 540
agcgggcctt gtagtgctag gaattcttgc gggtgggctt gtgattattc tttgctacct 600
atacacacct tgcttcactt tcttagtggt gttgtggtat tggtttaaaa aatggggccc 660
atactagtct tgcttgtttt actttcgctt ttggaaccgg gttctgccaa ttacgatcca 720
tgtctagact tcgacccaga aaactgcaca cttacttttg cacccgacac aagccgcatc 780
tgtggagttc atcgcctctc ttacgaactt ggcccccaac gacaaaaatt tacctgcatg 840

-continued gtgggaatca accccatagt tatcacccag caaagtggag atactaaggg ttgcattcac 900
tgctcctgcg attccatcga gtgcacctac accctgctga agaccctatg cggcctaaga 960
gacctgctac caatgaatta a 981

<210> SEQ ID NO 24
<211> LENGTH: 201
<212> TYPE: DNA
<213> ORGANISM: Artificial Sequence
<220> FEATURE:
<223> OTHER INFORMATION: A NON-CODING SEQUENCE SUITABLE FOR INCLUSION INTO BX

<400> SEQUENCE: 24
aaaatgatta ataaaaaatc acttacttga aatcagcaat aaggtctctg ttgaaatttt 60
ctcccagcag cacctcactt ccctcttccc aactctggta ttctaaaccc cgttcagcgg 120
catactttct ccatacttta aaggggatgt caaattttag ctcctctcct gtacccacaa 180
tcttcatgtc tttcttccca g 201

<210> SEQ ID NO 25
<211> LENGTH: 34
<212> TYPE: DNA
<213> ORGANISM: Artificial Sequence
<220> FEATURE:
<223> OTHER INFORMATION: A NON-CODING SEQUENCE SUITABLE FOR INCLUSION INTO BY

<400> SEQUENCE: 25
caaataaagt ttaacttgtt tatttgaaaa tcaa 34

<210> SEQ ID NO 26
<211> LENGTH: 8
<212> TYPE: PRT
<213> ORGANISM: Artificial Sequence
<220> FEATURE:
<223> OTHER INFORMATION: Hinge linker sequences

<400> SEQUENCE: 26

Asp Lys Thr His Thr Cys Ala Ala
1               5

<210> SEQ ID NO 27
<211> LENGTH: 11
<212> TYPE: PRT
<213> ORGANISM: Artificial Sequence
<220> FEATURE:
<223> OTHER INFORMATION: Hinge linker sequence

<400> SEQUENCE: 27

Asp Lys Thr His Thr Cys Pro Pro Cys Pro Ala
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Hinge linker sequence

<400> SEQUENCE: 28

Asp Lys Thr His Thr Cys Pro Pro Cys Pro Ala Thr Cys Pro Pro Cys
1               5                   10                  15

Pro Ala

```
<210> SEQ ID NO 29
<211> LENGTH: 25
<212> TYPE: PRT
<213> ORGANISM: Artificial Sequence
<220> FEATURE:
<223> OTHER INFORMATION: Hinge linker sequence

<400> SEQUENCE: 29

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25


<210> SEQ ID NO 30
<211> LENGTH: 30
<212> TYPE: PRT
<213> ORGANISM: Artificial Sequence
<220> FEATURE:
<223> OTHER INFORMATION: Hinge linker sequence

<400> SEQUENCE: 30

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30


<210> SEQ ID NO 31
<211> LENGTH: 31
<212> TYPE: PRT
<213> ORGANISM: Artificial Sequence
<220> FEATURE:
<223> OTHER INFORMATION: Hinge linker sequence

<400> SEQUENCE: 31

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30


<210> SEQ ID NO 32
<211> LENGTH: 15
<212> TYPE: PRT
<213> ORGANISM: Artificial Sequence
<220> FEATURE:
<223> OTHER INFORMATION: Hinge linker sequence

<400> SEQUENCE: 32

Asp Lys Thr His Thr Cys Cys Val Glu Cys Pro Pro Cys Pro Ala
1               5                   10                  15


<210> SEQ ID NO 33
<211> LENGTH: 26
<212> TYPE: PRT
<213> ORGANISM: Artificial Sequence
<220> FEATURE:
<223> OTHER INFORMATION: Hinge linker sequence

<400> SEQUENCE: 33

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25


<210> SEQ ID NO 34
```

<211> LENGTH: 11
<212> TYPE: PRT
<213> ORGANISM: Artificial Sequence
<220> FEATURE:
<223> OTHER INFORMATION: Hinge linker sequence

<400> SEQUENCE: 34

Asp Lys Thr His Thr Cys Pro Ser Cys Pro Ala
1 5 10

<210> SEQ ID NO 35
<211> LENGTH: 7
<212> TYPE: PRT
<213> ORGANISM: Artificial Sequence
<220> FEATURE:
<223> OTHER INFORMATION: FLEXIBLE LINKER SEQUENCE

<400> SEQUENCE: 35

Ser Gly Gly Gly Gly Ser Glu
1 5

<210> SEQ ID NO 36
<211> LENGTH: 6
<212> TYPE: PRT
<213> ORGANISM: Artificial Sequence
<220> FEATURE:
<223> OTHER INFORMATION: FLEXIBLE LINKER SEQUENCE

<400> SEQUENCE: 36

Asp Lys Thr His Thr Ser
1 5

<210> SEQ ID NO 37
<211> LENGTH: 6
<212> TYPE: PRT
<213> ORGANISM: Artificial Sequence
<220> FEATURE:
<223> OTHER INFORMATION: FLEXIBLE LINKER SEQUENCE

<400> SEQUENCE: 37

Ser Gly Gly Gly Gly Ser
1 5

<210> SEQ ID NO 38
<211> LENGTH: 11
<212> TYPE: PRT
<213> ORGANISM: Artificial Sequence
<220> FEATURE:
<223> OTHER INFORMATION: FLEXIBLE LINKER SEQUENCE

<400> SEQUENCE: 38

Ser Gly Gly Gly Gly Ser Gly Gly Gly Gly Ser
1 5 10

<210> SEQ ID NO 39
<211> LENGTH: 16
<212> TYPE: PRT
<213> ORGANISM: Artificial Sequence
<220> FEATURE:
<223> OTHER INFORMATION: FLEXIBLE LINKER SEQUENCE

<400> SEQUENCE: 39

Ser Gly Gly Gly Gly Ser Gly Gly Gly Gly Ser Gly Gly Gly Gly Ser
1 5 10 15

<210> SEQ ID NO 40
<211> LENGTH: 21

```
<212> TYPE: PRT
<213> ORGANISM: Artificial Sequence
<220> FEATURE:
<223> OTHER INFORMATION: FLEXIBLE LINKER SEQUENCE

<400> SEQUENCE: 40

Ser Gly Gly Gly Gly Ser Gly Gly Gly Gly Ser Gly Gly Gly Gly Ser
1               5                   10                  15

Gly Gly Gly Gly Ser
            20


<210> SEQ ID NO 41
<211> LENGTH: 26
<212> TYPE: PRT
<213> ORGANISM: Artificial Sequence
<220> FEATURE:
<223> OTHER INFORMATION: FLEXIBLE LINKER SEQUENCE

<400> SEQUENCE: 41

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25


<210> SEQ ID NO 42
<211> LENGTH: 11
<212> TYPE: PRT
<213> ORGANISM: Artificial Sequence
<220> FEATURE:
<223> OTHER INFORMATION: FLEXIBLE LINKER SEQUENCE

<400> SEQUENCE: 42

Ala Ala Ala Gly Ser Gly Gly Ala Ser Ala Ser
1               5                   10


<210> SEQ ID NO 43
<211> LENGTH: 16
<212> TYPE: PRT
<213> ORGANISM: Artificial Sequence
<220> FEATURE:
<223> OTHER INFORMATION: FLEXIBLE LINKER SEQUENCE
<220> FEATURE:
<221> NAME/KEY: misc_feature
<222> LOCATION: (7)..(7)
<223> OTHER INFORMATION: Xaa can be any naturally occurring amino acid

<400> SEQUENCE: 43

Ala Ala Ala Gly Ser Gly Xaa Gly Gly Gly Ser Gly Ala Ser Ala Ser
1               5                   10                  15


<210> SEQ ID NO 44
<211> LENGTH: 21
<212> TYPE: PRT
<213> ORGANISM: Artificial Sequence
<220> FEATURE:
<223> OTHER INFORMATION: FLEXIBLE LINKER SEQUENCE
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 44

Ala Ala Ala Gly Ser Gly Xaa Gly Gly Gly Ser Xaa Gly Gly Gly Ser
1               5                   10                  15
```

Gly Ala Ser Ala Ser
20

<210> SEQ ID NO 45
<211> LENGTH: 26
<212> TYPE: PRT
<213> ORGANISM: Artificial Sequence
<220> FEATURE:
<223> OTHER INFORMATION: FLEXIBLE LINKER SEQUENCE
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 45

Ala Ala Ala Gly Ser Gly Xaa Gly Gly Gly Ser Xaa Gly Gly Gly Ser
1 5 10 15

Xaa Gly Gly Gly Ser Gly Ala Ser Ala Ser
20 25

<210> SEQ ID NO 46
<211> LENGTH: 31
<212> TYPE: PRT
<213> ORGANISM: Artificial Sequence
<220> FEATURE:
<223> OTHER INFORMATION: FLEXIBLE LINKER SEQUENCE
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 46

Ala Ala Ala Gly Ser Gly Xaa Gly Gly Gly Ser Xaa Gly Gly Gly Ser
1 5 10 15

Xaa Gly Gly Gly Ser Xaa Gly Gly Gly Ser Gly Ala Ser Ala Ser
20 25 30

<210> SEQ ID NO 47
<211> LENGTH: 13
<212> TYPE: PRT
<213> ORGANISM: Artificial Sequence
<220> FEATURE:
<223> OTHER INFORMATION: FLEXIBLE LINKER SEQUENCE
<220> FEATURE:
<221> NAME/KEY: misc_feature
<222> LOCATION: (7)..(7)
<223> OTHER INFORMATION: Xaa can be any naturally occurring amino acid

<400> SEQUENCE: 47

Ala Ala Ala Gly Ser Gly Xaa Ser Gly Ala Ser Ala Ser 1 5 10

<210> SEQ ID NO 48
<211> LENGTH: 28
<212> TYPE: PRT
<213> ORGANISM: Artificial Sequence
<220> FEATURE:
<223> OTHER INFORMATION: FLEXIBLE LINKER SEQUENCE

<400> SEQUENCE: 48

Pro Gly Gly Asn Arg Gly Thr Thr Thr Thr Arg Arg Pro Ala Thr Thr
1 5 10 15

Thr Gly Ser Ser Pro Gly Pro Thr Gln Ser His Tyr
20 25

<210> SEQ ID NO 49
<211> LENGTH: 11
<212> TYPE: PRT
<213> ORGANISM: Artificial Sequence
<220> FEATURE:
<223> OTHER INFORMATION: FLEXIBLE LINKER SEQUENCE

<400> SEQUENCE: 49

Ala Thr Thr Thr Gly Ser Ser Pro Gly Pro Thr
1 5 10

<210> SEQ ID NO 50
<211> LENGTH: 6
<212> TYPE: PRT
<213> ORGANISM: Artificial Sequence
<220> FEATURE:
<223> OTHER INFORMATION: FLEXIBLE LINKER SEQUENCE

<400> SEQUENCE: 50

Ala Thr Thr Thr Gly Ser
1 5

<210> SEQ ID NO 51
<211> LENGTH: 21
<212> TYPE: PRT
<213> ORGANISM: Artificial Sequence
<220> FEATURE:
<223> OTHER INFORMATION: FLEXIBLE LINKER SEQUENCE

<400> SEQUENCE: 51

Glu Pro Ser Gly Pro Ile Ser Thr Ile Asn Ser Pro Pro Ser Lys Glu
1 5 10 15

Ser His Lys Ser Pro
20

<210> SEQ ID NO 52
<211> LENGTH: 15
<212> TYPE: PRT
<213> ORGANISM: Artificial Sequence
<220> FEATURE:
<223> OTHER INFORMATION: FLEXIBLE LINKER SEQUENCE

<400> SEQUENCE: 52

Gly Thr Val Ala Ala Pro Ser Val Phe Ile Phe Pro Pro Ser Asp
1 5 10 15

<210> SEQ ID NO 53
<211> LENGTH: 15
<212> TYPE: PRT
<213> ORGANISM: Artificial Sequence
<220> FEATURE:

<223> OTHER INFORMATION: FLEXIBLE LINKER SEQUENCE

<400> SEQUENCE: 53

Gly Gly Gly Gly Ile Ala Pro Ser Met Val Gly Gly Gly Gly Ser
1 5 10 15

<210> SEQ ID NO 54
<211> LENGTH: 15
<212> TYPE: PRT
<213> ORGANISM: Artificial Sequence
<220> FEATURE:
<223> OTHER INFORMATION: FLEXIBLE LINKER SEQUENCE

<400> SEQUENCE: 54

Gly Gly Gly Gly Lys Val Glu Gly Ala Gly Gly Gly Gly Gly Ser
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: FLEXIBLE LINKER SEQUENCE

<400> SEQUENCE: 55

Gly Gly Gly Gly Ser Met Lys Ser His Asp Gly Gly Gly Gly Ser
1 5 10 15

<210> SEQ ID NO 56
<211> LENGTH: 15
<212> TYPE: PRT
<213> ORGANISM: Artificial Sequence
<220> FEATURE:
<223> OTHER INFORMATION: FLEXIBLE LINKER SEQUENCE

<400> SEQUENCE: 56

Gly Gly Gly Gly Asn Leu Ile Thr Ile Val Gly Gly Gly Gly Ser
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: FLEXIBLE LINKER SEQUENCE

<400> SEQUENCE: 57

Gly Gly Gly Gly Val Val Pro Ser Leu Pro Gly Gly Gly Gly Ser
1 5 10 15

<210> SEQ ID NO 58
<211> LENGTH: 12
<212> TYPE: PRT
<213> ORGANISM: Artificial Sequence
<220> FEATURE:
<223> OTHER INFORMATION: FLEXIBLE LINKER SEQUENCE

<400> SEQUENCE: 58

Gly Gly Glu Lys Ser Ile Pro Gly Gly Gly Gly Ser
1 5 10

<210> SEQ ID NO 59
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 59

Arg Pro Leu Ser Tyr Arg Pro Pro Phe Pro Phe Gly Phe Pro Ser Val
1 5 10 15

Arg Pro

<210> SEQ ID NO 60
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 60

Tyr Pro Arg Ser Ile Tyr Ile Arg Arg Arg His Pro Ser Pro Ser Leu
1 5 10 15

Thr Thr

<210> SEQ ID NO 61
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 61

Thr Pro Ser His Leu Ser His Ile Leu Pro Ser Phe Gly Leu Pro Thr
1 5 10 15

Phe Asn

<210> SEQ ID NO 62
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 62

Arg Pro Val Ser Pro Phe Thr Phe Pro Arg Leu Ser Asn Ser Trp Leu
1 5 10 15

Pro Ala

<210> SEQ ID NO 63
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 63

Ser Pro Ala Ala His Phe Pro Arg Ser Ile Pro Arg Pro Gly Pro Ile
1 5 10 15

Arg Thr

<210> SEQ ID NO 64
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 64

Ala Pro Gly Pro Ser Ala Pro Ser His Arg Ser Leu Pro Ser Arg Ala 1 5 10 15

Phe Gly

<210> SEQ ID NO 65
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 65

Pro Arg Asn Ser Ile His Phe Leu His Pro Leu Leu Val Ala Pro Leu
1 5 10 15

Gly Ala

<210> SEQ ID NO 66
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 66

Met Pro Ser Leu Ser Gly Val Leu Gln Val Arg Tyr Leu Ser Pro Pro
1 5 10 15

Asp Leu

<210> SEQ ID NO 67
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 67

Ser Pro Gln Tyr Pro Ser Pro Leu Thr Leu Thr Leu Pro Pro His Pro
1 5 10 15

Ser Leu

<210> SEQ ID NO 68
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 68

Asn Pro Ser Leu Asn Pro Pro Ser Tyr Leu His Arg Ala Pro Ser Arg
1 5 10 15

Ile Ser

<210> SEQ ID NO 69
<211> LENGTH: 17
<212> TYPE: PRT
<213> ORGANISM: Artificial Sequence
<220> FEATURE:
<223> OTHER INFORMATION: FLEXIBLE LINKER SEQUENCE

<400> SEQUENCE: 69

Leu Pro Trp Arg Thr Ser Leu Leu Pro Ser Leu Pro Leu Arg Arg Arg
1 5 10 15

Pro

-continued

<210> SEQ ID NO 70
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 70

Pro Pro Leu Phe Ala Lys Gly Pro Val Gly Leu Leu Ser Arg Ser Phe
1 5 10 15

Pro Pro

<210> SEQ ID NO 71
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 71

Val Pro Pro Ala Pro Val Val Ser Leu Arg Ser Ala His Ala Arg Pro
1 5 10 15

Pro Tyr

<210> SEQ ID NO 72
<211> LENGTH: 17
<212> TYPE: PRT
<213> ORGANISM: Artificial Sequence
<220> FEATURE:
<223> OTHER INFORMATION: FLEXIBLE LINKER SEQUENCE

<400> SEQUENCE: 72

Leu Arg Pro Thr Pro Pro Arg Val Arg Ser Tyr Thr Cys Cys Pro Thr
1 5 10 15

Pro

<210> SEQ ID NO 73
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 73

Pro Asn Val Ala His Val Leu Pro Leu Leu Thr Val Pro Trp Asp Asn
1 5 10 15

Leu Arg

<210> SEQ ID NO 74
<211> LENGTH: 18
<212> TYPE: PRT
<213> ORGANISM: Artificial Sequence
<220> FEATURE:
<223> OTHER INFORMATION: FLEXIBLE LINKER SEQUENCE

<400> SEQUENCE: 74

Cys Asn Pro Leu Leu Pro Leu Cys Ala Arg Ser Pro Ala Val Arg Thr
1 5 10 15

Phe Pro

<210> SEQ ID NO 75
<211> LENGTH: 11
<212> TYPE: PRT

<213> ORGANISM: Artificial Sequence
<220> FEATURE:
<223> OTHER INFORMATION: Rigid linker sequence

<400> SEQUENCE: 75

Gly Ala Pro Ala Pro Ala Ala Pro Ala Pro Ala
1               5                   10

<210> SEQ ID NO 76
<211> LENGTH: 4
<212> TYPE: PRT
<213> ORGANISM: Artificial Sequence
<220> FEATURE:
<223> OTHER INFORMATION: Rigid linker sequence

<400> SEQUENCE: 76

Pro Pro Pro Pro
1

<210> SEQ ID NO 77
<211> LENGTH: 11
<212> TYPE: PRT
<213> ORGANISM: Artificial Sequence
<220> FEATURE:
<223> OTHER INFORMATION: LINKER SEQUENCE

<400> SEQUENCE: 77

Asp Leu Cys Leu Arg Asp Trp Gly Cys Leu Trp
1               5                   10

<210> SEQ ID NO 78
<211> LENGTH: 11
<212> TYPE: PRT
<213> ORGANISM: Artificial Sequence
<220> FEATURE:
<223> OTHER INFORMATION: LINKER SEQUENCE

<400> SEQUENCE: 78

Asp Ile Cys Leu Pro Arg Trp Gly Cys Leu Trp
1               5                   10

<210> SEQ ID NO 79
<211> LENGTH: 15
<212> TYPE: PRT
<213> ORGANISM: Artificial Sequence
<220> FEATURE:
<223> OTHER INFORMATION: LINKER SEQUENCE

<400> SEQUENCE: 79

Met Glu Asp Ile Cys Leu Pro Arg Trp Gly Cys Leu Trp Gly Asp
1               5                   10                  15

<210> SEQ ID NO 80
<211> LENGTH: 20
<212> TYPE: PRT
<213> ORGANISM: Artificial Sequence
<220> FEATURE:
<223> OTHER INFORMATION: LINKER SEQUENCE

<400> SEQUENCE: 80

Gln Arg Leu Met Glu Asp Ile Cys Leu Pro Arg Trp Gly Cys Leu Trp
1               5                   10                  15

Glu Asp Asp Glu
            20

<210> SEQ ID NO 81

<211> LENGTH: 20
<212> TYPE: PRT
<213> ORGANISM: Artificial Sequence
<220> FEATURE:
<223> OTHER INFORMATION: LINKER SEQUENCE

<400> SEQUENCE: 81

```
Gln Gly Leu Ile Gly Asp Ile Cys Leu Pro Arg Trp Gly Cys Leu Trp
1               5                   10                  15

Gly Arg Ser Val
            20
```

<210> SEQ ID NO 82
<211> LENGTH: 21
<212> TYPE: PRT
<213> ORGANISM: Artificial Sequence
<220> FEATURE:
<223> OTHER INFORMATION: LINKER SEQUENCE

<400> SEQUENCE: 82

```
Gln Gly Leu Ile Gly Asp Ile Cys Leu Pro Arg Trp Gly Cys Leu Trp
1               5                   10                  15

Gly Arg Ser Val Lys
            20
```

<210> SEQ ID NO 83
<211> LENGTH: 15
<212> TYPE: PRT
<213> ORGANISM: Artificial Sequence
<220> FEATURE:
<223> OTHER INFORMATION: LINKER SEQUENCE

<400> SEQUENCE: 83

```
Glu Asp Ile Cys Leu Pro Arg Trp Gly Cys Leu Trp Glu Asp Asp
1               5                   10                  15
```

<210> SEQ ID NO 84
<211> LENGTH: 18
<212> TYPE: PRT
<213> ORGANISM: Artificial Sequence
<220> FEATURE:
<223> OTHER INFORMATION: LINKER SEQUENCE

<400> SEQUENCE: 84

```
Arg Leu Met Glu Asp Ile Cys Leu Pro Arg Trp Gly Cys Leu Trp Glu
1               5                   10                  15

Asp Asp
```

<210> SEQ ID NO 85
<211> LENGTH: 16
<212> TYPE: PRT
<213> ORGANISM: Artificial Sequence
<220> FEATURE:
<223> OTHER INFORMATION: LINKER SEQUENCE

<400> SEQUENCE: 85

```
Met Glu Asp Ile Cys Leu Pro Arg Trp Gly Cys Leu Trp Glu Asp Asp
1               5                   10                  15
```

<210> SEQ ID NO 86
<211> LENGTH: 15
<212> TYPE: PRT
<213> ORGANISM: Artificial Sequence
<220> FEATURE:
<223> OTHER INFORMATION: LINKER SEQUENCE

<400> SEQUENCE: 86

Met Glu Asp Ile Cys Leu Pro Arg Trp Gly Cys Leu Trp Glu Asp
1 5 10 15

<210> SEQ ID NO 87
<211> LENGTH: 18
<212> TYPE: PRT
<213> ORGANISM: Artificial Sequence
<220> FEATURE:
<223> OTHER INFORMATION: LINKER SEQUENCE

<400> SEQUENCE: 87

Arg Leu Met Glu Asp Ile Cys Leu Ala Arg Trp Gly Cys Leu Trp Glu
1 5 10 15

Asp Asp

<210> SEQ ID NO 88
<211> LENGTH: 20
<212> TYPE: PRT
<213> ORGANISM: Artificial Sequence
<220> FEATURE:
<223> OTHER INFORMATION: LINKER SEQUENCE

<400> SEQUENCE: 88

Glu Val Arg Ser Phe Cys Thr Arg Trp Pro Ala Glu Lys Ser Cys Lys
1 5 10 15

Pro Leu Arg Gly
20

<210> SEQ ID NO 89
<211> LENGTH: 20
<212> TYPE: PRT
<213> ORGANISM: Artificial Sequence
<220> FEATURE:
<223> OTHER INFORMATION: LINKER SEQUENCE

<400> SEQUENCE: 89

Arg Ala Pro Glu Ser Phe Val Cys Tyr Trp Glu Thr Ile Cys Phe Glu
1 5 10 15

Arg Ser Glu Gln
20

<210> SEQ ID NO 90
<211> LENGTH: 11
<212> TYPE: PRT
<213> ORGANISM: Artificial Sequence
<220> FEATURE:
<223> OTHER INFORMATION: LINKER SEQUENCE

<400> SEQUENCE: 90

Glu Met Cys Tyr Phe Pro Gly Ile Cys Trp Met
1 5 10

<210> SEQ ID NO 91
<211> LENGTH: 20
<212> TYPE: PRT
<213> ORGANISM: Artificial Sequence
<220> FEATURE:
<223> OTHER INFORMATION: PDGFR RECEPTOR A

<400> SEQUENCE: 91

Ala Val Leu Val Leu Leu Val Ile Val Ile Ile Ser Leu Ile Val Leu
1 5 10 15

Val Val Ile Trp

20

<210> SEQ ID NO 92
<211> LENGTH: 21
<212> TYPE: PRT
<213> ORGANISM: Artificial Sequence
<220> FEATURE:
<223> OTHER INFORMATION: PDGFR RECEPTOR B

<400> SEQUENCE: 92

Val Val Ile Ser Ala Ile Leu Ala Leu Val Val Leu Thr Ile Ile Ser
1 5 10 15

Leu Ile Ile Leu Ile
20

<210> SEQ ID NO 93
<211> LENGTH: 24
<212> TYPE: PRT
<213> ORGANISM: Artificial Sequence
<220> FEATURE:
<223> OTHER INFORMATION: INSULIN-LIKE GROWTH FACTOR 1

<400> SEQUENCE: 93

Ile Ile Ile Gly Pro Pro Leu Ile Phe Val Phe Leu Phe Ser Val Val
1 5 10 15

Ile Gly Ser Ile Tyr Leu Phe Leu
20

<210> SEQ ID NO 94
<211> LENGTH: 28
<212> TYPE: PRT
<213> ORGANISM: Artificial Sequence
<220> FEATURE:
<223> OTHER INFORMATION: IL6-R

<400> SEQUENCE: 94

Ser Ser Ser Val Pro Leu Pro Thr Phe Leu Val Ala Gly Gly Ser Leu
1 5 10 15

Ala Phe Gly Thr Leu Leu Cys Ile Ala Ile Val Leu
20 25

<210> SEQ ID NO 95
<211> LENGTH: 27
<212> TYPE: PRT
<213> ORGANISM: Artificial Sequence
<220> FEATURE:
<223> OTHER INFORMATION: CD28

<400> SEQUENCE: 95

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 96
<211> LENGTH: 34522
<212> TYPE: DNA
<213> ORGANISM: Artificial Sequence
<220> FEATURE:
<223> OTHER INFORMATION: NG-348 virus genome sequence comprising a transgene cassette that encoding a membrane-anchored chimeric form an anti-human CD3e scFv, and CD80 inserted in the region BY

<400> SEQUENCE: 96
tctatctata taatatacct tatagatgga atggtgccaa tatgtaaatg aggtgatttt 60

-continued

```
aaaaagtgtg gatcgtgtgg tgattggctg tggggttaac ggctaaaagg ggcggtgcga    120
ccgtgggaaa atgacgtttt gtgggggtgg agttttttttg caagttgtcg cgggaaatgt    180
gacgcataaa aaggcttttt tctcacggaa ctacttagtt ttcccacggt atttaacagg    240
aaatgaggta gttttgaccg gatgcaagtg aaaattgttg attttcgcgc gaaaactgaa    300
tgaggaagtg tttttctgaa taatgtggta tttatggcag ggtggagtat ttgttcaggg    360
ccaggtagac tttgacccat tacgtggagg tttcgattac cgtgtttttt acctgaattt    420
ccgcgtaccg tgtcaaagtc ttctgttttt acgtaggtgt cagctgatcg ctagggtatt    480
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
```

-continued

```
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
```

```
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tgggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
```

-continued

```
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
```

aacctttcga cgaaagcgtc taaccagtca cagtcacaag gtaggctgag tacggcttct 9600
tgtgggcggg ggtggttatg tgttcggtct gggtcttctg tttcttcttc atctcgggaa 9660
ggtgagacga tgctgctggt gatgaaatta aagtaggcag ttctaagacg gcggatggtg 9720
gcgaggagca ccaggtcttt gggtccggct tgctggatac gcaggcgatt ggccattccc 9780
caagcattat cctgacatct agcaagatct ttgtagtagt cttgcatgag ccgttctacg 9840
ggcacttctt cctcacccgt tctgccatgc atacgtgtga gtccaaatcc gcgcattggt 9900
tgtaccagtg ccaagtcagc tacgactctt tcggcgagga tggcttgctg tacttgggta 9960
agggtggctt gaaagtcatc aaaatccaca aagcggtggt aagctcctgt attaatggtg 10020
taagcacagt tggccatgac tgaccagtta actgtctggt gaccagggcg cacgagctcg 10080
gtgtatttaa ggcgcgaata ggcgcgggtg tcaaagatgt aatcgttgca ggtgcgcacc 10140
agatactggt accctataag aaaatgcggc ggtggttggc ggtagagagg ccatcgttct 10200
gtagctggag cgccaggggc gaggtcttcc aacataaggc ggtgatagcc gtagatgtac 10260
ctggacatcc aggtgattcc tgcggcggta gtagaagccc gaggaaactc gcgtacgcgg 10320
ttccaaatgt tgcgtagcgg catgaagtag ttcattgtag gcacggtttg accagtgagg 10380
cgcgcgcagt cattgatgct ctatagacac ggagaaaatg aaagcgttca gcgactcgac 10440
tccgtagcct ggaggaacgt gaacgggttg ggtcgcggtg taccccggtt cgagacttgt 10500
actcgagccg gccggagccg cggctaacgt ggtattggca ctcccgtctc gacccagcct 10560
acaaaaatcc aggatacgga atcgagtcgt tttgctggtt tccgaatggc agggaagtga 10620
gtcctatttt tttttttgc cgctcagatg catcccgtgc tgcgacagat gcgcccccaa 10680
caacagcccc cctcgcagca gcagcagcag caatcacaaa aggctgtccc tgcaactact 10740
gcaactgccg ccgtgagcgg tgcgggacag cccgcctatg atctggactt ggaagagggc 10800
gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880

-continued

```
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgccccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
```

-continued

```
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg gggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
```

-continued

```
gcctggtctg ggggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
```

atcagaaagt cgaatatgat atcgacatgg agttttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg gggtgctgg ctggtcaagc gtctcagtta aatgcagtgg 19320
ttgacttgca ggacagaaac acagaacttt cttaccaact cttgcttgac tctctgggcg 19380
acagaaccag atactttagc atgtggaatc aggctgtgga cagttatgat cctgatgtac 19440
gtgttattga aaatcatggt gtggaagatg aacttcccaa ctactgtttt ccactggacg 19500
gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220
caaccaatat tcccatttcc attccttctc gcaactgggc ggctttcaga ggctggtcat 20280
ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360

-continued

```
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
```

ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac caccccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100

-continued

```
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
cccctttata aacccagggt ttatttcccc aaatggcttc acacaaagcc caaacggagt  28500
```

-continued

```
tcttacttta aaatgtttaa ccccactaac aaccacaggc ggatctctac agctaaaagt  28560
gggaggggga cttacagtgg atgacaccaa cggttttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc caccatggga tggagctgta tcatcctctt  29400
cttggtagca acagctacag gtgtccactc ccaggtgcag ctgcagcagt ctggggctga  29460
actggcaaga cctggggcct cagtgaagat gtcctgcaag gcttctggct acacctttac  29520
taggtacacg atgcactggg taaaacagag gcctggacag ggtctggaat ggattggata  29580
cattaatcct agccgtggtt atactaatta caatcagaag ttcaaggaca aggccacatt  29640
gactacagac aaatcctcca gcacagccta catgcaactg agcagcctga catctgagga  29700
ctctgcagtc tattactgtg caagatatta tgatgatcat tactgccttg actactgggg  29760
ccaaggcacc actctcacag tctcctcagg tggcggtggc tcgggcggtg gtggatctgg  29820
tggcggcgga tctgatatcg tgctcactca gtctccagca atcatgtctg catctccagg  29880
ggagaaggtc accatgacct gcagtgccag ctcaagtgta agttacatga actggtacca  29940
gcagaagtca ggcacctccc ccaaaagatg gatttatgac acatccaaac tggcttctgg  30000
agtccctgct cacttcaggg gcagtgggtc tgggacctct tactctctca caatcagcgg  30060
catggaggct gaagatgctg ccacttatta ctgccagcag tggagtagta acccattcac  30120
gttcggctcg gggacaaagt tggaaataaa ccggggatcc gaacaaaaac tcatctcaga  30180
agaggatctg aatgctgtgg gccaggacac gcaggaggtc atcgtggtgc cacactcctt  30240
gccctttaag gtggtggtga tctcagccat cctggccctg gtggtgctca ccatcatctc  30300
ccttatcatc ctcatcatgc tttggcagaa gaagccacgt ggaagcggag ctactaactt  30360
cagcctgctg aagcaggctg gagacgtgga ggagaaccct ggacctggcc acacacggag  30420
gcagggaaca tcaccatcca agtgtccata cctcaatttc tttcagctct tggtgctggc  30480
tggtctttct cacttctgtt caggtgttat ccacgtgacc aaggaagtga aagaagtggc  30540
aacgctgtcc tgtggtcaca atgtttctgt tgaagagctg gcacaaactc gcatctactg  30600
gcaaaaggag aagaaaatgg tgctgactat gatgtctggg gacatgaata tatggcccga  30660
gtacaagaac cggaccatct ttgatatcac taataacctc tccattgtga tcctggctct  30720
gcgcccatct gacgagggca catacgagtg tgttgttctg aagtatgaaa aagacgcttt  30780
caagcgggaa cacctggctg aagtgacgtt atcagtcaaa gctgacttcc ctacacctag  30840
```

-continued

```
tatatctgac tttgaaattc caacttctaa tattagaagg ataatttgct caacctctgg  30900
aggttttcca gagcctcacc tctcctggtt ggaaaatgga gaagaattaa atgccatcaa  30960
cacaacagtt tcccaagatc ctgaaactga gctctatgct gttagcagca aactggattt  31020
caatatgaca accaaccaca gcttcatgtg tctcatcaag tatggacatt taagagtgaa  31080
tcagaccttc aactggaata caaccaagca agagcatttt cctgataacc tgctcccatc  31140
ctgggccatt accttaatct cagtaaatgg aatttttgtg atatgctgcc tgacctactg  31200
ctttgcccca agatgcagag agagaaggag gaatgagaga ttgagaaggg aaagtgtacg  31260
ccctgtataa gctagcttga ctgactgaga tacagcgtac cttcagctca cagacatgat  31320
aagatacatt gatgagtttg gacaaaccac aactagaatg cagtgaaaaa aatgctttat  31380
ttgtgaaatt tgtgatgcta ttgctttatt tgtaaccatt ataagctgca ataaacaagt  31440
taacaacaac aattgcattc attttatgtt tcaggttcag ggggaggtgt gggaggtttt  31500
ttaaagcaag taaaacctct acaaatgtgg tagtcgtcag ctatcctgca ggaacttgtt  31560
tatttgaaaa tcaattcaca aaatccgagt agttattttg cctccccctt cccatttaac  31620
agaatacacc aatctctccc cacgcacagc tttaaacatt tggataccat tagatataga  31680
catggtttta gattccacat tccaaacagt ttcagagcga gccaatctgg ggtcagtgat  31740
agataaaaat ccatcgggat agtcttttaa agcgctttca cagtccaact gctgcggatg  31800
cgactccgga gtctggatca cggtcatctg gaagaagaac gatgggaatc ataatccgaa  31860
aacggtatcg gacgattgtg tctcatcaaa cccacaagca gccgctgtct gcgtcgctcc  31920
gtgcgactgc tgtttatggg atcagggtcc acagtgtcct gaagcatgat tttaatagcc  31980
cttaacatca actttctggt gcgatgcgcg cagcaacgca ttctgatttc actcaaatct  32040
ttgcagtagg tacaacacat tattacaata ttgtttaata aaccataatt aaaagcgctc  32100
cagccaaaac tcatatctga tataatcgcc cctgcatgac catcatacca aagtttaata  32160
taaattaaat gacgttccct caaaaacaca ctacccacat acatgatctc ttttggcatg  32220
tgcatattaa caatctgtct gtaccatgga caacgttggt taatcatgca acccaatata  32280
accttccgga accacactgc caacaccgct cccccagcca tgcattgaag tgaaccctgc  32340
tgattacaat gacaatgaag aacccaattc tctcgaccgt gaatcacttg agaatgaaaa  32400
atatctatag tggcacaaca tagacataaa tgcatgcatc ttctcataat ttttaactcc  32460
tcaggattta gaaacatatc ccagggaata ggaagctctt gcagaacagt aaagctggca  32520
gaacaaggaa gaccacgaac acaacttaca ctatgcatag tcatagtatc acaatctggc  32580
aacagcgggt ggtcttcagt catagaagct cgggtttcat tttcctcaca acgtggtaac  32640
tgggctctgg tgtaagggtg atgtctggcg catgatgtcg agcgtgcgcg caaccttgtc  32700
ataatggagt tgcttcctga cattctcgta ttttgtatag caaaacgcgg ccctggcaga  32760
acacactctt cttcgccttc tatcctgccg cttagcgtgt tccgtgtgat agttcaagta  32820
caaccacact cttaagttgg tcaaaagaat gctggcttca gttgtaatca aaactccatc  32880
gcatctaatc gttctgagga aatcatccaa gcaatgcaac tggattgtgt ttcaagcagg  32940
agaggagagg gaagagacgg aagaaccatg ttaattttta ttccaaacga tctcgcagta  33000
cttcaaattg tagatcgcgc agatggcatc tctcgccccc actgtgttgg tgaaaaagca  33060
cagctagatc aaaagaaatg cgattttcaa ggtgctcaac ggtggcttcc agcaaagcct  33120
ccacgcgcac atccaagaac aaaagaatac caaaagaagg agcattttct aactcctcaa  33180
tcatcatatt acattcctgc accattccca gataattttc agctttccag ccttgaatta  33240
```

-continued ttcgtgtcag ttcttgtggt aaatccaatc cacacattac aaacaggtcc cggagggcgc 33300
cctccaccac cattcttaaa cacaccctca taatgacaaa atatcttgct cctgtgtcac 33360
ctgtagcgaa ttgagaatgg caacatcaat tgacatgccc ttggctctaa gttcttcttt 33420
aagttctagt tgtaaaaact ctctcatatt atcaccaaac tgcttagcca gaagcccccc 33480
gggaacaaga gcaggggacg ctacagtgca gtacaagcgc agacctcccc aattggctcc 33540
agcaaaaaca agattggaat aagcatattg ggaaccgcca gtaatatcat cgaagttgct 33600
ggaaatataa tcaggcagag tttcttgtaa aaattgaata aaagaaaaat ttgccaaaaa 33660
aacattcaaa acctctggga tgcaaatgca ataggttacc gcgctgcgct ccaacattgt 33720
tagttttgaa ttagtctgca aaaataaaaa aaaaaacaag cgtcatatca tagtagcctg 33780
acgaacagat ggataaatca gtctttccat cacaagacaa gccacagggt ctccagctcg 33840
accctcgtaa aacctgtcat catgattaaa caacagcacc gaaagttcct cgcggtgacc 33900
agcatgaata attcttgatg aagcatacaa tccagacatg ttagcatcag ttaacgagaa 33960
aaaacagcca acatagcctt tgggtataat tatgcttaat cgtaagtata gcaaagccac 34020
ccctcgcgga tacaaagtaa aaggcacagg agaataaaaa atataattat ttctctgctg 34080
ctgttcaggc aacgtcgccc ccggtccctc taaatacaca tacaaagcct catcagccat 34140
ggcttaccag acaaagtaca gcgggcacac aaagcacaag ctctaaagtg actctccaac 34200
ctctccacaa tatatatata cacaagccct aaactgacgt aatgggagta aagtgtaaaa 34260
aatcccgcca aacccaacac acaccccgaa actgcgtcac cagggaaaag tacagtttca 34320
cttccgcaat cccaacaggc gtaacttcct ctttctcacg gtacgtgata tcccactaac 34380
ttgcaacgtc attttcccac ggtcgcaccg cccctttag ccgttaaccc cacagccaat 34440
caccacacga tccacacttt ttaaaatcac ctcatttaca tattggcacc attccatcta 34500
taaggtatat tatatagata ga 34522

<210> SEQ ID NO 97
<211> LENGTH: 966
<212> TYPE: DNA
<213> ORGANISM: Artificial Sequence
<220> FEATURE:
<223> OTHER INFORMATION: MEMBRANE TETHERED OKT3-SCFV NUCLEIC ACID SEQUENCE

<400> SEQUENCE: 97
atgggatgga gctgtatcat cctcttcttg gtagcaacag ctacaggtgt ccactcccag 60
gtgcagctgc agcagtctgg ggctgaactg gcaagacctg gggcctcagt gaagatgtcc 120
tgcaaggctt ctggctacac ctttactagg tacacgatgc actgggtaaa acagaggcct 180
ggacagggtc tggaatggat tggatacatt aatcctagcc gtggttatac taattacaat 240
cagaagttca aggacaaggc cacattgact acagacaaat cctccagcac agcctacatg 300
caactgagca gcctgacatc tgaggactct gcagtctatt actgtgcaag atattatgat 360
gatcattact gccttgacta ctggggccaa ggcaccactc tcacagtctc ctcaggtggc 420
ggtggctcgg gcggtggtgg atctggtggc ggcggatctg atatcgtgct cactcagtct 480
ccagcaatca tgtctgcatc tccaggggag aaggtcacca tgacctgcag tgccagctca 540
agtgtaagtt acatgaactg gtaccagcag aagtcaggca cctcccccaa aagatggatt 600
tatgacacat ccaaactggc ttctggagtc cctgctcact tcaggggcag tgggtctggg 660
acctcttact ctctcacaat cagcggcatg gaggctgaag atgctgccac ttattactgc 720
cagcagtgga gtagtaaccc attcacgttc ggctcgggga caaagttgga aataaaccgg 780
ggatccgaac aaaaactcat ctcagaagag gatctgaatg ctgtgggcca ggacacgcag 840
gaggtcatcg tggtgccaca ctccttgccc tttaaggtgg tggtgatctc agccatcctg 900
gccctggtgg tgctcaccat catctccctt atcatcctca tcatgctttg gcagaagaag 960
ccacgt 966

<210> SEQ ID NO 98
<211> LENGTH: 2196
<212> TYPE: DNA
<213> ORGANISM: Artificial Sequence
<220> FEATURE:
<223> OTHER INFORMATION: Transgene Cassette sequence - NG-348

<400> SEQUENCE: 98
gcgatcgcca ggcccaccat gggatggagc tgtatcatcc tcttcttggt agcaacagct 60
acaggtgtcc actcccaggt gcagctgcag cagtctgggg ctgaactggc aagacctggg 120
gcctcagtga agatgtcctg caaggcttct ggctacacct ttactaggta cacgatgcac 180
tgggtaaaac agaggcctgg acagggtctg gaatggattg gatacattaa tcctagccgt 240
ggttatacta attacaatca gaagttcaag gacaaggcca cattgactac agacaaatcc 300
tccagcacag cctacatgca actgagcagc ctgacatctg aggactctgc agtctattac 360
tgtgcaagat attatgatga tcattactgc cttgactact ggggccaagg caccactctc 420
acagtctcct caggtggcgg tggctcgggc ggtggtggat ctggtggcgg cggatctgat 480
atcgtgctca ctcagtctcc agcaatcatg tctgcatctc caggggagaa ggtcaccatg 540
acctgcagtg ccagctcaag tgtaagttac atgaactggt accagcagaa gtcaggcacc 600
tcccccaaaa gatggattta tgacacatcc aaactggctt ctggagtccc tgctcacttc 660
aggggcagtg ggtctgggac ctcttactct ctcacaatca gcggcatgga ggctgaagat 720
gctgccactt attactgcca gcagtggagt agtaacccat tcacgttcgg ctcggggaca 780
aagttggaaa taaaccgggg atccgaacaa aaactcatct cagaagagga tctgaatgct 840
gtgggccagg acacgcagga ggtcatcgtg gtgccacact ccttgccctt taaggtggtg 900
gtgatctcag ccatcctggc cctggtggtg ctcaccatca tctcccttat catcctcatc 960
atgctttggc agaagaagcc acgtggaagc ggagctacta acttcagcct gctgaagcag 1020
gctggagacg tggaggagaa ccctggacct ggccacacac ggaggcaggg aacatcacca 1080
tccaagtgtc catacctcaa tttctttcag ctcttggtgc tggctggtct ttctcacttc 1140
tgttcaggtg ttatccacgt gaccaaggaa gtgaaagaag tggcaacgct gtcctgtggt 1200
cacaatgttt ctgttgaaga gctggcacaa actcgcatct actggcaaaa ggagaagaaa 1260
atggtgctga ctatgatgtc tggggacatg aatatatggc ccgagtacaa gaaccggacc 1320
atctttgata tcactaataa cctctccatt gtgatcctgg ctctgcgccc atctgacgag 1380
ggcacatacg agtgtgttgt tctgaagtat gaaaaagacg ctttcaagcg ggaacacctg 1440
gctgaagtga cgttatcagt caaagctgac ttccctacac ctagtatatc tgactttgaa 1500
attccaactt ctaatattag aaggataatt tgctcaacct ctggaggttt tccagagcct 1560
cacctctcct ggttggaaaa tggagaagaa ttaaatgcca tcaacacaac agtttcccaa 1620
gatcctgaaa ctgagctcta tgctgttagc agcaaactgg atttcaatat gacaaccaac 1680
cacagcttca tgtgtctcat caagtatgga catttaagag tgaatcagac cttcaactgg 1740

-continued aatacaacca agcaagagca ttttcctgat aacctgctcc catcctgggc cattacctta 1800
atctcagtaa atggaatttt tgtgatatgc tgcctgacct actgctttgc cccaagatgc 1860
agagagagaa ggaggaatga gagattgaga agggaaagtg tacgccctgt ataagctagc 1920
ttgactgact gagatacagc gtaccttcag ctcacagaca tgataagata cattgatgag 1980
tttggacaaa ccacaactag aatgcagtga aaaaaatgct ttatttgtga aatttgtgat 2040
gctattgctt tatttgtaac cattataagc tgcaataaac aagttaacaa caacaattgc 2100
attcatttta tgtttcaggt tcaggggggag gtgtgggagg ttttttaaag caagtaaaac 2160
ctctacaaat gtggtagtcg tcagctatcc tgcagg 2196

<210> SEQ ID NO 99
<211> LENGTH: 333
<212> TYPE: PRT
<213> ORGANISM: Artificial Sequence
<220> FEATURE:
<223> OTHER INFORMATION: Membrane anchored form of the anti-human CD3
single chain Fv with C-terminal V5 tag

<400> SEQUENCE: 99

Met Gly Trp Ser Cys Ile Ile Leu Phe Leu Val Ala Thr Ala Thr Gly
1 5 10 15

Val His Ser Gln Val Gln Leu Gln Gln Ser Gly Ala Glu Leu Ala Arg
20 25 30

Pro Gly Ala Ser Val Lys Met Ser Cys Lys Ala Ser Gly Tyr Thr Phe
35 40 45

Thr Arg Tyr Thr Met His Trp Val Lys Gln Arg Pro Gly Gln Gly Leu
50 55 60

Glu Trp Ile Gly Tyr Ile Asn Pro Ser Arg Gly Tyr Thr Asn Tyr Asn
65 70 75 80

Gln Lys Phe Lys Asp Lys Ala Thr Leu Thr Thr Asp Lys Ser Ser Ser
85 90 95

Thr Ala Tyr Met Gln Leu Ser Ser Leu Thr Ser Glu Asp Ser Ala Val
100 105 110

Tyr Tyr Cys Ala Arg Tyr Tyr Asp Asp His Tyr Cys Leu Asp Tyr Trp
115 120 125

Gly Gln Gly Thr Thr Leu Thr Val Ser Ser Gly Gly Gly Gly Ser Gly
130 135 140

Gly Gly Gly Ser Gly Gly Gly Gly Ser Asp Ile Val Leu Thr Gln Ser
145 150 155 160

Pro Ala Ile Met Ser Ala Ser Pro Gly Glu Lys Val Thr Met Thr Cys
165 170 175

Ser Ala Ser Ser Ser Val Ser Tyr Met Asn Trp Tyr Gln Gln Lys Ser
180 185 190

Gly Thr Ser Pro Lys Arg Trp Ile Tyr Asp Thr Ser Lys Leu Ala Ser
195 200 205

Gly Val Pro Ala His Phe Arg Gly Ser Gly Ser Gly Thr Ser Tyr Ser
210 215 220

Leu Thr Ile Ser Gly Met Glu Ala Glu Asp Ala Ala Thr Tyr Tyr Cys
225 230 235 240

Gln Gln Trp Ser Ser Asn Pro Phe Thr Phe Gly Ser Gly Thr Lys Leu
245 250 255

Glu Ile Asn Arg Gly Ser Glu Gln Lys Leu Ile Ser Glu Glu Asp Leu
260 265 270

Asn Ala Val Gly Gln Asp Thr Gln Glu Val Ile Val Val Pro His Ser

-continued

```
        275                 280                 285

Leu Pro Phe Lys Val Val Val Ile Ser Ala Ile Leu Ala Leu Val Val
    290                 295                 300

Leu Thr Ile Ile Ser Leu Ile Ile Leu Ile Met Leu Trp Gln Lys Lys
305                 310                 315                 320

Pro Arg Gly Ser Ile Pro Asn Pro Leu Leu Gly Leu Asp
                325                 330
```

<210> SEQ ID NO 100
<211> LENGTH: 9
<212> TYPE: PRT
<213> ORGANISM: Artificial Sequence
<220> FEATURE:
<223> OTHER INFORMATION: V5 tag (9 amino acid variant)

<400> SEQUENCE: 100

```
Ile Pro Asn Pro Leu Leu Gly Leu Asp
1               5
```

<210> SEQ ID NO 101
<211> LENGTH: 34555
<212> TYPE: DNA
<213> ORGANISM: Artificial Sequence
<220> FEATURE:
<223> OTHER INFORMATION: NG-348A virus genome sequence comprising a transgene cassette encoding a membrane-anchored chimeric form of the anti-human CD3e scFv with C-terminal V5 tag and CD80 inserted in the region BY

<400> SEQUENCE: 101

```
tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540

tctgcgccgg cagtttaata ataaaaaaat gagagatttg cgatttctgc ctcaggaaat    600

aatctctgct gagactggaa atgaaatatt ggagcttgtg gtgcacgccc tgatgggaga    660

cgatccggag ccacctgtgc agctttttga gcctcctacg cttcaggaac tgtatgattt    720

agaggtagag ggatcggagg attctaatga ggaagctgta aatggctttt ttaccgattc    780

tatgctttta gctgctaatg aagggttaga attagatccg cctttggaca cttttgatac    840

tccaggggta attgtggaaa gcggtacagg tgtaagaaaa ttacctgatt tgagttccgt    900

ggactgtgat ttgcactgct atgaagacgg gtttcctccg agtgatgagg aggaccatga    960

aaaggagcag tccatgcaga ctgcagcggg tgagggagtg aaggctgcca atgttggttt   1020

tcagttggat tgcccggagc ttcctggaca tggctgtaag tcttgtgaat ttcacaggaa   1080

aaatactgga gtaaaggaac tgttatgttc gctttgttat atgagaacgc actgccactt   1140

tatttacagt aagtgtgttt aagttaaaat ttaaaggaat atgctgtttt tcacatgtat   1200

attgagtgtg agttttgtgc ttcttattat aggtcctgtg tctgatgctg atgaatcacc   1260
```

-continued

```
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
```

-continued

```
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tggggggggta taaaaggggg cggttctttg ctcttcctca ctgtcttccg gatcgctgtc   5940
caggaacgtc agctgttggg gtaggtattc cctctcgaag gcgggcatga cctctgcact   6000
```

-continued

```
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
```

-continued

```
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc cctgggattt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgccccc aa  10680
caacagcccc cctcgcagca gcagcagcag caatcacaaa aggctgtccc tgcaactact  10740
```

-continued

```
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
```

-continued

```
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caactttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
```

ccgtgttcgc ggacattttc gcgctccatg gggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccccctc gcacttagaa 15960 gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg ggggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220 gtttttttacc agccttaatt ccaattatcg ctgctgcaat tggcgcgata ccaggcatag 17280
cttccgtggc ggttcaggcc tcgcaacgac attgacattg gaaaaaaacg tataaataaa 17340
aaaaaaaaaa tacaatggac tctgacactc ctggtcctgt gactatgttt tcttagagat 17400
ggaagacatc aatttttcat ccttggctcc gcgacacggc acgaagccgt acatgggcac 17460
ctggagcgac atcggcacga gccaactgaa cgggggcgcc ttcaattgga gcagtatctg 17520
gagcgggctt aaaaatttttg gctcaaccat aaaaacatac gggaacaaag cttggaacag 17580
cagtacagga caggcgctta gaaataaact taaagaccag aacttccaac aaaaagtagt 17640
cgatgggata gcttccggca tcaatggagt ggtagatttg gctaaccagg ctgtgcagaa 17700
aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880

-continued

```
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
```

-continued

```
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
```

```
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
```

-continued

```
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
```

gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aatcacttta cttgaaatca 28200
gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
ccccctttata aacccagggt ttatttcccc aaatggcttc acacaaagcc caaacggagt 28500
tcttacttta aaatgtttaa ccccactaac aaccacaggc ggatctctac agctaaaagt 28560
gggagggggga cttacagtgg atgacaccaa cggtttttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc caccatggga tggagctgta tcatcctctt 29400
cttggtagca acagctacag gtgtccactc ccaggtgcag ctgcagcagt ctggggctga 29460
actggcaaga cctggggcct cagtgaagat gtcctgcaag gcttctggct acacctttac 29520
taggtacacg atgcactggg taaaacagag gcctggacag ggtctggaat ggattggata 29580
cattaatcct agccgtggtt atactaatta caatcagaag ttcaaggaca aggccacatt 29640
gactacagac aaatcctcca gcacagccta catgcaactg agcagcctga catctgagga 29700

-continued

```
ctctgcagtc tattactgtg caagatatta tgatgatcat tactgccttg actactgggg  29760
ccaaggcacc actctcacag tctcctcagg tggcggtggc tcgggcggtg gtggatctgg  29820
tggcggcgga tctgatatcg tgctcactca gtctccagca atcatgtctg catctccagg  29880
ggagaaggtc accatgacct gcagtgccag ctcaagtgta agttacatga actggtacca  29940
gcagaagtca ggcacctccc ccaaaagatg gatttatgac acatccaaac tggcttctgg  30000
agtccctgct cacttcaggg gcagtgggtc tgggacctct tactctctca caatcagcgg  30060
catggaggct gaagatgctg ccacttatta ctgccagcag tggagtagta acccattcac  30120
gttcggctcg gggacaaagt tggaaataaa ccggggatcc gaacaaaaac tcatctcaga  30180
agaggatctg aatgctgtgg gccaggacac gcaggaggtc atcgtggtgc cacactcctt  30240
gccctttaag gtggtggtga tctcagccat cctggccctg gtggtgctca ccatcatctc  30300
ccttatcatc ctcatcatgc tttggcagaa gaagccacgt ggttcaatcc ctaaccctct  30360
cctcggtctc gatggaagcg gagctactaa cttcagcctg ctgaagcagg ctggagacgt  30420
ggaggagaac cctggacctg gccacacacg gaggcaggga acatcaccat ccaagtgtcc  30480
atacctcaat ttctttcagc tcttggtgct ggctggtctt tctcacttct gttcaggtgt  30540
tatccacgtg accaaggaag tgaaagaagt ggcaacgctg tcctgtggtc acaatgtttc  30600
tgttgaagag ctggcacaaa ctcgcatcta ctggcaaaag gagaagaaaa tggtgctgac  30660
tatgatgtct ggggacatga atatatggcc cgagtacaag aaccggacca tctttgatat  30720
cactaataac ctctccattg tgatcctggc tctgcgccca tctgacgagg gcacatacga  30780
gtgtgttgtt ctgaagtatg aaaaagacgc tttcaagcgg gaacacctgg ctgaagtgac  30840
gttatcagtc aaagctgact tccctacacc tagtatatct gactttgaaa ttccaacttc  30900
taatattaga aggataattt gctcaacctc tggaggtttt ccagagcctc acctctcctg  30960
gttggaaaat ggagaagaat taaatgccat caacacaaca gtttcccaag atcctgaaac  31020
tgagctctat gctgttagca gcaaactgga tttcaatatg acaaccaacc acagcttcat  31080
gtgtctcatc aagtatggac atttaagagt gaatcagacc ttcaactgga atacaaccaa  31140
gcaagagcat tttcctgata acctgctccc atcctgggcc attaccttaa tctcagtaaa  31200
tggaattttt gtgatatgct gcctgaccta ctgctttgcc ccaagatgca gagagagaag  31260
gaggaatgag agattgagaa gggaaagtgt acgccctgta taagctagct tgactgactg  31320
agatacagcg taccttcagc tcacagacat gataagatac attgatgagt ttggacaaac  31380
cacaactaga atgcagtgaa aaaaatgctt tatttgtgaa atttgtgatg ctattgcttt  31440
atttgtaacc attataagct gcaataaaca agttaacaac aacaattgca ttcattttat  31500
gtttcaggtt cagggggagg tgtgggaggt tttttaaagc aagtaaaacc tctacaaatg  31560
tggtagtcgt cagctatcct gcaggaactt gtttatttga aaatcaattc acaaaatccg  31620
agtagttatt ttgcctcccc cttcccattt aacagaatac accaatctct ccccacgcac  31680
agctttaaac atttggatac cattagatat agacatggtt ttagattcca cattccaaac  31740
agtttcagag cgagccaatc tggggtcagt gatagataaa aatccatcgg gatagtcttt  31800
taaagcgctt tcacagtcca actgctgcgg atgcgactcc ggagtctgga tcacggtcat  31860
ctggaagaag aacgatggga atcataatcc gaaaacggta tcggacgatt gtgtctcatc  31920
aaacccacaa gcagccgctg tctgcgtcgc tccgtgcgac tgctgtttat gggatcaggg  31980
tccacagtgt cctgaagcat gattttaata gcccttaaca tcaactttct ggtgcgatgc  32040
gcgcagcaac gcattctgat ttcactcaaa tctttgcagt aggtacaaca cattattaca  32100
```

atattgttta ataaaccata attaaaagcg ctccagccaa aactcatatc tgatataatc 32160
gcccctgcat gaccatcata ccaaagttta atataaatta aatgacgttc cctcaaaaac 32220
acactaccca catacatgat ctcttttggc atgtgcatat taacaatctg tctgtaccat 32280
ggacaacgtt ggttaatcat gcaacccaat ataaccttcc ggaaccacac tgccaacacc 32340
gctcccccag ccatgcattg aagtgaaccc tgctgattac aatgacaatg aagaacccaa 32400
ttctctcgac cgtgaatcac ttgagaatga aaaatatcta tagtggcaca acatagacat 32460
aaatgcatgc atcttctcat aatttttaac tcctcaggat ttagaaacat atcccaggga 32520
ataggaagct cttgcagaac agtaaagctg gcagaacaag gaagaccacg aacacaactt 32580
acactatgca tagtcatagt atcacaatct ggcaacagcg ggtggtcttc agtcatagaa 32640
gctcgggttt cattttcctc acaacgtggt aactgggctc tggtgtaagg gtgatgtctg 32700
gcgcatgatg tcgagcgtgc gcgcaacctt gtcataatgg agttgcttcc tgacattctc 32760
gtattttgta tagcaaaacg cggccctggc agaacacact cttcttcgcc ttctatcctg 32820
ccgcttagcg tgttccgtgt gatagttcaa gtacaaccac actcttaagt tggtcaaaag 32880
aatgctggct tcagttgtaa tcaaaactcc atcgcatcta atcgttctga ggaaatcatc 32940
caagcaatgc aactggattg tgtttcaagc aggagaggag agggaagaga cggaagaacc 33000
atgttaattt ttattccaaa cgatctcgca gtacttcaaa ttgtagatcg cgcagatggc 33060
atctctcgcc cccactgtgt tggtgaaaaa gcacagctag atcaaaagaa atgcgatttt 33120
caaggtgctc aacggtggct tccagcaaag cctccacgcg cacatccaag aacaaaagaa 33180
taccaaaaga aggagcattt tctaactcct caatcatcat attacattcc tgcaccattc 33240
ccagataatt ttcagctttc cagccttgaa ttattcgtgt cagttcttgt ggtaaatcca 33300
atccacacat tacaaacagg tcccggaggg cgccctccac caccattctt aaacacaccc 33360
tcataatgac aaaatatctt gctcctgtgt cacctgtagc gaattgagaa tggcaacatc 33420
aattgacatg cccttggctc taagttcttc tttaagttct agttgtaaaa actctctcat 33480
attatcacca aactgcttag ccagaagccc cccgggaaca agagcagggg acgctacagt 33540
gcagtacaag cgcagacctc cccaattggc tccagcaaaa acaagattgg aataagcata 33600
ttgggaaccg ccagtaatat catcgaagtt gctggaaata taatcaggca gagtttcttg 33660
taaaaattga ataaaagaaa aatttgccaa aaaaacattc aaaacctctg ggatgcaaat 33720
gcaataggtt accgcgctgc gctccaacat tgttagtttt gaattagtct gcaaaaataa 33780
aaaaaaaaac aagcgtcata tcatagtagc ctgacgaaca gatggataaa tcagtctttc 33840
catcacaaga caagccacag ggtctccagc tcgaccctcg taaaacctgt catcatgatt 33900
aaacaacagc accgaaagtt cctcgcggtg accagcatga ataattcttg atgaagcata 33960
caatccagac atgttagcat cagttaacga gaaaaaacag ccaacatagc ctttgggtat 34020
aattatgctt aatcgtaagt atagcaaagc cacccctcgc ggatacaaag taaaaggcac 34080
aggagaataa aaaatataat tatttctctg ctgctgttca ggcaacgtcg cccccggtcc 34140
ctctaaatac acatacaaag cctcatcagc catggcttac cagacaaagt acagcgggca 34200
cacaaagcac aagctctaaa gtgactctcc aacctctcca caatatatat atacacaagc 34260
cctaaactga cgtaatggga gtaaagtgta aaaaatcccg ccaaacccaa cacacacccc 34320
gaaactgcgt caccagggaa aagtacagtt tcacttccgc aatcccaaca ggcgtaactt 34380
cctctttctc acggtacgtg atatcccact aacttgcaac gtcattttcc cacggtcgca 34440

-continued ccgccccttt tagccgttaa ccccacagcc aatcaccaca cgatccacac tttttaaaat 34500
cacctcattt acatattggc accattccat ctataaggta tattatatag ataga 34555

<210> SEQ ID NO 102
<211> LENGTH: 33595
<212> TYPE: DNA
<213> ORGANISM: Artificial Sequence
<220> FEATURE:
<223> OTHER INFORMATION: NG-420 virus genome sequence comprising a transgene cassette encoding a membrane-anchored chimeric form of the anti-human CD3e scFv inserted in the region BY

<400> SEQUENCE: 102
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540
tctgcgccgg cagtttaata ataaaaaaat gagagatttg cgatttctgc ctcaggaaat 600
aatctctgct gagactggaa atgaaatatt ggagcttgtg gtgcacgccc tgatgggaga 660
cgatccggag ccacctgtgc agctttttga gcctcctacg cttcaggaac tgtatgattt 720
agaggtagag ggatcggagg attctaatga ggaagctgta aatggctttt ttaccgattc 780
tatgctttta gctgctaatg aagggttaga attagatccg cctttggaca cttttgatac 840
tccaggggta attgtggaaa gcggtacagg tgtaagaaaa ttacctgatt tgagttccgt 900
ggactgtgat ttgcactgct atgaagacgg gtttcctccg agtgatgagg aggaccatga 960
aaaggagcag tccatgcaga ctgcagcggg tgagggagtg aaggctgcca atgttggttt 1020
tcagttggat tgcccggagc ttcctggaca tggctgtaag tcttgtgaat ttcacaggaa 1080
aaatactgga gtaaaggaac tgttatgttc gctttgttat atgagaacgc actgccactt 1140
tatttacagt aagtgtgttt aagttaaaat ttaaaggaat atgctgtttt tcacatgtat 1200
attgagtgtg agttttgtgc ttcttattat aggtcctgtg tctgatgctg atgaatcacc 1260
atctcctgat tctactacct cacctcctga gattcaagca cctgttcctg tggacgtgcg 1320
caagcccatt cctgtgaagc ttaagcctgg gaaacgtcca gcagtggaaa aacttgagga 1380
cttgttacag ggtggggacg gacctttgga cttgagtaca cggaaacgtc caagacaata 1440
agtgttccat atccgtgttt acttaaggtg acgtcaatat ttgtgtgaca gtgcaatgta 1500
ataaaaatat gttaactgtt cactggtttt tattgctttt tgggcgggga ctcaggtata 1560
taagtagaag cagacctgtg tggttagctc ataggagctg gctttcatcc atggaggttt 1620
gggccatttt ggaagacctt aggaagacta ggcaactgtt agagaacgct tcggacggag 1680
tctccggttt ttggagattc tggttcgcta gtgaattagc tagggtagtt tttaggataa 1740
aacaggacta taaacaagaa tttgaaaagt tgttggtaga ttgcccagga ctttttgaag 1800
ctcttaattt gggccatcag gttcacttta aagaaaaagt tttatcagtt ttagactttt 1860
caaccccagg tagaactgct gctgctgtgg cttttcttac ttttatatta gataaatgga 1920

-continued

```
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaacttttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
```

```
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tggggggcgta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
```

-continued

```
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
```

-continued

```
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa   10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
```

-continued gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740

-continued acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttctt gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccccctc gcacttagaa 15960 gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140

```
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
```

```
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
```

tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac cacccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960

-continued

```
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa atttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta ccccctatgaa gatgaaagca cctcccaaca  28440
cccctttata aacccagggt ttatttcccc aaatggcttc acacaaagcc caaacggagt  28500
tcttacttta aaatgtttaa ccccactaac aaccacaggc ggatctctac agctaaaagt  28560
gggagggggga cttacagtgg atgacaccaa cggtttttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc caccatggga tggagctgta tcatcctctt  29400
cttggtagca acagctacag gtgtccactc ccaggtgcag ctgcagcagt ctggggctga  29460
actggcaaga cctggggcct cagtgaagat gtcctgcaag gcttctggct acacctttac  29520
taggtacacg atgcactggg taaaacagag gcctggacag ggtctggaat ggattggata  29580
cattaatcct agccgtggtt atactaatta caatcagaag ttcaaggaca aggccacatt  29640
gactacagac aaatcctcca gcacagccta catgcaactg agcagcctga catctgagga  29700
ctctgcagtc tattactgtg caagatatta tgatgatcat tactgccttg actactgggg  29760
ccaaggcacc actctcacag tctcctcagg tggcggtggc tcgggcggtg gtggatctgg  29820
tggcggcgga tctgatatcg tgctcactca gtctccagca atcatgtctg catctccagg  29880
ggagaaggtc accatgacct gcagtgccag ctcaagtgta agttacatga actggtacca  29940
gcagaagtca ggcacctccc ccaaaagatg gatttatgac acatccaaac tggcttctgg  30000
agtccctgct cacttcaggg gcagtgggtc tgggacctct tactctctca caatcagcgg  30060
catggaggct gaagatgctg ccacttatta ctgccagcag tggagtagta acccattcac  30120
gttcggctcg gggacaaagt tggaaataaa ccggggatcc gaacaaaaac tcatctcaga  30180
agaggatctg aatgctgtgg gccaggacac gcaggaggtc atcgtggtgc cacactcctt  30240
gcccttttaag gtggtggtga tctcagccat cctggccctg gtggtgctca ccatcatctc  30300
ccttatcatc ctcatcatgc tttggcagaa gaagccacgt taagctagct tgactgactg  30360
```

agatacagcg taccttcagc tcacagacat gataagatac attgatgagt ttggacaaac 30420
cacaactaga atgcagtgaa aaaaatgctt tatttgtgaa atttgtgatg ctattgcttt 30480
atttgtaacc attataagct gcaataaaca agttaacaac aacaattgca ttcattttat 30540
gtttcaggtt cagggggagg tgtgggaggt tttttaaagc aagtaaaacc tctacaaatg 30600
tggtagtcgt cagctatcct gcaggaactt gtttatttga aaatcaattc acaaaatccg 30660
agtagttatt ttgcctcccc cttcccattt aacagaatac accaatctct ccccacgcac 30720
agctttaaac atttggatac cattagatat agacatggtt ttagattcca cattccaaac 30780
agtttcagag cgagccaatc tggggtcagt gatagataaa aatccatcgg gatagtcttt 30840
taaagcgctt tcacagtcca actgctgcgg atgcgactcc ggagtctgga tcacggtcat 30900
ctggaagaag aacgatggga atcataatcc gaaaacggta tcggacgatt gtgtctcatc 30960
aaacccacaa gcagccgctg tctgcgtcgc tccgtgcgac tgctgtttat gggatcaggg 31020
tccacagtgt cctgaagcat gattttaata gcccttaaca tcaactttct ggtgcgatgc 31080
gcgcagcaac gcattctgat ttcactcaaa tctttgcagt aggtacaaca cattattaca 31140
atattgttta ataaaccata attaaaagcg ctccagccaa aactcatatc tgatataatc 31200
gcccctgcat gaccatcata ccaaagttta atataaatta aatgacgttc cctcaaaaac 31260
acactaccca catacatgat ctcttttggc atgtgcatat taacaatctg tctgtaccat 31320
ggacaacgtt ggttaatcat gcaacccaat ataaccttcc ggaaccacac tgccaacacc 31380
gctcccccag ccatgcattg aagtgaaccc tgctgattac aatgacaatg aagaacccaa 31440
ttctctcgac cgtgaatcac ttgagaatga aaaatatcta tagtggcaca acatagacat 31500
aaatgcatgc atcttctcat aatttttaac tcctcaggat ttagaaacat atcccaggga 31560
ataggaagct cttgcagaac agtaaagctg gcagaacaag gaagaccacg aacacaactt 31620
acactatgca tagtcatagt atcacaatct ggcaacagcg ggtggtcttc agtcatagaa 31680
gctcgggttt cattttcctc acaacgtggt aactgggctc tggtgtaagg gtgatgtctg 31740
gcgcatgatg tcgagcgtgc gcgcaacctt gtcataatgg agttgcttcc tgacattctc 31800
gtattttgta tagcaaaacg cggccctggc agaacacact cttcttcgcc ttctatcctg 31860
ccgcttagcg tgttccgtgt gatagttcaa gtacaaccac actcttaagt tggtcaaaag 31920
aatgctggct tcagttgtaa tcaaaactcc atcgcatcta atcgttctga ggaaatcatc 31980
caagcaatgc aactggattg tgtttcaagc aggagaggag agggaagaga cggaagaacc 32040
atgttaattt ttattccaaa cgatctcgca gtacttcaaa ttgtagatcg cgcagatggc 32100
atctctcgcc cccactgtgt tggtgaaaaa gcacagctag atcaaaagaa atgcgatttt 32160
caaggtgctc aacggtggct tccagcaaag cctccacgcg cacatccaag aacaaaagaa 32220
taccaaaaga aggagcattt tctaactcct caatcatcat attacattcc tgcaccattc 32280
ccagataatt ttcagctttc cagccttgaa ttattcgtgt cagttcttgt ggtaaatcca 32340
atccacacat tacaaacagg tcccggaggg cgccctccac caccattctt aaacacaccc 32400
tcataatgac aaaatatctt gctcctgtgt cacctgtagc gaattgagaa tggcaacatc 32460
aattgacatg cccttggctc taagttcttc tttaagttct agttgtaaaa actctctcat 32520
attatcacca aactgcttag ccagaagccc cccgggaaca agagcagggg acgctacagt 32580
gcagtacaag cgcagacctc cccaattggc tccagcaaaa acaagattgg aataagcata 32640
ttgggaaccg ccagtaatat catcgaagtt gctggaaata taatcaggca gagtttcttg 32700

```
taaaaattga ataaaagaaa aatttgccaa aaaaacattc aaaacctctg ggatgcaaat  32760

gcaataggtt accgcgctgc gctccaacat tgttagtttt gaattagtct gcaaaaataa  32820

aaaaaaaaac aagcgtcata tcatagtagc ctgacgaaca gatggataaa tcagtctttc  32880

catcacaaga caagccacag ggtctccagc tcgaccctcg taaaacctgt catcatgatt  32940

aaacaacagc accgaaagtt cctcgcggtg accagcatga ataattcttg atgaagcata  33000

caatccagac atgttagcat cagttaacga gaaaaaacag ccaacatagc ctttgggtat  33060

aattatgctt aatcgtaagt atagcaaagc cacccctcgc ggatacaaag taaaaggcac  33120

aggagaataa aaaatataat tatttctctg ctgctgttca ggcaacgtcg cccccggtcc  33180

ctctaaatac acatacaaag cctcatcagc catggcttac cagacaaagt acagcgggca  33240

cacaaagcac aagctctaaa gtgactctcc aacctctcca caatatatat atacacaagc  33300

cctaaactga cgtaatggga gtaaagtgta aaaaatcccg ccaaacccaa cacacacccc  33360

gaaactgcgt caccagggaa aagtacagtt tcacttccgc aatcccaaca ggcgtaactt  33420

cctctttctc acggtacgtg atatcccact aacttgcaac gtcattttcc cacggtcgca  33480

ccgccccttt tagccgttaa ccccacagcc aatcaccaca cgatccacac tttttaaaat  33540

cacctcattt acatattggc accattccat ctataaggta tattatatag ataga       33595
```

<210> SEQ ID NO 103
<211> LENGTH: 33628
<212> TYPE: DNA
<213> ORGANISM: Artificial Sequence
<220> FEATURE:
<223> OTHER INFORMATION: NG-420 virus genome sequence comprising a transgene cassette encoding a membrane-anchored chimeric form of the anti-human CD3e scFv with a C-terminal V5 tag inserted in the region BY

<400> SEQUENCE: 103

```
tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540

tctgcgccgg cagtttaata ataaaaaaat gagagatttg cgatttctgc ctcaggaaat    600

aatctctgct gagactggaa atgaaatatt ggagcttgtg gtgcacgccc tgatgggaga    660

cgatccggag ccacctgtgc agctttttga gcctcctacg cttcaggaac tgtatgattt    720

agaggtagag ggatcggagg attctaatga ggaagctgta aatggctttt ttaccgattc    780

tatgctttta gctgctaatg aagggttaga attagatccg cctttggaca cttttgatac    840

tccaggggta attgtggaaa gcggtacagg tgtaagaaaa ttacctgatt tgagttccgt    900

ggactgtgat ttgcactgct atgaagacgg gtttcctccg agtgatgagg aggaccatga    960

aaaggagcag tccatgcaga ctgcagcggg tgagggagtg aaggctgcca atgttggttt   1020

tcagttggat tgcccggagc ttcctggaca tggctgtaag tcttgtgaat ttcacaggaa   1080
```

-continued

```
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg atagggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gttttttctg tcttgcagct   3480
```

```
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaacttttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
```

-continued

```
ttcaacatcc aggaatgtga ttggcttgta ggtgtatttc acgtgacctg gggtccccgc   5880
tggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
```

ggtcctgaga cgctgcggac tcaggttagt aggcagtgtc aggagattaa cttgcatgat 8280
cttttggagg gcgtgcggga ggttcagata gtacttgatc tcaacgggtc cgttggtgga 8340
gatgtcgatg gcttgcaggg ttccgtgtcc cttgggcgct accaccgtgc ccttgttttt 8400
cattttggac ggcggtggct ctgttgcttc ttgcatgttt agaagcggtg tcgagggcgc 8460
gcaccgggcg gcaggggcgg ctcgggaccc ggcggcatgg ctggcagtgg tacgtcggcg 8520
ccgcgcgcgg gtaggttctg gtactgcgcc ctgagaagac tcgcatgcgc gacgacgcgg 8580
cggttgacat cctggatctg acgcctctgg gtgaaagcta ccggccccgt gagcttgaac 8640
ctgaaagaga gttcaacaga atcaatctcg gtatcgttga cggcggcttg cctaaggatt 8700
tcttgcacgt caccagagtt gtcctggtag gcgatctccg ccatgaactg ctcgatctct 8760
tcctcttgaa gatctccgcg gcccgctctc tcgacggtgg ccgcgaggtc gttggagatg 8820
cgcccaatga gttgagagaa tgcattcatg cccgcctcgt tccagacgcg gctgtagacc 8880
acggccccca cgggatctct cgcgcgcatg accacctggg cgaggttgag ctccacgtgg 8940
cgggtgaaga ccgcatagtt gcataggcgc tggaaaaggt agttgagtgt ggtggcgatg 9000
tgctcggtga cgaagaaata catgatccat cgtctcagcg gcatctcgct gacatcgccc 9060
agagcttcca agcgctccat ggcctcgtag aagtccacgg caaaattaaa aaactgggag 9120
tttcgcgcgg acacggtcaa ctcctcttcc agaagacgga taagttcggc gatggtggtg 9180
cgcacctcgc gctcgaaagc ccctgggatt tcttcctcaa tctcttcttc ttccactaac 9240
atctcttcct cttcaggtgg ggctgcagga ggagggggaa cgcggcgacg ccggcggcgc 9300
acgggcagac ggtcgatgaa tctttcaatg acctctccgc ggcggcggcg catggtttca 9360
gtgacggcgc ggccgttctc gcgcggtcgc agagtaaaaa caccgccgcg catctcctta 9420
aagtggtgac tgggaggttc tccgtttggg agggagaggg cgctgattat acattttatt 9480
aattggcccg tagggactgc acgcagagat ctgatcgtgt caagatccac gggatctgaa 9540
aacctttcga cgaaagcgtc taaccagtca cagtcacaag gtaggctgag tacggcttct 9600
tgtgggcggg ggtggttatg tgttcggtct gggtcttctg tttcttcttc atctcgggaa 9660
ggtgagacga tgctgctggt gatgaaatta aagtaggcag ttctaagacg gcggatggtg 9720
gcgaggagca ccaggtcttt gggtccggct tgctggatac gcaggcgatt ggccattccc 9780
caagcattat cctgacatct agcaagatct ttgtagtagt cttgcatgag ccgttctacg 9840
ggcacttctt cctcacccgt tctgccatgc atacgtgtga gtccaaatcc gcgcattggt 9900
tgtaccagtg ccaagtcagc tacgactctt tcggcgagga tggcttgctg tacttgggta 9960
agggtggctt gaaagtcatc aaaatccaca aagcggtggt aagctcctgt attaatggtg 10020
taagcacagt tggccatgac tgaccagtta actgtctggt gaccagggcg cacgagctcg 10080
gtgtatttaa ggcgcgaata ggcgcgggtg tcaaagatgt aatcgttgca ggtgcgcacc 10140
agatactggt accctataag aaaatgcggc ggtggttggc ggtagagagg ccatcgttct 10200
gtagctggag cgccaggggc gaggtcttcc aacataaggc ggtgatagcc gtagatgtac 10260
ctggacatcc aggtgattcc tgcggcggta gtagaagccc gaggaaactc gcgtacgcgg 10320
ttccaaatgt tgcgtagcgg catgaagtag ttcattgtag gcacggtttg accagtgagg 10380
cgcgcgcagt cattgatgct ctatagacac ggagaaaatg aaagcgttca gcgactcgac 10440
tccgtagcct ggaggaacgt gaacgggttg ggtcgcggtg taccccggtt cgagacttgt 10500
actcgagccg gccggagccg cggctaacgt ggtattggca ctcccgtctc gacccagcct 10560

-continued

```
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
```

cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300

-continued

```
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
```

aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880
caccactaga ccgatagccc caatggccac cggggtgatg aaaccttctc agttgcatcg 17940
acccgtcacc ttggatttgc cccctccccc tgctgctact gctgtacccg cttctaagcc 18000
tgtcgctgcc ccgaaaccag tcgccgtagc caggtcacgt cccgggggcg ctcctcgtcc 18060
aaatgcgcac tggcaaaata ctctgaacag catcgtgggt ctaggcgtgc aaagtgtaaa 18120
acgccgtcgc tgcttttaat taaatatgga gtagcgctta acttgcctat ctgtgtatat 18180
gtgtcattac acgccgtcac agcagcagag gaaaaaagga agaggtcgtg cgtcgacgct 18240
gagttacttt caagatggcc accccatcga tgctgcccca atgggcatac atgcacatcg 18300
ccggacagga tgcttcggag tacctgagtc cgggtctggt gcagttcgcc cgcgccacag 18360
acacctactt caatctggga aataagttta gaaatcccac cgtagcgccg acccacgatg 18420
tgaccaccga ccgtagccag cggctcatgt tgcgcttcgt gcccgttgac cgggaggaca 18480
atacatactc ttacaaagtg cggtacaccc tggccgtggg cgacaacaga gtgctggata 18540
tggccagcac gttctttgac attaggggtg tgttggacag aggtcccagt ttcaaaccct 18600
attctggtac ggcttacaac tccctggctc ctaaaggcgc tccaaataca tctcagtgga 18660
ttgcagaagg tgtaaaaaat acaactggtg aggaacacgt aacagaagag gaaaccaata 18720
ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agtttttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg gggtgctgg ctggtcaagc gtctcagtta aatgcagtgg 19320
ttgacttgca ggacagaaac acagaacttt cttaccaact cttgcttgac tctctgggcg 19380
acagaaccag atactttagc atgtggaatc aggctgtgga cagttatgat cctgatgtac 19440
gtgttattga aaatcatggt gtggaagatg aacttcccaa ctactgtttt ccactggacg 19500
gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040

-continued

```
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
```

-continued tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780

-continued

```
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
```

-continued

```
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
ccccttttata aacccagggt ttatttcccc aaatggcttc acacaaagcc caaacggagt  28500
tcttacttta aaatgtttaa ccccactaac aaccacaggc ggatctctac agctaaaagt  28560
gggaggggga cttacagtgg atgacaccaa cggtttttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc caccatggga tggagctgta tcatcctctt  29400
cttggtagca acagctacag gtgtccactc ccaggtgcag ctgcagcagt ctggggctga  29460
actggcaaga cctggggcct cagtgaagat gtcctgcaag gcttctggct acacctttac  29520
```

-continued

```
taggtacacg atgcactggg taaaacagag gcctggacag ggtctggaat ggattggata  29580
cattaatcct agccgtggtt atactaatta caatcagaag ttcaaggaca aggccacatt  29640
gactacagac aaatcctcca gcacagccta catgcaactg agcagcctga catctgagga  29700
ctctgcagtc tattactgtg caagatatta tgatgatcat tactgccttg actactgggg  29760
ccaaggcacc actctcacag tctcctcagg tggcggtggc tcgggcggtg gtggatctgg  29820
tggcggcgga tctgatatcg tgctcactca gtctccagca atcatgtctg catctccagg  29880
ggagaaggtc accatgacct gcagtgccag ctcaagtgta agttacatga actggtacca  29940
gcagaagtca ggcacctccc ccaaaagatg gatttatgac acatccaaac tggcttctgg  30000
agtccctgct cacttcaggg gcagtgggtc tgggacctct tactctctca caatcagcgg  30060
catggaggct gaagatgctg ccacttatta ctgccagcag tggagtagta acccattcac  30120
gttcggctcg gggacaaagt tggaaataaa ccggggatcc gaacaaaaac tcatctcaga  30180
agaggatctg aatgctgtgg gccaggacac gcaggaggtc atcgtggtgc cacactcctt  30240
gccctttaag gtggtggtga tctcagccat cctggccctg gtggtgctca ccatcatctc  30300
ccttatcatc ctcatcatgc tttggcagaa gaagccacgt ggttcaatcc ctaaccctct  30360
cctcggtctc gattaagcta gcttgactga ctgagataca gcgtaccttc agctcacaga  30420
catgataaga tacattgatg agtttggaca aaccacaact agaatgcagt gaaaaaaatg  30480
ctttatttgt gaaatttgtg atgctattgc tttatttgta accattataa gctgcaataa  30540
acaagttaac aacaacaatt gcattcattt tatgtttcag gttcaggggg aggtgtggga  30600
ggttttttaa agcaagtaaa acctctacaa atgtggtagt cgtcagctat cctgcaggaa  30660
cttgtttatt tgaaaatcaa ttcacaaaat ccgagtagtt attttgcctc cccccttccca  30720
tttaacagaa tacaccaatc tctccccacg cacagcttta aacatttgga taccattaga  30780
tatagacatg gttttagatt ccacattcca aacagtttca gagcgagcca atctggggtc  30840
agtgatagat aaaaatccat cgggatagtc ttttaaagcg ctttcacagt ccaactgctg  30900
cggatgcgac tccggagtct ggatcacggt catctggaag aagaacgatg ggaatcataa  30960
tccgaaaacg gtatcggacg attgtgtctc atcaaaccca caagcagccg ctgtctgcgt  31020
cgctccgtgc gactgctgtt tatgggatca gggtccacag tgtcctgaag catgatttta  31080
atagccctta acatcaactt tctggtgcga tgcgcgcagc aacgcattct gatttcactc  31140
aaatctttgc agtaggtaca acacattatt acaatattgt ttaataaacc ataattaaaa  31200
gcgctccagc caaaactcat atctgatata atcgcccctg catgaccatc ataccaaagt  31260
ttaatataaa ttaaatgacg ttccctcaaa aacacactac ccacatacat gatctctttt  31320
ggcatgtgca tattaacaat ctgtctgtac catggacaac gttggttaat catgcaaccc  31380
aatataacct tccggaacca cactgccaac accgctcccc cagccatgca ttgaagtgaa  31440
ccctgctgat tacaatgaca atgaagaacc caattctctc gaccgtgaat cacttgagaa  31500
tgaaaaatat ctatagtggc acaacataga cataaatgca tgcatcttct cataattttt  31560
aactcctcag gatttagaaa catatcccag ggaataggaa gctcttgcag aacagtaaag  31620
ctggcagaac aaggaagacc acgaacacaa cttacactat gcatagtcat agtatcacaa  31680
tctggcaaca gcgggtggtc ttcagtcata gaagctcggg tttcattttc ctcacaacgt  31740
ggtaactggg ctctggtgta agggtgatgt ctggcgcatg atgtcgagcg tgcgcgcaac  31800
cttgtcataa tggagttgct tcctgacatt ctcgtatttt gtatagcaaa acgcggccct  31860
ggcagaacac actcttcttc gccttctatc ctgccgctta gcgtgttccg tgtgatagtt  31920
```

```
caagtacaac cacactctta agttggtcaa aagaatgctg gcttcagttg taatcaaaac  31980
tccatcgcat ctaatcgttc tgaggaaatc atccaagcaa tgcaactgga ttgtgtttca  32040
agcaggagag gagagggaag agacggaaga accatgttaa tttttattcc aaacgatctc  32100
gcagtacttc aaattgtaga tcgcgcagat ggcatctctc gcccccactg tgttggtgaa  32160
aaagcacagc tagatcaaaa gaaatgcgat tttcaaggtg ctcaacggtg gcttccagca  32220
aagcctccac gcgcacatcc aagaacaaaa gaataccaaa agaaggagca ttttctaact  32280
cctcaatcat catattacat tcctgcacca ttcccagata attttcagct ttccagcctt  32340
gaattattcg tgtcagttct tgtggtaaat ccaatccaca cattacaaac aggtcccgga  32400
gggcgccctc caccaccatt cttaaacaca ccctcataat gacaaaatat cttgctcctg  32460
tgtcacctgt agcgaattga gaatggcaac atcaattgac atgcccttgg ctctaagttc  32520
ttctttaagt tctagttgta aaaactctct catattatca ccaaactgct tagccagaag  32580
ccccccggga acaagagcag ggacgctac agtgcagtac aagcgcagac ctccccaatt  32640
ggctccagca aaaacaagat tggaataagc atattgggaa ccgccagtaa tatcatcgaa  32700
gttgctggaa atataatcag gcagagtttc ttgtaaaaat tgaataaaag aaaaatttgc  32760
caaaaaaaca ttcaaaacct ctgggatgca aatgcaatag gttaccgcgc tgcgctccaa  32820
cattgttagt tttgaattag tctgcaaaaa taaaaaaaaa aacaagcgtc atatcatagt  32880
agcctgacga acagatggat aaatcagtct ttccatcaca agacaagcca cagggtctcc  32940
agctcgaccc tcgtaaaacc tgtcatcatg attaaacaac agcaccgaaa gttcctcgcg  33000
gtgaccagca tgaataattc ttgatgaagc atacaatcca gacatgttag catcagttaa  33060
cgagaaaaaa cagccaacat agcctttggg tataattatg cttaatcgta agtatagcaa  33120
agccacccct cgcggataca aagtaaaagg cacaggagaa taaaaaatat aattatttct  33180
ctgctgctgt tcaggcaacg tcgcccccgg tccctctaaa tacacataca aagcctcatc  33240
agccatggct taccagacaa agtacagcgg gcacacaaag cacaagctct aaagtgactc  33300
tccaacctct ccacaatata tatatacaca agccctaaac tgacgtaatg ggagtaaagt  33360
gtaaaaaatc ccgccaaacc caacacacac cccgaaactg cgtcaccagg gaaaagtaca  33420
gtttcacttc cgcaatccca acaggcgtaa cttcctcttt ctcacggtac gtgatatccc  33480
actaacttgc aacgtcattt tcccacggtc gcaccgcccc ttttagccgt taaccccaca  33540
gccaatcacc acacgatcca cactttttaa aatcacctca tttacatatt ggcaccattc  33600
catctataag gtatattata tagataga                                    33628
```

<210> SEQ ID NO 104
<211> LENGTH: 15
<212> TYPE: PRT
<213> ORGANISM: Artificial Sequence
<220> FEATURE:
<223> OTHER INFORMATION: Linker

<400> SEQUENCE: 104

```
Gly Gly Gly Gly Ser Gly Gly Gly Gly Ser Gly Gly Gly Gly Ser
1               5                   10                  15
```

<210> SEQ ID NO 105
<211> LENGTH: 13
<212> TYPE: RNA
<213> ORGANISM: Artificial Sequence
<220> FEATURE:
<223> OTHER INFORMATION: Sequence comprising a start codon

<400> SEQUENCE: 105
gccgccrcca ugg 13

<210> SEQ ID NO 106
<211> LENGTH: 10
<212> TYPE: PRT
<213> ORGANISM: Artificial Sequence
<220> FEATURE:
<223> OTHER INFORMATION: c-myc tag

<400> SEQUENCE: 106

Glu Gln Lys Leu Ile Ser Glu Glu Asp Leu
1 5 10

<210> SEQ ID NO 107
<211> LENGTH: 13
<212> TYPE: PRT
<213> ORGANISM: Artificial Sequence
<220> FEATURE:
<223> OTHER INFORMATION: c-myc tag with amino acid spacer at the N and C-terminal

<400> SEQUENCE: 107

Gly Ser Glu Gln Lys Leu Ile Ser Glu Glu Asp Leu Asn
1 5 10

<210> SEQ ID NO 108
<211> LENGTH: 62
<212> TYPE: PRT
<213> ORGANISM: Artificial Sequence
<220> FEATURE:
<223> OTHER INFORMATION: spacer - c-myc tag -spacer PDGF TM domain

<400> SEQUENCE: 108

Gly Ser Glu Gln Lys Leu Ile Ser Glu Glu Asp Leu Asn Ala Val Gly
1 5 10 15

Gln Asp Thr Gln Glu Val Ile Val Val Pro His Ser Leu Pro Phe Lys
20 25 30

Val Val Val Ile Ser Ala Ile Leu Ala Leu Val Val Leu Thr Ile Ile
35 40 45

Ser Leu Ile Ile Leu Ile Met Leu Trp Gln Lys Lys Pro Arg
50 55 60

<210> SEQ ID NO 109
<211> LENGTH: 32345
<212> TYPE: DNA
<213> ORGANISM: Artificial Sequence
<220> FEATURE:
<223> OTHER INFORMATION: Fully synthetic EnAd genome with incorporated cloning site for transgene cassette insertion as in plasmid pEnAd2.4

<400> SEQUENCE: 109
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420

-continued

```
ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540

tctgcgccgg cagtttaata ataaaaaaat gagagatttg cgatttctgc ctcaggaaat    600

aatctctgct gagactggaa atgaaatatt ggagcttgtg gtgcacgccc tgatgggaga    660

cgatccggag ccacctgtgc agctttttga gcctcctacg cttcaggaac tgtatgattt    720

agaggtagag ggatcggagg attctaatga ggaagctgta aatggctttt ttaccgattc    780

tatgctttta gctgctaatg aagggttaga attagatccg cctttggaca cttttgatac    840

tccaggggta attgtggaaa gcggtacagg tgtaagaaaa ttacctgatt tgagttccgt    900

ggactgtgat ttgcactgct atgaagacgg gtttcctccg agtgatgagg aggaccatga    960

aaaggagcag tccatgcaga ctgcagcggg tgagggagtg aaggctgcca atgttggttt   1020

tcagttggat tgcccggagc ttcctggaca tggctgtaag tcttgtgaat ttcacaggaa   1080

aaatactgga gtaaaggaac tgttatgttc gctttgttat atgagaacgc actgccactt   1140

tatttacagt aagtgtgttt aagttaaaat ttaaaggaat atgctgtttt tcacatgtat   1200

attgagtgtg agttttgtgc ttcttattat aggtcctgtg tctgatgctg atgaatcacc   1260

atctcctgat tctactacct cacctcctga gattcaagca cctgttcctg tggacgtgcg   1320

caagcccatt cctgtgaagc ttaagcctgg gaaacgtcca gcagtggaaa aacttgagga   1380

cttgttacag ggtggggacg gacctttgga cttgagtaca cggaaacgtc caagacaata   1440

agtgttccat atccgtgttt acttaaggtg acgtcaatat ttgtgtgaca gtgcaatgta   1500

ataaaaatat gttaactgtt cactggtttt tattgctttt tgggcgggga ctcaggtata   1560

taagtagaag cagacctgtg tggttagctc ataggagctg gctttcatcc atggaggttt   1620

gggccatttt ggaagacctt aggaagacta ggcaactgtt agagaacgct tcggacggag   1680

tctccggttt ttggagattc tggttcgcta gtgaattagc tagggtagtt tttaggataa   1740

aacaggacta taaacaagaa tttgaaaagt tgttggtaga ttgcccagga ctttttgaag   1800

ctcttaattt gggccatcag gttcacttta aagaaaaagt tttatcagtt ttagactttt   1860

caaccccagg tagaactgct gctgctgtgg cttttcttac ttttatatta gataaatgga   1920

tcccgcagac tcatttcagc aggggatacg ttttggattt catagccaca gcattgtgga   1980

gaacatggaa ggttcgcaag atgaggacaa tcttaggtta ctggccagtg cagcctttgg   2040

gtgtagcggg aatcctgagg catccaccgg tcatgccagc ggttctggag gaggaacagc   2100

aagaggacaa cccgagagcc ggcctggacc ctccagtgga ggaggcggag tagctgactt   2160

gtctcctgaa ctgcaacggg tgcttactgg atctacgtcc actggacggg ataggggcgt   2220

taagagggag agggcatcta gtggtactga tgctagatct gagttggctt taagtttaat   2280

gagtcgcaga cgtcctgaaa ccatttggtg gcatgaggtt cagaaagagg gaagggatga   2340

agtttctgta ttgcaggaga aatattcact ggaacaggtg aaaacatgtt ggttggagcc   2400

tgaggatgat tgggaggtgg ccattaaaaa ttatgccaag atagctttga ggcctgataa   2460

acagtataag attactagac ggattaatat ccggaatgct tgttacatat ctggaaatgg   2520

ggctgaggtg gtaatagata ctcaagacaa ggcagttatt agatgctgca tgatggatat   2580

gtggcctggg gtagtcggta tggaagcagt aacttttgta aatgttaagt ttaggggaga   2640

tggttataat ggaatagtgt ttatggccaa taccaaactt atattgcatg gttgtagctt   2700

ttttggtttc aacaatacct gtgtagatgc ctggggacag gttagtgtac ggggatgtag   2760
```

-continued

```
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat ttttccagg atcctataga ggtgggattg aatgtttaga tacatgggca    4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
```

ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg gggtccccgc 5880 tggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060
tttcatgagg ttttcgtcca tctggtcaga aaacacaatt tttttattgt caagtttggt 6120
ggcaaatgat ccatacaggg cgttggataa aagtttggca atggatcgca tggtttggtt 6180
cttttccttg tccgcgcgct ctttggcggc gatgttgagt tggacatact cgcgtgccag 6240
gcacttccat tcggggaaga tagttgttaa ttcatctggc acgattctca cttgccaccc 6300
tcgattatgc aaggtaatta aatccacact ggtggccacc tcgcctcgaa ggggttcatt 6360
ggtccaacag agcctacctc ctttcctaga acagaaaggg ggaagtgggt ctagcataag 6420
ttcatcggga gggtctgcat ccatggtaaa gattcccgga agtaaatcct tatcaaaata 6480
gctgatggga gtggggtcat ctaaggccat ttgccattct cgagctgcca gtgcgcgctc 6540
atatgggtta aggggactgc cccatggcat gggatgggtg agtgcagagg catacatgcc 6600
acagatgtca tagacgtaga tgggatcctc aaagatgcct atgtaggttg gatagcatcg 6660 ccccctctg atacttgctc gcacatagtc atatagttca tgtgatggcg ctagcagccc 6720
cggacccaag ttggtgcgat tgggtttttc tgttctgtag acgatctggc gaaagatggc 6780
gtgagaattg gaagagatgg tgggtctttg aaaaatgttg aaatgggcat gaggtagacc 6840
tacagagtct ctgacaaagt gggcataaga ttcttgaagc ttggttacca gttcggcggt 6900
gacaagtacg tctagggcgc agtagtcaag tgtttcttga atgatgtcat aacctggttg 6960
gtttttcttt tcccacagtt cgcggttgag aaggtattct tcgcgatcct tccagtactc 7020
ttctagcgga aacccgtctt tgtctgcacg gtaagatcct agcatgtaga actgattaac 7080
tgccttgtaa gggcagcagc ccttctctac gggtagagag tatgcttgag cagcttttcg 7140
tagcgaagcg tgagtaaggg caaaggtgtc tctgaccatg actttgagga attggtattt 7200
gaagtcgatg tcgtcacagg ctccctgttc ccagagttgg aagtctaccc gtttcttgta 7260
ggcggggttg ggcaaagcga aagtaacatc attgaagaga atcttgccgg ccctgggcat 7320
gaaattgcga gtgatgcgaa aaggctgtgg tacttccgct cggttattga taacctgggc 7380
agctaggacg atctcgtcga aaccgttgat gttgtgtcct acgatgtata attctatgaa 7440
acgcggcgtg cctctgacgt gaggtagctt actgagctca tcaaaggtta ggtctgtggg 7500

-continued

```
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc cctgggatt tcttcctcaa tctcttcttc ttccactaac    9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
```

-continued

```
tgtaccagtg ccaagtcagc tacgactctt tcggcgagga tggcttgctg tacttgggta   9960

agggtggctt gaaagtcatc aaaatccaca aagcggtggt aagctcctgt attaatggtg  10020

taagcacagt tggccatgac tgaccagtta actgtctggt gaccagggcg cacgagctcg  10080

gtgtatttaa ggcgcgaata ggcgcgggtg tcaaagatgt aatcgttgca ggtgcgcacc  10140

agatactggt accctataag aaaatgcggc ggtggttggc ggtagagagg ccatcgttct  10200

gtagctggag cgccaggggc gaggtcttcc aacataaggc ggtgatagcc gtagatgtac  10260

ctggacatcc aggtgattcc tgcggcggta gtagaagccc gaggaaactc gcgtacgcgg  10320

ttccaaatgt tgcgtagcgg catgaagtag ttcattgtag gcacggtttg accagtgagg  10380

cgcgcgcagt cattgatgct ctatagacac ggagaaaatg aaagcgttca gcgactcgac  10440

tccgtagcct ggaggaacgt gaacgggttg ggtcgcggtg taccccggtt cgagacttgt  10500

actcgagccg gccggagccg cggctaacgt ggtattggca ctcccgtctc gacccagcct  10560

acaaaaatcc aggatacgga atcgagtcgt tttgctggtt tccgaatggc agggaagtga  10620

gtcctatttt tttttttgc cgctcagatg catcccgtgc tgcgacagat gcgcccccaa  10680

caacagcccc cctcgcagca gcagcagcag caatcacaaa aggctgtccc tgcaactact  10740

gcaactgccg ccgtgagcgg tgcgggacag cccgcctatg atctggactt ggaagagggc  10800

gaaggactgg cacgtctagg tgcgccttca cccgagcggc atccgcgagt tcaactgaaa  10860

aaagattctc gcgaggcgta tgtgccccaa cagaacctat ttagagacag aagcggcgag  10920

gagccggagg agatgcgagc ttcccgcttt aacgcgggtc gtgagctgcg tcacggtttg  10980

gaccgaagac gagtgttgcg ggacgaggat ttcgaagttg atgaaatgac agggatcagt  11040

cctgccaggg cacacgtggc tgcagccaac cttgtatcgg cttacgagca gacagtaaag  11100

gaagagcgta acttccaaaa gtcttttaat aatcatgtgc gaaccctgat tgcccgcgaa  11160

gaagttaccc ttggtttgat gcatttgtgg gatttgatgg aagctatcat tcagaaccct  11220

actagcaaac ctctgaccgc ccagctgttt ctggtggtgc aacacagcag agacaatgag  11280

gctttcagag aggcgctgct gaacatcacc gaacccgagg ggagatggtt gtatgatctt  11340

atcaacattc tacagagtat catagtgcag gagcggagcc tgggcctggc cgagaaggtg  11400

gctgccatca attactcggt tttgagcttg ggaaaatatt acgctcgcaa aatctacaag  11460

actccatacg ttcccataga caaggaggtg aagatagatg ggttctacat gcgcatgacg  11520

ctcaaggtct tgaccctgag cgatgatctt ggggtgtatc gcaatgacag aatgcatcgc  11580

gcggttagcg ccagcaggag gcgcgagtta agcgacaggg aactgatgca cagtttgcaa  11640

agagctctga ctggagctgg aaccgagggt gagaattact tcgacatggg agctgacttg  11700

cagtggcagc ctagtcgcag ggctctgagc gccgcgacgg caggatgtga gcttccttac  11760

atagaagagg cggatgaagg cgaggaggaa gagggcgagt acttggaaga ctgatggcac  11820

aacccgtgtt ttttgctaga tggaacagca agcaccggat cccgcaatgc gggcggcgct  11880

gcagagccag ccgtccggca ttaactcctc ggacgattgg acccaggcca tgcaacgtat  11940

catggcgttg acgactcgca accccgaagc ctttagacag caaccccagg ccaaccgtct  12000

atcggccatc atggaagctg tagtgccttc ccgctctaat cccactcatg agaaggtcct  12060

ggccatcgtg aacgcgttgg tggagaacaa agctattcgt ccagatgagg ccggactggt  12120

atacaacgct ctcttagaac gcgtggctcg ctacaacagt agcaatgtgc aaaccaattt  12180

ggaccgtatg ataacagatg tacgcgaagc cgtgtctcag cgcgaaaggt tccagcgtga  12240
```

-continued

```
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
```

```
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg gggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg ggcgcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
```

gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220
gttttttacc agccttaatt ccaattatcg ctgctgcaat tggcgcgata ccaggcatag 17280
cttccgtggc ggttcaggcc tcgcaacgac attgacattg gaaaaaaacg tataaataaa 17340
aaaaaaaaaa tacaatggac tctgacactc ctggtcctgt gactatgttt tcttagagat 17400
ggaagacatc aatttttcat ccttggctcc gcgacacggc acgaagccgt acatgggcac 17460
ctggagcgac atcggcacga gccaactgaa cgggggcgcc ttcaattgga gcagtatctg 17520
gagcgggctt aaaaattttg gctcaaccat aaaaacatac gggaacaaag cttggaacag 17580
cagtacagga caggcgctta gaaataaact taaagaccag aacttccaac aaaaagtagt 17640
cgatgggata gcttccggca tcaatggagt ggtagatttg gctaaccagg ctgtgcagaa 17700
aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880
caccactaga ccgatagccc caatggccac cggggtgatg aaaccttctc agttgcatcg 17940
acccgtcacc ttggatttgc cccctccccc tgctgctact gctgtacccg cttctaagcc 18000
tgtcgctgcc ccgaaaccag tcgccgtagc caggtcacgt cccgggggcg ctcctcgtcc 18060
aaatgcgcac tggcaaaata ctctgaacag catcgtgggt ctaggcgtgc aaagtgtaaa 18120
acgccgtcgc tgcttttaat taaatatgga gtagcgctta acttgcctat ctgtgtatat 18180
gtgtcattac acgccgtcac agcagcagag gaaaaaagga agaggtcgtg cgtcgacgct 18240
gagttacttt caagatggcc accccatcga tgctgcccca atgggcatac atgcacatcg 18300
ccggacagga tgcttcggag tacctgagtc cgggtctggt gcagttcgcc cgcgccacag 18360
acacctactt caatctggga aataagttta gaaatcccac cgtagcgccg acccacgatg 18420
tgaccaccga ccgtagccag cggctcatgt tgcgcttcgt gcccgttgac cgggaggaca 18480
atacatactc ttacaaagtg cggtacaccc tggccgtggg cgacaacaga gtgctggata 18540
tggccagcac gttctttgac attaggggtg tgttggacag aggtcccagt ttcaaaccct 18600
attctggtac ggcttacaac tccctggctc ctaaaggcgc tccaaataca tctcagtgga 18660
ttgcagaagg tgtaaaaaat acaactggtg aggaacacgt aacagaagag gaaaccaata 18720
ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agtttttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg gggggtgctgg ctggtcaagc gtctcagtta aatgcagtgg 19320
ttgacttgca ggacagaaac acagaacttt cttaccaact cttgcttgac tctctgggcg 19380

```
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
```

cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120

-continued cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac caccccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460

-continued

```
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
ccccttata aacccagggt ttatttcccc aaatggcttc acacaaagcc caaacggagt  28500
tcttacttta aaatgtttaa ccccactaac aaccacaggc ggatctctac agctaaaagt  28560
gggaggggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
```

```
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgctaccct gcaggaactt gtttatttga aaatcaattc  29400
acaaaatccg agtagttatt ttgcctcccc cttcccattt aacagaatac accaatctct  29460
ccccacgcac agctttaaac atttggatac cattagatat agacatggtt ttagattcca  29520
cattccaaac agtttcagag cgagccaatc tggggtcagt gatagataaa aatccatcgg  29580
gatagtcttt taaagcgctt tcacagtcca actgctgcgg atgcgactcc ggagtctgga  29640
tcacggtcat ctggaagaag aacgatggga atcataatcc gaaaacggta tcggacgatt  29700
gtgtctcatc aaacccacaa gcagccgctg tctgcgtcgc tccgtgcgac tgctgtttat  29760
gggatcaggg tccacagtgt cctgaagcat gattttaata gcccttaaca tcaactttct  29820
ggtgcgatgc gcgcagcaac gcattctgat ttcactcaaa tctttgcagt aggtacaaca  29880
cattattaca atattgttta ataaaccata attaaaagcg ctccagccaa aactcatatc  29940
tgatataatc gcccctgcat gaccatcata ccaaagttta atataaatta aatgacgttc  30000
cctcaaaaac acactaccca catacatgat ctcttttggc atgtgcatat taacaatctg  30060
tctgtaccat ggacaacgtt ggttaatcat gcaacccaat ataaccttcc ggaaccacac  30120
tgccaacacc gctcccccag ccatgcattg aagtgaaccc tgctgattac aatgacaatg  30180
aagaacccaa ttctctcgac cgtgaatcac ttgagaatga aaaatatcta tagtggcaca  30240
acatagacat aaatgcatgc atcttctcat aatttttaac tcctcaggat ttagaaacat  30300
atcccaggga ataggaagct cttgcagaac agtaaagctg gcagaacaag gaagaccacg  30360
aacacaactt acactatgca tagtcatagt atcacaatct ggcaacagcg ggtggtcttc  30420
agtcatagaa gctcgggttt cattttcctc acaacgtggt aactgggctc tggtgtaagg  30480
gtgatgtctg gcgcatgatg tcgagcgtgc gcgcaacctt gtcataatgg agttgcttcc  30540
tgacattctc gtattttgta tagcaaaacg cggccctggc agaacacact cttcttcgcc  30600
ttctatcctg ccgcttagcg tgttccgtgt gatagttcaa gtacaaccac actcttaagt  30660
tggtcaaaag aatgctggct tcagttgtaa tcaaaactcc atcgcatcta atcgttctga  30720
ggaaatcatc caagcaatgc aactggattg tgtttcaagc aggagaggag agggaagaga  30780
cggaagaacc atgttaattt ttattccaaa cgatctcgca gtacttcaaa ttgtagatcg  30840
cgcagatggc atctctcgcc cccactgtgt tggtgaaaaa gcacagctag atcaaaagaa  30900
atgcgatttt caaggtgctc aacggtggct tccagcaaag cctccacgcg cacatccaag  30960
aacaaaagaa taccaaaaga aggagcattt tctaactcct caatcatcat attacattcc  31020
tgcaccattc ccagataatt ttcagctttc cagccttgaa ttattcgtgt cagttcttgt  31080
ggtaaatcca atccacacat tacaaacagg tcccggaggg cgccctccac caccattctt  31140
aaacacaccc tcataatgac aaaatatctt gctcctgtgt cacctgtagc gaattgagaa  31200
```

-continued

```
tggcaacatc aattgacatg cccttggctc taagttcttc tttaagttct agttgtaaaa  31260

actctctcat attatcacca aactgcttag ccagaagccc cccgggaaca agagcagggg  31320

acgctacagt gcagtacaag cgcagacctc cccaattggc tccagcaaaa acaagattgg  31380

aataagcata ttgggaaccg ccagtaatat catcgaagtt gctggaaata taatcaggca  31440

gagtttcttg taaaaattga ataaaagaaa aatttgccaa aaaaacattc aaaacctctg  31500

ggatgcaaat gcaataggtt accgcgctgc gctccaacat tgttagtttt gaattagtct  31560

gcaaaaataa aaaaaaaaac aagcgtcata tcatagtagc ctgacgaaca gatggataaa  31620

tcagtctttc catcacaaga caagccacag ggtctccagc tcgaccctcg taaaacctgt  31680

catcatgatt aaacaacagc accgaaagtt cctcgcggtg accagcatga ataattcttg  31740

atgaagcata caatccagac atgttagcat cagttaacga gaaaaaacag ccaacatagc  31800

ctttgggtat aattatgctt aatcgtaagt atagcaaagc cacccctcgc ggatacaaag  31860

taaaaggcac aggagaataa aaaatataat tatttctctg ctgctgttca ggcaacgtcg  31920

cccccggtcc ctctaaatac acatacaaag cctcatcagc catggcttac cagacaaagt  31980

acagcgggca cacaaagcac aagctctaaa gtgactctcc aacctctcca caatatatat  32040

atacacaagc cctaaactga cgtaatggga gtaaagtgta aaaaatcccg ccaaacccaa  32100

cacacacccc gaaactgcgt caccagggaa aagtacagtt tcacttccgc aatcccaaca  32160

ggcgtaactt cctctttctc acggtacgtg atatcccact aacttgcaac gtcattttcc  32220

cacggtcgca ccgccccttt tagccgttaa ccccacagcc aatcaccaca cgatccacac  32280

tttttaaaat cacctcattt acatattggc accattccat ctataaggta tattatatag  32340

ataga                                                              32345
```